(12) United States Patent
Zhang et al.

(10) Patent No.: US 12,430,402 B2
(45) Date of Patent: Sep. 30, 2025

(54) CONFIDENCE GENERATION USING A NEURAL NETWORK

(71) Applicant: NVIDIA Corporation, Santa Clara, CA (US)

(72) Inventors: Eric Kangning Zhang, Plano, TX (US); Zoran Nikolic, Sugarland, TX (US); Branislav Kisacanin, Plano, TX (US); Eric Viscito, Shelburne, VT (US)

(73) Assignee: NVIDIA Corporation, Santa Ana, CA (US)

( * ) Notice: Subject to any disclaimer, the term of this patent is extended or adjusted under 35 U.S.C. 154(b) by 303 days.

(21) Appl. No.: 17/158,743

(22) Filed: Jan. 26, 2021

(65) Prior Publication Data

US 2022/0237414 A1    Jul. 28, 2022

(51) Int. Cl.
*G06F 18/21*     (2023.01)
*A01B 69/00*     (2006.01)
(Continued)

(52) U.S. Cl.
CPC .......... *G06F 18/217* (2023.01); *A01B 69/001* (2013.01); *A01C 21/005* (2013.01); *A01G 25/09* (2013.01); *A01G 25/16* (2013.01); *A01M 21/00* (2013.01); *B60W 10/04* (2013.01); *B60W 10/18* (2013.01); *B60W 30/09* (2013.01); *B60W 30/0956* (2013.01); *B60W 50/14* (2013.01); *B60W 60/0015* (2020.02); *G06F 18/2163* (2023.01); *G06F 18/24* (2023.01); *G06N 3/04* (2013.01); *G06N 3/08* (2013.01); *G06V 20/13* (2022.01); *G06V 20/56* (2022.01);
(Continued)

(58) Field of Classification Search
CPC .... A01B 69/001; A01C 21/005; A01G 25/09; A01G 25/16; A01M 21/00; B60W 10/04; B60W 10/18; B60W 2420/40; B60W 2556/45; B60W 30/09; B60W 30/0956; B60W 50/14; B60W 60/0015; G06F 18/2163; G06F 18/217; G06F 18/24; G06N 3/04; G06N 3/08; G06V 10/26; G06V 10/82; G06V 10/95; G06V 10/955; G06V 20/13; G06V 20/188; G06V 20/56; G06V 20/58; G06V 2201/03; G06V 2201/031; G16H 40/67
See application file for complete search history.

(56) References Cited

U.S. PATENT DOCUMENTS 10,726,303 B1 *   7/2020   Kim ...................... G05D 1/0061
11,200,429 B1 * 12/2021   Evans ................... G06V 10/62
(Continued)

OTHER PUBLICATIONS

Yingda et al., Nov. 3, 2020, "Synthesize then Compare: Detecting Failures and Anomalies for Semantic Segmentation" (Year: 2020).*
(Continued)

*Primary Examiner* — Babar Sarwar
(74) *Attorney, Agent, or Firm* — Davis Wright Tremaine LLP

(57) ABSTRACT

Apparatuses, systems, and techniques to generate one or more confidence values associated with one or more objects identified by one or more neural networks. In at least one embodiment, one or more confidence values associated with one or more objects identified by one or more neural networks are generated based on, for example, one or more neural network outputs.

34 Claims, 57 Drawing Sheets

(51) Int. Cl.

| | |
|---|---|
| *A01C 21/00* | (2006.01) |
| *A01G 25/09* | (2006.01) |
| *A01G 25/16* | (2006.01) |
| *A01M 21/00* | (2006.01) |
| *B60W 10/04* | (2006.01) |
| *B60W 10/18* | (2012.01) |
| *B60W 30/09* | (2012.01) |
| *B60W 30/095* | (2012.01) |
| *B60W 50/14* | (2020.01) |
| *B60W 60/00* | (2020.01) |
| *G06F 18/24* | (2023.01) |
| *G06N 3/04* | (2023.01) |
| *G06N 3/08* | (2023.01) |
| *G06V 20/13* | (2022.01) |
| *G06V 20/56* | (2022.01) |
| *G16H 40/67* | (2018.01) |

(52) U.S. Cl.
CPC ......... *G16H 40/67* (2018.01); *B60W 2420/40* (2013.01); *B60W 2556/45* (2020.02); *G06V 2201/03* (2022.01)

(56) References Cited

U.S. PATENT DOCUMENTS

| | | | |
|---|---|---|---|
| 11,409,304 B1* | 8/2022 | Cai | B60R 1/00 |
| 11,450,008 B1* | 9/2022 | Tyagi | G06N 3/0464 |
| 11,628,855 B1* | 4/2023 | Pradhan | G01S 17/58 |
| | | | 701/24 |
| 11,681,912 B2* | 6/2023 | Kim | G06N 3/08 |
| | | | 706/20 |
| 11,727,626 B2* | 8/2023 | Holzer | G06T 7/593 |
| | | | 345/419 |
| 2019/0258878 A1* | 8/2019 | Koivisto | G06V 10/46 |
| 2020/0311429 A1* | 10/2020 | Chen | A61B 5/1116 |
| 2021/0107487 A1* | 4/2021 | Oh | B60W 30/09 |
| 2021/0150230 A1* | 5/2021 | Smolyanskiy | G06V 10/82 |
| 2021/0209136 A1* | 7/2021 | Jha | G06F 16/29 |
| 2022/0138767 A1* | 5/2022 | Ashtekar | G06V 10/58 |
| | | | 705/7.22 |
| 2022/0234617 A1* | 7/2022 | Sholingar | B60W 30/0956 |
| 2022/0237414 A1* | 7/2022 | Zhang | A01M 21/00 |
| 2022/0245936 A1* | 8/2022 | Valk | G06V 20/13 |
| 2022/0269271 A1* | 8/2022 | Smolyanskiy | B62D 6/001 |
| 2022/0323030 A1* | 10/2022 | Manalad | A61B 6/482 |
| 2022/0343641 A1* | 10/2022 | Runge | G06N 3/045 |
| 2022/0388547 A1* | 12/2022 | Yangel | G06V 20/58 |
| 2022/0398827 A1* | 12/2022 | Lewis | G06N 3/045 |
| 2022/0402494 A1* | 12/2022 | Krutsch | B60W 30/18109 |
| 2023/0015771 A1* | 1/2023 | Nassi | G06N 3/08 |
| 2023/0023434 A1* | 1/2023 | Nowicka | G06V 20/00 |
| 2023/0039394 A1* | 2/2023 | Oestrich | B23K 9/0956 |
| 2023/0048222 A1* | 2/2023 | Yamamoto | G06V 10/56 |
| 2023/0065433 A1* | 3/2023 | Li | G06V 10/82 |
| 2023/0079886 A1* | 3/2023 | Amirghodsi | G06V 10/771 |
| | | | 706/25 |
| 2023/0171510 A1* | 6/2023 | Lindgren | H04N 23/745 |
| | | | 348/148 |
| 2023/0177682 A1* | 6/2023 | Xiao | G06T 7/11 |
| | | | 382/133 |
| 2023/0260270 A1* | 8/2023 | Iino | G06N 3/08 |
| | | | 382/156 |
| 2023/0326041 A1* | 10/2023 | Babazaki | G06T 7/248 |
| | | | 382/103 |
| 2024/0112035 A1* | 4/2024 | You | G06N 3/045 |

OTHER PUBLICATIONS

Chuan et al., Aug. 6, 2017, "On Calibration of Modern Neural Networks", (Year: 2017).*

Guo et al., "On Calibration of Modern Neural Networks," ICML: Proceedings of the 34th International Conference on Machine Learning, vol. 70, Aug. 6, 2017, 10 pages.

International Search Report and Written Opinion for Application No. PCT/US2022/013762, mailed Apr. 29, 2022, filed Jan. 25, 2022, 18 pages.

Xia et al., "Synthesize Then Compare: Detecting Failures and Anomalies for Semantic Segmentation," ECCV, Lecture Notes in Computer Science, Nov. 3, 2020, 17 pages.

Grosse, "Temperature Calibration of Proability Distributions," retrieved from Youtube, from https://www.youtube.com/watch?v=kup03Wfg4SA, Oct. 10, 2019, 3 pages.

IEEE, "IEEE Standard 754-2008 (Revision of IEEE Standard 754-1985): IEEE Standard for Floating-Point Arithmetic," Aug. 29, 2008, 70 pages.

Society of Automotive Engineers On-Road Automated Vehicle Standards Committee, "Taxonomy and Definitions for Terms Related to Driving Automation Systems for On-Road Motor Vehicles," Standard No. J3016-201609, issued Jan. 2014, revised Sep. 2016, 30 pages.

Society of Automotive Engineers On-Road Automated Vehicle Standards Committee, "Taxonomy and Definitions for Terms Related to Driving Automation Systems for On-Road Motor Vehicles," Standard No. J3016-201806, issued Jan. 2014, revised Jun. 2018, 35 pages.

Zhang, "Visual Semantic Segmentation," retrieved from, https://github.com/ekzhang/fastseg, Sep. 29, 2020, 10 pages.

* cited by examiner

CONFIDENCE GENERATION USING A NEURAL NETWORK

TECHNICAL FIELD

At least one embodiment pertains to processing resources used to generate confidence values associated with pixels, objects, or classes identified by one or more neural networks. For example, at least one embodiment pertains to processors or computing systems used to generate confidence values associated with pixels, objects, or classes identified by one or more neural networks according to various novel techniques described herein.

BACKGROUND

Classification of objects in images can present issues in various contexts. For example, a system processing an image provides a classification of an object depicted in the image, and even though confidence in the classification is very low, it is higher than other possibilities. This can result in errors that adversely affect systems that utilize the classification. For example, a system may perform operations based on provided classifications that may be influenced by confidences in the classifications.

DETAILED DESCRIPTION

In at least one embodiment, autonomous vehicles determine whether various objects in view are hazardous or not. In at least one embodiment, images captured by a vehicle are segmented using a neural network, and an output includes labels assigned to each pixel of an image. In at least one embodiment, there are instances when pixels are mislabeled. In at least one embodiment, an image depicts a road obstruction, but a vehicle's system could detect it as something else.

In at least one embodiment, a system assigns confidence values to an output of an image segmentation task in which confidence is computed as part of inferencing. In at least one embodiment, during inferencing, numerical values for each of multiple possible classes are computed. In at least one embodiment, numerical values are then used to indicate confidence in classifications. In at least one embodiment, systems such as object detection and collision in an autonomous vehicle can then use an image and confidence values together to determine more confidently objects in an image.

In at least one embodiment, a system for segmentation and confidence value determination is applicable to any system that obtains images and performs pixel labeling. In at least one embodiment, a system for image segmentation and confidence value determination is applicable to systems of various environments, such as transportation environments, medical environments, geosensing environments, and/or agriculture environments.

In at least one embodiment, techniques described herein achieve various technical advantages, including but not limited to: an ability to assess a quality of pixel-wise classifications, an ability to make actuation decisions or diagnoses based on confidence values of classifications, and various other technical advantages. In at least one embodiment, a system for segmentation and confidence value determination is used in autonomous driving and driver assistance. In at least one embodiment, segmentation results are fed into planning algorithms which use them to determine crucially important tasks such as driving path and speed, braking policy, and/or collision avoidance. In at least one embodiment, said planning algorithms can use per-pixel confidence data associated with their input data to select decision algorithms or fallback procedures when provided with unreliable input data.

Figure 1:
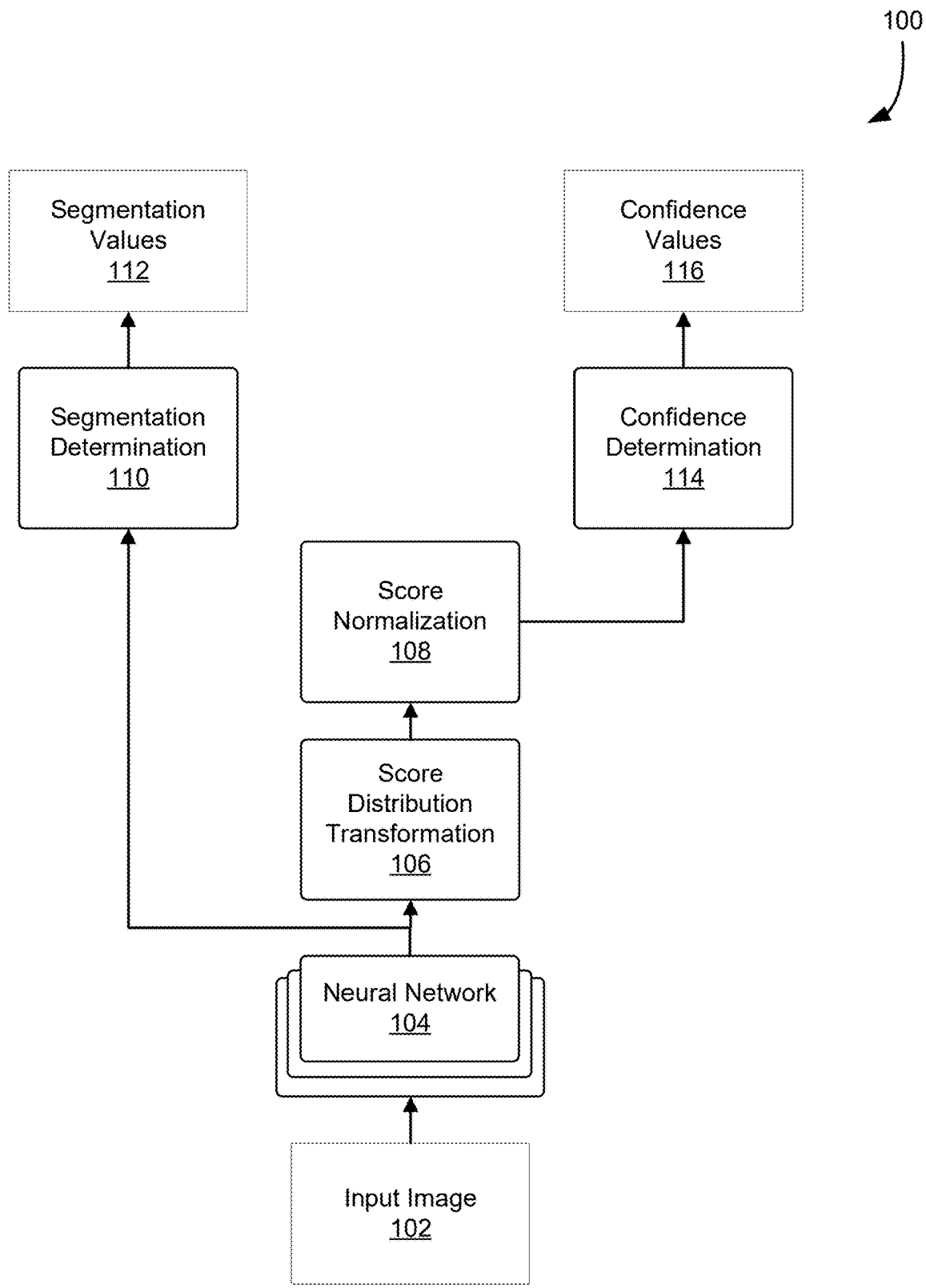
FIG. 1 illustrates an example of a system for segmentation and confidence value determination, according to at least one embodiment.

FIG. 1 illustrates an example 100 of a system for segmentation and confidence value determination, according to at least one embodiment. In at least one embodiment, a system for segmentation and confidence value determination comprises at least a neural network 104, a score distribution transformation 106, a score normalization 108, a segmentation determination 110, and a confidence determination 114. In at least one embodiment, a system for segmentation and confidence value determination receives or otherwise obtains an input image 102, and determines segmentation values 112 and confidence values 116.

In at least one embodiment, a system for segmentation and confidence value determination is a collection of one or more hardware and/or software computing resources with instructions that, when executed, processes an input image to determine segmentation values and confidence values from said input image. In at least one embodiment, a system for segmentation and confidence value determination is a software program executing on computer hardware, application executing on computer hardware, and/or variations thereof. In at least one embodiment, one or more processes of a system for segmentation and confidence value determination are performed by any suitable processing system or unit (e.g., graphics processing unit (GPU), parallel processing unit (PPU), central processing unit (CPU)), and in any suitable manner, including sequential, parallel, and/or variations thereof.

In at least one embodiment, an input image 102 is an image captured from one or more image and/or video capturing devices. In at least one embodiment, an input image 102 is an image depicting one or more objects that are to be identified. In at least one embodiment, an input image 102 is an image from a view of a vehicle, such as an autonomous vehicle, semi-autonomous vehicle, manual vehicle, and/or variations thereof. In at least one embodiment, an input image 102 is an image from one or more medical imaging devices. In at least one embodiment, an input image 102 is an image of an aerial or overhead view of terrain. In at least one embodiment, an input image 102 is an image of crops in one or more agriculture environments, such as farming or other crop cultivation environments.

In at least one embodiment, an input image 102 is a computer image file of any suitable format, such as a bitmap image file format. In at least one embodiment, an input image 102 is in compressed or uncompressed form. In at least one embodiment, an input image 102 is a red-green-blue (RGB) image. In at least one embodiment, an input image 102 is a black-and-white (BW) image. In at least one embodiment, an input image 102 is a grayscale image. In at least one embodiment, an input image 102 is obtained or otherwise received by a neural network 104. In at least one embodiment, an input image 102 is provided to a neural network 104 through one or more communication networks, data transfer operations, and/or variations thereof.

In at least one embodiment, a neural network 104 is one or more neural networks implemented on a collection of one or more hardware and/or software computing resources. In at least one embodiment, a neural network 104 is a collection of one or more hardware and/or software computing resources with instructions that, when executed, performs one or more processes of one or more neural networks. In at least one embodiment, a neural network 104 is a software program executing on computer hardware, application executing on computer hardware, and/or variations thereof. In at least one embodiment, a neural network 104 comprises various neural network models such as a perceptron model, a radial basis network (RBN), an auto encoder (AE), Boltzmann Machine (BM), Restricted Boltzmann Machine (RBM), deep belief network (DBN), deep convolutional network (DCN), extreme learning machine (ELM), deep residual network (DRN), support vector machines (SVM), and/or variations thereof.

In at least one embodiment, a neural network 104 comprises one or more image segmentation neural networks. In at least one embodiment, an image segmentation neural network refers to a neural network that partitions regions of an image into multiple segments (e.g., sets of pixels). In at least one embodiment, an image segmentation neural network processes an image to locate objects of said image. In at least one embodiment, an image segmentation neural network processes an image to assign labels to every pixel in said image such that pixels with a same label share various characteristics. In at least one embodiment, a neural network 104 (e.g., through one or more image segmentation neural networks) processes pixels of an image to determine scores for classes for each pixel, in which a score for a particular class for a particular pixel indicates a probability that said particular pixel corresponds to an object that belongs to said particular class. In at least one embodiment, a class, also referred to as an object class or segmentation class, refers to a classification or identifier of an object. In at least one embodiment, a neural network 104 identifies or otherwise classifies one or more objects of an input image 102 and generates confidence values (e.g., via determined scores) associated with said one or more objects.

In at least one embodiment, a neural network 104 comprises a region-based semantic segmentation network that performs semantic segmentation based on object detection results. In at least one embodiment, a neural network 104 comprises a region-based semantic segmentation network that utilizes selective search to extract object proposals, compute features for said object proposals, and classify regions using class-specific linear SVMs. In at least one embodiment, a neural network 104 comprises a fully convolutional network-based semantic segmentation network that learns a mapping from pixels to pixel, and may or may not extract region proposals. In at least one embodiment, a neural network 104 comprises a weakly supervised semantic segmentation network that is trained using annotations to iteratively improve estimated masks for semantic segmentation.

In at least one embodiment, a neural network 104 comprises various skip connection, pooling, convolution, upsampling, activation function, and/or other neural network operations. In at least one embodiment, skip connections refer to a process in which various output points of various processes of a neural network bypass or "skip" various operations of said neural network to be utilized as inputs to later points in said neural network. In at least one embodiment, pooling is a form of non-linear down-sampling in which an input is transformed into a reduced representation of said input. In at least one embodiment, a produced reduced representation of an input can comprise various details of said input, such as prominent details of said input, which can include edges, certain patterns and/or features, and/or variations thereof. In at least one embodiment, convolution is a mathematical operation on two inputs that produces an output that expresses how one input is affected by another input. In at least one embodiment, convolution is applied to an input along with a filter, which is denoted as a convolution filter. In at least one embodiment, convolution on an input with a filter transforms said input to enhance and/or reduce various features of said input.

In at least one embodiment, upsampling refers to various operations that upsample an input into an expanded representation of said input. In at least one embodiment, upsampling transforms an input by expanding data said input comprises, utilizing techniques such as resampling, interpolation, and/or variations thereof. In at least one embodiment, upsampling expands an input by performing other various operations that produce a higher density approximation and/or expanded representation of said input. In at least one embodiment, an activation function is a function that defines an output given an input or set of inputs. In at least one embodiment, an activation function processes an input to determine if said input should result in a particular output. In at least one embodiment, activation functions include at least ridge activation functions, which are univariate functions that process a linear combination of input variables, radial activation functions, which depend on distances between inputs and various fixed points, folding activation functions, which perform aggregation over inputs, and/or variations thereof.

In at least one embodiment, a neural network 104 is trained in connection with training data comprising training images and training labels. In at least one embodiment, training images comprise images such as an input image 102, and training labels comprise ground truth segmentation values for said training images. In at least one embodiment, a neural network 104 is trained by one or more systems and/or training frameworks that cause neural network 104 to process training images, compare training labels with values determined by neural network 104 from training images through one or more loss functions to calculate loss, and updating neural network 104 to minimize calculated loss. In at least one embodiment, a neural network 104 is trained by calculating loss and adjusting one or more weights, functions, processes, structural components, and/or variations thereof of neural network 104 such that loss is minimized. In at least one embodiment, a neural network 104 is trained with processes described in connection with FIG. 9.

In at least one embodiment, a neural network 104 is implemented with a set of segmentation classes of objects to detect within images. In at least one embodiment, segmentation classes utilized by a neural network 104 include classifications of objects of various environments, such as objects of transportation environments (e.g., pedestrians, vehicles, roads, road signs, road obstructions, etc.), medical environments (e.g., anatomical structures, medical abnormalities, etc.), geosensing environments (e.g., mountains, grassland, desert, water bodies, etc.), agriculture environments (e.g., crops, crop weeds, plants, etc.), and/or variations thereof. In at least one embodiment, a neural network 104 obtains an input image 102, processes input image 102 through one or more skip connection, pooling, convolution, upsampling, activation functions, and/or other neural network operations, in which said activation functions, based on features and other information determined through processes of neural network 104, determine a score for each segmentation class for each pixel of input image 102. In at least one embodiment, a neural network 104 processes an input image 102, in which scores for segmentation classes, also referred to as class scores, for each pixel of input image 102 are output from one or more hidden layers (e.g., a last hidden layer) of neural network 104. In at least one embodiment, a hidden layer of a neural network (e.g., a neural network 104) refers to a layer of one or more mathematical functions between an input and an output of said neural network. In at least one embodiment, a hidden layer performs linear transformations, nonlinear transformations, and/or variations thereof on inputs of a neural network.

In at least one embodiment, a neural network 104 processes an input image 102 and outputs a score for each segmentation class for each pixel of input image 102, in which a score for a particular class for a particular pixel indicates a probability that said particular pixel corresponds to an object that belongs to said particular class. In at least one embodiment, a score indicating a probability is represented as a decimal value (e.g., 0.1, 0.2), a percentage value (e.g., 10%, 20%), a numerical value (e.g., 10, 20), or any suitable representation. In at least one embodiment, a neural network 104 outputs a vector of scores, also referred to as logits, for pixels of an input image 102. In at least one embodiment, a vector of scores for a particular pixel comprises a score for each segmentation class for said particular pixel. In at least one embodiment, scores output by a neural network 104 are input to a score distribution transformation 106. In at least one embodiment, scores output by neural network 104 are also input to segmentation determination 110 to determine segmentation values 112, which is a collection of segmentation values determined for pixels of an input image 102. In at least one embodiment, a score distribution transformation 106 is a collection of one or more hardware and/or software computing resources with instructions that, when executed, transforms distributions of scores for segmentation classes for pixels of an image. In at least one embodiment, a score distribution transformation 106 is a software program executing on computer hardware, application executing on computer hardware, and/or variations thereof.

In at least one embodiment, a score distribution transformation 106 transforms scores such that an end distribution of class probabilities approximates a distribution in training data. In at least one embodiment, a score distribution transformation 106 performs any suitable calibration, scaling, or transformation process on scores output from a neural network 104 to transform said scores and/or a distribution of said scores. In at least one embodiment, a score distribution transformation 106 utilizes a calibration method such as temperature calibration, also referred to as temperature scaling, to transform output scores from a neural network 104. In at least one embodiment, temperature scaling refers to a method of transforming outputs of a classification model into a probability distribution over classes. In at least one embodiment, temperature scaling comprises scaling outputs of a neural network (e.g., a neural network 104) by a scalar parameter, which can be learned through training of said neural network. In at least one embodiment, temperature scaling uses a single scalar parameter to rescale scores output (e.g., a logits vector) from a neural network 104. In at least one embodiment, a scalar parameter for temperature scaling is determined through minimizing a negative log likelihood for a dataset for a neural network model (e.g., a neural network 104).

In at least one embodiment, a score distribution transformation 106 outputs transformed scores to a score normalization 108. In at least one embodiment, a score normalization 108 is a collection of one or more hardware and/or software computing resources with instructions that, when executed, performs one or more normalization processes on input values. In at least one embodiment, a score normalization 108 is a software program executing on computer hardware, application executing on computer hardware, and/or variations thereof. In at least one embodiment, a score normalization 108 normalizes scores output from a score distribution transformation 106 to one or more probability distributions.

In at least one embodiment, a score normalization 108 performs any suitable normalization process to normalize scores output from a score distribution transformation 106. In at least one embodiment, a score normalization 108 utilizes one or more softmax functions to normalize class scores. In at least one embodiment, a softmax function, also referred to as softargmax or a normalized exponential function, is a function that is a generalization of a logistic function to multiple dimensions. In at least one embodiment, a softmax function, based on an input vector of K real numbers, normalizes said input into a probability distribution of K probabilities proportional to exponentials of input numbers. In at least one embodiment, softmax function is defined by a following equation, although any variation thereof can be utilized:

$$\sigma(\vec{z})_i = \frac{e^{z_i}}{\sum_{j=1}^{K} e^{z_j}}$$

in which $\sigma$ denotes a softmax function, $\vec{z}$ denotes an input vector, $e^{z_i}$ denotes a standard exponential function for an input vector, K denotes a number of classes, and $e^{z_j}$ denotes a standard exponential function for an output vector.

In at least one embodiment, a score normalization 108 obtains scores (e.g., transformed scores output from a score distribution transformation 106) and normalizes said scores into a probability distribution using a formula such as described above. In at least one embodiment, a score normalization 108 normalizes scores for segmentation classes for pixels of an input image 102 such that all probabilities for classes for each pixel of input image 102 sum up to a value of 1. In at least one embodiment, a score normalization 108 normalizes scores such that scores indicating probabilities for segmentation classes for each pixel of an input image 102 sum up to a value of 1.

In at least one embodiment, a score normalization 108 outputs normalized scores comprising a set of scores (e.g., scores corresponding to each segmentation class) for each pixel of an input image 102. In at least one embodiment, a score normalization 108 provides normalized scores to a segmentation determination 110 and a confidence determination 114. In at least one embodiment, a segmentation determination 110 is a collection of one or more hardware and/or software computing resources with instructions that, when executed, determines segmentation values for pixels of an image. In at least one embodiment, a segmentation determination 110 is a software program executing on computer hardware, application executing on computer hardware, and/or variations thereof. In at least one embodiment, a segmentation value refers to a value or other identifier corresponding to a particular class, and can be a label, number, letter(s), and/or variations thereof.

In at least one embodiment, a segmentation determination 110 uses one or more arg max functions to determine a segmentation value for each pixel of an input image 102. In at least one embodiment, an arg max, or arguments of a maxima, function is a function that determines input arguments at which output values are maximized. In at least one embodiment, a segmentation determination 110, based on sets of scores for pixels of an input image 102 indicating class probabilities, determines a segmentation value for each pixel of input image 102. In at least one embodiment, a segmentation determination 110, for a set of scores for a particular pixel of an input image 102, determines a class that corresponds to a highest or maximum score of said set of scores, and assigns a segmentation value corresponding to said class to said particular pixel. In at least one embodiment, a segmentation determination 110 determines segmentation values 112, which is a collection of segmentation values determined for pixels of an input image 102. In at least one embodiment, a segmentation determination 110 performs semantic segmentation, which is represented mathematically by a following formula, although any variation thereof can be utilized: Semantic Segmentation=arg max (SoftMax).

In at least one embodiment, segmentation values 112 are visualized in connection with an input image 102. In at least one embodiment, visual semantic segmentation comprises an image in which each pixel has a value corresponding to a most probable class of objects. In at least one embodiment, for visualization purposes, each value is associated with a color code. In at least one embodiment, segmentation values 112 comprise a segmentation value for each pixel of an input image 102, in which each segmentation value is associated with a color, in which segmentation values 112 are visualized through a segmentation map which visualizes each pixel of an input image 102 with its associated segmentation value color. In at least one embodiment, a segmentation value of a pixel indicates a prediction of a class that an object corresponding to said pixel belongs to. Further information regarding a segmentation map can be found in description of FIG. 2.

In at least one embodiment, a confidence determination 114 is a collection of one or more hardware and/or software computing resources with instructions that, when executed, determines confidence values for pixels of an image. In at least one embodiment, a confidence determination 114 is a software program executing on computer hardware, application executing on computer hardware, and/or variations thereof. In at least one embodiment, a confidence or confidence value refers to a value of probability for an output, and can be represented as a fraction, decimal, percent, or any suitable representation. In at least one embodiment, for example, a neural network output has a confidence value of 0.95 or 95%, which indicates that said neural network has determined that said output is correct with a probability of 0.95 or 95%.

In at least one embodiment, a confidence determination 114 uses one or more functions to determine a confidence value for each pixel of an input image 102. In at least one embodiment, a confidence determination 114 utilizes a monotonic non-linear function, which refers to a non-linear function between sets that preserves, reverses, or otherwise transforms a given order of said sets. In at least one embodiment, a confidence determination 114, based on sets of scores for pixels of an input image 102 indicating class probabilities, determines a confidence value for each pixel of input image 102. In at least one embodiment, a confidence determination 114, for a set of scores for a particular pixel of an input image 102, determines a class that corresponds to a highest or maximum score of said set of scores, and assigns a confidence value for said pixel as said highest or maximum score. In at least one embodiment, a confidence determination 114 inputs assigned confidence values for pixels of an input image 102 to one or more functions (e.g., one or more monotonic non-linear functions) to determine final confidence values. In at least one embodiment, a confidence determination 114 does not input assigned confidence values for pixels of an input image 102 to one or more functions and utilizes said assigned confidence values as final confidence values. In at least one embodiment, a confidence determination 114 saves a maximum probability value for each pixel, which is otherwise discarded in various neural network environments, computed in a SoftMax block (e.g., a score normalization 108), and uses them to compute confidence values.

In at least one embodiment, a confidence determination 114 determines confidence values 116, which is a collection of final confidence values determined for pixels for an input image 102. In at least one embodiment, confidence values 116 are unmodified maximum probability values. In at least one embodiment, confidence values 116 are probability values passed through a monotonic linear function, denoted by F, such that output probabilities satisfy various defined constraints. In at least one embodiment, confidence is represented mathematically by a following formula, although any variation thereof can be utilized: Confidence=F(max (SoftMax)), in which F denotes a monotonic linear function. In at least one embodiment, each value of confidence values 116 corresponds to a value of segmentation values 112. In at least one embodiment, each pixel of an input image 102 is associated with a particular value of segmentation values 112 and a corresponding value of confidence values 116. In at least one embodiment, for a particular pixel, associated segmentation value, and corresponding confidence value, said associated segmentation value indicates a prediction of a class that an object corresponding to said particular pixel belongs to, and said corresponding confidence value indicates a probability determined by one or more neural networks that said prediction is correct.

In at least one embodiment, confidence values 116 are visualized in connection with an input image 102. In at least one embodiment, confidence values 116 comprise a confidence value for each pixel of an input image 102, in which confidence values of confidence values 116 are associated with a color gradient (e.g., lower values correspond to darker colors, higher values correspond to lighter colors, and/or variations thereof), in which confidence values 116 are visualized through a confidence map which visualizes each pixel of an input image 102 with its corresponding confidence value color on said color gradient. In at least one embodiment, confidence values 116 are visualized through a confidence map using numerical values of confidence values 116. Further information regarding a confidence map can be found in description of FIG. 2.

In at least one embodiment, a confidence determination 114 determines multiple confidence values for each pixel of an input image 102 as confidence values 116. In at least one embodiment, a confidence determination 114, for a set of scores for a particular pixel of an input image 102, determines classes that correspond to maximum set of scores (e.g., a first maximum, a second maximum, and so on) of said set of scores, and assigns confidence values for said pixel as said highest or maximum set of scores. In at least one embodiment, confidence values 116 comprise one or more data structures, such as multi-dimensional arrays, that indicate one or more confidence values for each pixel of an input image 102.

In at least one embodiment, an input image 102 is any suitable data and a neural network 104 is any suitable data labeling algorithm, in which neural network 104 outputs scores for classes of data detected within input image 102, in which said scores are processed by a score distribution transformation 106, a score normalization 108, a segmentation determination 110, and a confidence determination 114 to determine segmentation values 112, which comprise segmentation values indicating particular classes of said classes of data, and confidence values 116, which comprise confidence values for said particular classes.

In at least one embodiment, confidence values 116 are input to one or more systems that perform various actions based at least in part on confidences indicated by confidence values 116. Further information regarding processes performed utilizing confidence values can be found in description of FIGS. 3-7. In at least one embodiment, a neural network 104 is any suitable labeling algorithm in which confidence values 116 are generated and utilized to perform one or more processes in connection with labeling algorithms including but not limited to: semantic segmentation, instance segmentation, panoptic segmentation, optical flow, stereo disparity, classification, and detection.

In at least one embodiment, semantic segmentation algorithms refer to algorithms that link or classify each pixel of an image to a class or class label, in which confidence information is usable to determine a reliability or quality of classifications. In at least one embodiment, instance segmentation algorithms refer to algorithms that identify instances of objects within an image at a pixel level, in which confidence information is usable to determine a reliability or quality of identified instances, or classifications. In at least one embodiment, panoptic segmentation algorithms refer to algorithms that perform semantic segmentation and instance segmentation. In at least one embodiment, optical flow algorithms refer to algorithms that determine relative motions of objects of an image, in which confidence information is usable to determine a reliability or quality of determined relative motions of objects. In at least one embodiment, stereo disparity algorithms refer to algorithms that determine apparent pixel differences or motions between stereo images, in which confidence information is usable to determine a reliability or quality of determined apparent pixel differences or motions. In at least one embodiment, classification algorithms refer to algorithms that classify objects of an image, in which confidence information is usable to determine a reliability or quality of classifications of objects. In at least one embodiment, detection algorithms refer to algorithms that detect and/or localize objects of an image, in which confidence information is usable to determine a reliability or quality of detected and/or localized objects.

Figure 2:
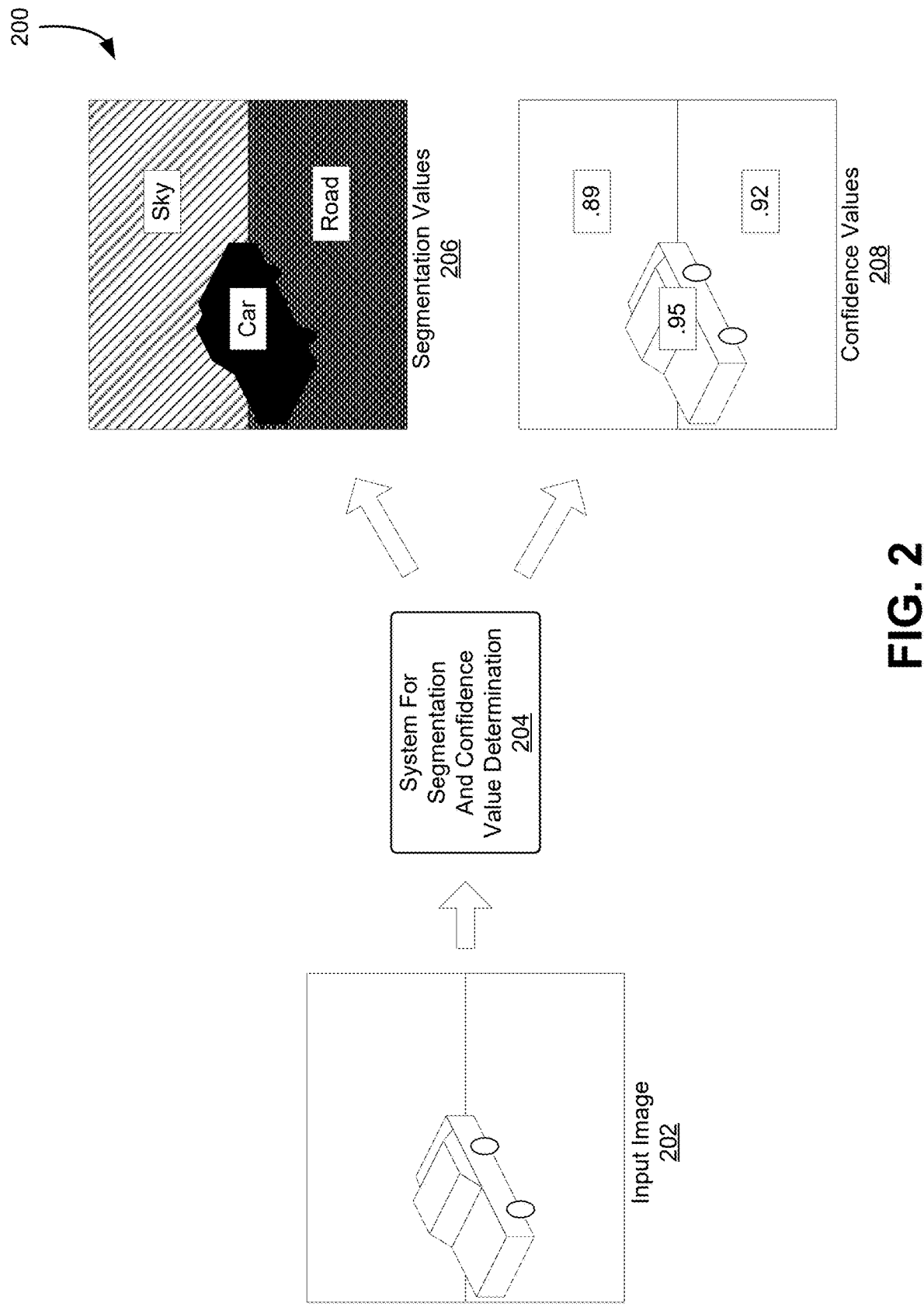
FIG. 2 illustrates an example of segmentation values and confidence values, according to at least one embodiment.

FIG. 2 illustrates an example 200 of segmentation values and confidence values, according to at least one embodiment. In at least one embodiment, an input image 202, a system for segmentation and confidence value determination 204, segmentation values 206, and confidence values 208 are in accordance with those discussed in connection with FIG. 1.

In at least one embodiment, an input image 202 is an image captured from one or more image and/or video capturing devices that depicts one or more objects. In at least one embodiment, an input image 202 is at least an RGB image, BW image, grayscale image, and/or variations thereof. In at least one embodiment, an input image 202 is an image from a view of a vehicle, such as an autonomous vehicle, semi-autonomous vehicle, manual vehicle, and/or variations thereof. In at least one embodiment, an input image 202 is an image from one or more medical imaging devices. In at least one embodiment, an input image 202 is an image, captured by a drone, of an aerial or overhead view of terrain. In at least one embodiment, an input image 202 is an image, captured by a robotic device, of crops in one or more agriculture environments, such as farming or other crop cultivation environments. In at least one embodiment, referring to FIG. 2, an input image 202 depicts a car object, a sky object, and a road object.

In at least one embodiment, an input image 202 is obtained and processed by a system for segmentation and confidence value determination 204. In at least one embodiment, a system for segmentation and confidence value determination 204 processes an input image 202 through one or more neural network, score distribution transformation, score normalization, segmentation determination, and confidence determination processes to determine segmentation values 206 and confidence values 208. Further information regarding a system for segmentation and confidence value determination processing an input image to determine segmentation values and confidence values can be found in description of FIG. 1.

In at least one embodiment, segmentation values 206 comprise a segmentation value for each pixel of an input image 202. In at least one embodiment, referring to FIG. 2, a system for segmentation and confidence value determination 204 is implemented with segmentation classes including at least a car object, a sky object, and a road object, in which segmentation values 206 comprise segmentation values indicating which pixels of an input image 202 correspond to a car object, a sky object, and a road object. In at least one embodiment, referring to FIG. 2, segmentation values 206 are visualized as a segmentation map. In at least one embodiment, referring to FIG. 2, a segmentation map visualization of segmentation values 206 depicts pixels of an input image 202 that correspond to a car object as solid color, pixels of input image 202 that correspond to a sky object as a first patterned color, and pixels of input image 202 that correspond to a road object as a second patterned color.

In at least one embodiment, confidence values 208 comprise a confidence value for each pixel of an input image 202. In at least one embodiment, referring to FIG. 2, a system for segmentation and confidence value determination 204 is implemented with segmentation classes including at least a car object, a sky object, and a road object, in which confidence values 208 comprise confidence values of pixels of an input image 202 that correspond to a car object, a sky object, and a road object. In at least one embodiment, referring to FIG. 2, confidence values 208 are visualized as a confidence map. In at least one embodiment, referring to FIG. 2, a confidence map visualization of confidence values 208 depicts a confidence value of "0.95" for pixels of an input image 202 that correspond to a car object, a confidence value of "0.89" for pixels of input image 202 that correspond to a sky object, and a confidence value of "0.92" for pixels of input image 202 that correspond to a road object.

In at least one embodiment, a confidence value refers to a value of a probability that an output of a neural network is correct. In at least one embodiment, a system for segmentation and confidence value determination 204 obtains an input image 202 and determines a set of pixels that correspond to a car object with a probability for said set of pixels of 95%. In at least one embodiment, a system for segmentation and confidence value determination 204, instead of discarding determined probabilities, utilizes determined probabilities to generate a confidence map such that one or more entities are provided with confidence values and information indicating that a classification of a set of pixels as a car object has a probability of 95% of being correct.

In at least one embodiment, input image 202 is obtained and processed by a system to produce both segmentation values 206 and confidence values 208 in a single output where the confidence values 208 accompany segmentation values 208. In at least one embodiment, a confidence map visualization of both segmentation values 206 and confidence values 208 are combined and illustrated as "sky 0.92." In at least one embodiment, while a confidence map of FIG. 2 depicts a single confidence value for each set of pixels that correspond to a particular object, a confidence map can depict a confidence value for each pixel, which can be represented in various forms, such as through numerical values (e.g., such as in accordance with a confidence map of FIG. 2), a color gradient (e.g., a confidence map comprising colors, in which lower confidence values correspond to darker colors, higher confidence values correspond to lighter colors, and/or variations thereof), a defined color scheme (e.g., a confidence map comprising colors, in which particular confidence values correspond to particular colors), and/or variations thereof. In at least one embodiment, confidence values 208 are utilized by one or more systems that perform various processes in response to values of confidence values 208. Further information regarding processes performed utilizing confidence values can be found in description of FIGS. 3-7.

Figure 3:
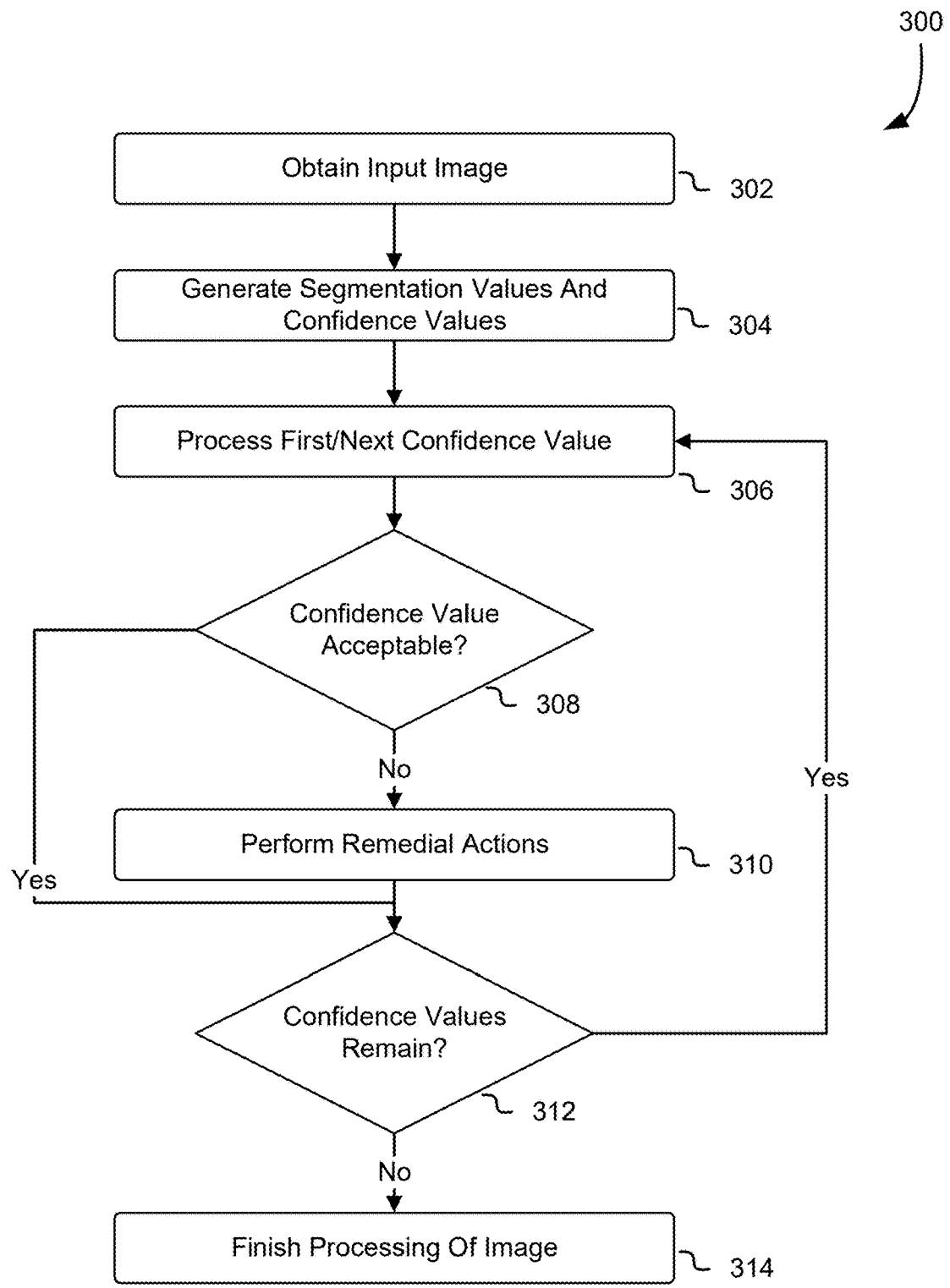
FIG. 3 shows an illustrative example of a process to process an image and perform actions based at least in part on confidence values, according to at least one embodiment.

FIG. 3 shows an illustrative example of a process 300 to process an image and perform actions based at least in part on confidence values, according to at least one embodiment. In at least one embodiment, some or all of process 300 (or any other processes described herein, or variations and/or combinations thereof) is performed under control of one or more computer systems configured with computer-executable instructions and is implemented as code (e.g., computer-executable instructions, one or more computer programs, or one or more applications) executing collectively on one or more processors, by hardware, software, or combinations thereof. In at least one embodiment, code is stored on a computer-readable storage medium in form of a computer program comprising a plurality of computer-readable instructions executable by one or more processors. In at least one embodiment, a computer-readable storage medium is a non-transitory computer-readable medium. In at least one embodiment, at least some computer-readable instructions usable to perform process 300 are not stored solely using transitory signals (e.g., a propagating transient electric or electromagnetic transmission). A non-transitory computer-readable medium does not necessarily include non-transitory data storage circuitry (e.g., buffers, caches, and queues) within transceivers of transitory signals. In at least one embodiment, process 300 is performed at least in part on a computer system such as those described elsewhere in this disclosure. In at least one embodiment, process 300 is performed by one or more systems such as those described in connection with FIGS. 1-2.

In at least one embodiment, a system performing at least a part of process 300 includes executable code to obtain 302 an input image. In at least one embodiment, an input image is an image from a view of a vehicle, such as an autonomous vehicle, semi-autonomous vehicle, manual vehicle, and/or variations thereof. In at least one embodiment, an input image is an image from one or more medical imaging devices. In at least one embodiment, an input image is an image of an aerial or overhead view of terrain. In at least one embodiment, an input image is an image of crops in one or more agriculture environments, such as farming or other crop cultivation environments.

In at least one embodiment, a system performing at least a part of process 300 includes executable code to generate 304 segmentation values and confidence values. In at least one embodiment, a system (e.g., a system for segmentation and confidence value determination) processes an input image through one or more neural network, score distribution transformation, score normalization, segmentation determination, and confidence determination processes to determine segmentation values and confidence values. In at least one embodiment, a system performing at least a part of process 300 provides an input image to one or more neural networks that process said input image and identify or otherwise classify one or more objects of said input image. In at least one embodiment, a system performing at least a part of process 300 generates one or more confidence values associated with one or more objects identified or otherwise classified by one or more neural networks. Further information regarding generating segmentation values and confidence values can be found in description of FIG. 1.

In at least one embodiment, segmentation values indicate predictions of classes of objects that pixels of an image belong to, and confidence values indicate confidence values of said predictions. In at least one embodiment, a confidence value of a prediction indicates a probability determined by one or more neural networks that said prediction is correct. In at least one embodiment, segmentation values indicate predictions of classes of objects of transportation environments, such as pedestrians, vehicles, roads, road signs, road obstructions, animals, street lights, or other transportation environment objects. In at least one embodiment, segmentation values indicate predictions of classes of objects of medical environments, such as anatomical structures, medical abnormalities, bones, connective tissues, epithelial tissues, muscle tissues, nervous tissues, or other medical environment objects. In at least one embodiment, segmentation values indicate predictions of classes of objects of geosensing environments, such as mountains, grassland, desert, water bodies, forests, marshes, cities, or other geosensing environment objects. In at least one embodiment, segmentation values indicate predictions of classes of objects of agriculture environments, such as crops, crop weeds, soil, pests, or other agriculture environment objects.

In at least one embodiment, a system performing at least a part of process 300 includes executable code to process 306 first/next confidence value. In at least one embodiment, a system processes confidence values determined in connection with segmentation values for pixels of an image. In at least one embodiment, a system processes each confidence value for each pixel of an image. In at least one embodiment, a system performing at least a part of process 300 includes executable code to determine 308 whether a confidence value is acceptable. In at least one embodiment, one or more systems define a threshold that indicates whether a confidence value is acceptable, in which values lower than said threshold are unacceptable, and values higher than or equal to said threshold are acceptable. In at least one embodiment, for example, a threshold is defined as a value of 0.5, in which a confidence value of 0.6 is determined to be acceptable, and a confidence value of 0.4 is determined to be unacceptable. In at least one embodiment, generated confidence values are filtered in a way where outliers or those that are deemed below a threshold are removed. In at least one embodiment, confidence values associated with a same label in a same image are aggregated. In at least one embodiment, aggregating confidence values comprises averaging all generated confidence values for a pixel, a set of pixels, an object, or a classification to determine an averaged confidence value. In at least one embodiment, select decision algorithms or fallback procedures are then performed based on said averaged confidence value. In at least one embodiment, a system performing at least a part of process 300 includes executable code to, if a confidence value is determined to be acceptable, proceed to 312 of process 300.

In at least one embodiment, a system performing at least a part of process 300 includes executable code to, if a confidence value is determined to be not acceptable, perform 310 remedial actions. In at least one embodiment, a remedial action refers to one or more processes, actions, or events that one or more systems perform in response to an unacceptable confidence value. In at least one embodiment, a system performs remedial actions based on a segmentation class that a confidence value corresponds to. In at least one embodiment, a system performs a remedial action to modify one or more actions, processes, or states of said system in response to an unacceptable confidence value.

In at least one embodiment, a system of a transportation environment, such as a system of a vehicle, performs remedial actions such as activating one or more acceleration, braking, or warning vehicle systems, transmitting one or more notifications to other various systems, refining determined segmentation values and confidence values, re-determining determined segmentation values and confidence values, and/or variations thereof, based on unacceptable determined confidence values. In at least one embodiment, for example, a system of a vehicle that is travelling in a transportation environment (e.g., a road) obtains or otherwise receives an image captured from a view of said vehicle (e.g., through a camera mounted on said vehicle), processes said image to determine segmentation values and confidence values of pixels of said image, determines that a region of pixels of said image corresponding to an object that has been predicted to be a road object has a corresponding unacceptable confidence value, and performs a remedial action of activating one or more braking systems of said vehicle. Further information regarding a system of a transportation environment can be found in description of FIG. 4.

In at least one embodiment, a system of a medical environment, such as a system of a medical device, performs remedial actions such as activating one or more warning systems, transmitting one or more notifications to other various systems, refining determined segmentation values and confidence values, re-determining determined segmentation values and confidence values, and/or variations thereof, based on unacceptable determined confidence values. In at least one embodiment, for example, a system of a medical device obtains or otherwise receives an image captured from a medical imaging device (e.g., a medical scanner), processes said image to determine segmentation values and confidence values of pixels of said image, determines that a region of pixels of said image corresponding to an object that has been predicted to be a normal organ has a corresponding unacceptable confidence value, and performs a remedial action of notifying one or more systems of a potential organ abnormality. Further information regarding a system of a medical environment can be found in description of FIG. 5.

In at least one embodiment, a system of a geosensing environment, such as a system of a geosensing device, performs remedial actions such as activating one or more warning systems, transmitting one or more notifications to other various systems, refining determined segmentation values and confidence values, re-determining determined segmentation values and confidence values, and/or variations thereof, based on unacceptable determined confidence values. In at least one embodiment, for example, a system of a geosensing device obtains or otherwise receives an image captured from a geosensing imaging device (e.g., a geosensing satellite), processes said image to determine segmentation values and confidence values of pixels of said image, determines that a region of pixels of said image corresponding to an object that has been predicted to be a body of water has a corresponding unacceptable confidence value, and performs a remedial action of notifying one or more warning systems that said predicted body of water may not be a body of water. Further information regarding a system of a geosensing environment can be found in description of FIG. 6.

In at least one embodiment, a system of an agriculture environment, such as a system of an agriculture device, performs remedial actions such as activating one or more fertilization, watering, or weeding agriculture systems, transmitting one or more notifications to other various systems, refining determined segmentation values and confidence values, re-determining determined segmentation values and confidence values, and/or variations thereof, based on unacceptable determined confidence values. In at least one embodiment, for example, a system of an agriculture device obtains or otherwise receives an image captured from an agriculture imaging device, processes said image to determine segmentation values and confidence values of pixels of said image, determines that a region of pixels of said image corresponding to an object that has been predicted to be a healthy crop has a corresponding unacceptable confidence value, and performs a remedial action of causing one or more fertilization systems to increase amounts of fertilizer. Further information regarding a system of an agriculture environment can be found in description of FIG. 7.

In at least one embodiment, a system performing at least a part of process 300 includes executable code to determine 312 whether confidence values remain. In at least one embodiment, a system tracks processed confidence values to determine if confidence values remain for pixels of an input image. In at least one embodiment, a system performing at least a part of process 300 includes executable code to, if confidence values remain, proceed to 306 of process 300. In at least one embodiment, a system performing at least a part of process 300 includes executable code to process each confidence value determined for an input image. In at least one embodiment, a system performing at least a part of process 300 includes executable code to, if no confidence values remain, finish 314 processing of image. In at least one embodiment, an input image is an image of a set of images, in which a system processes each image of said set of images.

Figure 4:
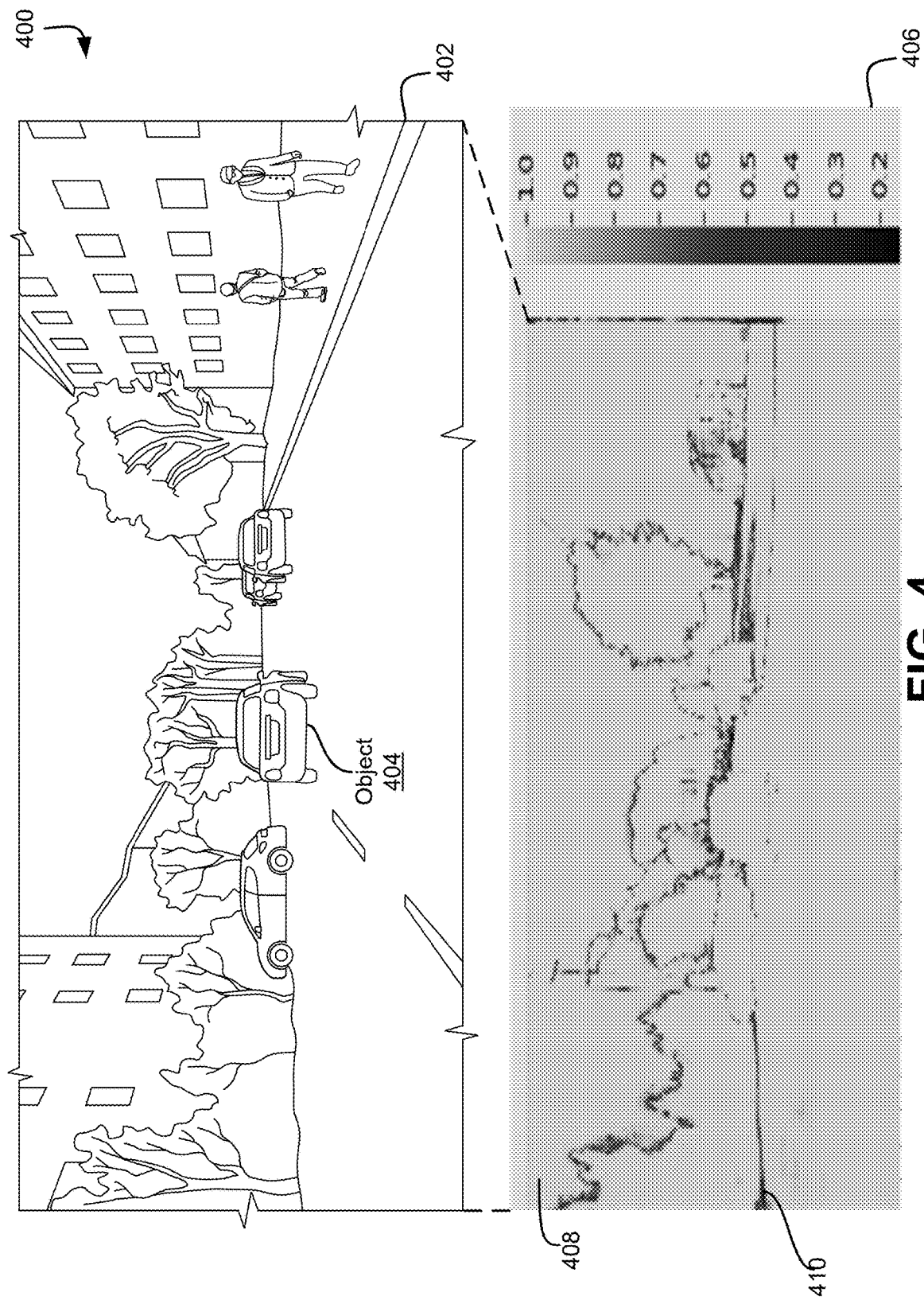
FIG. 4 illustrates an example of a transportation environment where a neural network is used to output confidence values assigned to pixels of objects in one or more images captured by a device in said transportation environment, according to at least one embodiment.

FIG. 4 illustrates an example 400 of a transportation environment where a neural network is used to output confidence values assigned to pixels of objects in one or more images captured by a device in said transportation environment, according to at least one embodiment. In at least one embodiment, example 400 depicts an image 402 captured from a view of a vehicle. In at least one embodiment, an image 402 is an image captured from one or more cameras of a vehicle, such as an autonomous vehicle, semi-autonomous vehicle, manual vehicle, and/or variations thereof. In at least one embodiment, an image 402 depicts a view from a vehicle that is travelling through an environment.

In at least one embodiment, a system for segmentation and confidence value determination is implemented as part of one or more vehicle systems. In at least one embodiment, a system for segmentation and confidence value determination is implemented with one or more segmentation classes corresponding to objects of transportation environments, such as pedestrians, vehicles, roads, road signs, road obstructions, animals, street lights, or other transportation environment objects. In at least one embodiment, a system for segmentation and confidence value determination processes an image 402 to determine segmentation values and confidence values for pixels of image 402. In at least one embodiment, a system for segmentation and confidence value determination predicts classifications (e.g., via segmentation values) of objects of an image 402 and generates associated confidence values corresponding to said predicted classifications. In at least one embodiment, a system for segmentation and confidence value determination predicts a classification (e.g., indicated via segmentation values) and confidence values for an object 404 depicted in an image 402. In at least one embodiment, a system for segmentation and confidence value determination predicts classifications of objects of an image and corresponding probabilities of predicted classifications for one or more users of a transportation environment system, such as an autonomous vehicle, such that said one or more users can determine a reliability and/or accuracy of predicted classifications. In at least one embodiment, a system for segmentation and confidence value determination generates a visualization of a semantic segmentation of an image 402, in which pixels are assigned colors corresponding to predicted classifications of said pixels (e.g., a first color is assigned to pixels predicted to correspond to a sidewalk, a second color is assigned to pixels predicted to correspond to trees, and so on).

In at least one embodiment, a system for segmentation and confidence value determination generates a confidence map 406 that corresponds to a semantic segmentation of an image 402, in which pixels are assigned colors corresponding to confidences of predicted classifications of said pixels (e.g., pixels with high confidence values are assigned light colors, pixels with low confidence values are assigned dark colors, and so on). In at least one embodiment, confidence values close to a value of 1 indicate high confidences in predicted semantic segmentations (e.g., predicted classifications), and confidence values close to a value of 0 indicate low confidences in predicted semantic segmentations.

In at least one embodiment, a confidence map 406 is a visualization of confidence values corresponding to a semantic segmentation of an image 402. In at least one embodiment, a confidence map 406 is a visualization of confidence values based on a color gradient, in which pixels corresponding to lower confidence values are assigned darker colors and pixels corresponding to higher confidence values are assigned lighter colors. In at least one embodiment, a confidence map 406 comprises a region 408 of pixels assigned lighter colors (e.g., light pink in a colored confidence value map or light gray in a greyscale confidence value map), indicating that region 408 corresponds to pixels with predicted classifications with high confidences. In at least one embodiment, pixels of a region 408 are predicted to correspond to a building object with high confidence, in which said pixels are assigned lighter colors to correspond to said high confidence. In at least one embodiment, a confidence map 406 comprises a region 410 of pixels assigned darker colors (e.g., black), indicating that region 410 corresponds to pixels with predicted classifications with low confidence. In at least one embodiment, pixels of a region 410 are predicted to correspond to a ground object with low confidence, in which said pixels are assigned darker colors to correspond to said low confidence. In at least one embodiment, pixels of a confidence map 406 corresponding to pixels of an object 404 of an image 402 are lighter colored, indicating a high confidence of a predicted classification of object 404. In at least one embodiment, a confidence map 406 is any suitable visualization of confidence values of pixels, such as a color gradient (e.g., a confidence map comprising colors, in which lower confidence values correspond to darker colors, higher confidence values correspond to lighter colors, and/or variations thereof), a defined color scheme (e.g., a confidence map comprising colors, in which particular confidence values correspond to particular colors), and/or variations thereof.

In at least one embodiment, a system for segmentation and confidence value determination performs one or more remedial actions in response to determined segmentation and confidence values. In at least one embodiment, a remedial action of activating steering systems of a vehicle comprises a system transmitting one or more signals to steering systems (e.g., electronic power steering systems) to cause said vehicle to steer in one or more directions, such as to avoid collision with one or more objects. In at least one embodiment, a remedial action of activating acceleration systems of a vehicle comprises a system transmitting one or more signals to acceleration systems (e.g., throttle body and associated components) to cause said vehicle to accelerate or reduce acceleration. In at least one embodiment, a remedial action of activating braking systems of a vehicle comprises a system transmitting one or more signals to braking systems (e.g., electronic braking system (EBS)) to cause said vehicle to apply brakes to slow or stop. In at least one embodiment, a remedial action of activating warning systems of a vehicle comprises transmitting one or more signals to warning systems (e.g., an onboard computer) to cause said vehicle to activate warning indicators, or transmit one or more notifications to other systems via one or more networks.

In at least one embodiment, a system for segmentation and confidence value determination generates segmentation values that indicate that an object 404 is a car object and associated confidence values that indicate a high level of confidence, in which said system performs one or more remedial actions such as causing a vehicle to activate braking systems to slow or maintain distance from said car object.

In at least one embodiment, a system for segmentation and confidence value determination generates segmentation values that indicate that an object 404 is a car object and associated confidence values that indicate a low level of confidence, in which said system performs one or more remedial actions such as causing one or more systems of a vehicle to capture more images of object 404 to generate additional segmentation and confidence values such that a confidence level of a prediction of a classification of object 404 can be increased. In at least one embodiment, a system for segmentation and confidence value determination (e.g., in response to low/unacceptable confidence values) generates additional segmentation and confidence values through one or more systems, such as via said system for segmentation and confidence value determination, additional image segmentation neural networks, image classification/detection systems, or other systems of a vehicle.

In at least one embodiment, a system for segmentation and confidence value determination generates segmentation values that indicate that an object 404 is a road object and associated confidence values that indicate a low level of confidence, in which said system performs one or more remedial actions such as causing a vehicle to activate braking systems to avoid potential collision with object 404, and/or causing one or more systems of a vehicle to capture more images of object 404 to generate additional segmentation and confidence values to determine a different prediction of a classification of object 404 and/or increase a confidence level of a prediction of a classification of object 404.

Figure 5:
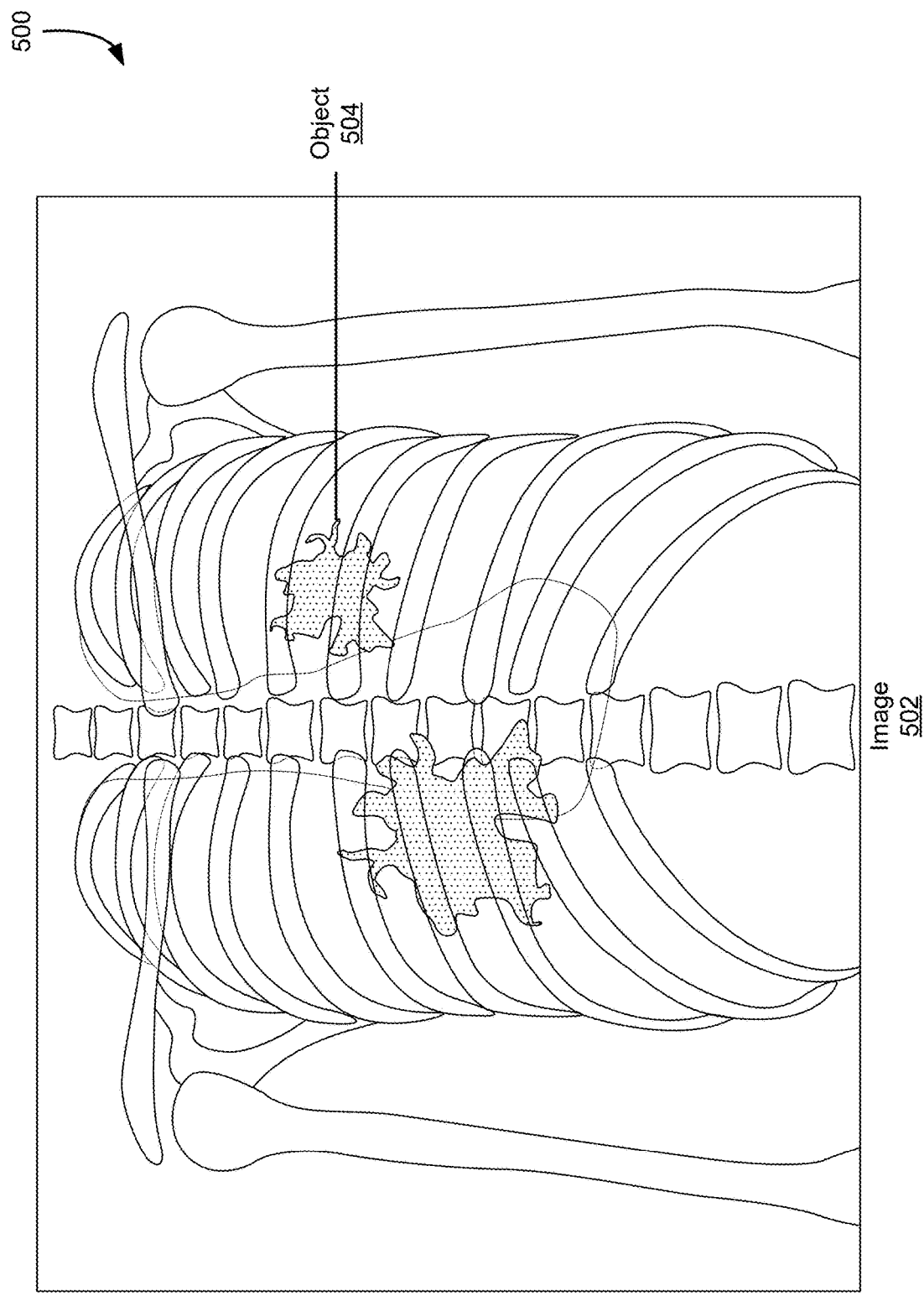
FIG. 5 illustrates an example of a medical environment where a neural network is used to output confidence values assigned to pixels of objects in one or more images captured by a device in said medical environment, according to at least one embodiment.

FIG. 5 illustrates an example 500 of a medical environment where a neural network is used to output confidence values assigned to pixels of objects in one or more images captured by a device in said medical environment, according to at least one embodiment. In at least one embodiment, example 500 depicts an image 502 captured from a medical imaging device, such as an X-ray imaging device, computed tomography (CT) scanner, magnetic resonance imaging (MRI) device, ultrasound device, and/or variations thereof. In at least one embodiment, an image 502 depicts an X-ray view of a human chest.

In at least one embodiment, a system for segmentation and confidence value determination is implemented as part of one or more medical imaging device systems. In at least one embodiment, a system for segmentation and confidence value determination is implemented with one or more segmentation classes corresponding to objects of medical environments, such as anatomical structures, medical abnormalities, medically normal regions, bones, connective tissues, epithelial tissues, muscle tissues, nervous tissues, or other medical environment objects. In at least one embodiment, a system for segmentation and confidence value determination processes an image 502 to determine segmentation values and confidence values for pixels of image 502. In at least one embodiment, a system for segmentation and confidence value determination predicts classifications (e.g., via segmentation values) of objects of an image 502 and generates associated confidence values corresponding to said predicted classifications. In at least one embodiment, a system for segmentation and confidence value determination predicts a classification (e.g., indicated via segmentation values) and confidence values for an object 504 depicted in an image 502. In at least one embodiment, a system for segmentation and confidence value determination predicts classifications of objects of an image and corresponding probabilities of predicted classifications for one or more users (e.g., medical personnel) of a medical environment system, such as a medical imaging device, such that said one or more users can determine a reliability and/or accuracy of predicted classifications.

In at least one embodiment, a system for segmentation and confidence value determination performs one or more remedial actions in response to determined segmentation and confidence values. In at least one embodiment, a remedial action of activating one or more medical warning systems comprises a system transmitting one or more notifications to one or more medical warning systems and/or monitoring equipment indicating a potential medical emergency or warning.

In at least one embodiment, a system for segmentation and confidence value determination generates segmentation values that indicate that an object 504 is a medical abnormality and associated confidence values that indicate a high level of confidence, in which said system performs one or more remedial actions such as notifying one or more medical systems of a potential medical abnormality.

In at least one embodiment, a system for segmentation and confidence value determination generates segmentation values that indicate that an object 504 is a medical abnormality and associated confidence values that indicate a low level of confidence, in which said system performs one or more remedial actions such as causing one or more medical imaging device systems to capture more images of object 504 to generate additional segmentation and confidence values such that a confidence level of a prediction of a classification of object 504 can be increased. In at least one embodiment, a system for segmentation and confidence value determination (e.g., in response to low/unacceptable confidence values) generates additional segmentation and confidence values through one or more systems, such as via said system for segmentation and confidence value determination, additional image segmentation neural networks, image classification/detection systems, or other systems of one or more medical imaging device systems.

In at least one embodiment, a system for segmentation and confidence value determination generates segmentation values that indicate that an object 504 is a medically normal region and associated confidence values that indicate a low level of confidence, in which said system performs one or more remedial actions such as notifying one or more medical systems that object 504 potentially does not correspond to a medically normal region, or causing one or more medical imaging device systems to capture more images of object 504 to generate additional segmentation and confidence values to determine a different prediction of a classification of object 504 and/or increase a confidence level of a prediction of a classification of object 504.

Figure 6:
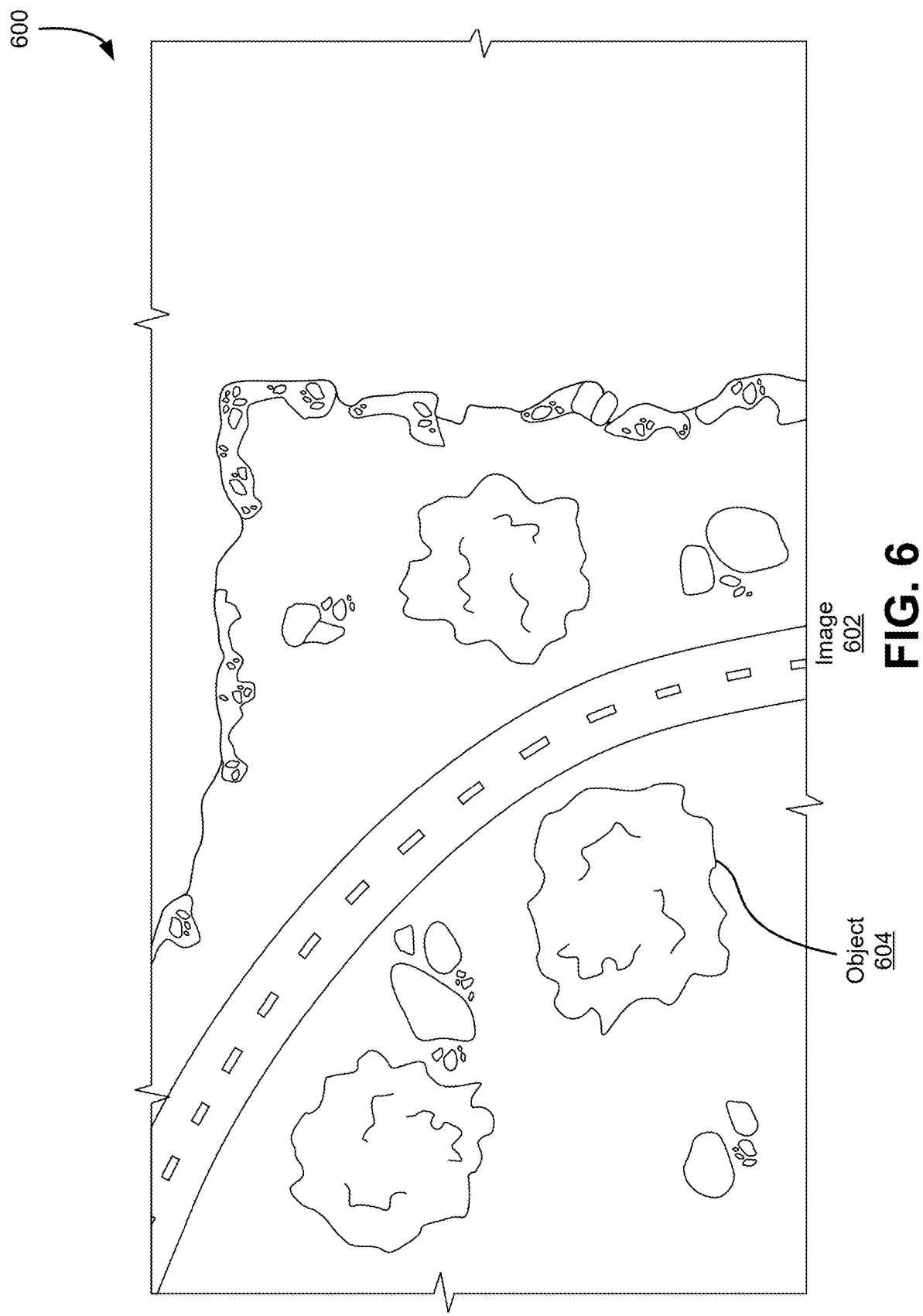
FIG. 6 illustrates an example of a geosensing environment where a neural network is used to output confidence values assigned to pixels of objects in one or more images captured by a device in said geosensing environment, according to at least one embodiment.

FIG. 6 illustrates an example 600 of a geosensing environment where a neural network is used to output confidence values assigned to pixels of objects in one or more images captured by a device in said geosensing environment, according to at least one embodiment. In at least one embodiment, geosensing refers to one or more systems and processes operating in connection with various environmental and geographic phenomena associated with various terrain. In at least one embodiment, example 600 depicts an image 602 captured of an overhead view of terrain. In at least one embodiment, an image 602 is captured from one or more cameras of one or more geosensing imaging systems (e.g., satellites).

In at least one embodiment, a system for segmentation and confidence value determination is implemented as part of one or more geosensing systems. In at least one embodiment, a system for segmentation and confidence value determination is implemented with one or more segmentation classes corresponding to objects of geosensing environments, such as mountains, grassland, desert, water bodies, forests, marshes, cities, or other geosensing environment objects. In at least one embodiment, a system for segmentation and confidence value determination processes an image 602 to determine segmentation values and confidence values for pixels of image 602. In at least one embodiment, a system for segmentation and confidence value determination predicts classifications (e.g., via segmentation values) of objects of an image 602 and generates associated confidence values corresponding to said predicted classifications.

In at least one embodiment, a system for segmentation and confidence value determination predicts a classification (e.g., indicated via segmentation values) and confidence values for an object 604 depicted in an image 602. In at least one embodiment, a system for segmentation and confidence value determination predicts classifications of objects of an image and corresponding probabilities of predicted classifications for one or more users of a geosensing environment system, such as a geosensing imaging system, such that said one or more users can determine a reliability and/or accuracy of predicted classifications. In at least one embodiment, a system for segmentation and confidence value determination performs one or more remedial actions in response to determined segmentation and confidence values.

In at least one embodiment, a system for segmentation and confidence value determination generates segmentation values that indicate that an object 604 is a mountain object and associated confidence values that indicate a high level of confidence, in which said system performs one or more remedial actions such as transmitting one or more notifications to one or more geosensing systems (e.g., equipment such as surveying motor vehicles or rovers) indicating that object 604 is a mountain object.

In at least one embodiment, a system for segmentation and confidence value determination generates segmentation values that indicate that an object 604 is a mountain object and associated confidence values that indicate a low level of confidence, in which said system performs one or more remedial actions such as causing one or more geosensing imaging systems to capture more images of object 604 to generate additional segmentation and confidence values such that a confidence level of a prediction of a classification of object 604 can be increased. In at least one embodiment, a system for segmentation and confidence value determination (e.g., in response to low/unacceptable confidence values) generates additional segmentation and confidence values through one or more systems, such as via said system for segmentation and confidence value determination, additional image segmentation neural networks, image classification/detection systems, or other systems of one or more geosensing systems.

In at least one embodiment, a system for segmentation and confidence value determination generates segmentation values that indicate that an object 604 is a water body object and associated confidence values that indicate a low level of confidence, in which said system performs one or more remedial actions such as transmitting one or more notifications to one or more geosensing systems (e.g., equipment such as surveying motor vehicles or rovers) indicating that object 604 potentially does not correspond to a water body, or causing one or more geosensing imaging systems to capture more images of object 604 to generate additional segmentation and confidence values to determine a different prediction of a classification of object 604 and/or increase a confidence level of a prediction of a classification of object 604.

Figure 7:
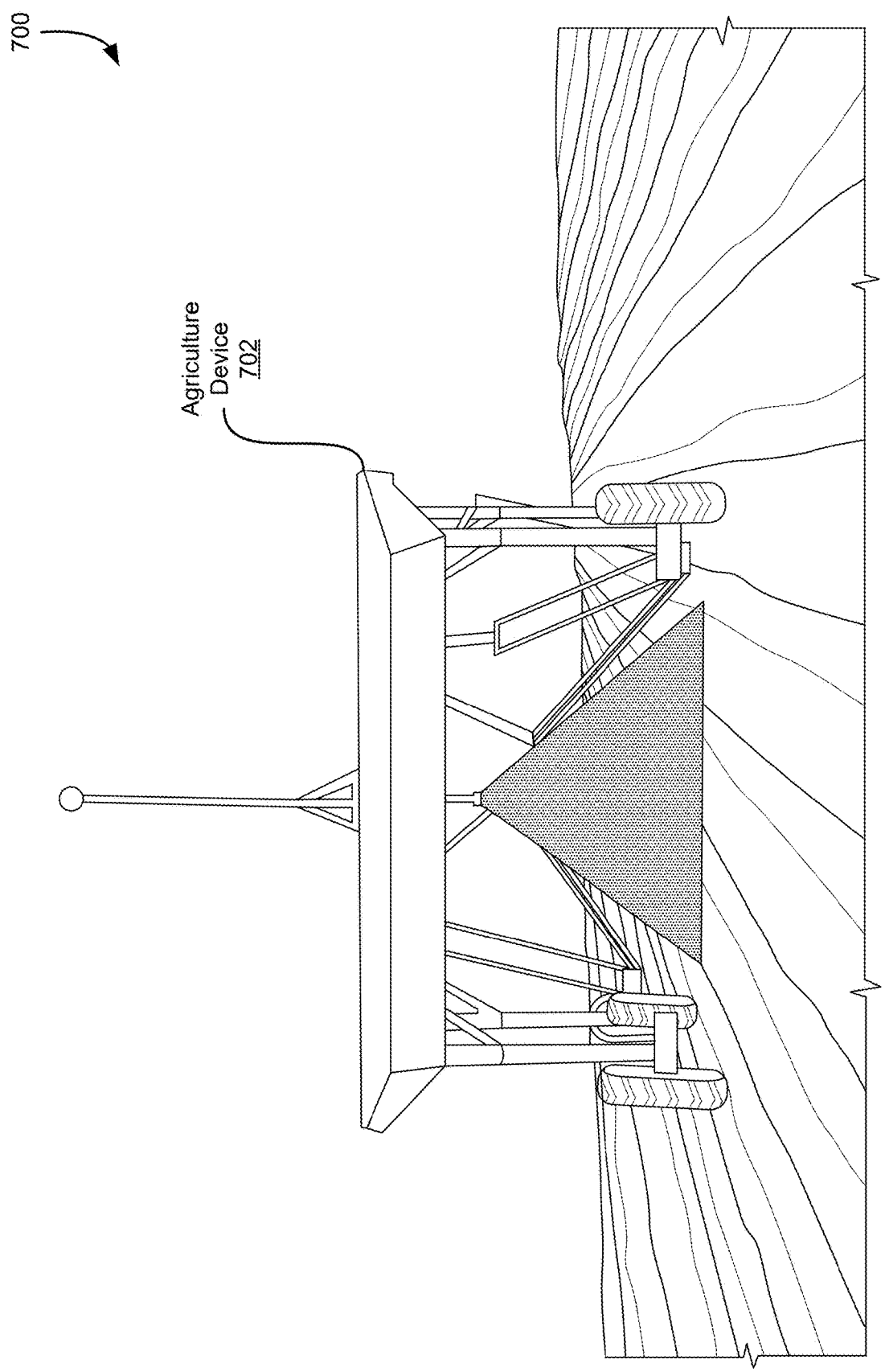
FIG. 7 illustrates an example of an agriculture environment where a neural network is used to output confidence values assigned to pixels of objects in one or more images captured by a device in said agriculture environment, according to at least one embodiment.

FIG. 7 illustrates an example 700 of an agriculture environment where a neural network is used to output confidence values assigned to pixels of objects in one or more images captured by a device in said agriculture environment, according to at least one embodiment. In at least one embodiment, example 700 depicts an agriculture device 702 operating in an agriculture environment, such as a farm. In at least one embodiment, an agriculture device 702 is a robotic system that comprises various agriculture systems, such as fertilization systems, watering systems, weeding systems, crop planting systems, and/or variations thereof. In at least one embodiment, an agriculture device 702 comprises one or more computing systems and one or more image capture devices (e.g., cameras). In at least one embodiment, example 700 depicts an agriculture environment of a land region for cultivating plants, such as a farm.

In at least one embodiment, a system for segmentation and confidence value determination is implemented as part of an agriculture device 702. In at least one embodiment, a system for segmentation and confidence value determination is implemented with one or more segmentation classes corresponding to objects of agriculture environments, such as healthy crops, unhealthy crops, crop weeds, soil, pests, or other agriculture environment objects. In at least one embodiment, a system for segmentation and confidence value determination processes an image captured from an agriculture device 702 to determine segmentation values and confidence values for pixels of said image. In at least one embodiment, a system for segmentation and confidence value determination predicts classifications (e.g., via segmentation values) of objects of an image captured from an agriculture device 702 and generates associated confidence values corresponding to said predicted classifications. In at least one embodiment, a system for segmentation and confidence value determination predicts a classification (e.g., indicated via segmentation values) and confidence values for an object depicted in an image captured from an agriculture device 702. In at least one embodiment, a system for segmentation and confidence value determination predicts classifications of objects of an image and corresponding probabilities of predicted classifications for one or more users of an agriculture environment system, such as an agriculture monitoring system that monitors various agriculture land spaces, such that said one or more users can determine a reliability and/or accuracy of predicted classifications.

In at least one embodiment, a system for segmentation and confidence value determination performs one or more remedial actions in response to determined segmentation and confidence values. In at least one embodiment, a remedial action of activating one or more fertilization systems of an agriculture device comprises a system transmitting one or more notifications to said one or more fertilization systems to cause fertilizer to be output or otherwise dispensed. In at least one embodiment, a remedial action of activating one or more watering systems of an agriculture device comprises a system transmitting one or more notifications to said one or more watering systems to cause water to be output or otherwise dispensed. In at least one embodiment, a remedial action of activating one or more weeding systems of an agriculture device comprises a system transmitting one or more notifications to said one or more weeding systems to cause one or more weeding operations to be performed, such as activating one or more robotic components that remove weeds from ground.

In at least one embodiment, a system for segmentation and confidence value determination generates segmentation values that indicate that an object of an image captured from an agriculture device 702 is an unhealthy crop object and associated confidence values that indicate a high level of confidence, in which said system performs one or more remedial actions such as causing one or more fertilization and/or water systems to provide fertilizer and/or additional water or notifying one or more systems that said object corresponds to an unhealthy crop.

In at least one embodiment, a system for segmentation and confidence value determination generates segmentation values that indicate that an object of an image captured from an agriculture device 702 is an unhealthy crop object and associated confidence values that indicate a low level of confidence, in which said system performs one or more remedial actions such as causing agriculture device 702 to capture more images of said object to generate additional segmentation and confidence values such that a confidence level of a prediction of a classification of said object can be increased. In at least one embodiment, a system for segmentation and confidence value determination (e.g., in response to low/unacceptable confidence values) generates additional segmentation and confidence values through one or more systems, such as via said system for segmentation and confidence value determination, additional image segmentation neural networks, image classification/detection systems, or other systems of one or more agriculture systems.

In at least one embodiment, a system for segmentation and confidence value determination generates segmentation values that indicate that an object of an image captured from an agriculture device 702 is a healthy crop object and associated confidence values that indicate a low level of confidence, in which said system performs one or more remedial actions such as causing one or more fertilization and/or water systems to provide fertilizer and/or additional water, notifying one or more systems that said object potentially does not correspond to a healthy crop, or causing agriculture device 702 to capture more images of said object to generate additional segmentation and confidence values to determine a different prediction of a classification of said object and/or increase a confidence level of a prediction of a classification of said object.

Inference and Training Logic

Figure 8A:
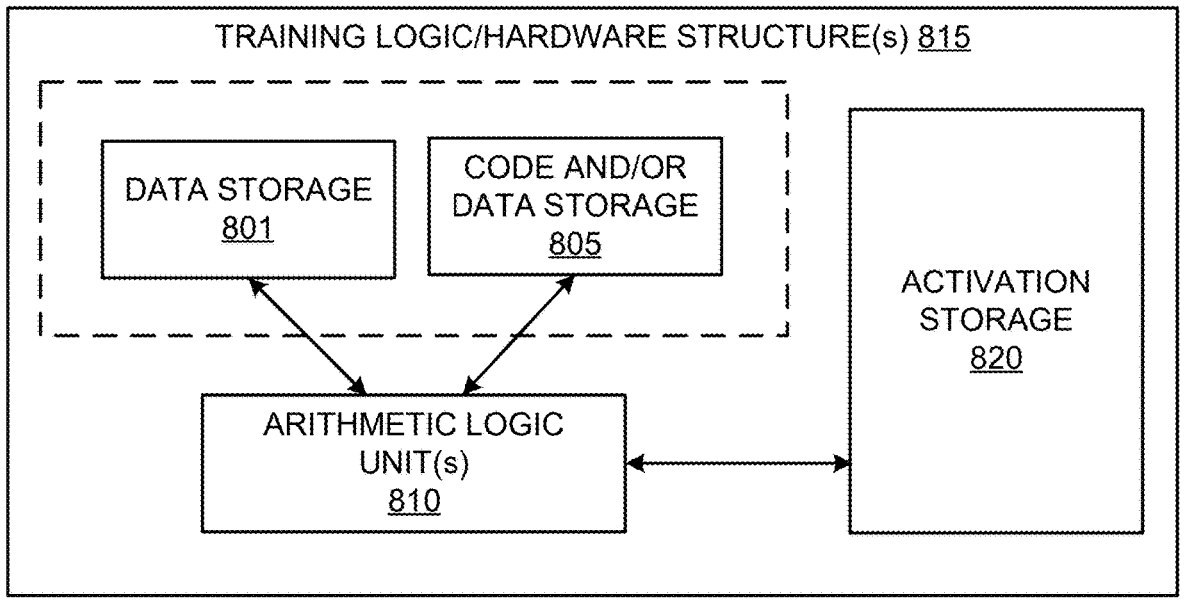
FIG. 8A illustrates inference and/or training logic, according to at least one embodiment.

FIG. 8A illustrates inference and/or training logic 815 used to perform inferencing and/or training operations associated with one or more embodiments. Details regarding inference and/or training logic 815 are provided below in conjunction with FIGS. 8A and/or 8B.

In at least one embodiment, inference and/or training logic 815 may include, without limitation, code and/or data storage 801 to store forward and/or output weight and/or input/output data, and/or other parameters to configure neurons or layers of a neural network trained and/or used for inferencing in aspects of one or more embodiments. In at least one embodiment, training logic 815 may include, or be coupled to code and/or data storage 801 to store graph code or other software to control timing and/or order, in which weight and/or other parameter information is to be loaded to configure, logic, including integer and/or floating point units (collectively, arithmetic logic units (ALUs)). In at least one embodiment, code, such as graph code, loads weight or other parameter information into processor ALUs based on an architecture of a neural network to which such code corresponds. In at least one embodiment, code and/or data storage 801 stores weight parameters and/or input/output data of each layer of a neural network trained or used in conjunction with one or more embodiments during forward propagation of input/output data and/or weight parameters during training and/or inferencing using aspects of one or more embodiments. In at least one embodiment, any portion of code and/or data storage 801 may be included with other on-chip or off-chip data storage, including a processor's L1, L2, or L3 cache or system memory.

In at least one embodiment, any portion of code and/or data storage 801 may be internal or external to one or more processors or other hardware logic devices or circuits. In at least one embodiment, code and/or code and/or data storage 801 may be cache memory, dynamic randomly addressable memory ("DRAM"), static randomly addressable memory ("SRAM"), non-volatile memory (e.g., flash memory), or other storage. In at least one embodiment, a choice of whether code and/or code and/or data storage 801 is internal or external to a processor, for example, or comprising DRAM, SRAM, flash or some other storage type may depend on available storage on-chip versus off-chip, latency requirements of training and/or inferencing functions being performed, batch size of data used in inferencing and/or training of a neural network, or some combination of these factors.

In at least one embodiment, inference and/or training logic 815 may include, without limitation, a code and/or data storage 805 to store backward and/or output weight and/or input/output data corresponding to neurons or layers of a neural network trained and/or used for inferencing in aspects of one or more embodiments. In at least one embodiment, code and/or data storage 805 stores weight parameters and/or input/output data of each layer of a neural network trained or used in conjunction with one or more embodiments during backward propagation of input/output data and/or weight parameters during training and/or inferencing using aspects of one or more embodiments. In at least one embodiment, training logic 815 may include, or be coupled to code and/or data storage 805 to store graph code or other software to control timing and/or order, in which weight and/or other parameter information is to be loaded to configure, logic, including integer and/or floating point units (collectively, arithmetic logic units (ALUs)).

In at least one embodiment, code, such as graph code, causes the loading of weight or other parameter information into processor ALUs based on an architecture of a neural network to which such code corresponds. In at least one embodiment, any portion of code and/or data storage 805 may be included with other on-chip or off-chip data storage, including a processor's L1, L2, or L3 cache or system memory. In at least one embodiment, any portion of code and/or data storage 805 may be internal or external to one or more processors or other hardware logic devices or circuits. In at least one embodiment, code and/or data storage 805 may be cache memory, DRAM, SRAM, non-volatile memory (e.g., flash memory), or other storage. In at least one embodiment, a choice of whether code and/or data storage 805 is internal or external to a processor, for example, or comprising DRAM, SRAM, flash memory or some other storage type may depend on available storage on-chip versus off-chip, latency requirements of training and/or inferencing functions being performed, batch size of data used in inferencing and/or training of a neural network, or some combination of these factors.

In at least one embodiment, code and/or data storage 801 and code and/or data storage 805 may be separate storage structures. In at least one embodiment, code and/or data storage 801 and code and/or data storage 805 may be a combined storage structure. In at least one embodiment, code and/or data storage 801 and code and/or data storage 805 may be partially combined and partially separate. In at least one embodiment, any portion of code and/or data storage 801 and code and/or data storage 805 may be included with other on-chip or off-chip data storage, including a processor's L1, L2, or L3 cache or system memory.

In at least one embodiment, inference and/or training logic 815 may include, without limitation, one or more arithmetic logic unit(s) ("ALU(s)") 810, including integer and/or floating point units, to perform logical and/or mathematical operations based, at least in part on, or indicated by, training and/or inference code (e.g., graph code), a result of which may produce activations (e.g., output values from layers or neurons within a neural network) stored in an activation storage 820 that are functions of input/output and/or weight parameter data stored in code and/or data storage 801 and/or code and/or data storage 805. In at least one embodiment, activations stored in activation storage 820 are generated according to linear algebraic and or matrix-based mathematics performed by ALU(s) 810 in response to performing instructions or other code, wherein weight values stored in code and/or data storage 805 and/or data storage 801 are used as operands along with other values, such as bias values, gradient information, momentum values, or other parameters or hyperparameters, any or all of which may be stored in code and/or data storage 805 or code and/or data storage 801 or another storage on or off-chip.

In at least one embodiment, ALU(s) 810 are included within one or more processors or other hardware logic devices or circuits, whereas in another embodiment, ALU(s) 810 may be external to a processor or other hardware logic device or circuit that uses them (e.g., a co-processor). In at least one embodiment, ALUs 810 may be included within a processor's execution units or otherwise within a bank of ALUs accessible by a processor's execution units either within same processor or distributed between different processors of different types (e.g., central processing units, graphics processing units, fixed function units, etc.). In at least one embodiment, code and/or data storage 801, code and/or data storage 805, and activation storage 820 may share a processor or other hardware logic device or circuit, whereas in another embodiment, they may be in different processors or other hardware logic devices or circuits, or some combination of same and different processors or other hardware logic devices or circuits. In at least one embodiment, any portion of activation storage 820 may be included with other on-chip or off-chip data storage, including a processor's L1, L2, or L3 cache or system memory. Furthermore, inferencing and/or training code may be stored with other code accessible to a processor or other hardware logic or circuit and fetched and/or processed using a processor's fetch, decode, scheduling, execution, retirement and/or other logical circuits.

In at least one embodiment, activation storage 820 may be cache memory, DRAM, SRAM, non-volatile memory (e.g., flash memory), or other storage. In at least one embodiment, activation storage 820 may be completely or partially within or external to one or more processors or other logical circuits. In at least one embodiment, a choice of whether activation storage 820 is internal or external to a processor, for example, or comprising DRAM, SRAM, flash memory or some other storage type may depend on available storage on-chip versus off-chip, latency requirements of training and/or inferencing functions being performed, batch size of data used in inferencing and/or training of a neural network, or some combination of these factors.

In at least one embodiment, inference and/or training logic 815 illustrated in FIG. 8A may be used in conjunction with an application-specific integrated circuit ("ASIC"), such as a TensorFlow® Processing Unit from Google, an inference processing unit (IPU) from Graphcore™, or a Nervana® (e.g., "Lake Crest") processor from Intel Corp. In at least one embodiment, inference and/or training logic 815 illustrated in FIG. 8A may be used in conjunction with central processing unit ("CPU") hardware, graphics processing unit ("GPU") hardware or other hardware, such as field programmable gate arrays ("FPGAs").

Figure 8B:
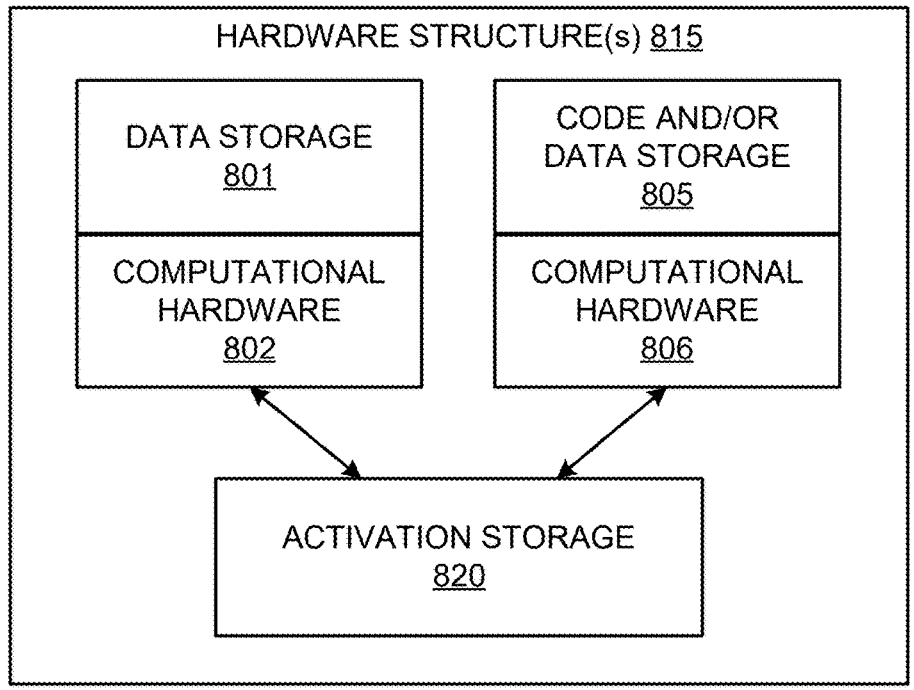
FIG. 8B illustrates inference and/or training logic, according to at least one embodiment.

FIG. 8B illustrates inference and/or training logic 815, according to at least one embodiment. In at least one embodiment, inference and/or training logic 815 may include, without limitation, hardware logic in which computational resources are dedicated or otherwise exclusively used in conjunction with weight values or other information corresponding to one or more layers of neurons within a neural network. In at least one embodiment, inference and/or training logic 815 illustrated in FIG. 8B may be used in conjunction with an application-specific integrated circuit (ASIC), such as TensorFlow® Processing Unit from Google, an inference processing unit (IPU) from Graphcore™, or a Nervana® (e.g., "Lake Crest") processor from Intel Corp. In at least one embodiment, inference and/or training logic 815 illustrated in FIG. 8B may be used in conjunction with central processing unit (CPU) hardware, graphics processing unit (GPU) hardware or other hardware, such as field programmable gate arrays (FPGAs). In at least one embodiment, inference and/or training logic 815 includes, without limitation, code and/or data storage 801 and code and/or data storage 805, which may be used to store code (e.g., graph code), weight values and/or other information, including bias values, gradient information, momentum values, and/or other parameter or hyperparameter information. In at least one embodiment illustrated in FIG. 8B, each of code and/or data storage 801 and code and/or data storage 805 is associated with a dedicated computational resource, such as computational hardware 802 and computational hardware 806, respectively. In at least one embodiment, each of computational hardware 802 and computational hardware 806 comprises one or more ALUs that perform mathematical functions, such as linear algebraic functions, only on information stored in code and/or data storage 801 and code and/or data storage 805, respectively, result of which is stored in activation storage 820.

In at least one embodiment, each of code and/or data storage 801 and 805 and corresponding computational hardware 802 and 806, respectively, correspond to different layers of a neural network, such that resulting activation from one storage/computational pair 801/802 of code and/or data storage 801 and computational hardware 802 is provided as an input to a next storage/computational pair 805/806 of code and/or data storage 805 and computational hardware 806, in order to mirror a conceptual organization of a neural network. In at least one embodiment, each of storage/computational pairs 801/802 and 805/806 may correspond to more than one neural network layer. In at least one embodiment, additional storage/computation pairs (not shown) subsequent to or in parallel with storage/computation pairs 801/802 and 805/806 may be included in inference and/or training logic 815.

In at least one embodiment, one or more systems depicted in FIG. 8 are utilized to generate segmentation and confidence values for pixels of an image. In at least one embodiment, one or more systems depicted in FIG. 8 are utilized to implement one or more networks and processes such as those described in connection with FIGS. 1-7. In at least one embodiment, one or more systems depicted in FIG. 8 are utilized to implement a system for segmentation and confidence value determination.

Neural Network Training and Deployment

Figure 9:
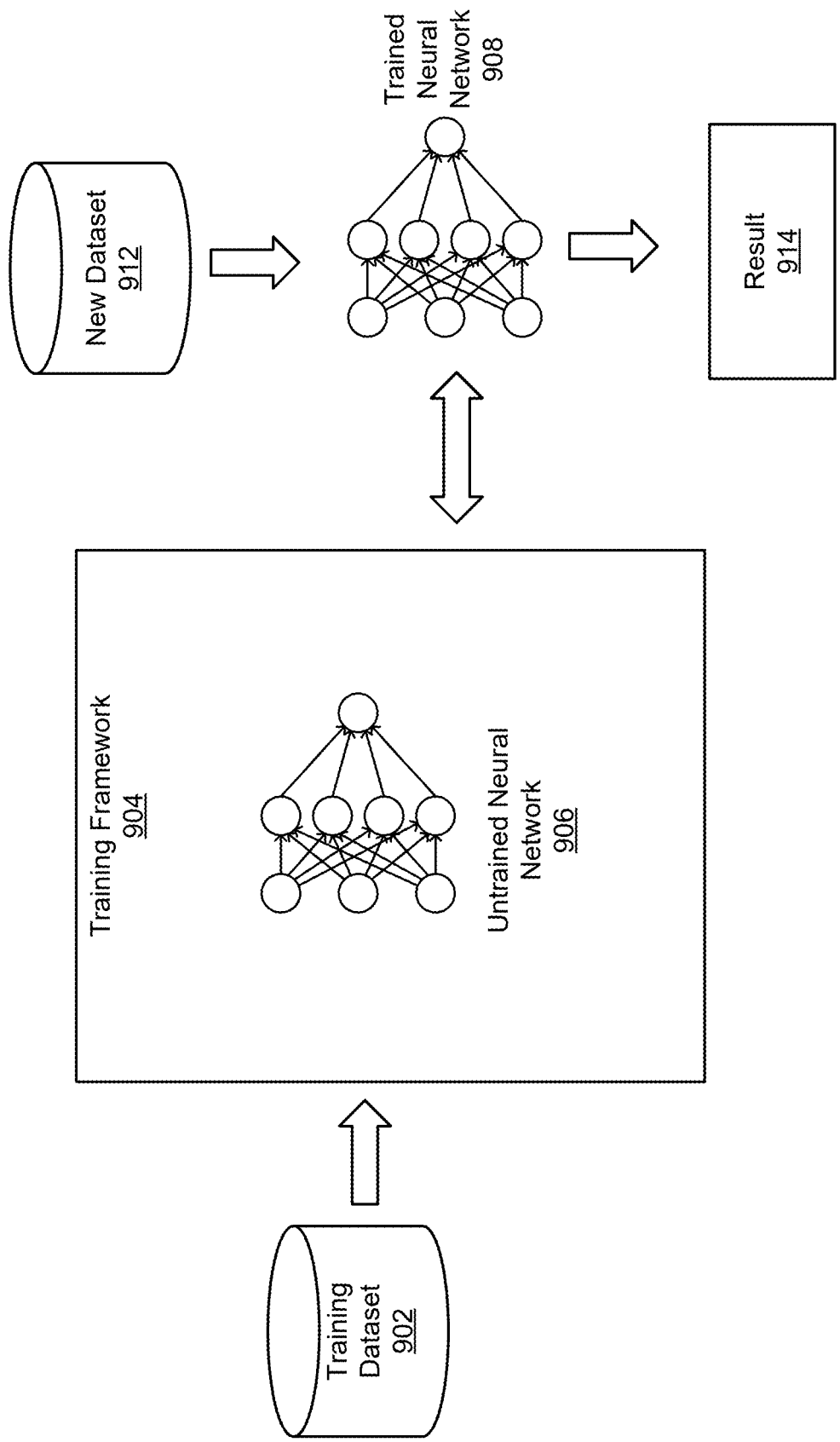
FIG. 9 illustrates training and deployment of a neural network, according to at least one embodiment.

FIG. 9 illustrates training and deployment of a deep neural network, according to at least one embodiment. In at least one embodiment, untrained neural network 906 is trained using a training dataset 902. In at least one embodiment, training framework 904 is a PyTorch framework, whereas in other embodiments, training framework 904 is a TensorFlow, Boost, Caffe, Microsoft Cognitive Toolkit/CNTK, MXNet, Chainer, Keras, Deeplearning4j, or other training framework. In at least one embodiment, training framework 904 trains an untrained neural network 906 and enables it to be trained using processing resources described herein to generate a trained neural network 908. In at least one embodiment, weights may be chosen randomly or by pre-training using a deep belief network. In at least one embodiment, training may be performed in either a supervised, partially supervised, or unsupervised manner.

In at least one embodiment, untrained neural network 906 is trained using supervised learning, wherein training dataset 902 includes an input paired with a desired output for an input, or where training dataset 902 includes input having a known output and an output of neural network 906 is manually graded. In at least one embodiment, untrained neural network 906 is trained in a supervised manner and processes inputs from training dataset 902 and compares resulting outputs against a set of expected or desired outputs. In at least one embodiment, errors are then propagated back through untrained neural network 906. In at least one embodiment, training framework 904 adjusts weights that control untrained neural network 906. In at least one embodiment, training framework 904 includes tools to monitor how well untrained neural network 906 is converging towards a model, such as trained neural network 908, suitable to generating correct answers, such as in result 914, based on input data such as a new dataset 912. In at least one embodiment, training framework 904 trains untrained neural network 906 repeatedly while adjust weights to refine an output of untrained neural network 906 using a loss function and adjustment algorithm, such as stochastic gradient descent. In at least one embodiment, training framework 904 trains untrained neural network 906 until untrained neural network 906 achieves a desired accuracy. In at least one embodiment, trained neural network 908 can then be deployed to implement any number of machine learning operations.

In at least one embodiment, untrained neural network 906 is trained using unsupervised learning, wherein untrained neural network 906 attempts to train itself using unlabeled data. In at least one embodiment, unsupervised learning training dataset 902 will include input data without any associated output data or "ground truth" data. In at least one embodiment, untrained neural network 906 can learn groupings within training dataset 902 and can determine how individual inputs are related to untrained dataset 902. In at least one embodiment, unsupervised training can be used to generate a self-organizing map in trained neural network 908 capable of performing operations useful in reducing dimensionality of new dataset 912. In at least one embodiment, unsupervised training can also be used to perform anomaly detection, which allows classification of data points in new dataset 912 that deviate from normal patterns of new dataset 912.

In at least one embodiment, semi-supervised learning may be used, which is a technique in which in training dataset 902 includes a mix of labeled and unlabeled data. In at least one embodiment, training framework 904 may be used to perform incremental learning, such as through transferred learning techniques. In at least one embodiment, incremental learning enables trained neural network 908 to adapt to new dataset 912 without forgetting knowledge instilled within trained neural network 908 during initial training.

In at least one embodiment, one or more systems depicted in FIG. 9 are utilized to generate segmentation and confidence values for pixels of an image. In at least one embodiment, one or more systems depicted in FIG. 9 are utilized to implement one or more networks and processes such as those described in connection with FIGS. 1-7. In at least one embodiment, one or more systems depicted in FIG. 9 are utilized to implement a system for segmentation and confidence value determination.

Data Center

Figure 10:
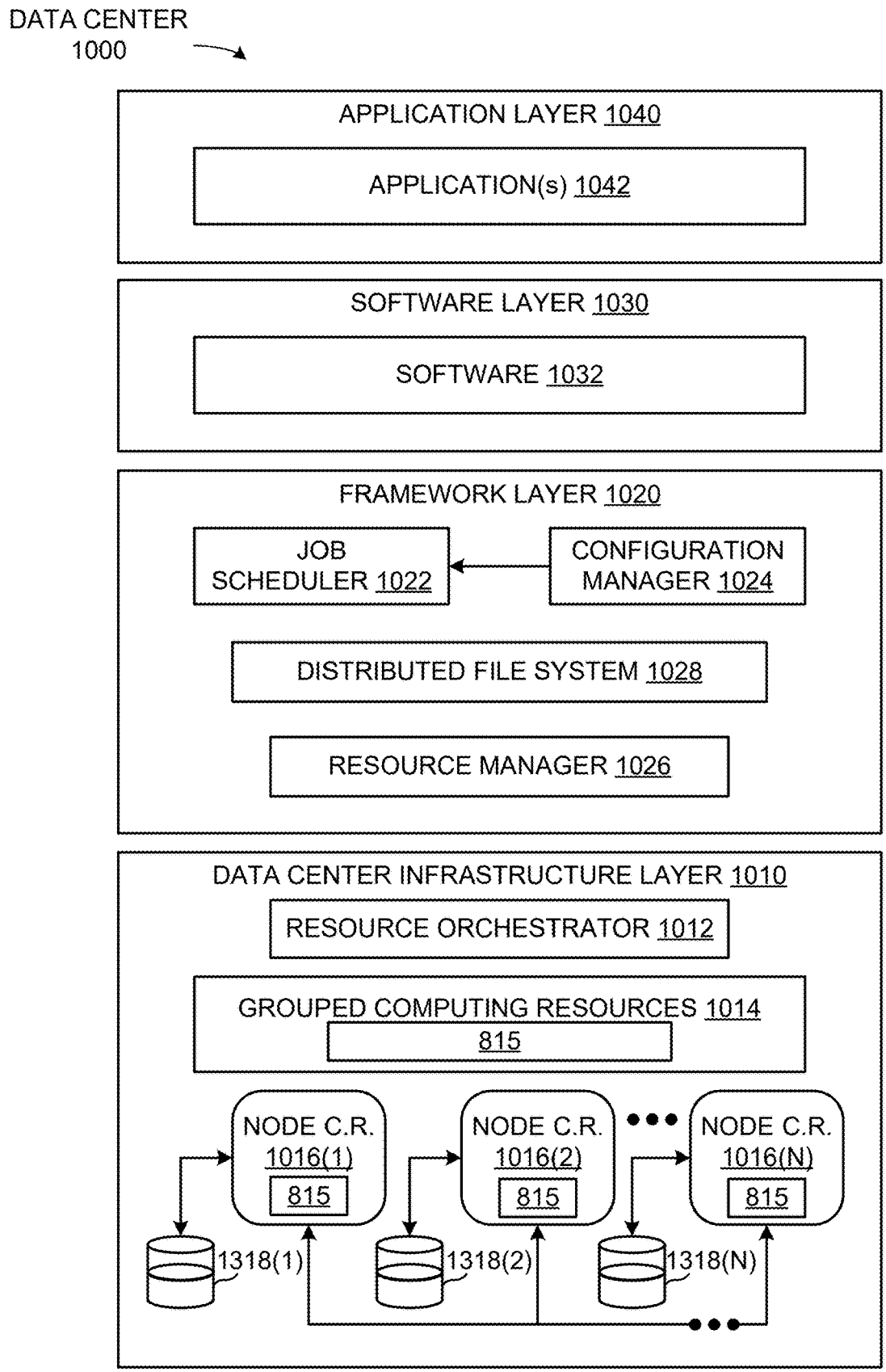
FIG. 10 illustrates an example data center system, according to at least one embodiment.

FIG. 10 illustrates an example data center 1000, in which at least one embodiment may be used. In at least one embodiment, data center 1000 includes a data center infrastructure layer 1010, a framework layer 1020, a software layer 1030 and an application layer 1040.

In at least one embodiment, as shown in FIG. 10, data center infrastructure layer 1010 may include a resource orchestrator 1012, grouped computing resources 1014, and node computing resources ("node C.R.s") 1016(1)-1016(N), where "N" represents a positive integer (which may be a different integer "N" than used in other figures). In at least one embodiment, node C.R.s 1016(1)-1016(N) may include, but are not limited to, any number of central processing units ("CPUs") or other processors (including accelerators, field programmable gate arrays (FPGAs), graphics processors, etc.), memory storage devices 1018(1)-1018(N) (e.g., dynamic read-only memory, solid state storage or disk drives), network input/output ("NW I/O") devices, network switches, virtual machines ("VMs"), power modules, and cooling modules, etc. In at least one embodiment, one or more node C.R.s from among node C.R.s 1016(1)-1016(N) may be a server having one or more of above-mentioned computing resources.

In at least one embodiment, grouped computing resources 1014 may include separate groupings of node C.R.s housed within one or more racks (not shown), or many racks housed in data centers at various geographical locations (also not shown). In at least one embodiment, separate groupings of node C.R.s within grouped computing resources 1014 may include grouped compute, network, memory or storage resources that may be configured or allocated to support one or more workloads. In at least one embodiment, several node C.R.s including CPUs or processors may grouped within one or more racks to provide compute resources to support one or more workloads. In at least one embodiment, one or more racks may also include any number of power modules, cooling modules, and network switches, in any combination.

In at least one embodiment, resource orchestrator 1012 may configure or otherwise control one or more node C.R.s 1016(1)-1016(N) and/or grouped computing resources 1014. In at least one embodiment, resource orchestrator 1012 may include a software design infrastructure ("SDI") management entity for data center 1000. In at least one embodiment, resource orchestrator 812 may include hardware, software or some combination thereof.

In at least one embodiment, as shown in FIG. 10, framework layer 1020 includes a job scheduler 1022, a configuration manager 1024, a resource manager 1026 and a distributed file system 1028. In at least one embodiment, framework layer 1020 may include a framework to support software 1032 of software layer 1030 and/or one or more application(s) 1042 of application layer 1040. In at least one embodiment, software 1032 or application(s) 1042 may respectively include web-based service software or applications, such as those provided by Amazon Web Services, Google Cloud and Microsoft Azure. In at least one embodiment, framework layer 1020 may be, but is not limited to, a type of free and open-source software web application framework such as Apache Spark™ (hereinafter "Spark") that may utilize distributed file system 1028 for large-scale data processing (e.g., "big data"). In at least one embodiment, job scheduler 1032 may include a Spark driver to facilitate scheduling of workloads supported by various layers of data center 1000. In at least one embodiment, configuration manager 1024 may be capable of configuring different layers such as software layer 1030 and framework layer 1020 including Spark and distributed file system 1028 for supporting large-scale data processing. In at least one embodiment, resource manager 1026 may be capable of managing clustered or grouped computing resources mapped to or allocated for support of distributed file system 1028 and job scheduler 1022. In at least one embodiment, clustered or grouped computing resources may include grouped computing resources 1014 at data center infrastructure layer 1010. In at least one embodiment, resource manager 1026 may coordinate with resource orchestrator 1012 to manage these mapped or allocated computing resources.

In at least one embodiment, software 1032 included in software layer 1030 may include software used by at least portions of node C.R.s 1016(1)-1016(N), grouped computing resources 1014, and/or distributed file system 1028 of framework layer 1020. In at least one embodiment, one or more types of software may include, but are not limited to, Internet web page search software, e-mail virus scan software, database software, and streaming video content software.

In at least one embodiment, application(s) 1042 included in application layer 1040 may include one or more types of applications used by at least portions of node C.R.s 1016(1)-1016(N), grouped computing resources 1014, and/or distributed file system 1028 of framework layer 1020. In at least one embodiment, one or more types of applications may include, but are not limited to, any number of a genomics application, a cognitive compute, application and a machine learning application, including training or inferencing software, machine learning framework software (e.g., PyTorch, TensorFlow, Caffe, etc.) or other machine learning applications used in conjunction with one or more embodiments.

In at least one embodiment, any of configuration manager 1024, resource manager 1026, and resource orchestrator 1012 may implement any number and type of self-modifying actions based on any amount and type of data acquired in any technically feasible fashion. In at least one embodiment, self-modifying actions may relieve a data center operator of data center 1000 from making possibly bad configuration decisions and possibly avoiding underutilized and/or poor performing portions of a data center.

In at least one embodiment, data center 1000 may include tools, services, software or other resources to train one or more machine learning models or predict or infer information using one or more machine learning models according to one or more embodiments described herein. For example, in at least one embodiment, a machine learning model may be trained by calculating weight parameters according to a neural network architecture using software and computing resources described above with respect to data center 1000. In at least one embodiment, trained machine learning models corresponding to one or more neural networks may be used to infer or predict information using resources described above with respect to data center 1000 by using weight parameters calculated through one or more training techniques described herein.

In at least one embodiment, data center may use CPUs, application-specific integrated circuits (ASICs), GPUs, FPGAs, or other hardware to perform training and/or inferencing using above-described resources. Moreover, one or more software and/or hardware resources described above may be configured as a service to allow users to train or performing inferencing of information, such as image recognition, speech recognition, or other artificial intelligence services.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, inference and/or training logic 815 may be used in system FIG. 10 for inferencing or predicting operations based, at least in part, on weight parameters calculated using neural network training operations, neural network functions and/or architectures, or neural network use cases described herein.

In at least one embodiment, one or more systems depicted in FIG. 10 are utilized to generate segmentation and confidence values for pixels of an image. In at least one embodiment, one or more systems depicted in FIG. 10 are utilized to implement one or more networks and processes such as those described in connection with FIGS. 1-7. In at least one embodiment, one or more systems depicted in FIG. 10 are utilized to implement a system for segmentation and confidence value determination.

Autonomous Vehicle

Figure 11A:
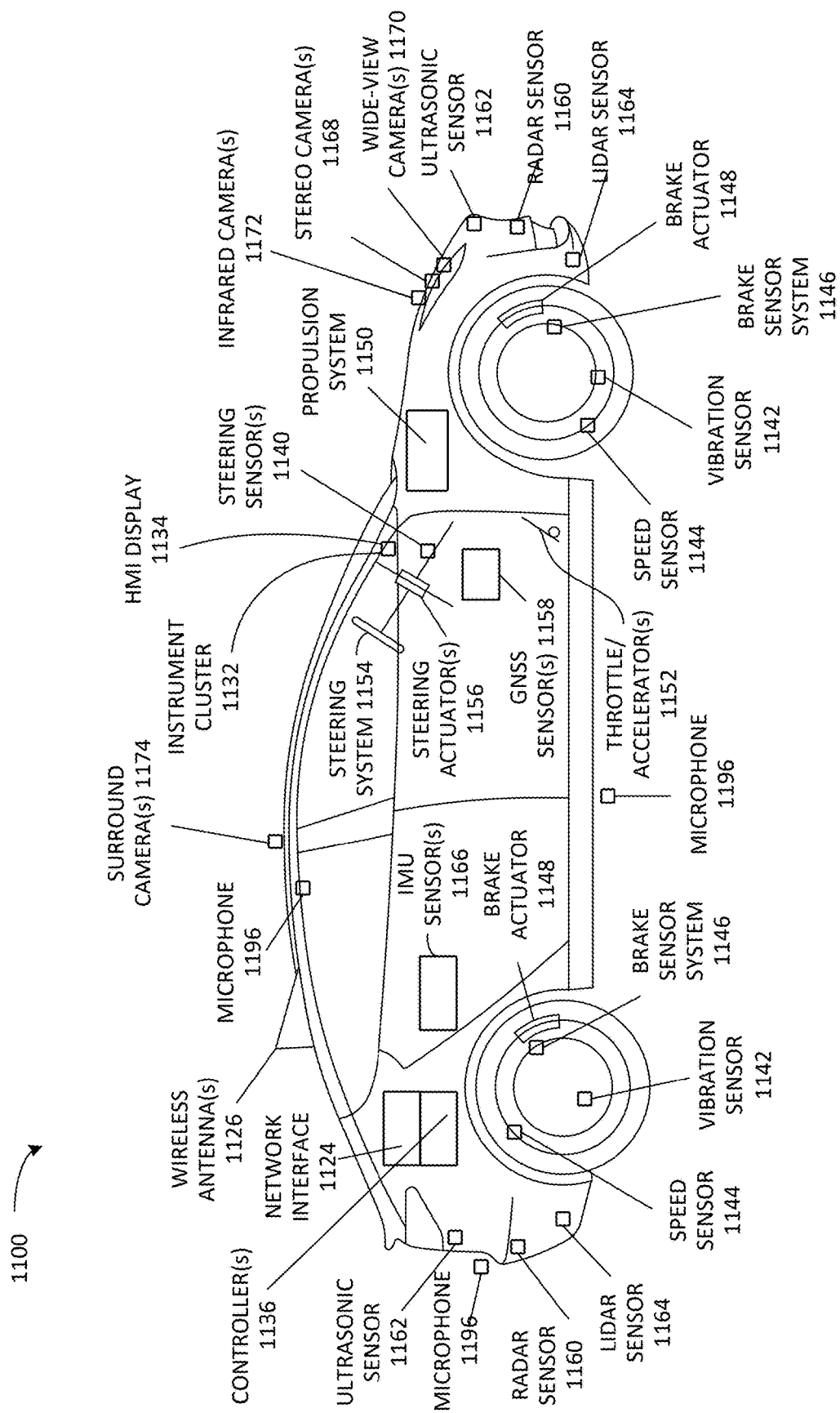
FIG. 11A illustrates an example of an autonomous vehicle, according to at least one embodiment.

FIG. 11A illustrates an example of an autonomous vehicle 1100, according to at least one embodiment. In at least one embodiment, autonomous vehicle 1100 (alternatively referred to herein as "vehicle 1100") may be, without limitation, a passenger vehicle, such as a car, a truck, a bus, and/or another type of vehicle that accommodates one or more passengers. In at least one embodiment, vehicle 1100 may be a semi-tractor-trailer truck used for hauling cargo. In at least one embodiment, vehicle 1100 may be an airplane, robotic vehicle, or other kind of vehicle.

Autonomous vehicles may be described in terms of automation levels, defined by National Highway Traffic Safety Administration ("NHTSA"), a division of US Department of Transportation, and Society of Automotive Engineers ("SAE") "Taxonomy and Definitions for Terms Related to Driving Automation Systems for On-Road Motor Vehicles" (e.g., Standard No. J3016-201806, published on Jun. 15, 2018, Standard No. J3016-201609, published on Sep. 30, 2016, and previous and future versions of this standard). In at least one embodiment, vehicle 1100 may be capable of functionality in accordance with one or more of Level 1 through Level 5 of autonomous driving levels. For example, in at least one embodiment, vehicle 1100 may be capable of conditional automation (Level 3), high automation (Level 4), and/or full automation (Level 5), depending on embodiment.

In at least one embodiment, vehicle 1100 may include, without limitation, components such as a chassis, a vehicle body, wheels (e.g., 2, 4, 6, 8, 18, etc.), tires, axles, and other components of a vehicle. In at least one embodiment, vehicle 1100 may include, without limitation, a propulsion system 1150, such as an internal combustion engine, hybrid electric power plant, an all-electric engine, and/or another propulsion system type. In at least one embodiment, propulsion system 1150 may be connected to a drive train of vehicle 1100, which may include, without limitation, a transmission, to enable propulsion of vehicle 1100. In at least one embodiment, propulsion system 1150 may be controlled in response to receiving signals from a throttle/accelerator(s) 1152.

In at least one embodiment, a steering system 1154, which may include, without limitation, a steering wheel, is used to steer vehicle 1100 (e.g., along a desired path or route) when propulsion system 1150 is operating (e.g., when vehicle 1100 is in motion). In at least one embodiment, steering system 1154 may receive signals from steering actuator(s) 1156. In at least one embodiment, a steering wheel may be optional for full automation (Level 5) functionality. In at least one embodiment, a brake sensor system 1146 may be used to operate vehicle brakes in response to receiving signals from brake actuator(s) 1148 and/or brake sensors.

In at least one embodiment, controller(s) 1136, which may include, without limitation, one or more system on chips ("SoCs") (not shown in FIG. 11A) and/or graphics processing unit(s) ("GPU(s)"), provide signals (e.g., representative of commands) to one or more components and/or systems of vehicle 1100. For instance, in at least one embodiment, controller(s) 1136 may send signals to operate vehicle brakes via brake actuator(s) 1148, to operate steering system 1154 via steering actuator(s) 1156, to operate propulsion system 1150 via throttle/accelerator(s) 1152. In at least one embodiment, controller(s) 1136 may include one or more onboard (e.g., integrated) computing devices that process sensor signals, and output operation commands (e.g., signals representing commands) to enable autonomous driving and/or to assist a human driver in driving vehicle 1100. In at least one embodiment, controller(s) 1136 may include a first controller for autonomous driving functions, a second controller for functional safety functions, a third controller for artificial intelligence functionality (e.g., computer vision), a fourth controller for infotainment functionality, a fifth controller for redundancy in emergency conditions, and/or other controllers. In at least one embodiment, a single controller may handle two or more of above functionalities, two or more controllers may handle a single functionality, and/or any combination thereof.

In at least one embodiment, controller(s) 1136 provide signals for controlling one or more components and/or systems of vehicle 1100 in response to sensor data received from one or more sensors (e.g., sensor inputs). In at least one embodiment, sensor data may be received from, for example and without limitation, global navigation satellite systems ("GNSS") sensor(s) 1158 (e.g., Global Positioning System sensor(s)), RADAR sensor(s) 1160, ultrasonic sensor(s) 1162, LIDAR sensor(s) 1164, inertial measurement unit ("IMU") sensor(s) 1166 (e.g., accelerometer(s), gyroscope(s), a magnetic compass or magnetic compasses, magnetometer(s), etc.), microphone(s) 1196, stereo camera(s) 1168, wide-view camera(s) 1170 (e.g., fisheye cameras), infrared camera(s) 1172, surround camera(s) 1174 (e.g., 360 degree cameras), long-range cameras (not shown in FIG. 11A), mid-range camera(s) (not shown in FIG. 11A), speed sensor(s) 1144 (e.g., for measuring speed of vehicle 1100), vibration sensor(s) 1142, steering sensor(s) 1140, brake sensor(s) (e.g., as part of brake sensor system 1146), and/or other sensor types.

In at least one embodiment, one or more of controller(s) 1136 may receive inputs (e.g., represented by input data) from an instrument cluster 1132 of vehicle 1100 and provide outputs (e.g., represented by output data, display data, etc.) via a human-machine interface ("HMI") display 1134, an audible annunciator, a loudspeaker, and/or via other components of vehicle 1100. In at least one embodiment, outputs may include information such as vehicle velocity, speed, time, map data (e.g., a High Definition map (not shown in FIG. 11A)), location data (e.g., vehicle's 1100 location, such as on a map), direction, location of other vehicles (e.g., an occupancy grid), information about objects and status of objects as perceived by controller(s) 1136, etc. For example, in at least one embodiment, HMI display 1134 may display information about presence of one or more objects (e.g., a street sign, caution sign, traffic light changing, etc.), and/or information about driving maneuvers vehicle has made, is making, or will make (e.g., changing lanes now, taking exit 34B in two miles, etc.).

In at least one embodiment, vehicle 1100 further includes a network interface 1124 which may use wireless antenna(s) 1126 and/or modem(s) to communicate over one or more networks. For example, in at least one embodiment, network interface 1124 may be capable of communication over Long-Term Evolution ("LTE"), Wideband Code Division Multiple Access ("WCDMA"), Universal Mobile Telecommunications System ("UMTS"), Global System for Mobile communication ("GSM"), IMT-CDMA Multi-Carrier ("CDMA2000") networks, etc. In at least one embodiment, wireless antenna(s) 1126 may also enable communication between objects in environment (e.g., vehicles, mobile devices, etc.), using local area network(s), such as Bluetooth, Bluetooth Low Energy ("LE"), Z-Wave, ZigBee, etc., and/or low power wide-area network(s) ("LPWANs"), such as LoRaWAN, SigFox, etc. protocols.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, inference and/or training logic 815 may be used in system FIG. 11A for inferencing or predicting operations based, at least in part, on weight parameters calculated using neural network training operations, neural network functions and/or architectures, or neural network use cases described herein.

Figure 11B:
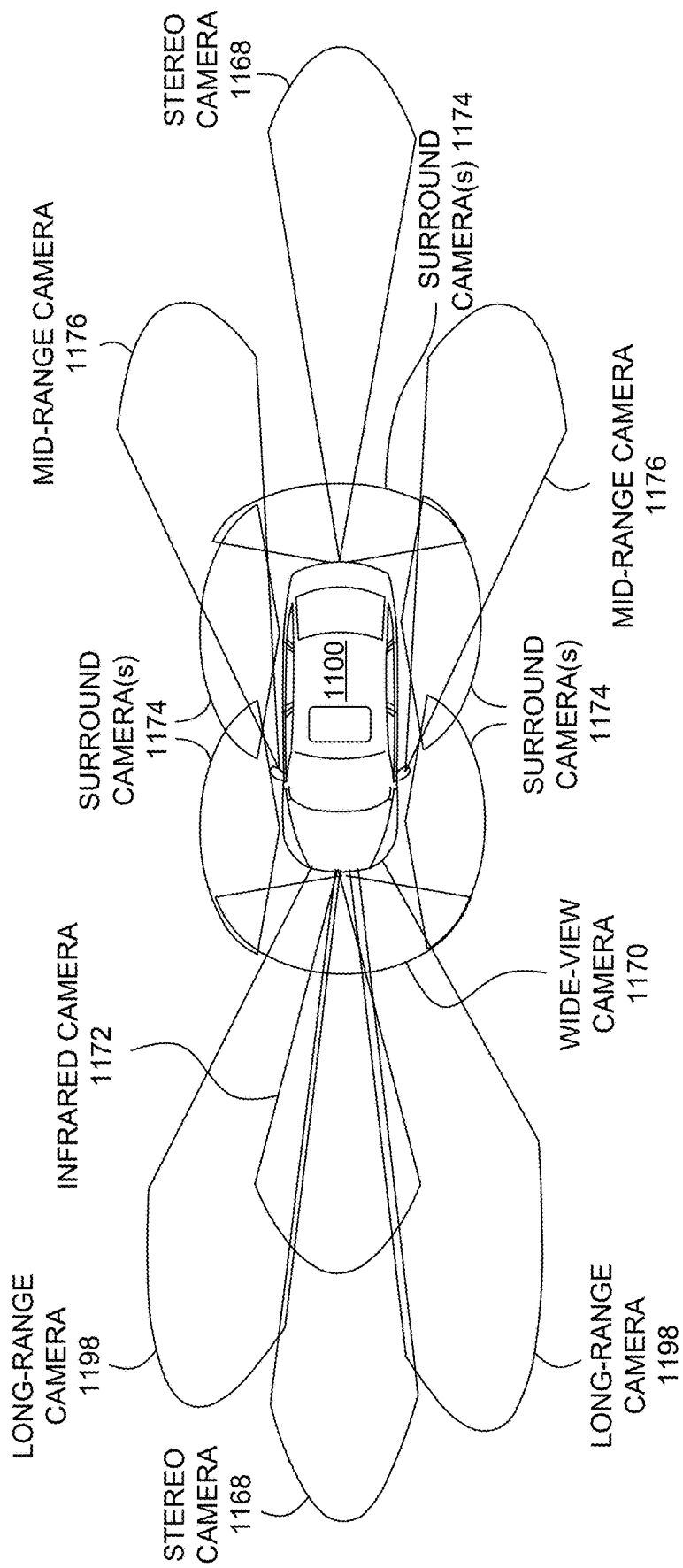
FIG. 11B illustrates an example of camera locations and fields of view for the autonomous vehicle of FIG. 11A, according to at least one embodiment.

FIG. 11B illustrates an example of camera locations and fields of view for autonomous vehicle 1100 of FIG. 11A, according to at least one embodiment. In at least one embodiment, cameras and respective fields of view are one example embodiment and are not intended to be limiting. For instance, in at least one embodiment, additional and/or alternative cameras may be included and/or cameras may be located at different locations on vehicle 1100.

In at least one embodiment, camera types for cameras may include, but are not limited to, digital cameras that may be adapted for use with components and/or systems of vehicle 1100. In at least one embodiment, camera(s) may operate at automotive safety integrity level ("ASIL") B and/or at another ASIL. In at least one embodiment, camera types may be capable of any image capture rate, such as 60 frames per second (fps), 1220 fps, 240 fps, etc., depending on embodiment. In at least one embodiment, cameras may be capable of using rolling shutters, global shutters, another type of shutter, or a combination thereof. In at least one embodiment, color filter array may include a red clear clear clear ("RCCC") color filter array, a red clear clear blue ("RCCB") color filter array, a red blue green clear ("RBGC") color filter array, a Foveon X3 color filter array, a Bayer sensors ("RGGB") color filter array, a monochrome sensor color filter array, and/or another type of color filter array. In at least one embodiment, clear pixel cameras, such as cameras with an RCCC, an RCCB, and/or an RBGC color filter array, may be used in an effort to increase light sensitivity.

In at least one embodiment, one or more of camera(s) may be used to perform advanced driver assistance systems ("ADAS") functions (e.g., as part of a redundant or fail-safe design). For example, in at least one embodiment, a Multi-Function Mono Camera may be installed to provide functions including lane departure warning, traffic sign assist and intelligent headlamp control. In at least one embodiment, one or more of camera(s) (e.g., all cameras) may record and provide image data (e.g., video) simultaneously.

In at least one embodiment, one or more camera may be mounted in a mounting assembly, such as a custom designed (three-dimensional ("3D") printed) assembly, in order to cut out stray light and reflections from within vehicle 1100 (e.g., reflections from dashboard reflected in windshield mirrors) which may interfere with camera image data capture abilities. With reference to wing-mirror mounting assemblies, in at least one embodiment, wing-mirror assemblies may be custom 3D printed so that a camera mounting plate matches a shape of a wing-mirror. In at least one embodiment, camera(s) may be integrated into wing-mirrors. In at least one embodiment, for side-view cameras, camera(s) may also be integrated within four pillars at each corner of a cabin.

In at least one embodiment, cameras with a field of view that include portions of an environment in front of vehicle 1100 (e.g., front-facing cameras) may be used for surround view, to help identify forward facing paths and obstacles, as well as aid in, with help of one or more of controller(s) 1136 and/or control SoCs, providing information critical to generating an occupancy grid and/or determining preferred vehicle paths. In at least one embodiment, front-facing cameras may be used to perform many similar ADAS functions as LIDAR, including, without limitation, emergency braking, pedestrian detection, and collision avoidance. In at least one embodiment, front-facing cameras may also be used for ADAS functions and systems including, without limitation, Lane Departure Warnings ("LDW"), Autonomous Cruise Control ("ACC"), and/or other functions such as traffic sign recognition.

In at least one embodiment, a variety of cameras may be used in a front-facing configuration, including, for example, a monocular camera platform that includes a CMOS ("complementary metal oxide semiconductor") color imager. In at least one embodiment, a wide-view camera 1170 may be used to perceive objects coming into view from a periphery (e.g., pedestrians, crossing traffic or bicycles). Although only one wide-view camera 1170 is illustrated in FIG. 11B, in other embodiments, there may be any number (including zero) wide-view cameras on vehicle 1100. In at least one embodiment, any number of long-range camera(s) 1198 (e.g., a long-view stereo camera pair) may be used for depth-based object detection, especially for objects for which a neural network has not yet been trained. In at least one embodiment, long-range camera(s) 1198 may also be used for object detection and classification, as well as basic object tracking.

In at least one embodiment, any number of stereo camera(s) 1168 may also be included in a front-facing configuration. In at least one embodiment, one or more of stereo camera(s) 1168 may include an integrated control unit comprising a scalable processing unit, which may provide a programmable logic ("FPGA") and a multi-core microprocessor with an integrated Controller Area Network ("CAN") or Ethernet interface on a single chip. In at least one embodiment, such a unit may be used to generate a 3D map of an environment of vehicle 1100, including a distance estimate for all points in an image. In at least one embodiment, one or more of stereo camera(s) 1168 may include, without limitation, compact stereo vision sensor(s) that may include, without limitation, two camera lenses (one each on left and right) and an image processing chip that may measure distance from vehicle 1100 to target object and use generated information (e.g., metadata) to activate autonomous emergency braking and lane departure warning functions. In at least one embodiment, other types of stereo camera(s) 1168 may be used in addition to, or alternatively from, those described herein.

In at least one embodiment, cameras with a field of view that include portions of environment to sides of vehicle 1100 (e.g., side-view cameras) may be used for surround view, providing information used to create and update an occupancy grid, as well as to generate side impact collision warnings. For example, in at least one embodiment, surround camera(s) 1174 (e.g., four surround cameras as illustrated in FIG. 11B) could be positioned on vehicle 1100. In at least one embodiment, surround camera(s) 1174 may include, without limitation, any number and combination of wide-view cameras, fisheye camera(s), 360 degree camera(s), and/or similar cameras. For instance, in at least one embodiment, four fisheye cameras may be positioned on a front, a rear, and sides of vehicle 1100. In at least one embodiment, vehicle 1100 may use three surround camera(s) 1174 (e.g., left, right, and rear), and may leverage one or more other camera(s) (e.g., a forward-facing camera) as a fourth surround-view camera.

In at least one embodiment, cameras with a field of view that include portions of an environment behind vehicle 1100 (e.g., rear-view cameras) may be used for parking assistance, surround view, rear collision warnings, and creating and updating an occupancy grid. In at least one embodiment, a wide variety of cameras may be used including, but not limited to, cameras that are also suitable as a front-facing camera(s) (e.g., long-range cameras 1198 and/or mid-range camera(s) 1176, stereo camera(s) 1168), infrared camera(s) 1172, etc., as described herein.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, inference and/or training logic 815 may be used in system FIG. 11B for inferencing or predicting operations based, at least in part, on weight parameters calculated using neural network training operations, neural network functions and/or architectures, or neural network use cases described herein.

Figure 11C:
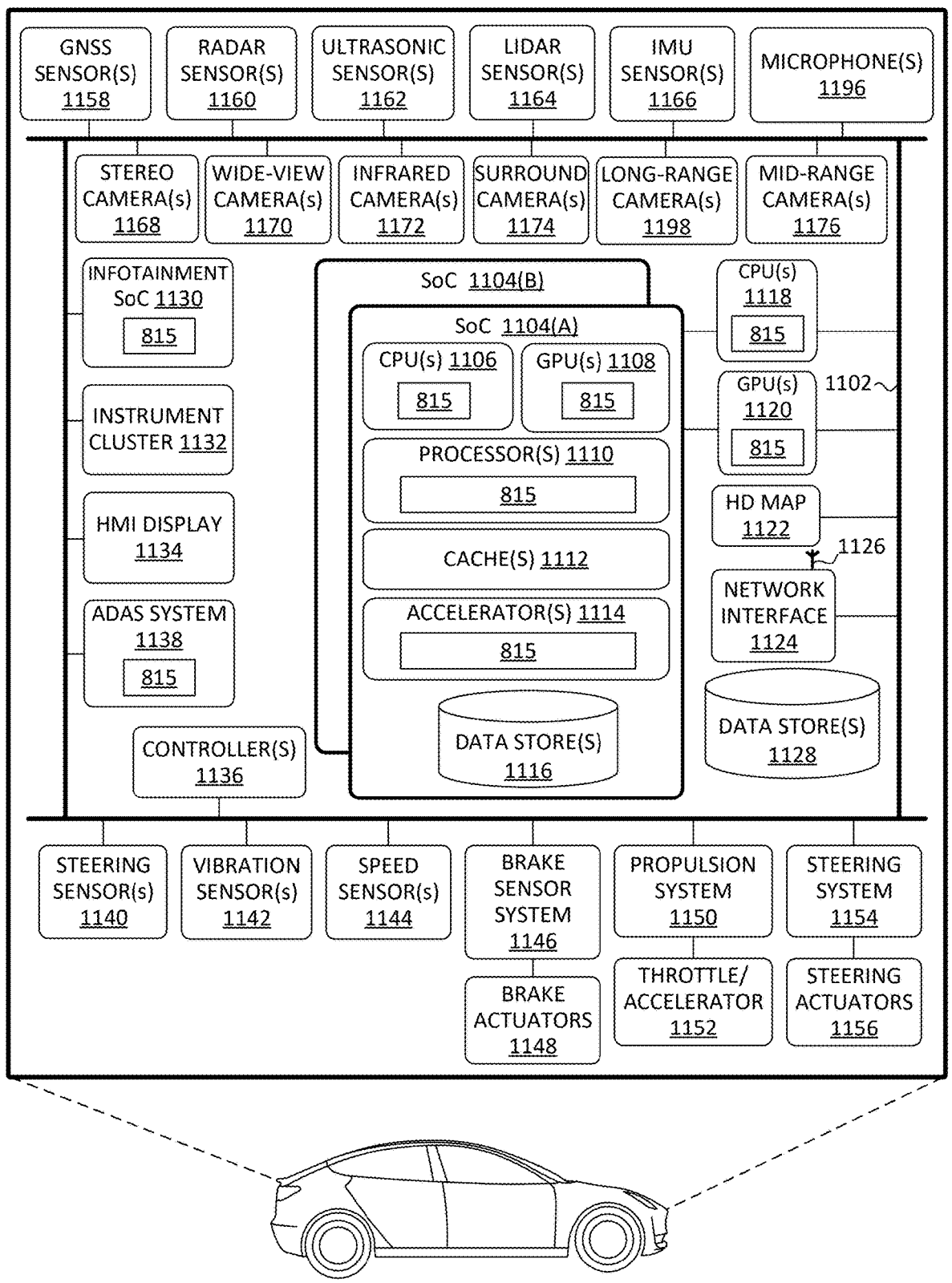
FIG. 11C is a block diagram illustrating an example system architecture for the autonomous vehicle of FIG. 11A, according to at least one embodiment.

FIG. 11C is a block diagram illustrating an example system architecture for autonomous vehicle 1100 of FIG. 11A, according to at least one embodiment. In at least one embodiment, each of components, features, and systems of vehicle 1100 in FIG. 11C is illustrated as being connected via a bus 1102. In at least one embodiment, bus 1102 may include, without limitation, a CAN data interface (alternatively referred to herein as a "CAN bus"). In at least one embodiment, a CAN may be a network inside vehicle 1100 used to aid in control of various features and functionality of vehicle 1100, such as actuation of brakes, acceleration, braking, steering, windshield wipers, etc. In at least one embodiment, bus 1102 may be configured to have dozens or even hundreds of nodes, each with its own unique identifier (e.g., a CAN ID). In at least one embodiment, bus 1102 may be read to find steering wheel angle, ground speed, engine revolutions per minute ("RPMs"), button positions, and/or other vehicle status indicators. In at least one embodiment, bus 1102 may be a CAN bus that is ASIL B compliant.

In at least one embodiment, in addition to, or alternatively from CAN, FlexRay and/or Ethernet protocols may be used. In at least one embodiment, there may be any number of busses forming bus 1102, which may include, without limitation, zero or more CAN busses, zero or more FlexRay busses, zero or more Ethernet busses, and/or zero or more other types of busses using different protocols. In at least one embodiment, two or more busses may be used to perform different functions, and/or may be used for redundancy. For example, a first bus may be used for collision avoidance functionality and a second bus may be used for actuation control. In at least one embodiment, each bus of bus 1102 may communicate with any of components of vehicle 1100, and two or more busses of bus 1102 may communicate with corresponding components. In at least one embodiment, each of any number of system(s) on chip(s) ("SoC(s)") 1104 (such as SoC 1104(A) and SoC 1104(B)), each of controller(s) 1136, and/or each computer within vehicle may have access to same input data (e.g., inputs from sensors of vehicle 1100), and may be connected to a common bus, such CAN bus.

In at least one embodiment, vehicle 1100 may include one or more controller(s) 1136, such as those described herein with respect to FIG. 11A. In at least one embodiment, controller(s) 1136 may be used for a variety of functions. In at least one embodiment, controller(s) 1136 may be coupled to any of various other components and systems of vehicle 1100, and may be used for control of vehicle 1100, artificial intelligence of vehicle 1100, infotainment for vehicle 1100, and/or other functions.

In at least one embodiment, vehicle 1100 may include any number of SoCs 1104. In at least one embodiment, each of SoCs 1104 may include, without limitation, central processing units ("CPU(s)") 1106, graphics processing units ("GPU(s)") 1108, processor(s) 1110, cache(s) 1112, accelerator(s) 1114, data store(s) 1116, and/or other components and features not illustrated. In at least one embodiment, SoC(s) 1104 may be used to control vehicle 1100 in a variety of platforms and systems. For example, in at least one embodiment, SoC(s) 1104 may be combined in a system (e.g., system of vehicle 1100) with a High Definition ("HD") map 1122 which may obtain map refreshes and/or updates via network interface 1124 from one or more servers (not shown in FIG. 11C).

In at least one embodiment, CPU(s) 1106 may include a CPU cluster or CPU complex (alternatively referred to herein as a "CCPLEX"). In at least one embodiment, CPU(s) 1106 may include multiple cores and/or level two ("L2") caches. For instance, in at least one embodiment, CPU(s) 1106 may include eight cores in a coherent multi-processor configuration. In at least one embodiment, CPU(s) 1106 may include four dual-core clusters where each cluster has a dedicated L2 cache (e.g., a 2 megabyte (MB) L2 cache). In at least one embodiment, CPU(s) 1106 (e.g., CCPLEX) may be configured to support simultaneous cluster operations enabling any combination of clusters of CPU(s) 1106 to be active at any given time.

In at least one embodiment, one or more of CPU(s) 1106 may implement power management capabilities that include, without limitation, one or more of following features: individual hardware blocks may be clock-gated automatically when idle to save dynamic power; each core clock may be gated when such core is not actively executing instructions due to execution of Wait for Interrupt ("WFI")/Wait for Event ("WFE") instructions; each core may be independently power-gated; each core cluster may be independently clock-gated when all cores are clock-gated or power-gated; and/or each core cluster may be independently power-gated when all cores are power-gated. In at least one embodiment, CPU(s) 1106 may further implement an enhanced algorithm for managing power states, where allowed power states and expected wakeup times are specified, and hardware/microcode determines which best power state to enter for core, cluster, and CCPLEX. In at least one embodiment, processing cores may support simplified power state entry sequences in software with work offloaded to microcode.

In at least one embodiment, GPU(s) 1108 may include an integrated GPU (alternatively referred to herein as an "iGPU"). In at least one embodiment, GPU(s) 1108 may be programmable and may be efficient for parallel workloads. In at least one embodiment, GPU(s) 1108 may use an enhanced tensor instruction set. In at least one embodiment, GPU(s) 1108 may include one or more streaming microprocessors, where each streaming microprocessor may include a level one ("L1") cache (e.g., an L1 cache with at least 96 KB storage capacity), and two or more streaming microprocessors may share an L2 cache (e.g., an L2 cache with a 512 KB storage capacity). In at least one embodiment, GPU(s) 1108 may include at least eight streaming microprocessors. In at least one embodiment, GPU(s) 1108 may use compute application programming interface(s) (API(s)). In at least one embodiment, GPU(s) 1108 may use one or more parallel computing platforms and/or programming models (e.g., NVIDIA's CUDA model).

In at least one embodiment, one or more of GPU(s) 1108 may be power-optimized for best performance in automotive and embedded use cases. For example, in at least one embodiment, GPU(s) 1108 could be fabricated on Fin field-effect transistor ("FinFET") circuitry. In at least one embodiment, each streaming microprocessor may incorporate a number of mixed-precision processing cores partitioned into multiple blocks. For example, and without limitation, 64 PF32 cores and 32 PF64 cores could be partitioned into four processing blocks. In at least one embodiment, each processing block could be allocated 16 FP32 cores, 8 FP64 cores, 16 INT32 cores, two mixed-precision NVIDIA Tensor cores for deep learning matrix arithmetic, a level zero ("L0") instruction cache, a warp scheduler, a dispatch unit, and/or a 64 KB register file. In at least one embodiment, streaming microprocessors may include independent parallel integer and floating-point data paths to provide for efficient execution of workloads with a mix of computation and addressing calculations. In at least one embodiment, streaming microprocessors may include independent thread scheduling capability to enable finer-grain synchronization and cooperation between parallel threads. In at least one embodiment, streaming microprocessors may include a combined L1 data cache and shared memory unit in order to improve performance while simplifying programming.

In at least one embodiment, one or more of GPU(s) 1108 may include a high bandwidth memory ("HBM") and/or a 16 GB HBM2 memory subsystem to provide, in some examples, about 900 GB/second peak memory bandwidth. In at least one embodiment, in addition to, or alternatively from, HBM memory, a synchronous graphics random-access memory ("SGRAM") may be used, such as a graphics double data rate type five synchronous random-access memory ("GDDR5").

In at least one embodiment, GPU(s) 1108 may include unified memory technology. In at least one embodiment, address translation services ("ATS") support may be used to allow GPU(s) 1108 to access CPU(s) 1106 page tables directly. In at least one embodiment, embodiment, when a GPU of GPU(s) 1108 memory management unit ("MMU") experiences a miss, an address translation request may be transmitted to CPU(s) 1106. In response, 2 CPU of CPU(s) 1106 may look in its page tables for a virtual-to-physical mapping for an address and transmit translation back to GPU(s) 1108, in at least one embodiment. In at least one embodiment, unified memory technology may allow a single unified virtual address space for memory of both CPU(s) 1106 and GPU(s) 1108, thereby simplifying GPU(s) 1108 programming and porting of applications to GPU(s) 1108.

In at least one embodiment, GPU(s) 1108 may include any number of access counters that may keep track of frequency of access of GPU(s) 1108 to memory of other processors. In at least one embodiment, access counter(s) may help ensure that memory pages are moved to physical memory of a processor that is accessing pages most frequently, thereby improving efficiency for memory ranges shared between processors.

In at least one embodiment, one or more of SoC(s) 1104 may include any number of cache(s) 1112, including those described herein. For example, in at least one embodiment, cache(s) 1112 could include a level three ("L3") cache that is available to both CPU(s) 1106 and GPU(s) 1108 (e.g., that is connected to CPU(s) 1106 and GPU(s) 1108). In at least one embodiment, cache(s) 1112 may include a write-back cache that may keep track of states of lines, such as by using a cache coherence protocol (e.g., MEI, MESI, MSI, etc.). In at least one embodiment, a L3 cache may include 4 MB of memory or more, depending on embodiment, although smaller cache sizes may be used.

In at least one embodiment, one or more of SoC(s) 1104 may include one or more accelerator(s) 1114 (e.g., hardware accelerators, software accelerators, or a combination thereof). In at least one embodiment, SoC(s) 1104 may include a hardware acceleration cluster that may include optimized hardware accelerators and/or large on-chip memory. In at least one embodiment, large on-chip memory (e.g., 4 MB of SRAM), may enable a hardware acceleration cluster to accelerate neural networks and other calculations. In at least one embodiment, a hardware acceleration cluster may be used to complement GPU(s) 1108 and to off-load some of tasks of GPU(s) 1108 (e.g., to free up more cycles of GPU(s) 1108 for performing other tasks). In at least one embodiment, accelerator(s) 1114 could be used for targeted workloads (e.g., perception, convolutional neural networks ("CNNs"), recurrent neural networks ("RNNs"), etc.) that are stable enough to be amenable to acceleration. In at least one embodiment, a CNN may include a region-based or regional convolutional neural networks ("RCNNs") and Fast RCNNs (e.g., as used for object detection) or other type of CNN.

In at least one embodiment, accelerator(s) 1114 (e.g., hardware acceleration cluster) may include one or more deep learning accelerator ("DLA"). In at least one embodiment, DLA(s) may include, without limitation, one or more Tensor processing units ("TPUs") that may be configured to provide an additional ten trillion operations per second for deep learning applications and inferencing. In at least one embodiment, TPUs may be accelerators configured to, and optimized for, performing image processing functions (e.g., for CNNs, RCNNs, etc.). In at least one embodiment, DLA(s) may further be optimized for a specific set of neural network types and floating point operations, as well as inferencing. In at least one embodiment, design of DLA(s) may provide more performance per millimeter than a typical general-purpose GPU, and typically vastly exceeds performance of a CPU. In at least one embodiment, TPU(s) may perform several functions, including a single-instance convolution function, supporting, for example, INT8, INT16, and FP16 data types for both features and weights, as well as post-processor functions. In at least one embodiment, DLA(s) may quickly and efficiently execute neural networks, especially CNNs, on processed or unprocessed data for any of a variety of functions, including, for example and without limitation: a CNN for object identification and detection using data from camera sensors; a CNN for distance estimation using data from camera sensors; a CNN for emergency vehicle detection and identification and detection using data from microphones; a CNN for facial recognition and vehicle owner identification using data from camera sensors; and/or a CNN for security and/or safety related events.

In at least one embodiment, DLA(s) may perform any function of GPU(s) 1108, and by using an inference accelerator, for example, a designer may target either DLA(s) or GPU(s) 1108 for any function. For example, in at least one embodiment, a designer may focus processing of CNNs and floating point operations on DLA(s) and leave other functions to GPU(s) 1108 and/or accelerator(s) 1114.

In at least one embodiment, accelerator(s) 1114 may include programmable vision accelerator ("PVA"), which may alternatively be referred to herein as a computer vision accelerator. In at least one embodiment, PVA may be designed and configured to accelerate computer vision algorithms for advanced driver assistance system ("ADAS") 1138, autonomous driving, augmented reality ("AR") applications, and/or virtual reality ("VR") applications. In at least one embodiment, PVA may provide a balance between performance and flexibility. For example, in at least one embodiment, each PVA may include, for example and without limitation, any number of reduced instruction set computer ("RISC") cores, direct memory access ("DMA"), and/or any number of vector processors.

In at least one embodiment, RISC cores may interact with image sensors (e.g., image sensors of any cameras described herein), image signal processor(s), etc. In at least one embodiment, each RISC core may include any amount of memory. In at least one embodiment, RISC cores may use any of a number of protocols, depending on embodiment. In at least one embodiment, RISC cores may execute a real-time operating system ("RTOS"). In at least one embodiment, RISC cores may be implemented using one or more integrated circuit devices, application specific integrated circuits ("ASICs"), and/or memory devices. For example, in at least one embodiment, RISC cores could include an instruction cache and/or a tightly coupled RAM.

In at least one embodiment, DMA may enable components of PVA to access system memory independently of CPU(s) 1106. In at least one embodiment, DMA may support any number of features used to provide optimization to a PVA including, but not limited to, supporting multi-dimensional addressing and/or circular addressing. In at least one embodiment, DMA may support up to six or more dimensions of addressing, which may include, without limitation, block width, block height, block depth, horizontal block stepping, vertical block stepping, and/or depth stepping.

In at least one embodiment, vector processors may be programmable processors that may be designed to efficiently and flexibly execute programming for computer vision algorithms and provide signal processing capabilities. In at least one embodiment, a PVA may include a PVA core and two vector processing subsystem partitions. In at least one embodiment, a PVA core may include a processor subsystem, DMA engine(s) (e.g., two DMA engines), and/or other peripherals. In at least one embodiment, a vector processing subsystem may operate as a primary processing engine of a PVA, and may include a vector processing unit ("VPU"), an instruction cache, and/or vector memory (e.g., "VMEM"). In at least one embodiment, VPU core may include a digital signal processor such as, for example, a single instruction, multiple data ("SIMD"), very long instruction word ("VLIW") digital signal processor. In at least one embodiment, a combination of SIMD and VLIW may enhance throughput and speed.

In at least one embodiment, each of vector processors may include an instruction cache and may be coupled to dedicated memory. As a result, in at least one embodiment, each of vector processors may be configured to execute independently of other vector processors. In at least one embodiment, vector processors that are included in a particular PVA may be configured to employ data parallelism. For instance, in at least one embodiment, plurality of vector processors included in a single PVA may execute a common computer vision algorithm, but on different regions of an image. In at least one embodiment, vector processors included in a particular PVA may simultaneously execute different computer vision algorithms, on one image, or even execute different algorithms on sequential images or portions of an image. In at least one embodiment, among other things, any number of PVAs may be included in hardware acceleration cluster and any number of vector processors may be included in each PVA. In at least one embodiment, PVA may include additional error correcting code ("ECC") memory, to enhance overall system safety.

In at least one embodiment, accelerator(s) 1114 may include a computer vision network on-chip and static random-access memory ("SRAM"), for providing a high-bandwidth, low latency SRAM for accelerator(s) 1114. In at least one embodiment, on-chip memory may include at least 4 MB SRAM, comprising, for example and without limitation, eight field-configurable memory blocks, that may be accessible by both a PVA and a DLA. In at least one embodiment, each pair of memory blocks may include an advanced peripheral bus ("APB") interface, configuration circuitry, a controller, and a multiplexer. In at least one embodiment, any type of memory may be used. In at least one embodiment, a PVA and a DLA may access memory via a backbone that provides a PVA and a DLA with high-speed access to memory. In at least one embodiment, a backbone may include a computer vision network on-chip that interconnects a PVA and a DLA to memory (e.g., using APB).

In at least one embodiment, a computer vision network on-chip may include an interface that determines, before transmission of any control signal/address/data, that both a PVA and a DLA provide ready and valid signals. In at least one embodiment, an interface may provide for separate phases and separate channels for transmitting control signals/addresses/data, as well as burst-type communications for continuous data transfer. In at least one embodiment, an interface may comply with International Organization for Standardization ("ISO") 26262 or International Electrotechnical Commission ("IEC") 61508 standards, although other standards and protocols may be used.

In at least one embodiment, one or more of SoC(s) 1104 may include a real-time ray-tracing hardware accelerator. In at least one embodiment, real-time ray-tracing hardware accelerator may be used to quickly and efficiently determine positions and extents of objects (e.g., within a world model), to generate real-time visualization simulations, for RADAR signal interpretation, for sound propagation synthesis and/or analysis, for simulation of SONAR systems, for general wave propagation simulation, for comparison to LIDAR data for purposes of localization and/or other functions, and/or for other uses.

In at least one embodiment, accelerator(s) 1114 can have a wide array of uses for autonomous driving. In at least one embodiment, a PVA may be used for key processing stages in ADAS and autonomous vehicles. In at least one embodiment, a PVA's capabilities are a good match for algorithmic domains needing predictable processing, at low power and low latency. In other words, a PVA performs well on semi-dense or dense regular computation, even on small data sets, which might require predictable run-times with low latency and low power. In at least one embodiment, such as in vehicle 1100, PVAs might be designed to run classic computer vision algorithms, as they can be efficient at object detection and operating on integer math.

For example, according to at least one embodiment of technology, a PVA is used to perform computer stereo vision. In at least one embodiment, a semi-global matching-based algorithm may be used in some examples, although this is not intended to be limiting. In at least one embodiment, applications for Level 3-5 autonomous driving use motion estimation/stereo matching on-the-fly (e.g., structure from motion, pedestrian recognition, lane detection, etc.). In at least one embodiment, a PVA may perform computer stereo vision functions on inputs from two monocular cameras.

In at least one embodiment, a PVA may be used to perform dense optical flow. For example, in at least one embodiment, a PVA could process raw RADAR data (e.g., using a 4D Fast Fourier Transform) to provide processed RADAR data. In at least one embodiment, a PVA is used for time of flight depth processing, by processing raw time of flight data to provide processed time of flight data, for example.

In at least one embodiment, a DLA may be used to run any type of network to enhance control and driving safety, including for example and without limitation, a neural network that outputs a measure of confidence for each object detection. In at least one embodiment, confidence may be represented or interpreted as a probability, or as providing a relative "weight" of each detection compared to other detections. In at least one embodiment, a confidence measure enables a system to make further decisions regarding which detections should be considered as true positive detections rather than false positive detections. In at least one embodiment, a system may set a threshold value for confidence and consider only detections exceeding threshold value as true positive detections. In an embodiment in which an automatic emergency braking ("AEB") system is used, false positive detections would cause vehicle to automatically perform emergency braking, which is obviously undesirable. In at least one embodiment, highly confident detections may be considered as triggers for AEB. In at least one embodiment, a DLA may run a neural network for regressing confidence value. In at least one embodiment, neural network may take as its input at least some subset of parameters, such as bounding box dimensions, ground plane estimate obtained (e.g., from another subsystem), output from IMU sensor(s) 1166 that correlates with vehicle 1100 orientation, distance, 3D location estimates of object obtained from neural network and/or other sensors (e.g., LIDAR sensor(s) 1164 or RADAR sensor(s) 1160), among others.

In at least one embodiment, one or more of SoC(s) 1104 may include data store(s) 1116 (e.g., memory). In at least one embodiment, data store(s) 1116 may be on-chip memory of SoC(s) 1104, which may store neural networks to be executed on GPU(s) 1108 and/or a DLA. In at least one embodiment, data store(s) 1116 may be large enough in capacity to store multiple instances of neural networks for redundancy and safety. In at least one embodiment, data store(s) 1116 may comprise L2 or L3 cache(s).

In at least one embodiment, one or more of SoC(s) 1104 may include any number of processor(s) 1110 (e.g., embedded processors). In at least one embodiment, processor(s) 1110 may include a boot and power management processor that may be a dedicated processor and subsystem to handle boot power and management functions and related security enforcement. In at least one embodiment, a boot and power management processor may be a part of a boot sequence of SoC(s) 1104 and may provide runtime power management services. In at least one embodiment, a boot power and management processor may provide clock and voltage programming, assistance in system low power state transitions, management of SoC(s) 1104 thermals and temperature sensors, and/or management of SoC(s) 1104 power states. In at least one embodiment, each temperature sensor may be implemented as a ring-oscillator whose output frequency is proportional to temperature, and SoC(s) 1104 may use ring-oscillators to detect temperatures of CPU(s) 1106, GPU(s) 1108, and/or accelerator(s) 1114. In at least one embodiment, if temperatures are determined to exceed a threshold, then a boot and power management processor may enter a temperature fault routine and put SoC(s) 1104 into a lower power state and/or put vehicle 1100 into a chauffeur to safe stop mode (e.g., bring vehicle 1100 to a safe stop).

In at least one embodiment, processor(s) 1110 may further include a set of embedded processors that may serve as an audio processing engine which may be an audio subsystem that enables full hardware support for multi-channel audio over multiple interfaces, and a broad and flexible range of audio I/O interfaces. In at least one embodiment, an audio processing engine is a dedicated processor core with a digital signal processor with dedicated RAM.

In at least one embodiment, processor(s) 1110 may further include an always-on processor engine that may provide necessary hardware features to support low power sensor management and wake use cases. In at least one embodiment, an always-on processor engine may include, without limitation, a processor core, a tightly coupled RAM, supporting peripherals (e.g., timers and interrupt controllers), various I/O controller peripherals, and routing logic.

In at least one embodiment, processor(s) 1110 may further include a safety cluster engine that includes, without limitation, a dedicated processor subsystem to handle safety management for automotive applications. In at least one embodiment, a safety cluster engine may include, without limitation, two or more processor cores, a tightly coupled RAM, support peripherals (e.g., timers, an interrupt controller, etc.), and/or routing logic. In a safety mode, two or more cores may operate, in at least one embodiment, in a lockstep mode and function as a single core with comparison logic to detect any differences between their operations. In at least one embodiment, processor(s) 1110 may further include a real-time camera engine that may include, without limitation, a dedicated processor subsystem for handling real-time camera management. In at least one embodiment, processor(s) 1110 may further include a high-dynamic range signal processor that may include, without limitation, an image signal processor that is a hardware engine that is part of a camera processing pipeline.

In at least one embodiment, processor(s) 1110 may include a video image compositor that may be a processing block (e.g., implemented on a microprocessor) that implements video post-processing functions needed by a video playback application to produce a final image for a player window. In at least one embodiment, a video image compositor may perform lens distortion correction on wide-view camera(s) 1170, surround camera(s) 1174, and/or on in-cabin monitoring camera sensor(s). In at least one embodiment, in-cabin monitoring camera sensor(s) are preferably monitored by a neural network running on another instance of SoC 1104, configured to identify in cabin events and respond accordingly. In at least one embodiment, an in-cabin system may perform, without limitation, lip reading to activate cellular service and place a phone call, dictate emails, change a vehicle's destination, activate or change a vehicle's infotainment system and settings, or provide voice-activated web surfing. In at least one embodiment, certain functions are available to a driver when a vehicle is operating in an autonomous mode and are disabled otherwise.

In at least one embodiment, a video image compositor may include enhanced temporal noise reduction for both spatial and temporal noise reduction. For example, in at least one embodiment, where motion occurs in a video, noise reduction weights spatial information appropriately, decreasing weights of information provided by adjacent frames. In at least one embodiment, where an image or portion of an image does not include motion, temporal noise reduction performed by video image compositor may use information from a previous image to reduce noise in a current image.

In at least one embodiment, a video image compositor may also be configured to perform stereo rectification on input stereo lens frames. In at least one embodiment, a video image compositor may further be used for user interface composition when an operating system desktop is in use, and GPU(s) 1108 are not required to continuously render new surfaces. In at least one embodiment, when GPU(s) 1108 are powered on and active doing 3D rendering, a video image compositor may be used to offload GPU(s) 1108 to improve performance and responsiveness.

In at least one embodiment, one or more SoC of SoC(s) 1104 may further include a mobile industry processor interface ("MIPI") camera serial interface for receiving video and input from cameras, a high-speed interface, and/or a video input block that may be used for a camera and related pixel input functions. In at least one embodiment, one or more of SoC(s) 1104 may further include an input/output controller(s) that may be controlled by software and may be used for receiving I/O signals that are uncommitted to a specific role.

In at least one embodiment, one or more Soc of SoC(s) 1104 may further include a broad range of peripheral interfaces to enable communication with peripherals, audio encoders/decoders ("codecs"), power management, and/or other devices. In at least one embodiment, SoC(s) 1104 may be used to process data from cameras (e.g., connected over Gigabit Multimedia Serial Link and Ethernet channels), sensors (e.g., LIDAR sensor(s) 1164, RADAR sensor(s) 1160, etc. that may be connected over Ethernet channels), data from bus 1102 (e.g., speed of vehicle 1100, steering wheel position, etc.), data from GNSS sensor(s) 1158 (e.g., connected over a Ethernet bus or a CAN bus), etc. In at least one embodiment, one or more SoC of SoC(s) 1104 may further include dedicated high-performance mass storage controllers that may include their own DMA engines, and that may be used to free CPU(s) 1106 from routine data management tasks.

In at least one embodiment, SoC(s) 1104 may be an end-to-end platform with a flexible architecture that spans automation Levels 3-5, thereby providing a comprehensive functional safety architecture that leverages and makes efficient use of computer vision and ADAS techniques for diversity and redundancy, and provides a platform for a flexible, reliable driving software stack, along with deep learning tools. In at least one embodiment, SoC(s) 1104 may be faster, more reliable, and even more energy-efficient and space-efficient than conventional systems. For example, in at least one embodiment, accelerator(s) 1114, when combined with CPU(s) 1106, GPU(s) 1108, and data store(s) 1116, may provide for a fast, efficient platform for Level 3-5 autonomous vehicles.

In at least one embodiment, computer vision algorithms may be executed on CPUs, which may be configured using a high-level programming language, such as C, to execute a wide variety of processing algorithms across a wide variety of visual data. However, in at least one embodiment, CPUs are oftentimes unable to meet performance requirements of many computer vision applications, such as those related to execution time and power consumption, for example. In at least one embodiment, many CPUs are unable to execute complex object detection algorithms in real-time, which is used in in-vehicle ADAS applications and in practical Level 3-5 autonomous vehicles.

Embodiments described herein allow for multiple neural networks to be performed simultaneously and/or sequentially, and for results to be combined together to enable Level 3-5 autonomous driving functionality. For example, in at least one embodiment, a CNN executing on a DLA or a discrete GPU (e.g., GPU(s) 1120) may include text and word recognition, allowing reading and understanding of traffic signs, including signs for which a neural network has not been specifically trained. In at least one embodiment, a DLA may further include a neural network that is able to identify, interpret, and provide semantic understanding of a sign, and to pass that semantic understanding to path planning modules running on a CPU Complex.

In at least one embodiment, multiple neural networks may be run simultaneously, as for Level 3, 4, or 5 driving. For example, in at least one embodiment, a warning sign stating "Caution: flashing lights indicate icy conditions," along with an electric light, may be independently or collectively interpreted by several neural networks. In at least one embodiment, such warning sign itself may be identified as a traffic sign by a first deployed neural network (e.g., a neural network that has been trained), text "flashing lights indicate icy conditions" may be interpreted by a second deployed neural network, which informs a vehicle's path planning software (preferably executing on a CPU Complex) that when flashing lights are detected, icy conditions exist. In at least one embodiment, a flashing light may be identified by operating a third deployed neural network over multiple frames, informing a vehicle's path-planning software of a presence (or an absence) of flashing lights. In at least one embodiment, all three neural networks may run simultaneously, such as within a DLA and/or on GPU(s) 1108.

In at least one embodiment, a CNN for facial recognition and vehicle owner identification may use data from camera sensors to identify presence of an authorized driver and/or owner of vehicle 1100. In at least one embodiment, an always-on sensor processing engine may be used to unlock a vehicle when an owner approaches a driver door and turns on lights, and, in a security mode, to disable such vehicle when an owner leaves such vehicle. In this way, SoC(s) 1104 provide for security against theft and/or carjacking.

In at least one embodiment, a CNN for emergency vehicle detection and identification may use data from microphones 1196 to detect and identify emergency vehicle sirens. In at least one embodiment, SoC(s) 1104 use a CNN for classifying environmental and urban sounds, as well as classifying visual data. In at least one embodiment, a CNN running on a DLA is trained to identify a relative closing speed of an emergency vehicle (e.g., by using a Doppler effect). In at least one embodiment, a CNN may also be trained to identify emergency vehicles specific to a local area in which a vehicle is operating, as identified by GNSS sensor(s) 1158. In at least one embodiment, when operating in Europe, a CNN will seek to detect European sirens, and when in North America, a CNN will seek to identify only North American sirens. In at least one embodiment, once an emergency vehicle is detected, a control program may be used to execute an emergency vehicle safety routine, slowing a vehicle, pulling over to a side of a road, parking a vehicle, and/or idling a vehicle, with assistance of ultrasonic sensor(s) 1162, until emergency vehicles pass.

In at least one embodiment, vehicle 1100 may include CPU(s) 1118 (e.g., discrete CPU(s), or dCPU(s)), that may be coupled to SoC(s) 1104 via a high-speed interconnect (e.g., PCIe). In at least one embodiment, CPU(s) 1118 may include an X86 processor, for example. CPU(s) 1118 may be used to perform any of a variety of functions, including arbitrating potentially inconsistent results between ADAS sensors and SoC(s) 1104, and/or monitoring status and health of controller(s) 1136 and/or an infotainment system on a chip ("infotainment SoC") 1130, for example.

In at least one embodiment, vehicle 1100 may include GPU(s) 1120 (e.g., discrete GPU(s), or dGPU(s)), that may be coupled to SoC(s) 1104 via a high-speed interconnect (e.g., NVIDIA's NVLINK channel). In at least one embodiment, GPU(s) 1120 may provide additional artificial intelligence functionality, such as by executing redundant and/or different neural networks, and may be used to train and/or update neural networks based at least in part on input (e.g., sensor data) from sensors of a vehicle 1100.

In at least one embodiment, vehicle 1100 may further include network interface 1124 which may include, without limitation, wireless antenna(s) 1126 (e.g., one or more wireless antennas for different communication protocols, such as a cellular antenna, a Bluetooth antenna, etc.). In at least one embodiment, network interface 1124 may be used to enable wireless connectivity to Internet cloud services (e.g., with server(s) and/or other network devices), with other vehicles, and/or with computing devices (e.g., client devices of passengers). In at least one embodiment, to communicate with other vehicles, a direct link may be established between vehicle 110 and another vehicle and/or an indirect link may be established (e.g., across networks and over the Internet). In at least one embodiment, direct links may be provided using a vehicle-to-vehicle communication link. In at least one embodiment, a vehicle-to-vehicle communication link may provide vehicle 1100 information about vehicles in proximity to vehicle 1100 (e.g., vehicles in front of, on a side of, and/or behind vehicle 1100). In at least one embodiment, such aforementioned functionality may be part of a cooperative adaptive cruise control functionality of vehicle 1100.

In at least one embodiment, network interface 1124 may include an SoC that provides modulation and demodulation functionality and enables controller(s) 1136 to communicate over wireless networks. In at least one embodiment, network interface 1124 may include a radio frequency front-end for up-conversion from baseband to radio frequency, and down conversion from radio frequency to baseband. In at least one embodiment, frequency conversions may be performed in any technically feasible fashion. For example, frequency conversions could be performed through well-known processes, and/or using super-heterodyne processes. In at least one embodiment, radio frequency front end functionality may be provided by a separate chip. In at least one embodiment, network interfaces may include wireless functionality for communicating over LTE, WCDMA, UMTS, GSM, CDMA2000, Bluetooth, Bluetooth LE, Wi-Fi, Z-Wave, ZigBee, LoRaWAN, and/or other wireless protocols.

In at least one embodiment, vehicle 1100 may further include data store(s) 1128 which may include, without limitation, off-chip (e.g., off SoC(s) 1104) storage. In at least one embodiment, data store(s) 1128 may include, without limitation, one or more storage elements including RAM, SRAM, dynamic random-access memory ("DRAM"), video random-access memory ("VRAM"), flash memory, hard disks, and/or other components and/or devices that may store at least one bit of data.

In at least one embodiment, vehicle 1100 may further include GNSS sensor(s) 1158 (e.g., GPS and/or assisted GPS sensors), to assist in mapping, perception, occupancy grid generation, and/or path planning functions. In at least one embodiment, any number of GNSS sensor(s) 1158 may be used, including, for example and without limitation, a GPS using a USB connector with an Ethernet-to-Serial (e.g., RS-232) bridge.

In at least one embodiment, vehicle 1100 may further include RADAR sensor(s) 1160. In at least one embodiment, RADAR sensor(s) 1160 may be used by vehicle 1100 for long-range vehicle detection, even in darkness and/or severe weather conditions. In at least one embodiment, RADAR functional safety levels may be ASIL B. In at least one embodiment, RADAR sensor(s) 1160 may use a CAN bus and/or bus 1102 (e.g., to transmit data generated by RADAR sensor(s) 1160) for control and to access object tracking data, with access to Ethernet channels to access raw data in some examples. In at least one embodiment, a wide variety of RADAR sensor types may be used. For example, and without limitation, RADAR sensor(s) 1160 may be suitable for front, rear, and side RADAR use. In at least one embodiment, one or more sensor of RADAR sensors(s) 1160 is a Pulse Doppler RADAR sensor.

In at least one embodiment, RADAR sensor(s) 1160 may include different configurations, such as long-range with narrow field of view, short-range with wide field of view, short-range side coverage, etc. In at least one embodiment, long-range RADAR may be used for adaptive cruise control functionality. In at least one embodiment, long-range RADAR systems may provide a broad field of view realized by two or more independent scans, such as within a 250 m (meter) range. In at least one embodiment, RADAR sensor(s) 1160 may help in distinguishing between static and moving objects, and may be used by ADAS system 1138 for emergency brake assist and forward collision warning. In at least one embodiment, sensors 1160(*s*) included in a long-range RADAR system may include, without limitation, monostatic multimodal RADAR with multiple (e.g., six or more) fixed RADAR antennae and a high-speed CAN and FlexRay interface. In at least one embodiment, with six antennae, a central four antennae may create a focused beam pattern, designed to record vehicle's 1100 surroundings at higher speeds with minimal interference from traffic in adjacent lanes. In at least one embodiment, another two antennae may expand field of view, making it possible to quickly detect vehicles entering or leaving a lane of vehicle 1100.

In at least one embodiment, mid-range RADAR systems may include, as an example, a range of up to 160 m (front) or 80 m (rear), and a field of view of up to 42 degrees (front) or 150 degrees (rear). In at least one embodiment, short-range RADAR systems may include, without limitation, any number of RADAR sensor(s) 1160 designed to be installed at both ends of a rear bumper. When installed at both ends of a rear bumper, in at least one embodiment, a RADAR sensor system may create two beams that constantly monitor blind spots in a rear direction and next to a vehicle. In at least one embodiment, short-range RADAR systems may be used in ADAS system 1138 for blind spot detection and/or lane change assist.

In at least one embodiment, vehicle 1100 may further include ultrasonic sensor(s) 1162. In at least one embodiment, ultrasonic sensor(s) 1162, which may be positioned at a front, a back, and/or side location of vehicle 1100, may be used for parking assist and/or to create and update an occupancy grid. In at least one embodiment, a wide variety of ultrasonic sensor(s) 1162 may be used, and different ultrasonic sensor(s) 1162 may be used for different ranges of detection (e.g., 2.5 m, 4 m). In at least one embodiment, ultrasonic sensor(s) 1162 may operate at functional safety levels of ASIL B.

In at least one embodiment, vehicle 1100 may include LIDAR sensor(s) 1164. In at least one embodiment, LIDAR sensor(s) 1164 may be used for object and pedestrian detection, emergency braking, collision avoidance, and/or other functions. In at least one embodiment, LIDAR sensor(s) 1164 may operate at functional safety level ASIL B. In at least one embodiment, vehicle 1100 may include multiple LIDAR sensors 1164 (e.g., two, four, six, etc.) that may use an Ethernet channel (e.g., to provide data to a Gigabit Ethernet switch).

In at least one embodiment, LIDAR sensor(s) 1164 may be capable of providing a list of objects and their distances for a 360-degree field of view. In at least one embodiment, commercially available LIDAR sensor(s) 1164 may have an advertised range of approximately 100 m, with an accuracy of 2 cm to 3 cm, and with support for a 100 Mbps Ethernet connection, for example. In at least one embodiment, one or more non-protruding LIDAR sensors may be used. In such an embodiment, LIDAR sensor(s) 1164 may include a small device that may be embedded into a front, a rear, a side, and/or a corner location of vehicle 1100. In at least one embodiment, LIDAR sensor(s) 1164, in such an embodiment, may provide up to a 120-degree horizontal and 35-degree vertical field-of-view, with a 200 m range even for low-reflectivity objects. In at least one embodiment, front-mounted LIDAR sensor(s) 1164 may be configured for a horizontal field of view between 45 degrees and 135 degrees.

In at least one embodiment, LIDAR technologies, such as 3D flash LIDAR, may also be used. In at least one embodiment, 3D flash LIDAR uses a flash of a laser as a transmission source, to illuminate surroundings of vehicle 1100 up to approximately 200 m. In at least one embodiment, a flash LIDAR unit includes, without limitation, a receptor, which records laser pulse transit time and reflected light on each pixel, which in turn corresponds to a range from vehicle 1100 to objects. In at least one embodiment, flash LIDAR may allow for highly accurate and distortion-free images of surroundings to be generated with every laser flash. In at least one embodiment, four flash LIDAR sensors may be deployed, one at each side of vehicle 1100. In at least one embodiment, 3D flash LIDAR systems include, without limitation, a solid-state 3D staring array LIDAR camera with no moving parts other than a fan (e.g., a non-scanning LIDAR device). In at least one embodiment, flash LIDAR device may use a 5 nanosecond class I (eye-safe) laser pulse per frame and may capture reflected laser light as a 3D range point cloud and co-registered intensity data.

In at least one embodiment, vehicle 1100 may further include IMU sensor(s) 1166. In at least one embodiment, IMU sensor(s) 1166 may be located at a center of a rear axle of vehicle 1100. In at least one embodiment, IMU sensor(s) 1166 may include, for example and without limitation, accelerometer(s), magnetometer(s), gyroscope(s), a magnetic compass, magnetic compasses, and/or other sensor types. In at least one embodiment, such as in six-axis applications, IMU sensor(s) 1166 may include, without limitation, accelerometers and gyroscopes. In at least one embodiment, such as in nine-axis applications, IMU sensor(s) 1166 may include, without limitation, accelerometers, gyroscopes, and magnetometers.

In at least one embodiment, IMU sensor(s) 1166 may be implemented as a miniature, high performance GPS-Aided Inertial Navigation System ("GPS/INS") that combines micro-electro-mechanical systems ("MEMS") inertial sensors, a high-sensitivity GPS receiver, and advanced Kalman filtering algorithms to provide estimates of position, velocity, and attitude. In at least one embodiment, IMU sensor(s) 1166 may enable vehicle 1100 to estimate its heading without requiring input from a magnetic sensor by directly observing and correlating changes in velocity from a GPS to IMU sensor(s) 1166. In at least one embodiment, IMU sensor(s) 1166 and GNSS sensor(s) 1158 may be combined in a single integrated unit.

In at least one embodiment, vehicle 1100 may include microphone(s) 1196 placed in and/or around vehicle 1100. In at least one embodiment, microphone(s) 1196 may be used for emergency vehicle detection and identification, among other things.

In at least one embodiment, vehicle 1100 may further include any number of camera types, including stereo camera(s) 1168, wide-view camera(s) 1170, infrared camera(s) 1172, surround camera(s) 1174, long-range camera(s) 1198, mid-range camera(s) 1176, and/or other camera types. In at least one embodiment, cameras may be used to capture image data around an entire periphery of vehicle 1100. In at least one embodiment, which types of cameras used depends on vehicle 1100. In at least one embodiment, any combination of camera types may be used to provide necessary coverage around vehicle 1100. In at least one embodiment, a number of cameras deployed may differ depending on embodiment. For example, in at least one embodiment, vehicle 1100 could include six cameras, seven cameras, ten cameras, twelve cameras, or another number of cameras. In at least one embodiment, cameras may support, as an example and without limitation, Gigabit Multimedia Serial Link ("GMSL") and/or Gigabit Ethernet communications. In at least one embodiment, each camera might be as described with more detail previously herein with respect to FIG. 11A and FIG. 11B.

In at least one embodiment, vehicle 1100 may further include vibration sensor(s) 1142. In at least one embodiment, vibration sensor(s) 1142 may measure vibrations of components of vehicle 1100, such as axle(s). For example, in at least one embodiment, changes in vibrations may indicate a change in road surfaces. In at least one embodiment, when two or more vibration sensors 1142 are used, differences between vibrations may be used to determine friction or slippage of road surface (e.g., when a difference in vibration is between a power-driven axle and a freely rotating axle).

In at least one embodiment, vehicle 1100 may include ADAS system 1138. In at least one embodiment, ADAS system 1138 may include, without limitation, an SoC, in some examples. In at least one embodiment, ADAS system 1138 may include, without limitation, any number and combination of an autonomous/adaptive/automatic cruise control ("ACC") system, a cooperative adaptive cruise control ("CACC") system, a forward crash warning ("FCW") system, an automatic emergency braking ("AEB") system, a lane departure warning ("LDW")" system, a lane keep assist ("LKA") system, a blind spot warning ("BSW") system, a rear cross-traffic warning ("RCTW") system, a collision warning ("CW") system, a lane centering ("LC") system, and/or other systems, features, and/or functionality.

In at least one embodiment, ACC system may use RADAR sensor(s) 1160, LIDAR sensor(s) 1164, and/or any number of camera(s). In at least one embodiment, ACC system may include a longitudinal ACC system and/or a lateral ACC system. In at least one embodiment, a longitudinal ACC system monitors and controls distance to another vehicle immediately ahead of vehicle 1100 and automatically adjusts speed of vehicle 1100 to maintain a safe distance from vehicles ahead. In at least one embodiment, a lateral ACC system performs distance keeping, and advises vehicle 1100 to change lanes when necessary. In at least one embodiment, a lateral ACC is related to other ADAS applications, such as LC and CW.

In at least one embodiment, a CACC system uses information from other vehicles that may be received via network interface 1124 and/or wireless antenna(s) 1126 from other vehicles via a wireless link, or indirectly, over a network connection (e.g., over the Internet). In at least one embodiment, direct links may be provided by a vehicle-to-vehicle ("V2V") communication link, while indirect links may be provided by an infrastructure-to-vehicle ("I2V") communication link. In general, V2V communication provides information about immediately preceding vehicles (e.g., vehicles immediately ahead of and in same lane as vehicle 1100), while I2V communication provides information about traffic further ahead. In at least one embodiment, a CACC system may include either or both I2V and V2V information sources. In at least one embodiment, given information of vehicles ahead of vehicle 1100, a CACC system may be more reliable and it has potential to improve traffic flow smoothness and reduce congestion on road.

In at least one embodiment, an FCW system is designed to alert a driver to a hazard, so that such driver may take corrective action. In at least one embodiment, an FCW system uses a front-facing camera and/or RADAR sensor(s) 1160, coupled to a dedicated processor, DSP, FPGA, and/or ASIC, that is electrically coupled to provide driver feedback, such as a display, speaker, and/or vibrating component. In at least one embodiment, an FCW system may provide a warning, such as in form of a sound, visual warning, vibration and/or a quick brake pulse.

In at least one embodiment, an AEB system detects an impending forward collision with another vehicle or other object, and may automatically apply brakes if a driver does not take corrective action within a specified time or distance parameter. In at least one embodiment, AEB system may use front-facing camera(s) and/or RADAR sensor(s) 1160, coupled to a dedicated processor, DSP, FPGA, and/or ASIC. In at least one embodiment, when an AEB system detects a hazard, it will typically first alert a driver to take corrective action to avoid collision and, if that driver does not take corrective action, that AEB system may automatically apply brakes in an effort to prevent, or at least mitigate, an impact of a predicted collision. In at least one embodiment, an AEB system may include techniques such as dynamic brake support and/or crash imminent braking.

In at least one embodiment, an LDW system provides visual, audible, and/or tactile warnings, such as steering wheel or seat vibrations, to alert driver when vehicle 1100 crosses lane markings. In at least one embodiment, an LDW system does not activate when a driver indicates an intentional lane departure, such as by activating a turn signal. In at least one embodiment, an LDW system may use front-side facing cameras, coupled to a dedicated processor, DSP, FPGA, and/or ASIC, that is electrically coupled to provide driver feedback, such as a display, speaker, and/or vibrating component. In at least one embodiment, an LKA system is a variation of an LDW system. In at least one embodiment, an LKA system provides steering input or braking to correct vehicle 1100 if vehicle 1100 starts to exit its lane.

In at least one embodiment, a BSW system detects and warns a driver of vehicles in an automobile's blind spot. In at least one embodiment, a BSW system may provide a visual, audible, and/or tactile alert to indicate that merging or changing lanes is unsafe. In at least one embodiment, a BSW system may provide an additional warning when a driver uses a turn signal. In at least one embodiment, a BSW system may use rear-side facing camera(s) and/or RADAR sensor(s) 1160, coupled to a dedicated processor, DSP, FPGA, and/or ASIC, that is electrically coupled to driver feedback, such as a display, speaker, and/or vibrating component.

In at least one embodiment, an RCTW system may provide visual, audible, and/or tactile notification when an object is detected outside a rear-camera range when vehicle 1100 is backing up. In at least one embodiment, an RCTW system includes an AEB system to ensure that vehicle brakes are applied to avoid a crash. In at least one embodiment, an RCTW system may use one or more rear-facing RADAR sensor(s) 1160, coupled to a dedicated processor, DSP, FPGA, and/or ASIC, that is electrically coupled to provide driver feedback, such as a display, speaker, and/or vibrating component.

In at least one embodiment, conventional ADAS systems may be prone to false positive results which may be annoying and distracting to a driver, but typically are not catastrophic, because conventional ADAS systems alert a driver and allow that driver to decide whether a safety condition truly exists and act accordingly. In at least one embodiment, vehicle 1100 itself decides, in case of conflicting results, whether to heed result from a primary computer or a secondary computer (e.g., a first controller or a second controller of controllers 1136). For example, in at least one embodiment, ADAS system 1138 may be a backup and/or secondary computer for providing perception information to a backup computer rationality module. In at least one embodiment, a backup computer rationality monitor may run redundant diverse software on hardware components to detect faults in perception and dynamic driving tasks. In at least one embodiment, outputs from ADAS system 1138 may be provided to a supervisory MCU. In at least one embodiment, if outputs from a primary computer and outputs from a secondary computer conflict, a supervisory MCU determines how to reconcile conflict to ensure safe operation.

In at least one embodiment, a primary computer may be configured to provide a supervisory MCU with a confidence score, indicating that primary computer's confidence in a chosen result. In at least one embodiment, if that confidence score exceeds a threshold, that supervisory MCU may follow that primary computer's direction, regardless of whether that secondary computer provides a conflicting or inconsistent result. In at least one embodiment, where a confidence score does not meet a threshold, and where primary and secondary computers indicate different results (e.g., a conflict), a supervisory MCU may arbitrate between computers to determine an appropriate outcome.

In at least one embodiment, a supervisory MCU may be configured to run a neural network(s) that is trained and configured to determine, based at least in part on outputs from a primary computer and outputs from a secondary computer, conditions under which that secondary computer provides false alarms. In at least one embodiment, neural network(s) in a supervisory MCU may learn when a secondary computer's output may be trusted, and when it cannot. For example, in at least one embodiment, when that secondary computer is a RADAR-based FCW system, a neural network(s) in that supervisory MCU may learn when an FCW system is identifying metallic objects that are not, in fact, hazards, such as a drainage grate or manhole cover that triggers an alarm. In at least one embodiment, when a secondary computer is a camera-based LDW system, a neural network in a supervisory MCU may learn to override LDW when bicyclists or pedestrians are present and a lane departure is, in fact, a safest maneuver. In at least one embodiment, a supervisory MCU may include at least one of a DLA or a GPU suitable for running neural network(s) with associated memory. In at least one embodiment, a supervisory MCU may comprise and/or be included as a component of SoC(s) 1104.

In at least one embodiment, ADAS system 1138 may include a secondary computer that performs ADAS functionality using traditional rules of computer vision. In at least one embodiment, that secondary computer may use classic computer vision rules (if-then), and presence of a neural network(s) in a supervisory MCU may improve reliability, safety and performance. For example, in at least one embodiment, diverse implementation and intentional non-identity makes an overall system more fault-tolerant, especially to faults caused by software (or software-hardware interface) functionality. For example, in at least one embodiment, if there is a software bug or error in software running on a primary computer, and non-identical software code running on a secondary computer provides a consistent overall result, then a supervisory MCU may have greater confidence that an overall result is correct, and a bug in software or hardware on that primary computer is not causing a material error.

In at least one embodiment, an output of ADAS system 1138 may be fed into a primary computer's perception block and/or a primary computer's dynamic driving task block. For example, in at least one embodiment, if ADAS system 1138 indicates a forward crash warning due to an object immediately ahead, a perception block may use this information when identifying objects. In at least one embodiment, a secondary computer may have its own neural network that is trained and thus reduces a risk of false positives, as described herein.

In at least one embodiment, vehicle 1100 may further include infotainment SoC 1130 (e.g., an in-vehicle infotainment system (IVI)). Although illustrated and described as an SoC, infotainment system SoC 1130, in at least one embodiment, may not be an SoC, and may include, without limitation, two or more discrete components. In at least one embodiment, infotainment SoC 1130 may include, without limitation, a combination of hardware and software that may be used to provide audio (e.g., music, a personal digital assistant, navigational instructions, news, radio, etc.), video (e.g., TV, movies, streaming, etc.), phone (e.g., hands-free calling), network connectivity (e.g., LTE, WiFi, etc.), and/or information services (e.g., navigation systems, rear-parking assistance, a radio data system, vehicle related information such as fuel level, total distance covered, brake fuel level, oil level, door open/close, air filter information, etc.) to vehicle 1100. For example, infotainment SoC 1130 could include radios, disk players, navigation systems, video players, USB and Bluetooth connectivity, carputers, in-car entertainment, WiFi, steering wheel audio controls, hands free voice control, a heads-up display ("HUD"), HMI display 1134, a telematics device, a control panel (e.g., for controlling and/or interacting with various components, features, and/or systems), and/or other components. In at least one embodiment, infotainment SoC 1130 may further be used to provide information (e.g., visual and/or audible) to user(s) of vehicle 1100, such as information from ADAS system 1138, autonomous driving information such as planned vehicle maneuvers, trajectories, surrounding environment information (e.g., intersection information, vehicle information, road information, etc.), and/or other information.

In at least one embodiment, infotainment SoC 1130 may include any amount and type of GPU functionality. In at least one embodiment, infotainment SoC 1130 may communicate over bus 1102 with other devices, systems, and/or components of vehicle 1100. In at least one embodiment, infotainment SoC 1130 may be coupled to a supervisory MCU such that a GPU of an infotainment system may perform some self-driving functions in event that primary controller(s) 1136 (e.g., primary and/or backup computers of vehicle 1100) fail. In at least one embodiment, infotainment SoC 1130 may put vehicle 1100 into a chauffeur to safe stop mode, as described herein.

In at least one embodiment, vehicle 1100 may further include instrument cluster 1132 (e.g., a digital dash, an electronic instrument cluster, a digital instrument panel, etc.). In at least one embodiment, instrument cluster 1132 may include, without limitation, a controller and/or supercomputer (e.g., a discrete controller or supercomputer). In at least one embodiment, instrument cluster 1132 may include, without limitation, any number and combination of a set of instrumentation such as a speedometer, fuel level, oil pressure, tachometer, odometer, turn indicators, gearshift position indicator, seat belt warning light(s), parking-brake warning light(s), engine-malfunction light(s), supplemental restraint system (e.g., airbag) information, lighting controls, safety system controls, navigation information, etc. In some examples, information may be displayed and/or shared among infotainment SoC 1130 and instrument cluster 1132. In at least one embodiment, instrument cluster 1132 may be included as part of infotainment SoC 1130, or vice versa.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, inference and/or training logic 815 may be used in system FIG. 11C for inferencing or predicting operations based, at least in part, on weight parameters calculated using neural network training operations, neural network functions and/or architectures, or neural network use cases described herein.

Figure 11D:
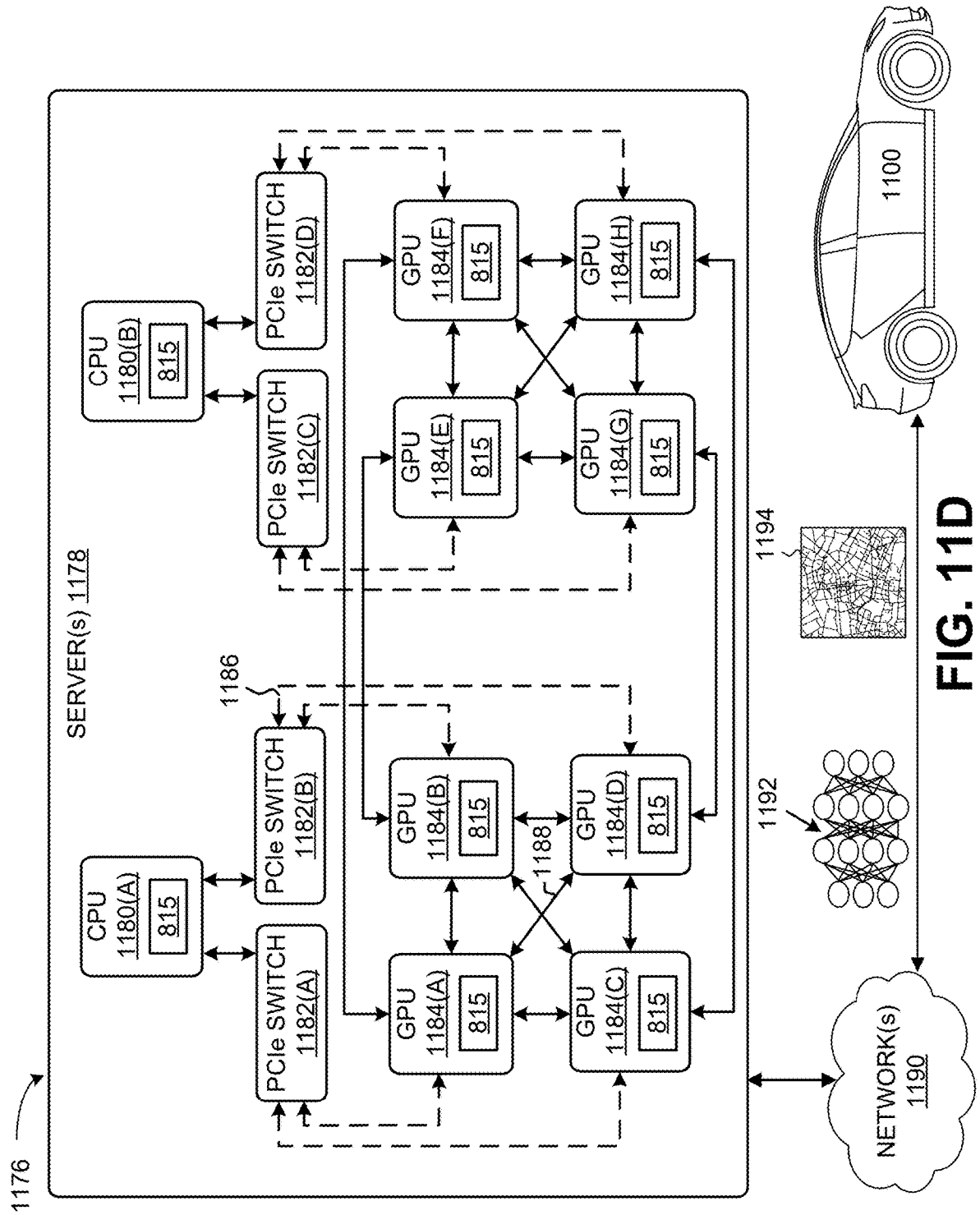
FIG. 11D is a diagram illustrating a system for communication between cloud-based server(s) and the autonomous vehicle of FIG. 11A, according to at least one embodiment.

FIG. 11D is a diagram of a system 1176 for communication between cloud-based server(s) and autonomous vehicle 1100 of FIG. 11A, according to at least one embodiment. In at least one embodiment, system 1176 may include, without limitation, server(s) 1178, network(s) 1190, and any number and type of vehicles, including vehicle 1100. In at least one embodiment, server(s) 1178 may include, without limitation, a plurality of GPUs 1184(A)-1184(H) (collectively referred to herein as GPUs 1184), PCIe switches 1182(A)-1182(D) (collectively referred to herein as PCIe switches 1182), and/or CPUs 1180(A)-1180(B) (collectively referred to herein as CPUs 1180). In at least one embodiment, GPUs 1184, CPUs 1180, and PCIe switches 1182 may be interconnected with high-speed interconnects such as, for example and without limitation, NVLink interfaces 1188 developed by NVIDIA and/or PCIe connections 1186. In at least one embodiment, GPUs 1184 are connected via an NVLink and/or NVSwitch SoC and GPUs 1184 and PCIe switches 1182 are connected via PCIe interconnects. Although eight GPUs 1184, two CPUs 1180, and four PCIe switches 1182 are illustrated, this is not intended to be limiting. In at least one embodiment, each of server(s) 1178 may include, without limitation, any number of GPUs 1184, CPUs 1180, and/or PCIe switches 1182, in any combination. For example, in at least one embodiment, server(s) 1178 could each include eight, sixteen, thirty-two, and/or more GPUs 1184.

In at least one embodiment, server(s) 1178 may receive, over network(s) 1190 and from vehicles, image data representative of images showing unexpected or changed road conditions, such as recently commenced road-work. In at least one embodiment, server(s) 1178 may transmit, over network(s) 1190 and to vehicles, neural networks 1192, updated or otherwise, and/or map information 1194, including, without limitation, information regarding traffic and road conditions. In at least one embodiment, updates to map information 1194 may include, without limitation, updates for HD map 1122, such as information regarding construction sites, potholes, detours, flooding, and/or other obstructions. In at least one embodiment, neural networks 1192, and/or map information 1194 may have resulted from new training and/or experiences represented in data received from any number of vehicles in an environment, and/or based at least in part on training performed at a data center (e.g., using server(s) 1178 and/or other servers).

In at least one embodiment, server(s) 1178 may be used to train machine learning models (e.g., neural networks) based at least in part on training data. In at least one embodiment, training data may be generated by vehicles, and/or may be generated in a simulation (e.g., using a game engine). In at least one embodiment, any amount of training data is tagged (e.g., where associated neural network benefits from supervised learning) and/or undergoes other preprocessing. In at least one embodiment, any amount of training data is not tagged and/or pre-processed (e.g., where associated neural network does not require supervised learning). In at least one embodiment, once machine learning models are trained, machine learning models may be used by vehicles (e.g., transmitted to vehicles over network(s) 1190), and/or machine learning models may be used by server(s) 1178 to remotely monitor vehicles.

In at least one embodiment, server(s) 1178 may receive data from vehicles and apply data to up-to-date real-time neural networks for real-time intelligent inferencing. In at least one embodiment, server(s) 1178 may include deep-learning supercomputers and/or dedicated AI computers powered by GPU(s) 1184, such as a DGX and DGX Station machines developed by NVIDIA. However, in at least one embodiment, server(s) 1178 may include deep learning infrastructure that uses CPU-powered data centers.

In at least one embodiment, deep-learning infrastructure of server(s) 1178 may be capable of fast, real-time inferencing, and may use that capability to evaluate and verify health of processors, software, and/or associated hardware in vehicle 1100. For example, in at least one embodiment, deep-learning infrastructure may receive periodic updates from vehicle 1100, such as a sequence of images and/or objects that vehicle 1100 has located in that sequence of images (e.g., via computer vision and/or other machine learning object classification techniques). In at least one embodiment, deep-learning infrastructure may run its own neural network to identify objects and compare them with objects identified by vehicle 1100 and, if results do not match and deep-learning infrastructure concludes that AI in vehicle 1100 is malfunctioning, then server(s) 1178 may transmit a signal to vehicle 1100 instructing a fail-safe computer of vehicle 1100 to assume control, notify passengers, and complete a safe parking maneuver.

In at least one embodiment, server(s) 1178 may include GPU(s) 1184 and one or more programmable inference accelerators (e.g., NVIDIA's TensorRT 3 devices). In at least one embodiment, a combination of GPU-powered servers and inference acceleration may make real-time responsiveness possible. In at least one embodiment, such as where performance is less critical, servers powered by CPUs, FPGAs, and other processors may be used for inferencing. In at least one embodiment, hardware structure(s) 815 are used to perform one or more embodiments. Details regarding hardware structure(x) 815 are provided herein in conjunction with FIGS. 8A and/or 8B.

In at least one embodiment, one or more systems depicted in FIGS. 11A-11D are utilized to generate segmentation and confidence values for pixels of an image. In at least one embodiment, one or more systems depicted in FIGS. 11A-11D are utilized to implement one or more networks and processes such as those described in connection with FIGS. 1-7. In at least one embodiment, one or more systems depicted in FIGS. 11A-11D are utilized to implement a system for segmentation and confidence value determination.

Computer Systems

Figure 12:
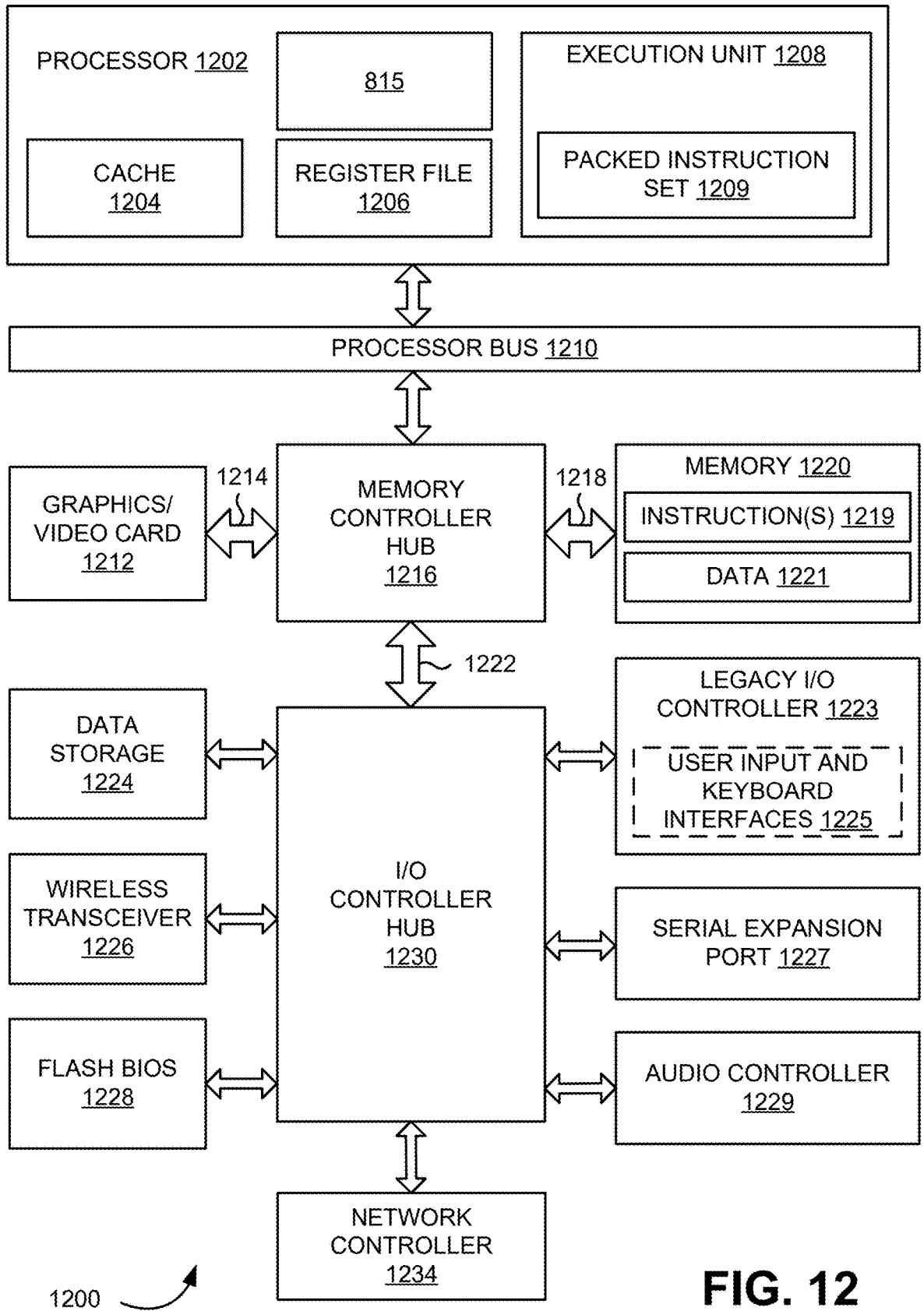
FIG. 12 is a block diagram illustrating a computer system, according to at least one embodiment.

FIG. 12 is a block diagram illustrating an exemplary computer system, which may be a system with interconnected devices and components, a system-on-a-chip (SOC) or some combination thereof formed with a processor that may include execution units to execute an instruction, according to at least one embodiment. In at least one embodiment, a computer system 1200 may include, without limitation, a component, such as a processor 1202 to employ execution units including logic to perform algorithms for process data, in accordance with present disclosure, such as in embodiment described herein. In at least one embodiment, computer system 1200 may include processors, such as PENTIUM® Processor family, Xeon™ Itanium®, XScale™ and/or StrongARM™, Intel® Core™, or Intel® Nervana™ microprocessors available from Intel Corporation of Santa Clara, California, although other systems (including PCs having other microprocessors, engineering workstations, set-top boxes and like) may also be used. In at least one embodiment, computer system 1200 may execute a version of WINDOWS operating system available from Microsoft Corporation of Redmond, Wash., although other operating systems (UNIX and Linux, for example), embedded software, and/or graphical user interfaces, may also be used.

Embodiments may be used in other devices such as handheld devices and embedded applications. Some examples of handheld devices include cellular phones, Internet Protocol devices, digital cameras, personal digital assistants ("PDAs"), and handheld PCs. In at least one embodiment, embedded applications may include a microcontroller, a digital signal processor ("DSP"), system on a chip, network computers ("NetPCs"), set-top boxes, network hubs, wide area network ("WAN") switches, or any other system that may perform one or more instructions in accordance with at least one embodiment.

In at least one embodiment, computer system 1200 may include, without limitation, processor 1202 that may include, without limitation, one or more execution units 1208 to perform machine learning model training and/or inferencing according to techniques described herein. In at least one embodiment, computer system 1200 is a single processor desktop or server system, but in another embodiment, computer system 1200 may be a multiprocessor system. In at least one embodiment, processor 1202 may include, without limitation, a complex instruction set computer ("CISC") microprocessor, a reduced instruction set computing ("RISC") microprocessor, a very long instruction word ("VLIW") microprocessor, a processor implementing a combination of instruction sets, or any other processor device, such as a digital signal processor, for example. In at least one embodiment, processor 1202 may be coupled to a processor bus 1210 that may transmit data signals between processor 1202 and other components in computer system 1200.

In at least one embodiment, processor 1202 may include, without limitation, a Level 1 ("L1") internal cache memory ("cache") 1204. In at least one embodiment, processor 1202 may have a single internal cache or multiple levels of internal cache. In at least one embodiment, cache memory may reside external to processor 1202. Other embodiments may also include a combination of both internal and external caches depending on particular implementation and needs. In at least one embodiment, a register file 1206 may store different types of data in various registers including, without limitation, integer registers, floating point registers, status registers, and an instruction pointer register.

In at least one embodiment, execution unit 1208, including, without limitation, logic to perform integer and floating point operations, also resides in processor 1202. In at least one embodiment, processor 1202 may also include a microcode ("ucode") read only memory ("ROM") that stores microcode for certain macro instructions. In at least one embodiment, execution unit 1208 may include logic to handle a packed instruction set 1209. In at least one embodiment, by including packed instruction set 1209 in an instruction set of a general-purpose processor, along with associated circuitry to execute instructions, operations used by many multimedia applications may be performed using packed data in processor 1202. In at least one embodiment, many multimedia applications may be accelerated and executed more efficiently by using a full width of a processor's data bus for performing operations on packed data, which may eliminate a need to transfer smaller units of data across that processor's data bus to perform one or more operations one data element at a time.

In at least one embodiment, execution unit 1208 may also be used in microcontrollers, embedded processors, graphics devices, DSPs, and other types of logic circuits. In at least one embodiment, computer system 1200 may include, without limitation, a memory 1220. In at least one embodiment, memory 1220 may be a Dynamic Random Access Memory ("DRAM") device, a Static Random Access Memory ("SRAM") device, a flash memory device, or another memory device. In at least one embodiment, memory 1220 may store instruction(s) 1219 and/or data 1221 represented by data signals that may be executed by processor 1202.

In at least one embodiment, a system logic chip may be coupled to processor bus 1210 and memory 1220. In at least one embodiment, a system logic chip may include, without limitation, a memory controller hub ("MCH") 1216, and processor 1202 may communicate with MCH 1216 via processor bus 1210. In at least one embodiment, MCH 1216 may provide a high bandwidth memory path 1218 to memory 1220 for instruction and data storage and for storage of graphics commands, data and textures. In at least one embodiment, MCH 1216 may direct data signals between processor 1202, memory 1220, and other components in computer system 1200 and to bridge data signals between processor bus 1210, memory 1220, and a system I/O interface 1222. In at least one embodiment, a system logic chip may provide a graphics port for coupling to a graphics controller. In at least one embodiment, MCH 1216 may be coupled to memory 1220 through high bandwidth memory path 1218 and a graphics/video card 1212 may be coupled to MCH 1216 through an Accelerated Graphics Port ("AGP") interconnect 1214.

In at least one embodiment, computer system 1200 may use system I/O interface 1222 as a proprietary hub interface bus to couple MCH 1216 to an I/O controller hub ("ICH") 1230. In at least one embodiment, ICH 1230 may provide direct connections to some I/O devices via a local I/O bus. In at least one embodiment, a local I/O bus may include, without limitation, a high-speed I/O bus for connecting peripherals to memory 1220, a chipset, and processor 1202. Examples may include, without limitation, an audio controller 1229, a firmware hub ("flash BIOS") 1228, a wireless transceiver 1226, a data storage 1224, a legacy I/O controller 1223 containing user input and keyboard interfaces 1225, a serial expansion port 1227, such as a Universal Serial Bus ("USB") port, and a network controller 1234. In at least one embodiment, data storage 1224 may comprise a hard disk drive, a floppy disk drive, a CD-ROM device, a flash memory device, or other mass storage device.

In at least one embodiment, FIG. 12 illustrates a system, which includes interconnected hardware devices or "chips", whereas in other embodiments, FIG. 12 may illustrate an exemplary SoC. In at least one embodiment, devices illustrated in FIG. 12 may be interconnected with proprietary interconnects, standardized interconnects (e.g., PCIe) or some combination thereof. In at least one embodiment, one or more components of computer system 1200 are interconnected using compute express link (CXL) interconnects.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, inference and/or training logic 815 may be used in system FIG. 12 for inferencing or predicting operations based, at least in part, on weight parameters calculated using neural network training operations, neural network functions and/or architectures, or neural network use cases described herein.

In at least one embodiment, one or more systems depicted in FIG. 12 are utilized to generate segmentation and confidence values for pixels of an image. In at least one embodiment, one or more systems depicted in FIG. 12 are utilized to implement one or more networks and processes such as those described in connection with FIGS. 1-7. In at least one embodiment, one or more systems depicted in FIG. 12 are utilized to implement a system for segmentation and confidence value determination.

Figure 13:
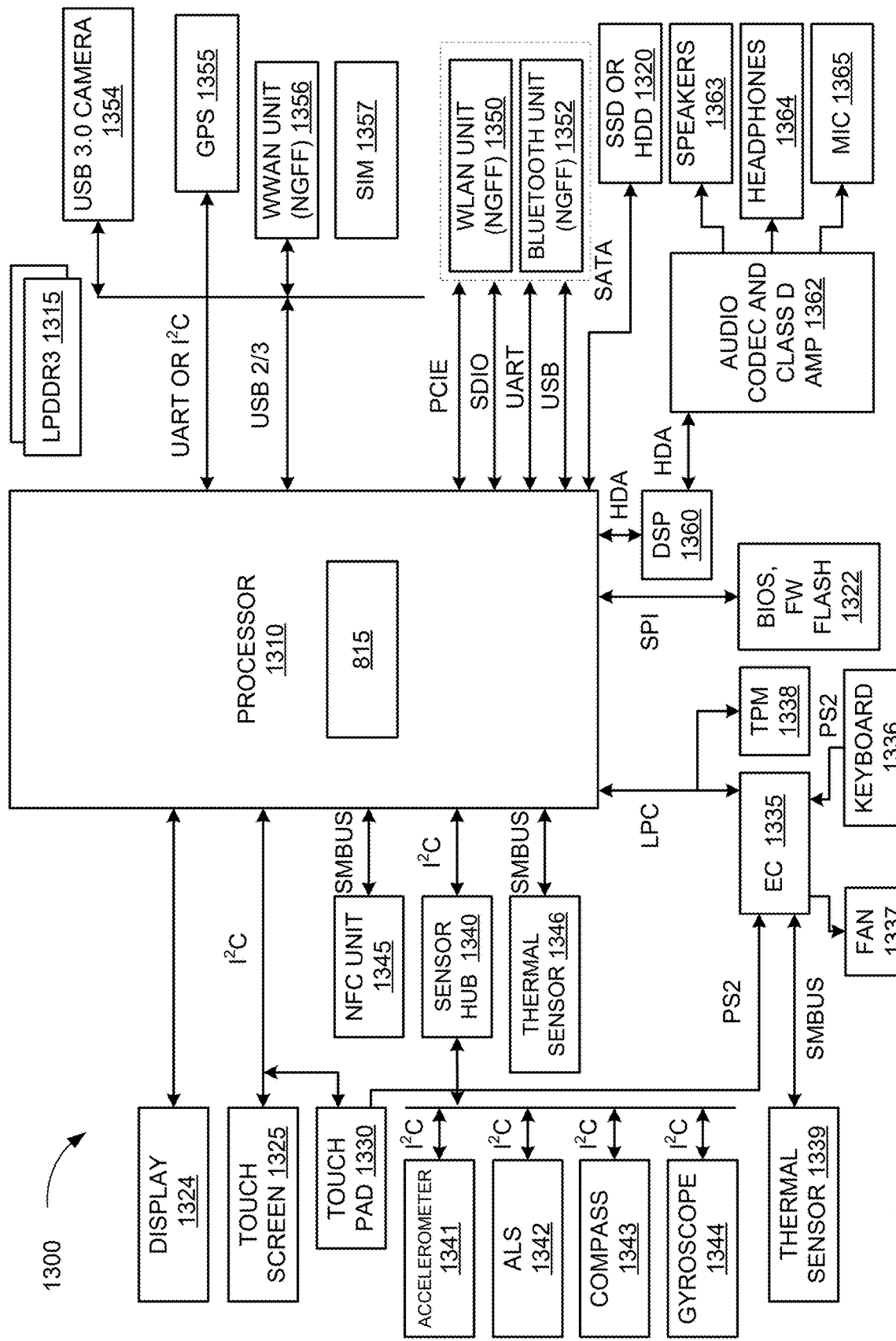
FIG. 13 is a block diagram illustrating a computer system, according to at least one embodiment.

FIG. 13 is a block diagram illustrating an electronic device 1300 for utilizing a processor 1310, according to at least one embodiment. In at least one embodiment, electronic device 1300 may be, for example and without limitation, a notebook, a tower server, a rack server, a blade server, a laptop, a desktop, a tablet, a mobile device, a phone, an embedded computer, or any other suitable electronic device.

In at least one embodiment, electronic device 1300 may include, without limitation, processor 1310 communicatively coupled to any suitable number or kind of components, peripherals, modules, or devices. In at least one embodiment, processor 1310 is coupled using a bus or interface, such as a PC bus, a System Management Bus ("SMBus"), a Low Pin Count (LPC) bus, a Serial Peripheral Interface ("SPI"), a High Definition Audio ("HDA") bus, a Serial Advance Technology Attachment ("SATA") bus, a Universal Serial Bus ("USB") (versions 1, 2, 3, etc.), or a Universal Asynchronous Receiver/Transmitter ("UART") bus. In at least one embodiment, FIG. 13 illustrates a system, which includes interconnected hardware devices or "chips", whereas in other embodiments, FIG. 13 may illustrate an exemplary SoC. In at least one embodiment, devices illustrated in FIG. 13 may be interconnected with proprietary interconnects, standardized interconnects (e.g., PCIe) or some combination thereof. In at least one embodiment, one or more components of FIG. 13 are interconnected using compute express link (CXL) interconnects.

In at least one embodiment, FIG. 13 may include a display 1324, a touch screen 1325, a touch pad 1330, a Near Field Communications unit ("NFC") 1345, a sensor hub 1340, a thermal sensor 1346, an Express Chipset ("EC") 1335, a Trusted Platform Module ("TPM") 1338, BIOS/firmware/flash memory ("BIOS, FW Flash") 1322, a DSP 1360, a drive 1320 such as a Solid State Disk ("SSD") or a Hard Disk Drive ("HDD"), a wireless local area network unit ("WLAN") 1350, a Bluetooth unit 1352, a Wireless Wide Area Network unit ("WWAN") 1356, a Global Positioning System (GPS) unit 1355, a camera ("USB 3.0 camera") 1354 such as a USB 3.0 camera, and/or a Low Power Double Data Rate ("LPDDR") memory unit ("LPDDR3") 1315 implemented in, for example, an LPDDR3 standard. These components may each be implemented in any suitable manner.

In at least one embodiment, other components may be communicatively coupled to processor 1310 through components described herein. In at least one embodiment, an accelerometer 1341, an ambient light sensor ("ALS") 1342, a compass 1343, and a gyroscope 1344 may be communicatively coupled to sensor hub 1340. In at least one embodiment, a thermal sensor 1339, a fan 1337, a keyboard 1336, and touch pad 1330 may be communicatively coupled to EC 1335. In at least one embodiment, speakers 1363, headphones 1364, and a microphone ("mic") 1365 may be communicatively coupled to an audio unit ("audio codec and class D amp") 1362, which may in turn be communicatively coupled to DSP 1360. In at least one embodiment, audio unit 1362 may include, for example and without limitation, an audio coder/decoder ("codec") and a class D amplifier. In at least one embodiment, a SIM card ("SIM") 1357 may be communicatively coupled to WWAN unit 1356. In at least one embodiment, components such as WLAN unit 1350 and Bluetooth unit 1352, as well as WWAN unit 1356 may be implemented in a Next Generation Form Factor ("NGFF").

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, inference and/or training logic 815 may be used in system FIG. 13 for inferencing or predicting operations based, at least in part, on weight parameters calculated using neural network training operations, neural network functions and/or architectures, or neural network use cases described herein.

In at least one embodiment, one or more systems depicted in FIG. 13 are utilized to generate segmentation and confidence values for pixels of an image. In at least one embodiment, one or more systems depicted in FIG. 13 are utilized to implement one or more networks and processes such as those described in connection with FIGS. 1-7. In at least one embodiment, one or more systems depicted in FIG. 13 are utilized to implement a system for segmentation and confidence value determination.

Figure 14:
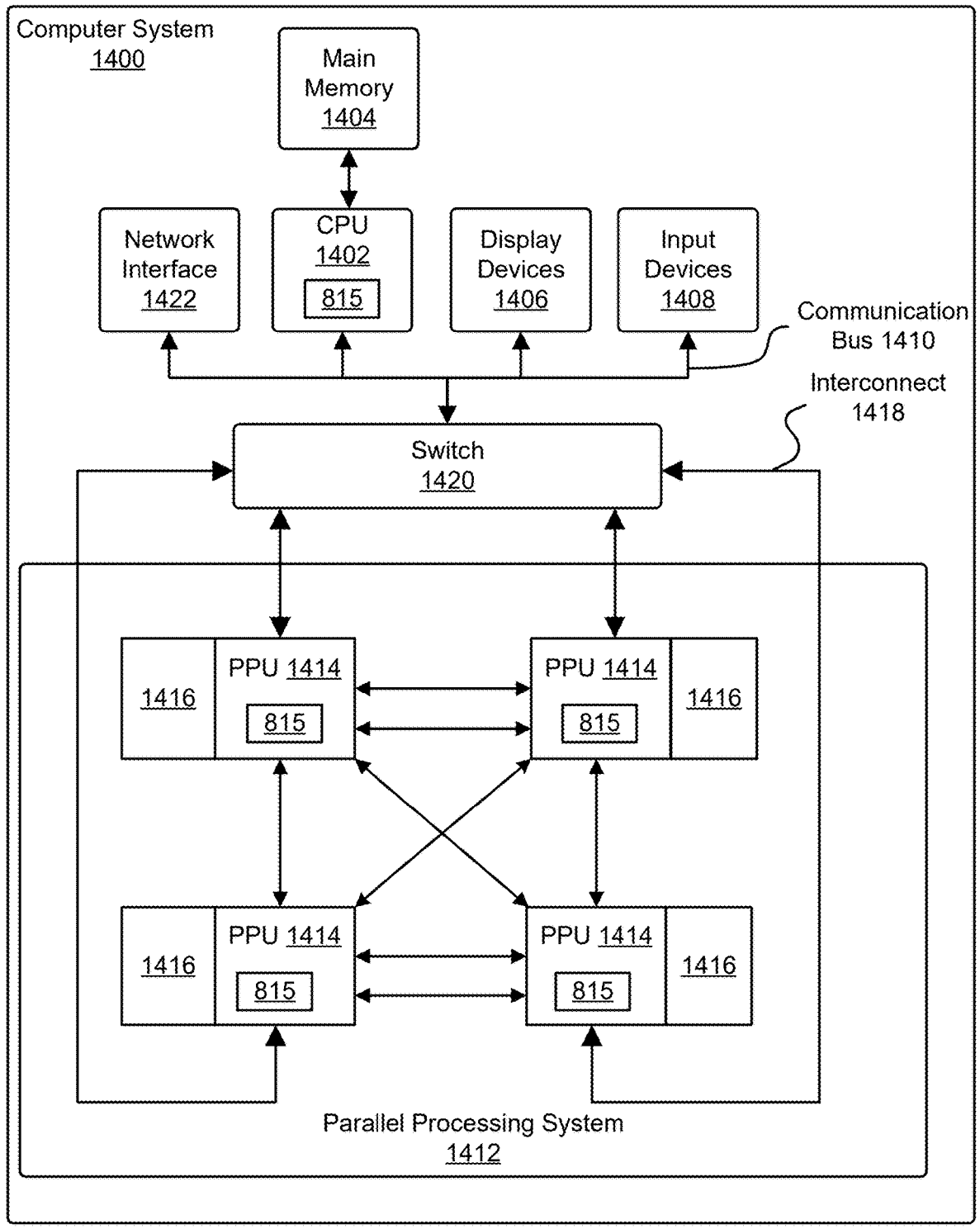
FIG. 14 illustrates a computer system, according to at least one embodiment.

FIG. 14 illustrates a computer system 1400, according to at least one embodiment. In at least one embodiment, computer system 1400 is configured to implement various processes and methods described throughout this disclosure.

In at least one embodiment, computer system 1400 comprises, without limitation, at least one central processing unit ("CPU") 1402 that is connected to a communication bus 1410 implemented using any suitable protocol, such as PCI ("Peripheral Component Interconnect"), peripheral component interconnect express ("PCI-Express"), AGP ("Accelerated Graphics Port"), HyperTransport, or any other bus or point-to-point communication protocol(s). In at least one embodiment, computer system 1400 includes, without limitation, a main memory 1404 and control logic (e.g., implemented as hardware, software, or a combination thereof) and data are stored in main memory 1404, which may take form of random access memory ("RAM"). In at least one embodiment, a network interface subsystem ("network interface") 1422 provides an interface to other computing devices and networks for receiving data from and transmitting data to other systems with computer system 1400.

In at least one embodiment, computer system 1400, in at least one embodiment, includes, without limitation, input devices 1408, a parallel processing system 1412, and display devices 1406 that can be implemented using a conventional cathode ray tube ("CRT"), a liquid crystal display ("LCD"), a light emitting diode ("LED") display, a plasma display, or other suitable display technologies. In at least one embodiment, user input is received from input devices 1408 such as keyboard, mouse, touchpad, microphone, etc. In at least one embodiment, each module described herein can be situated on a single semiconductor platform to form a processing system.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, inference and/or training logic 815 may be used in system FIG. 14 for inferencing or predicting operations based, at least in part, on weight parameters calculated using neural network training operations, neural network functions and/or architectures, or neural network use cases described herein.

In at least one embodiment, one or more systems depicted in FIG. 14 are utilized to generate segmentation and confidence values for pixels of an image. In at least one embodiment, one or more systems depicted in FIG. 14 are utilized to implement one or more networks and processes such as those described in connection with FIGS. 1-7. In at least one embodiment, one or more systems depicted in FIG. 14 are utilized to implement a system for segmentation and confidence value determination.

Figure 15:
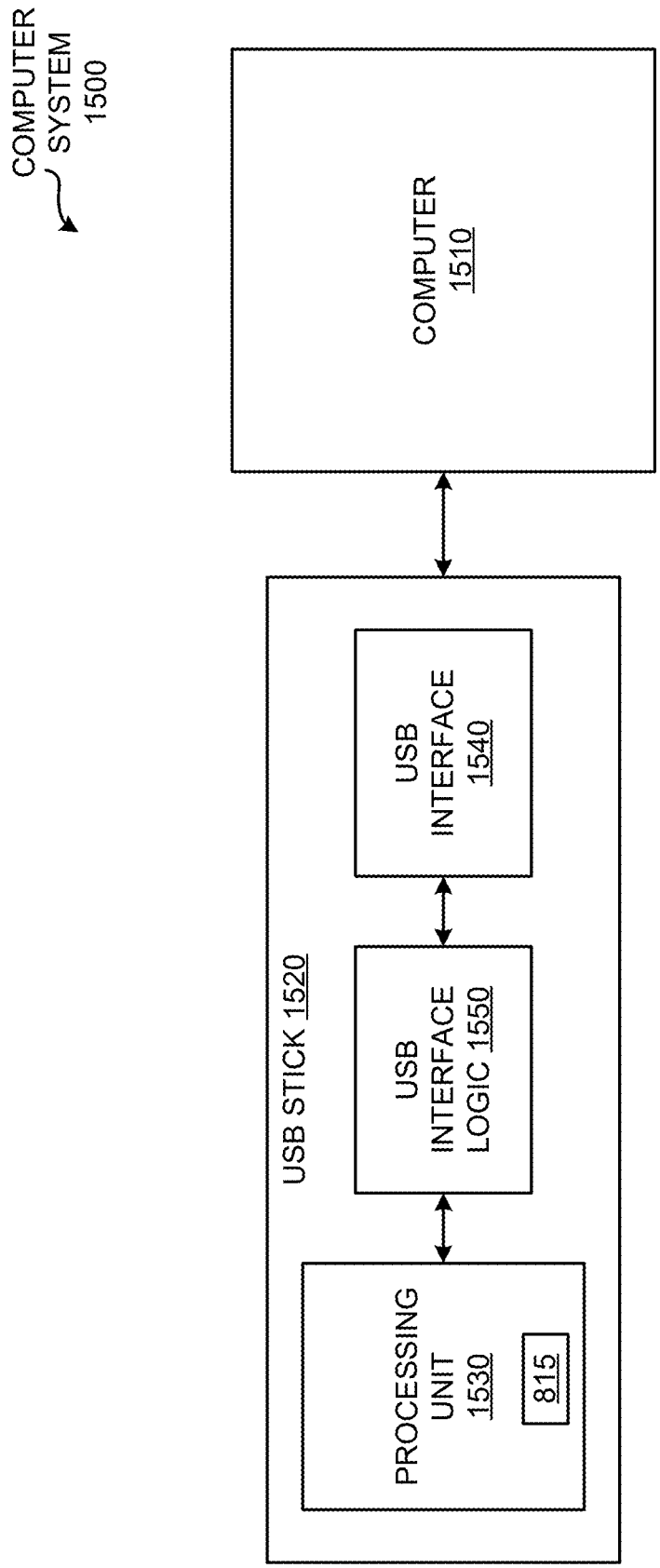
FIG. 15 illustrates a computer system, according to at least one embodiment.

FIG. 15 illustrates a computer system 1500, according to at least one embodiment. In at least one embodiment, computer system 1500 includes, without limitation, a computer 1510 and a USB stick 1520. In at least one embodiment, computer 1510 may include, without limitation, any number and type of processor(s) (not shown) and a memory (not shown). In at least one embodiment, computer 1510 includes, without limitation, a server, a cloud instance, a laptop, and a desktop computer.

In at least one embodiment, USB stick 1520 includes, without limitation, a processing unit 1530, a USB interface 1540, and USB interface logic 1550. In at least one embodiment, processing unit 1530 may be any instruction execution system, apparatus, or device capable of executing instructions. In at least one embodiment, processing unit 1530 may include, without limitation, any number and type of processing cores (not shown). In at least one embodiment, processing unit 1530 comprises an application specific integrated circuit ("ASIC") that is optimized to perform any amount and type of operations associated with machine learning. For instance, in at least one embodiment, processing unit 1530 is a tensor processing unit ("TPC") that is optimized to perform machine learning inference operations. In at least one embodiment, processing unit 1530 is a vision processing unit ("VPU") that is optimized to perform machine vision and machine learning inference operations.

In at least one embodiment, USB interface 1540 may be any type of USB connector or USB socket. For instance, in at least one embodiment, USB interface 1540 is a USB 3.0 Type-C socket for data and power. In at least one embodiment, USB interface 1540 is a USB 3.0 Type-A connector. In at least one embodiment, USB interface logic 1550 may include any amount and type of logic that enables processing unit 1530 to interface with devices (e.g., computer 1510) via USB connector 1540.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, inference and/or training logic 815 may be used in system FIG. 15 for inferencing or predicting operations based, at least in part, on weight parameters calculated using neural network training operations, neural network functions and/or architectures, or neural network use cases described herein.

In at least one embodiment, one or more systems depicted in FIG. 15 are utilized to generate segmentation and confidence values for pixels of an image. In at least one embodiment, one or more systems depicted in FIG. 15 are utilized to implement one or more networks and processes such as those described in connection with FIGS. 1-7. In at least one embodiment, one or more systems depicted in FIG. 15 are utilized to implement a system for segmentation and confidence value determination.

Figure 16A:
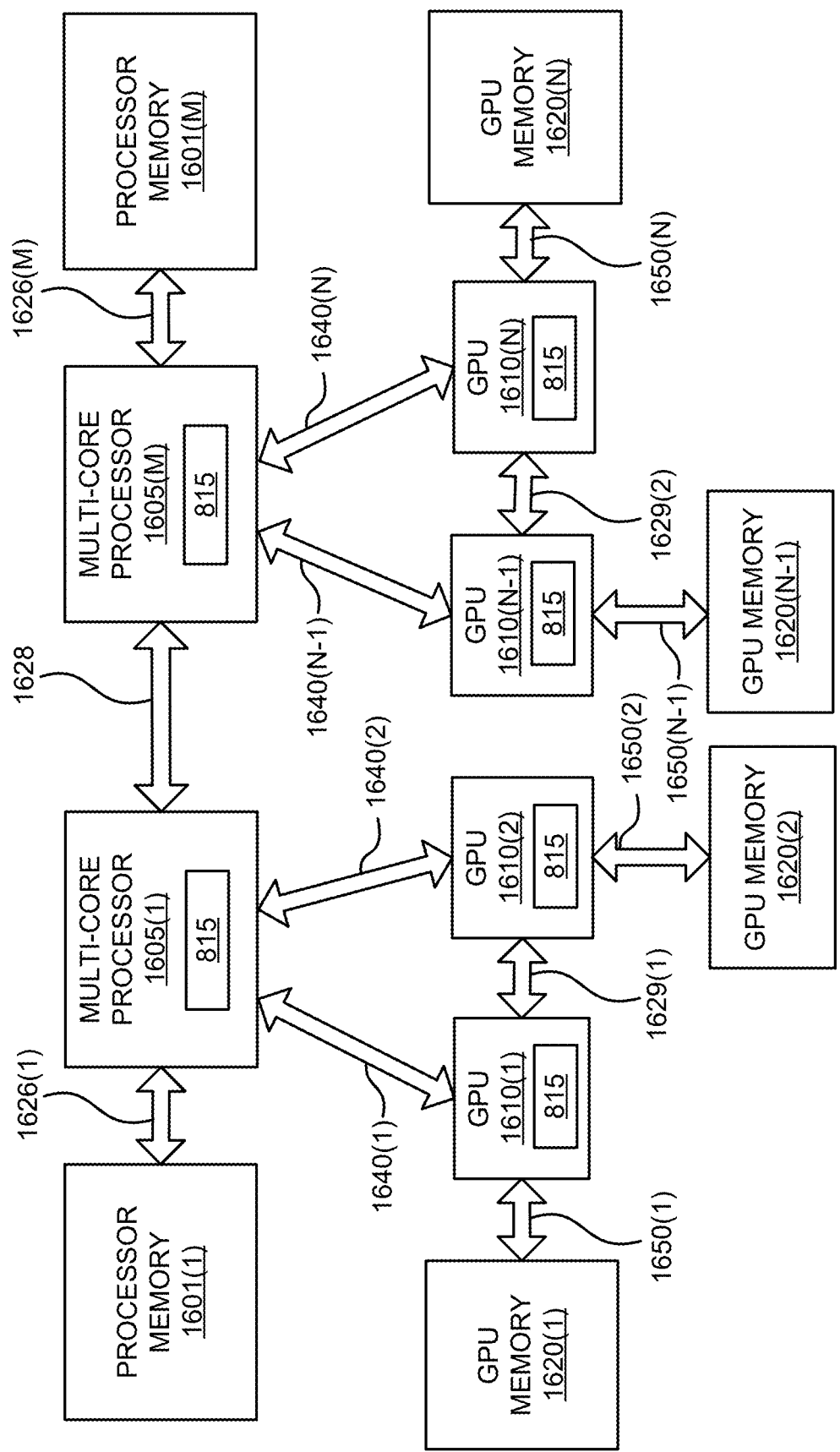
FIG. 16A illustrates a computer system, according to at least one embodiment.

FIG. 16A illustrates an exemplary architecture in which a plurality of GPUs 1610(1)-1610(N) is communicatively coupled to a plurality of multi-core processors 1605(1)-1605(M) over high-speed links 1640(1)-1640(N) (e.g., buses, point-to-point interconnects, etc.). In at least one embodiment, high-speed links 1640(1)-1640(N) support a communication throughput of 4 GB/s, 30 GB/s, 80 GB/s or higher. In at least one embodiment, various interconnect protocols may be used including, but not limited to, PCIe 4.0 or 5.0 and NVLink 2.0. In various figures, "N" and "M" represent positive integers, values of which may be different from figure to figure.

In addition, and in at least one embodiment, two or more of GPUs 1610 are interconnected over high-speed links 1629(1)-1629(2), which may be implemented using similar or different protocols/links than those used for high-speed links 1640(1)-1640(N). Similarly, two or more of multi-core processors 1605 may be connected over a high-speed link 1628 which may be symmetric multi-processor (SMP) buses operating at 20 GB/s, 30 GB/s, 120 GB/s or higher. Alternatively, all communication between various system components shown in FIG. 16A may be accomplished using similar protocols/links (e.g., over a common interconnection fabric).

In at least one embodiment, each multi-core processor 1605 is communicatively coupled to a processor memory 1601(1)-1601(M), via memory interconnects 1626(1)-1626(M), respectively, and each GPU 1610(1)-1610(N) is communicatively coupled to GPU memory 1620(1)-1620(N) over GPU memory interconnects 1650(1)-1650(N), respectively. In at least one embodiment, memory interconnects 1626 and 1650 may utilize similar or different memory access technologies. By way of example, and not limitation, processor memories 1601(1)-1601(M) and GPU memories 1620 may be volatile memories such as dynamic random access memories (DRAMs) (including stacked DRAMs), Graphics DDR SDRAM (GDDR) (e.g., GDDR5, GDDR6), or High Bandwidth Memory (HBM) and/or may be non-volatile memories such as 3D XPoint or Nano-Ram. In at least one embodiment, some portion of processor memories 1601 may be volatile memory and another portion may be non-volatile memory (e.g., using a two-level memory (2LM) hierarchy).

As described herein, although various multi-core processors 1605 and GPUs 1610 may be physically coupled to a particular memory 1601, 1620, respectively, and/or a unified memory architecture may be implemented in which a virtual system address space (also referred to as "effective address" space) is distributed among various physical memories. For example, processor memories 1601(1)-1601(M) may each comprise 64 GB of system memory address space and GPU memories 1620(1)-1620(N) may each comprise 32 GB of system memory address space resulting in a total of 256 GB addressable memory when M=2 and N=4. Other values for N and M are possible.

Figure 16B:
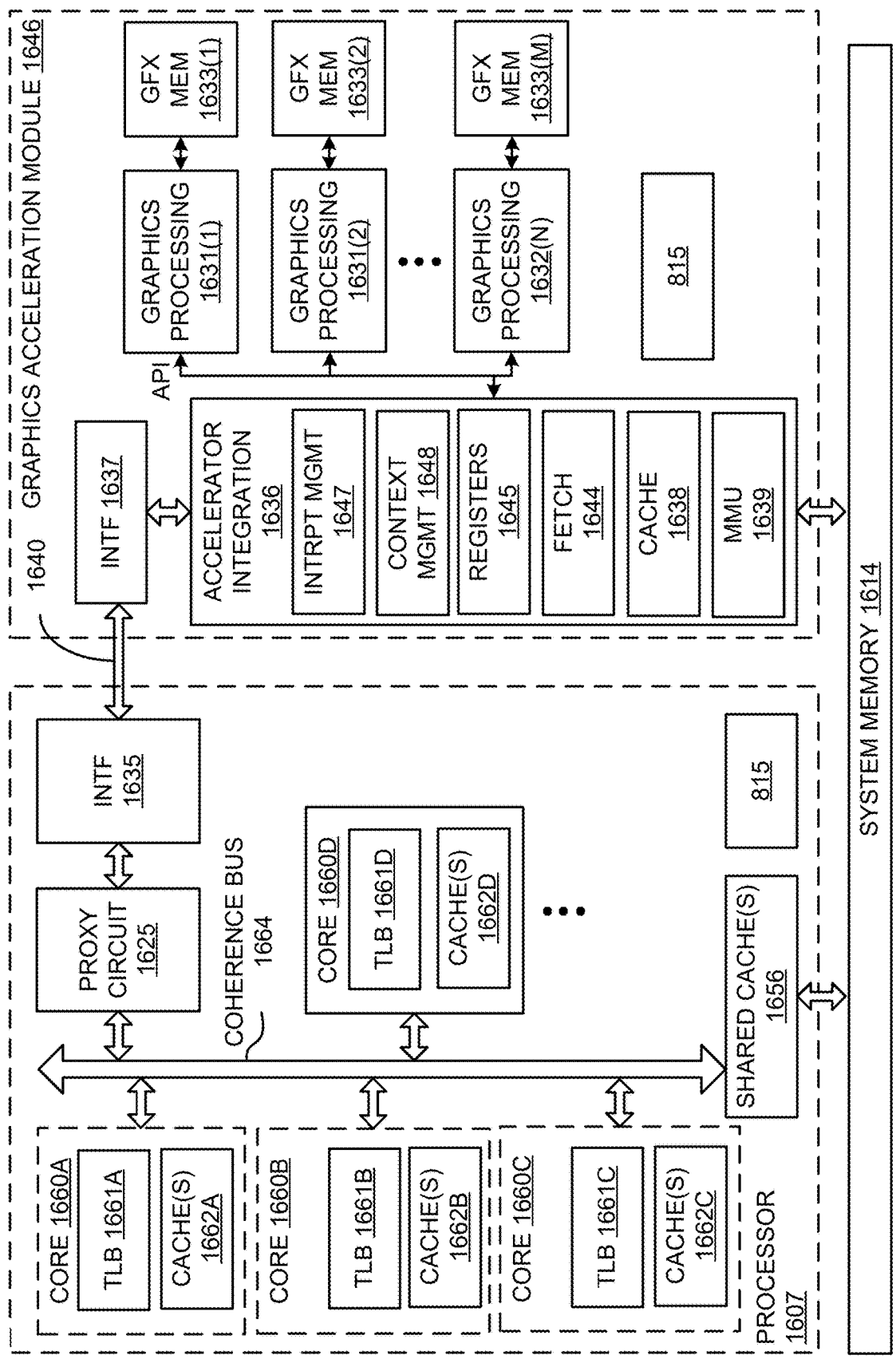
FIG. 16B illustrates a computer system, according to at least one embodiment.

FIG. 16B illustrates additional details for an interconnection between a multi-core processor 1607 and a graphics acceleration module 1646 in accordance with one exemplary embodiment. In at least one embodiment, graphics acceleration module 1646 may include one or more GPU chips integrated on a line card which is coupled to processor 1607 via high-speed link 1640 (e.g., a PCIe bus, NVLink, etc.). In at least one embodiment, graphics acceleration module 1646 may alternatively be integrated on a package or chip with processor 1607.

In at least one embodiment, processor 1607 includes a plurality of cores 1660A-1660D, each with a translation lookaside buffer ("TLB") 1661A-1661D and one or more caches 1662A-1662D. In at least one embodiment, cores 1660A-1660D may include various other components for executing instructions and processing data that are not illustrated. In at least one embodiment, caches 1662A-1662D may comprise Level 1 (L1) and Level 2 (L2) caches. In addition, one or more shared caches 1656 may be included in caches 1662A-1662D and shared by sets of cores 1660A-1660D. For example, one embodiment of processor 1607 includes 24 cores, each with its own L1 cache, twelve shared L2 caches, and twelve shared L3 caches. In this embodiment, one or more L2 and L3 caches are shared by two adjacent cores. In at least one embodiment, processor 1607 and graphics acceleration module 1646 connect with system memory 1614, which may include processor memories 1601(1)-1601(M) of FIG. 16A.

In at least one embodiment, coherency is maintained for data and instructions stored in various caches 1662A-1662D, 1656 and system memory 1614 via inter-core communication over a coherence bus 1664. In at least one embodiment, for example, each cache may have cache coherency logic/circuitry associated therewith to communicate to over coherence bus 1664 in response to detected reads or writes to particular cache lines. In at least one embodiment, a cache snooping protocol is implemented over coherence bus 1664 to snoop cache accesses.

In at least one embodiment, a proxy circuit 1625 communicatively couples graphics acceleration module 1646 to coherence bus 1664, allowing graphics acceleration module 1646 to participate in a cache coherence protocol as a peer of cores 1660A-1660D. In particular, in at least one embodiment, an interface 1635 provides connectivity to proxy circuit 1625 over high-speed link 1640 and an interface 1637 connects graphics acceleration module 1646 to high-speed link 1640.

In at least one embodiment, an accelerator integration circuit 1636 provides cache management, memory access, context management, and interrupt management services on behalf of a plurality of graphics processing engines 1631(1)-1631(N) of graphics acceleration module 1646. In at least one embodiment, graphics processing engines 1631(1)-1631(N) may each comprise a separate graphics processing unit (GPU). In at least one embodiment, graphics processing engines 1631(1)-1631(N) alternatively may comprise different types of graphics processing engines within a GPU, such as graphics execution units, media processing engines (e.g., video encoders/decoders), samplers, and blit engines. In at least one embodiment, graphics acceleration module 1646 may be a GPU with a plurality of graphics processing engines 1631(1)-1631(N) or graphics processing engines 1631(1)-1631(N) may be individual GPUs integrated on a common package, line card, or chip.

In at least one embodiment, accelerator integration circuit 1636 includes a memory management unit (MMU) 1639 for performing various memory management functions such as virtual-to-physical memory translations (also referred to as effective-to-real memory translations) and memory access protocols for accessing system memory 1614. In at least one embodiment, MMU 1639 may also include a translation lookaside buffer (TLB) (not shown) for caching virtual/effective to physical/real address translations. In at least one embodiment, a cache 1638 can store commands and data for efficient access by graphics processing engines 1631(1)-1631(N). In at least one embodiment, data stored in cache 1638 and graphics memories 1633(1)-1633(M) is kept coherent with core caches 1662A-1662D, 1656 and system memory 1614, possibly using a fetch unit 1644. As mentioned, this may be accomplished via proxy circuit 1625 on behalf of cache 1638 and memories 1633(1)-1633(M) (e.g., sending updates to cache 1638 related to modifications/accesses of cache lines on processor caches 1662A-1662D, 1656 and receiving updates from cache 1638).

In at least one embodiment, a set of registers 1645 store context data for threads executed by graphics processing engines 1631(1)-1631(N) and a context management circuit 1648 manages thread contexts. For example, context management circuit 1648 may perform save and restore operations to save and restore contexts of various threads during contexts switches (e.g., where a first thread is saved and a second thread is stored so that a second thread can be execute by a graphics processing engine). For example, on a context switch, context management circuit 1648 may store current register values to a designated region in memory (e.g., identified by a context pointer). It may then restore register values when returning to a context. In at least one embodiment, an interrupt management circuit 1647 receives and processes interrupts received from system devices.

In at least one embodiment, virtual/effective addresses from a graphics processing engine 1631 are translated to real/physical addresses in system memory 1614 by MMU 1639. In at least one embodiment, accelerator integration circuit 1636 supports multiple (e.g., 4, 8, 16) graphics accelerator modules 1646 and/or other accelerator devices. In at least one embodiment, graphics accelerator module 1646 may be dedicated to a single application executed on processor 1607 or may be shared between multiple applications. In at least one embodiment, a virtualized graphics execution environment is presented in which resources of graphics processing engines 1631(1)-1631(N) are shared with multiple applications or virtual machines (VMs). In at least one embodiment, resources may be subdivided into "slices" which are allocated to different VMs and/or applications based on processing requirements and priorities associated with VMs and/or applications.

In at least one embodiment, accelerator integration circuit 1636 performs as a bridge to a system for graphics acceleration module 1646 and provides address translation and system memory cache services. In addition, in at least one embodiment, accelerator integration circuit 1636 may provide virtualization facilities for a host processor to manage virtualization of graphics processing engines 1631(1)-1631(N), interrupts, and memory management.

In at least one embodiment, because hardware resources of graphics processing engines 1631(1)-1631(N) are mapped explicitly to a real address space seen by host processor 1607, any host processor can address these resources directly using an effective address value. In at least one embodiment, one function of accelerator integration circuit 1636 is physical separation of graphics processing engines 1631(1)-1631(N) so that they appear to a system as independent units.

In at least one embodiment, one or more graphics memories 1633(1)-1633(M) are coupled to each of graphics processing engines 1631(1)-1631(N), respectively and N=M. In at least one embodiment, graphics memories 1633(1)-1633(M) store instructions and data being processed by each of graphics processing engines 1631(1)-1631(N). In at least one embodiment, graphics memories 1633(1)-1633(M) may be volatile memories such as DRAMs (including stacked DRAMs), GDDR memory (e.g., GDDR5, GDDR6), or HBM, and/or may be non-volatile memories such as 3D XPoint or Nano-Ram.

In at least one embodiment, to reduce data traffic over high-speed link 1640, biasing techniques can be used to ensure that data stored in graphics memories 1633(1)-1633(M) is data that will be used most frequently by graphics processing engines 1631(1)-1631(N) and preferably not used by cores 1660A-1660D (at least not frequently). Similarly, in at least one embodiment, a biasing mechanism attempts to keep data needed by cores (and preferably not graphics processing engines 1631(1)-1631(N)) within caches 1662A-1662D, 1656 and system memory 1614.

Figure 16C:
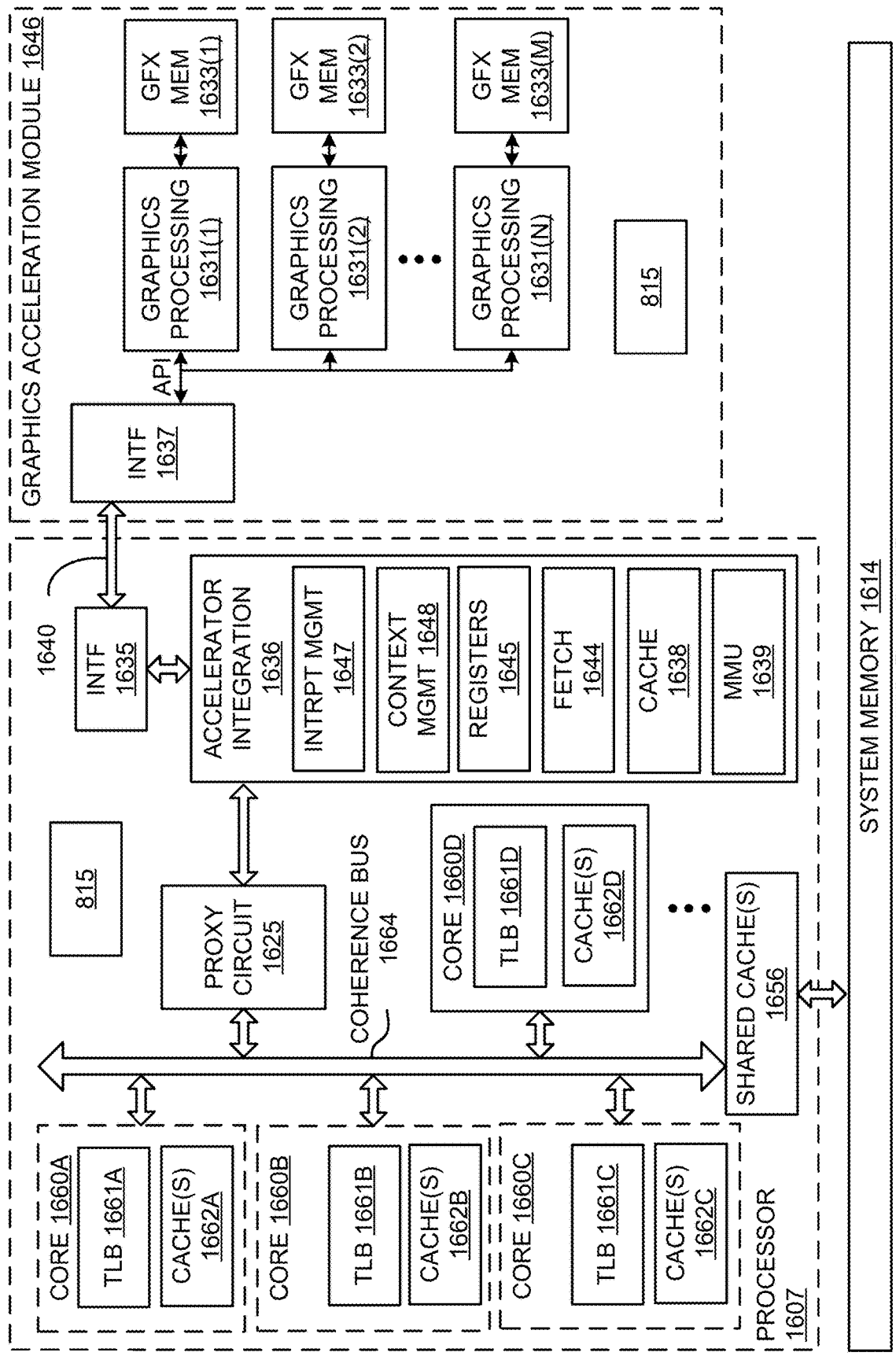
FIG. 16C illustrates a computer system, according to at least one embodiment.

FIG. 16C illustrates another exemplary embodiment in which accelerator integration circuit 1636 is integrated within processor 1607. In this embodiment, graphics processing engines 1631(1)-1631(N) communicate directly over high-speed link 1640 to accelerator integration circuit 1636 via interface 1637 and interface 1635 (which, again, may be any form of bus or interface protocol). In at least one embodiment, accelerator integration circuit 1636 may perform similar operations as those described with respect to FIG. 16B, but potentially at a higher throughput given its close proximity to coherence bus 1664 and caches 1662A-1662D, 1656. In at least one embodiment, an accelerator integration circuit supports different programming models including a dedicated-process programming model (no graphics acceleration module virtualization) and shared programming models (with virtualization), which may include programming models which are controlled by accelerator integration circuit 1636 and programming models which are controlled by graphics acceleration module 1646.

In at least one embodiment, graphics processing engines 1631(1)-1631(N) are dedicated to a single application or process under a single operating system. In at least one embodiment, a single application can funnel other application requests to graphics processing engines 1631(1)-1631(N), providing virtualization within a VM/partition.

In at least one embodiment, graphics processing engines 1631(1)-1631(N), may be shared by multiple VM/application partitions. In at least one embodiment, shared models may use a system hypervisor to virtualize graphics processing engines 1631(1)-1631(N) to allow access by each operating system. In at least one embodiment, for single-partition systems without a hypervisor, graphics processing engines 1631(1)-1631(N) are owned by an operating system. In at least one embodiment, an operating system can virtualize graphics processing engines 1631(1)-1631(N) to provide access to each process or application.

In at least one embodiment, graphics acceleration module 1646 or an individual graphics processing engine 1631(1)-1631(N) selects a process element using a process handle. In at least one embodiment, process elements are stored in system memory 1614 and are addressable using an effective address to real address translation technique described herein. In at least one embodiment, a process handle may be an implementation-specific value provided to a host process when registering its context with graphics processing engine 1631(1)-1631(N) (that is, calling system software to add a process element to a process element linked list). In at least one embodiment, a lower 16-bits of a process handle may be an offset of a process element within a process element linked list.

Figure 16D:
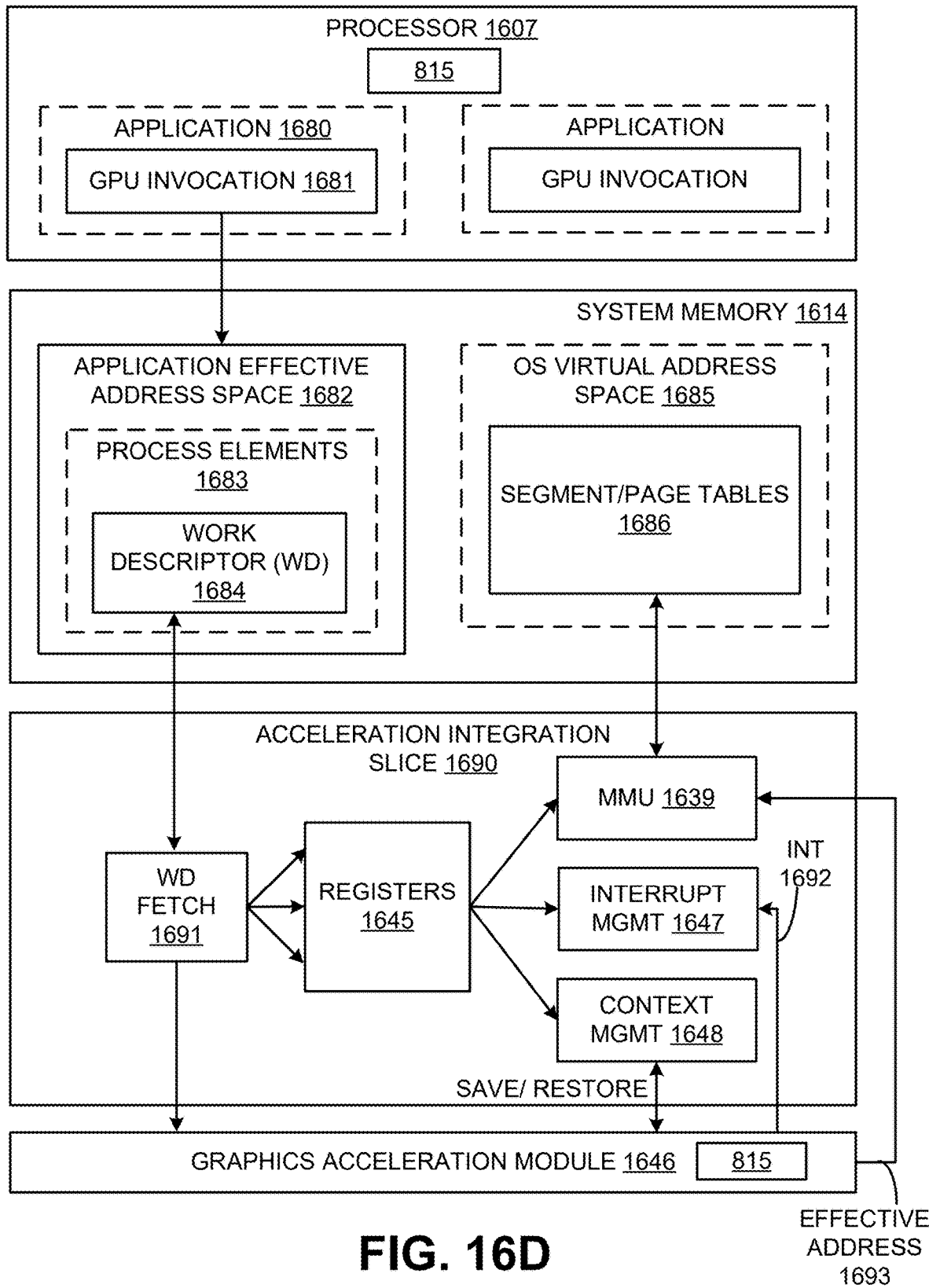
FIG. 16D illustrates a computer system, according to at least one embodiment.

FIG. 16D illustrates an exemplary accelerator integration slice 1690. In at least one embodiment, a "slice" comprises a specified portion of processing resources of accelerator integration circuit 1636. In at least one embodiment, an application is effective address space 1682 within system memory 1614 stores process elements 1683. In at least one embodiment, process elements 1683 are stored in response to GPU invocations 1681 from applications 1680 executed on processor 1607. In at least one embodiment, a process element 1683 contains process state for corresponding application 1680. In at least one embodiment, a work descriptor (WD) 1684 contained in process element 1683 can be a single job requested by an application or may contain a pointer to a queue of jobs. In at least one embodiment, WD 1684 is a pointer to a job request queue in an application's effective address space 1682.

In at least one embodiment, graphics acceleration module 1646 and/or individual graphics processing engines 1631(1)-1631(N) can be shared by all or a subset of processes in a system. In at least one embodiment, an infrastructure for setting up process states and sending a WD 1684 to a graphics acceleration module 1646 to start a job in a virtualized environment may be included.

In at least one embodiment, a dedicated-process programming model is implementation-specific. In at least one embodiment, in this model, a single process owns graphics acceleration module 1646 or an individual graphics processing engine 1631. In at least one embodiment, when graphics acceleration module 1646 is owned by a single process, a hypervisor initializes accelerator integration circuit 1636 for an owning partition and an operating system initializes accelerator integration circuit 1636 for an owning process when graphics acceleration module 1646 is assigned.

In at least one embodiment, in operation, a WD fetch unit 1691 in accelerator integration slice 1690 fetches next WD 1684, which includes an indication of work to be done by one or more graphics processing engines of graphics acceleration module 1646. In at least one embodiment, data from WD 1684 may be stored in registers 1645 and used by MMU 1639, interrupt management circuit 1647 and/or context management circuit 1648 as illustrated. For example, one embodiment of MMU 1639 includes segment/page walk circuitry for accessing segment/page tables 1686 within an OS virtual address space 1685. In at least one embodiment, interrupt management circuit 1647 may process interrupt events 1692 received from graphics acceleration module 1646. In at least one embodiment, when performing graphics operations, an effective address 1693 generated by a graphics processing engine 1631(1)-1631(N) is translated to a real address by MMU 1639.

In at least one embodiment, registers 1645 are duplicated for each graphics processing engine 1631(1)-1631(N) and/or graphics acceleration module 1646 and may be initialized by a hypervisor or an operating system. In at least one embodiment, each of these duplicated registers may be included in an accelerator integration slice 1690. Exemplary registers that may be initialized by a hypervisor are shown in Table 1.

TABLE 1

Hypervisor Initialized Registers

| Register # | Description |
|---|---|
| 1 | Slice Control Register |
| 2 | Real Address (RA) Scheduled Processes Area Pointer |
| 3 | Authority Mask Override Register |
| 4 | Interrupt Vector Table Entry Offset |
| 5 | Interrupt Vector Table Entry Limit |
| 6 | State Register |
| 7 | Logical Partition ID |
| 8 | Real address (RA) Hypervisor Accelerator Utilization Record Pointer |
| 9 | Storage Description Register |

Exemplary registers that may be initialized by an operating system are shown in Table 2.

TABLE 2

Operating System Initialized Registers

| Register # | Description |
|---|---|
| 1 | Process and Thread Identification |
| 2 | Effective Address (EA) Context Save/Restore Pointer |
| 3 | Virtual Address (VA) Accelerator Utilization Record Pointer |
| 4 | Virtual Address (VA) Storage Segment Table Pointer |
| 5 | Authority Mask |
| 6 | Work descriptor |

In at least one embodiment, each WD 1684 is specific to a particular graphics acceleration module 1646 and/or graphics processing engines 1631(1)-1631(N). In at least one embodiment, it contains all information required by a graphics processing engine 1631(1)-1631(N) to do work, or it can be a pointer to a memory location where an application has set up a command queue of work to be completed.

Figure 16E:
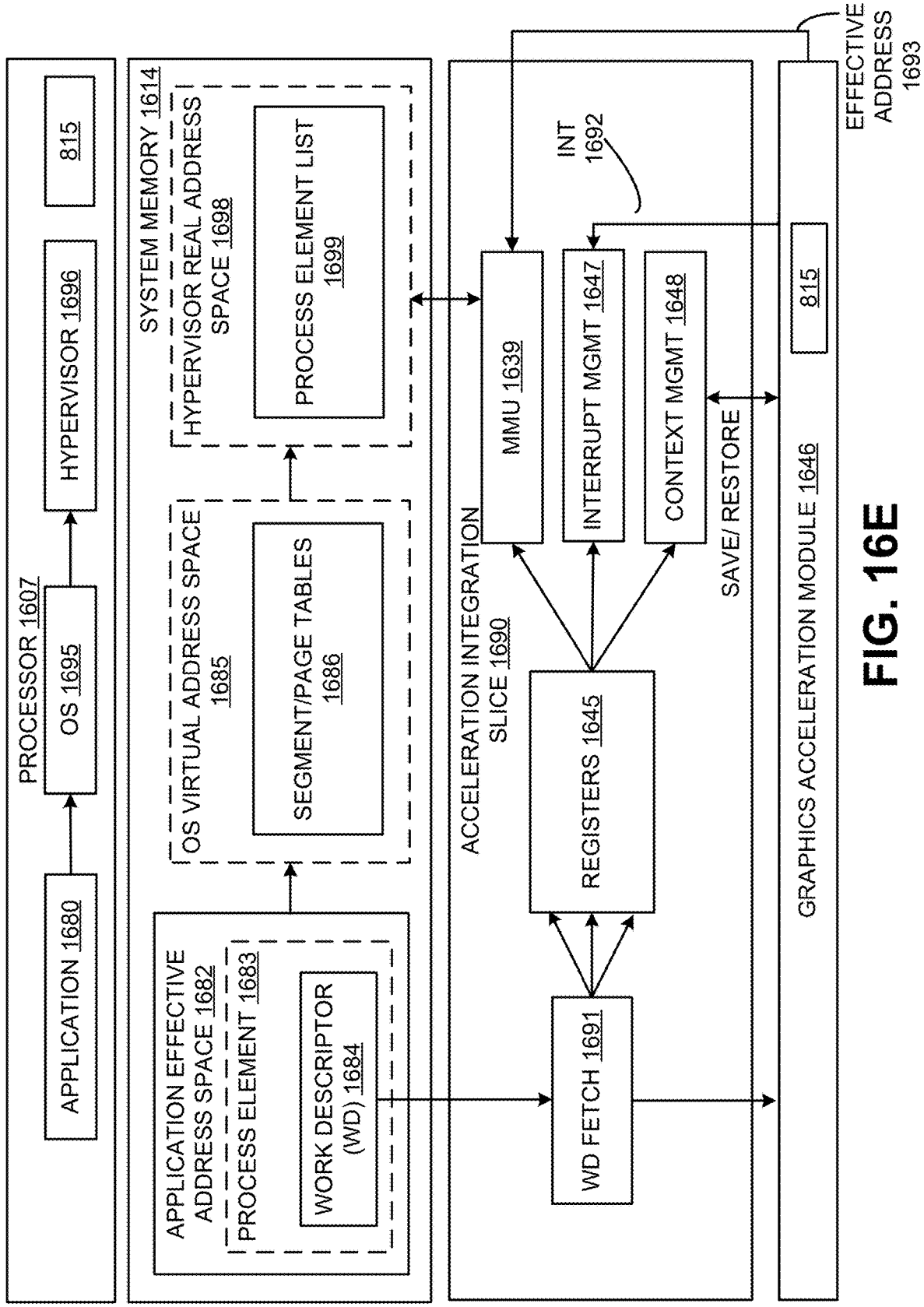
FIGS. 16E and 16F illustrate a shared programming model, according to at least one embodiment.

FIG. 16E illustrates additional details for one exemplary embodiment of a shared model. This embodiment includes a hypervisor real address space 1698 in which a process element list 1699 is stored. In at least one embodiment, hypervisor real address space 1698 is accessible via a hypervisor 1696 which virtualizes graphics acceleration module engines for operating system 1695.

In at least one embodiment, shared programming models allow for all or a subset of processes from all or a subset of partitions in a system to use a graphics acceleration module 1646. In at least one embodiment, there are two programming models where graphics acceleration module 1646 is shared by multiple processes and partitions, namely time-sliced shared and graphics directed shared.

In at least one embodiment, in this model, system hypervisor 1696 owns graphics acceleration module 1646 and makes its function available to all operating systems 1695. In at least one embodiment, for a graphics acceleration module 1646 to support virtualization by system hypervisor 1696, graphics acceleration module 1646 may adhere to certain requirements, such as (1) an application's job request must be autonomous (that is, state does not need to be maintained between jobs), or graphics acceleration module 1646 must provide a context save and restore mechanism, (2) an application's job request is guaranteed by graphics acceleration module 1646 to complete in a specified amount of time, including any translation faults, or graphics acceleration module 1646 provides an ability to preempt processing of a job, and (3) graphics acceleration module 1646 must be guaranteed fairness between processes when operating in a directed shared programming model.

In at least one embodiment, application 1680 is required to make an operating system 1695 system call with a graphics acceleration module type, a work descriptor (WD), an authority mask register (AMR) value, and a context save/restore area pointer (CSRP). In at least one embodiment, graphics acceleration module type describes a targeted acceleration function for a system call. In at least one embodiment, graphics acceleration module type may be a system-specific value. In at least one embodiment, WD is formatted specifically for graphics acceleration module 1646 and can be in a form of a graphics acceleration module 1646 command, an effective address pointer to a user-defined structure, an effective address pointer to a queue of commands, or any other data structure to describe work to be done by graphics acceleration module 1646.

In at least one embodiment, an AMR value is an AMR state to use for a current process. In at least one embodiment, a value passed to an operating system is similar to an application setting an AMR. In at least one embodiment, if accelerator integration circuit 1636 (not shown) and graphics acceleration module 1646 implementations do not support a User Authority Mask Override Register (UAMOR), an operating system may apply a current UAMOR value to an AMR value before passing an AMR in a hypervisor call. In at least one embodiment, hypervisor 1696 may optionally apply a current Authority Mask Override Register (AMOR) value before placing an AMR into process element 1683. In at least one embodiment, CSRP is one of registers 1645 containing an effective address of an area in an application's effective address space 1682 for graphics acceleration module 1646 to save and restore context state. In at least one embodiment, this pointer is optional if no state is required to be saved between jobs or when a job is preempted. In at least one embodiment, context save/restore area may be pinned system memory.

Upon receiving a system call, operating system 1695 may verify that application 1680 has registered and been given authority to use graphics acceleration module 1646. In at least one embodiment, operating system 1695 then calls hypervisor 1696 with information shown in Table 3.

TABLE 3

OS to Hypervisor Call Parameters

| Parameter # | Description |
| --- | --- |
| 1 | A work descriptor (WD) |
| 2 | An Authority Mask Register (AMR) value (potentially masked) |
| 3 | An effective address (EA) Context Save/Restore Area Pointer (CSRP) |
| 4 | A process ID (PID) and optional thread ID (TID) |
| 5 | A virtual address (VA) accelerator utilization record pointer (AURP) |
| 6 | Virtual address of storage segment table pointer (SSTP) |
| 7 | A logical interrupt service number (LISN) |

In at least one embodiment, upon receiving a hypervisor call, hypervisor 1696 verifies that operating system 1695 has registered and been given authority to use graphics acceleration module 1646. In at least one embodiment, hypervisor 1696 then puts process element 1683 into a process element linked list for a corresponding graphics acceleration module 1646 type. In at least one embodiment, a process element may include information shown in Table 4.

TABLE 4

Process Element Information

| Element # | Description |
| --- | --- |
| 1 | A work descriptor (WD) |
| 2 | An Authority Mask Register (AMR) value (potentially masked). |
| 3 | An effective address (EA) Context Save/Restore Area Pointer (CSRP) |
| 4 | A process ID (PID) and optional thread ID (TID) |
| 5 | A virtual address (VA) accelerator utilization record pointer (AURP) |
| 6 | Virtual address of storage segment table pointer (SSTP) |
| 7 | A logical interrupt service number (LISN) |
| 8 | Interrupt vector table, derived from hypervisor call parameters |
| 9 | A state register (SR) value |
| 10 | A logical partition ID (LPID) |
| 11 | A real address (RA) hypervisor accelerator utilization record pointer |
| 12 | Storage Descriptor Register (SDR) |

In at least one embodiment, hypervisor initializes a plurality of accelerator integration slice 1690 registers 1645.

Figure 16F:
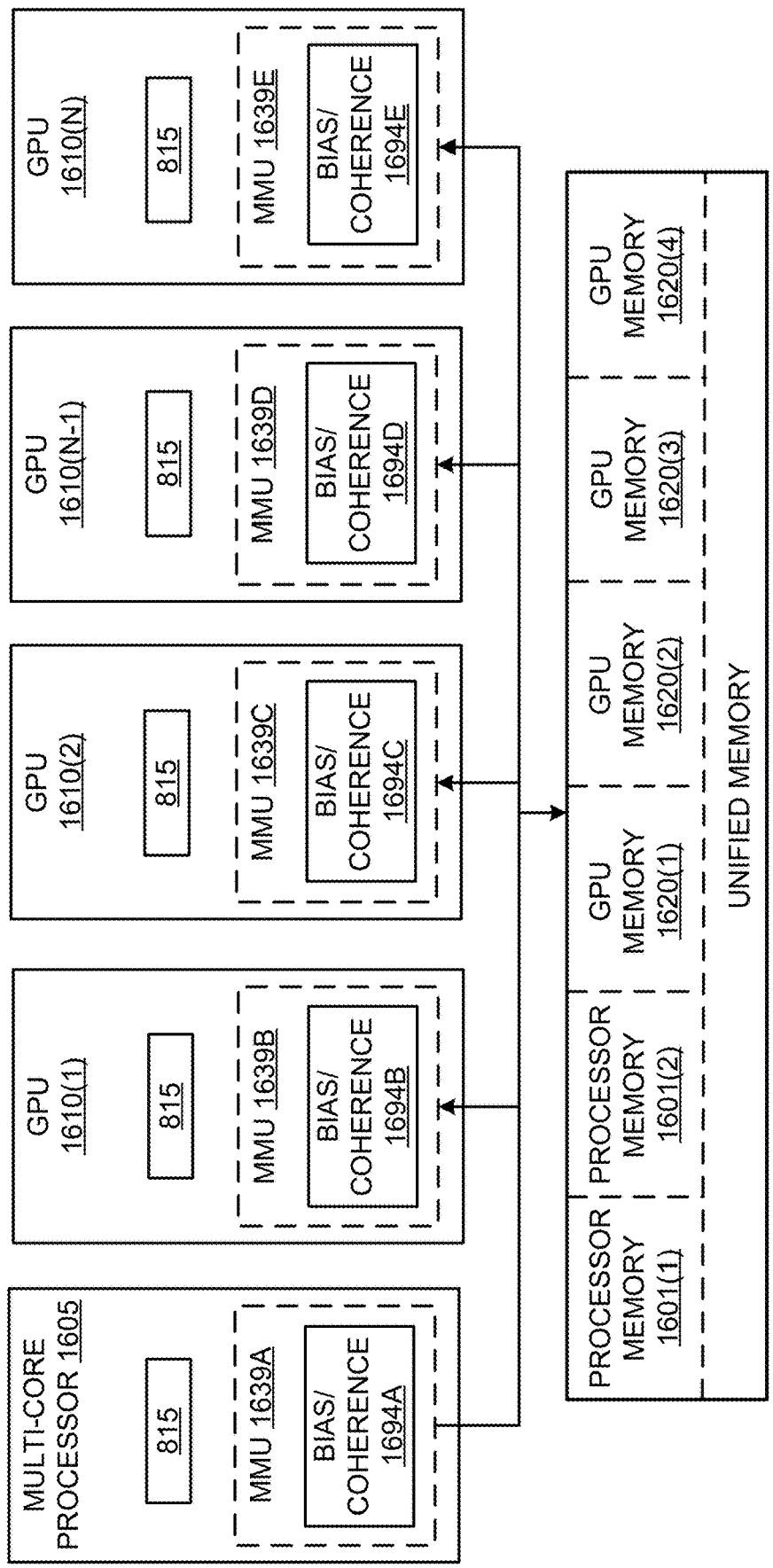

As illustrated in FIG. 16F, in at least one embodiment, a unified memory is used, addressable via a common virtual memory address space used to access physical processor memories 1601(1)-1601(N) and GPU memories 1620(1)-1620(N). In this implementation, operations executed on GPUs 1610(1)-1610(N) utilize a same virtual/effective memory address space to access processor memories 1601(1)-1601(M) and vice versa, thereby simplifying programmability. In at least one embodiment, a first portion of a virtual/effective address space is allocated to processor memory 1601(1), a second portion to second processor memory 1601(N), a third portion to GPU memory 1620(1), and so on. In at least one embodiment, an entire virtual/effective memory space (sometimes referred to as an effective address space) is thereby distributed across each of processor memories 1601 and GPU memories 1620, allowing any processor or GPU to access any physical memory with a virtual address mapped to that memory.

In at least one embodiment, bias/coherence management circuitry 1694A-1694E within one or more of MMUs 1639A-1639E ensures cache coherence between caches of one or more host processors (e.g., 1605) and GPUs 1610 and implements biasing techniques indicating physical memories in which certain types of data should be stored. In at least one embodiment, while multiple instances of bias/coherence management circuitry 1694A-1694E are illustrated in FIG. 16F, bias/coherence circuitry may be implemented within an MMU of one or more host processors 1605 and/or within accelerator integration circuit 1636.

One embodiment allows GPU memories 1620 to be mapped as part of system memory, and accessed using shared virtual memory (SVM) technology, but without suffering performance drawbacks associated with full system cache coherence. In at least one embodiment, an ability for GPU memories 1620 to be accessed as system memory without onerous cache coherence overhead provides a beneficial operating environment for GPU offload. In at least one embodiment, this arrangement allows software of host processor 1605 to setup operands and access computation results, without overhead of tradition I/O DMA data copies. In at least one embodiment, such traditional copies involve driver calls, interrupts and memory mapped I/O (MMIO) accesses that are all inefficient relative to simple memory accesses. In at least one embodiment, an ability to access GPU memories 1620 without cache coherence overheads can be critical to execution time of an offloaded computation. In at least one embodiment, in cases with substantial streaming write memory traffic, for example, cache coherence overhead can significantly reduce an effective write bandwidth seen by a GPU 1610. In at least one embodiment, efficiency of operand setup, efficiency of results access, and efficiency of GPU computation may play a role in determining effectiveness of a GPU offload.

In at least one embodiment, selection of GPU bias and host processor bias is driven by a bias tracker data structure. In at least one embodiment, a bias table may be used, for example, which may be a page-granular structure (e.g., controlled at a granularity of a memory page) that includes 1 or 2 bits per GPU-attached memory page. In at least one embodiment, a bias table may be implemented in a stolen memory range of one or more GPU memories 1620, with or without a bias cache in a GPU 1610 (e.g., to cache frequently/recently used entries of a bias table). Alternatively, in at least one embodiment, an entire bias table may be maintained within a GPU.

In at least one embodiment, a bias table entry associated with each access to a GPU attached memory 1620 is accessed prior to actual access to a GPU memory, causing following operations. In at least one embodiment, local requests from a GPU 1610 that find their page in GPU bias are forwarded directly to a corresponding GPU memory 1620. In at least one embodiment, local requests from a GPU that find their page in host bias are forwarded to processor 1605 (e.g., over a high-speed link as described herein). In at least one embodiment, requests from processor 1605 that find a requested page in host processor bias complete a request like a normal memory read. Alternatively, requests directed to a GPU-biased page may be forwarded to a GPU 1610. In at least one embodiment, a GPU may then transition a page to a host processor bias if it is not currently using a page. In at least one embodiment, a bias state of a page can be changed either by a software-based mechanism, a hardware-assisted software-based mechanism, or, for a limited set of cases, a purely hardware-based mechanism.

In at least one embodiment, one mechanism for changing bias state employs an API call (e.g., OpenCL), which, in turn, calls a GPU's device driver which, in turn, sends a message (or enqueues a command descriptor) to a GPU directing it to change a bias state and, for some transitions, perform a cache flushing operation in a host. In at least one embodiment, a cache flushing operation is used for a transition from host processor 1605 bias to GPU bias, but is not for an opposite transition.

In at least one embodiment, cache coherency is maintained by temporarily rendering GPU-biased pages uncacheable by host processor 1605. In at least one embodiment, to access these pages, processor 1605 may request access from GPU 1610, which may or may not grant access right away. In at least one embodiment, thus, to reduce communication between processor 1605 and GPU 1610 it is beneficial to ensure that GPU-biased pages are those which are required by a GPU but not host processor 1605 and vice versa.

Hardware structure(s) 815 are used to perform one or more embodiments. Details regarding a hardware structure(s) 815 may be provided herein in conjunction with FIGS. 8A and/or 8B.

In at least one embodiment, one or more systems depicted in FIGS. 16A-16F are utilized to generate segmentation and confidence values for pixels of an image. In at least one embodiment, one or more systems depicted in FIGS. 16A-16F are utilized to implement one or more networks and processes such as those described in connection with FIGS. 1-7. In at least one embodiment, one or more systems depicted in FIGS. 16A-16F are utilized to implement a system for segmentation and confidence value determination.

Figure 17:
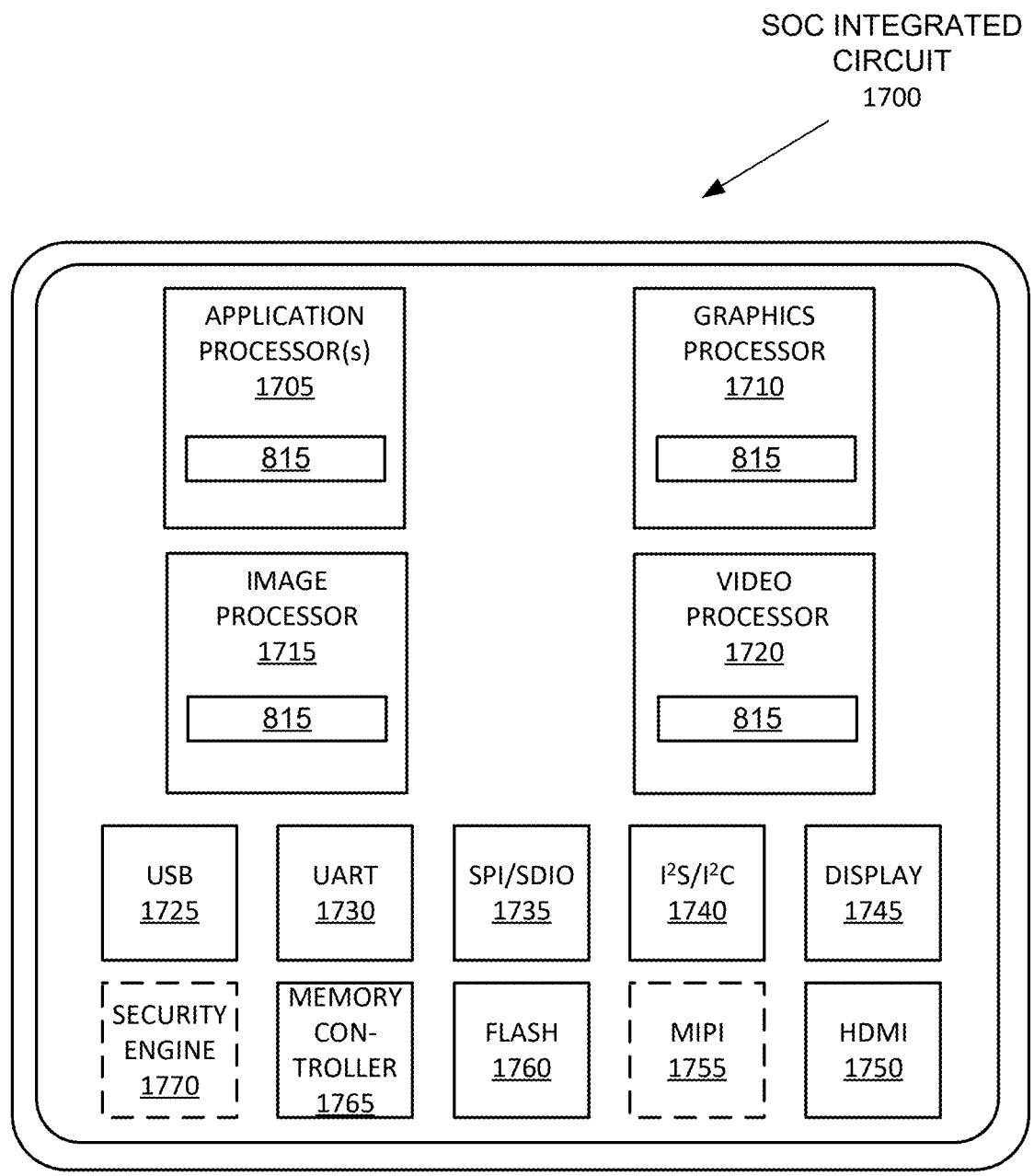
FIG. 17 illustrates exemplary integrated circuits and associated graphics processors, according to at least one embodiment.

FIG. 17 illustrates exemplary integrated circuits and associated graphics processors that may be fabricated using one or more IP cores, according to various embodiments described herein. In addition to what is illustrated, other logic and circuits may be included in at least one embodiment, including additional graphics processors/cores, peripheral interface controllers, or general-purpose processor cores.

FIG. 17 is a block diagram illustrating an exemplary system on a chip integrated circuit 1700 that may be fabricated using one or more IP cores, according to at least one embodiment. In at least one embodiment, integrated circuit 1700 includes one or more application processor(s) 1705 (e.g., CPUs), at least one graphics processor 1710, and may additionally include an image processor 1715 and/or a video processor 1720, any of which may be a modular IP core. In at least one embodiment, integrated circuit 1700 includes peripheral or bus logic including a USB controller 1725, a UART controller 1730, an SPI/SDIO controller 1735, and an I$^2$S/I$^2$C controller 1740. In at least one embodiment, integrated circuit 1700 can include a display device 1745 coupled to one or more of a high-definition multimedia interface (HDMI) controller 1750 and a mobile industry processor interface (MIPI) display interface 1755. In at least one embodiment, storage may be provided by a flash memory subsystem 1760 including flash memory and a flash memory controller. In at least one embodiment, a memory interface may be provided via a memory controller 1765 for access to SDRAM or SRAM memory devices. In at least one embodiment, some integrated circuits additionally include an embedded security engine 1770.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, inference and/or training logic 815 may be used in integrated circuit 1700 for inferencing or predicting operations based, at least in part, on weight parameters calculated using neural network training operations, neural network functions and/or architectures, or neural network use cases described herein.

In at least one embodiment, one or more systems depicted in FIG. 17 are utilized to generate segmentation and confidence values for pixels of an image. In at least one embodiment, one or more systems depicted in FIG. 17 are utilized to implement one or more networks and processes such as those described in connection with FIGS. 1-7. In at least one embodiment, one or more systems depicted in FIG. 17 are utilized to implement a system for segmentation and confidence value determination.

Figure 18A:
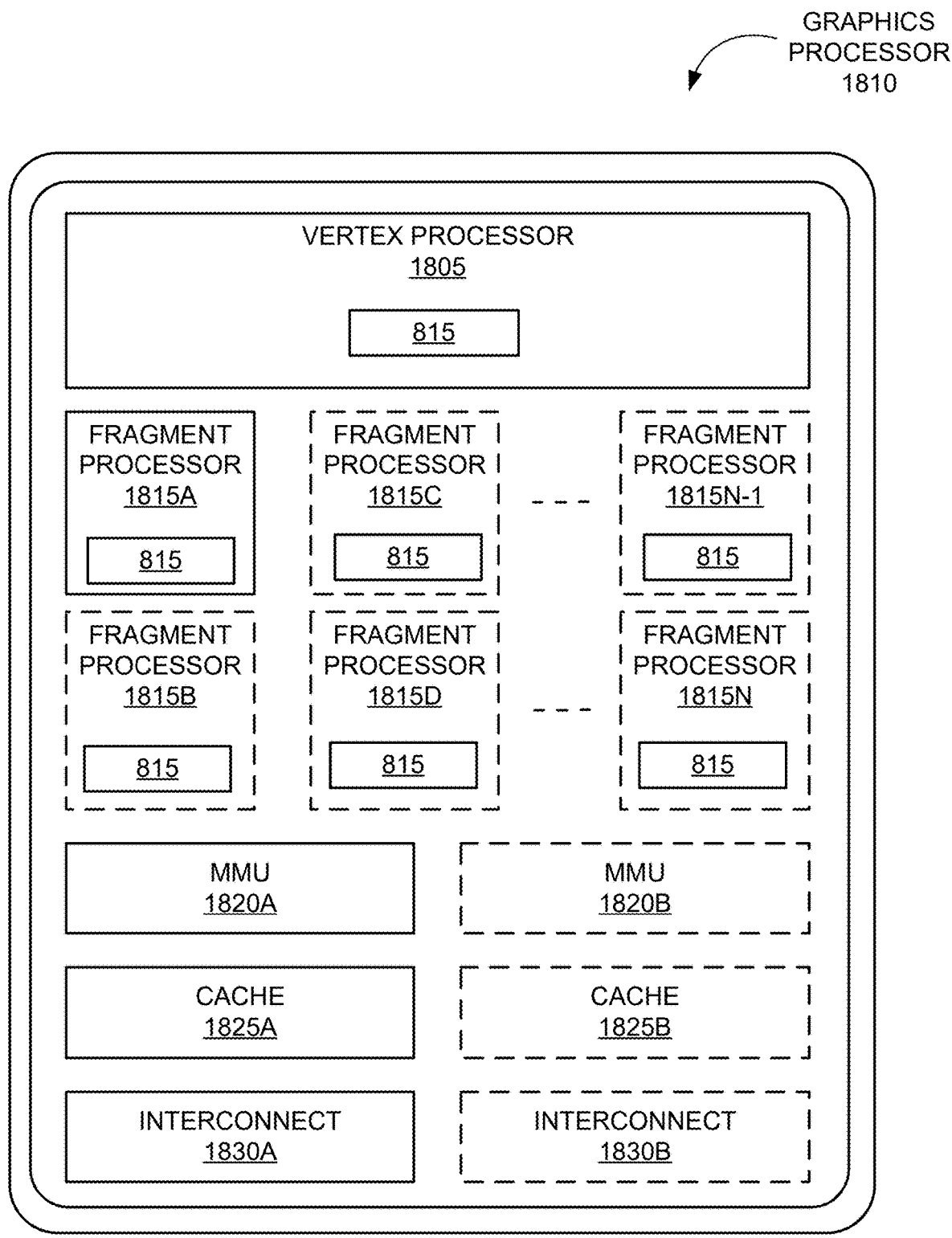
FIGS. 18A and 18B illustrate exemplary integrated circuits and associated graphics processors, according to at least one embodiment.
Figure 18B:
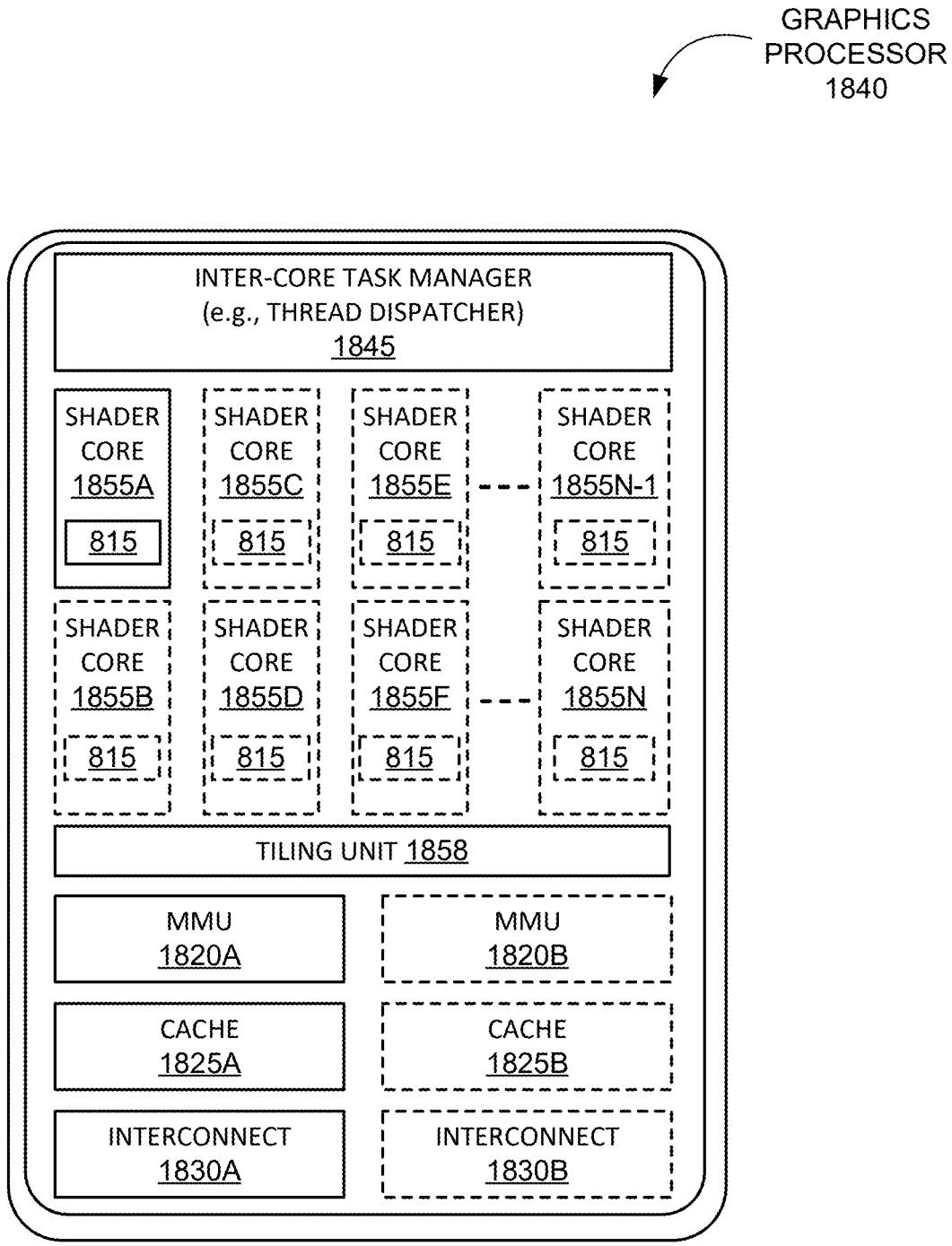

FIGS. 18A-18B illustrate exemplary integrated circuits and associated graphics processors that may be fabricated using one or more IP cores, according to various embodiments described herein. In addition to what is illustrated, other logic and circuits may be included in at least one embodiment, including additional graphics processors/cores, peripheral interface controllers, or general-purpose processor cores.

FIGS. 18A-18B are block diagrams illustrating exemplary graphics processors for use within an SoC, according to embodiments described herein. FIG. 18A illustrates an exemplary graphics processor 1810 of a system on a chip integrated circuit that may be fabricated using one or more IP cores, according to at least one embodiment. FIG. 18B illustrates an additional exemplary graphics processor 1840 of a system on a chip integrated circuit that may be fabricated using one or more IP cores, according to at least one embodiment. In at least one embodiment, graphics processor 1810 of FIG. 18A is a low power graphics processor core. In at least one embodiment, graphics processor 1840 of FIG. 18B is a higher performance graphics processor core. In at least one embodiment, each of graphics processors 1810, 1840 can be variants of graphics processor 1710 of FIG. 17.

In at least one embodiment, graphics processor 1810 includes a vertex processor 1805 and one or more fragment processor(s) 1815A-1815N (e.g., 1815A, 1815B, 1815C, 1815D, through 1815N-1, and 1815N). In at least one embodiment, graphics processor 1810 can execute different shader programs via separate logic, such that vertex processor 1805 is optimized to execute operations for vertex shader programs, while one or more fragment processor(s) 1815A-1815N execute fragment (e.g., pixel) shading operations for fragment or pixel shader programs. In at least one embodiment, vertex processor 1805 performs a vertex processing stage of a 3D graphics pipeline and generates primitives and vertex data. In at least one embodiment, fragment processor(s) 1815A-1815N use primitive and vertex data generated by vertex processor 1805 to produce a framebuffer that is displayed on a display device. In at least one embodiment, fragment processor(s) 1815A-1815N are optimized to execute fragment shader programs as provided for in an OpenGL API, which may be used to perform similar operations as a pixel shader program as provided for in a Direct 3D API.

In at least one embodiment, graphics processor 1810 additionally includes one or more memory management units (MMUs) 1820A-1820B, cache(s) 1825A-1825B, and circuit interconnect(s) 1830A-1830B. In at least one embodiment, one or more MMU(s) 1820A-1820B provide for virtual to physical address mapping for graphics processor 1810, including for vertex processor 1805 and/or fragment processor(s) 1815A-1815N, which may reference vertex or image/texture data stored in memory, in addition to vertex or image/texture data stored in one or more cache(s) 1825A-1825B. In at least one embodiment, one or more MMU(s) 1820A-1820B may be synchronized with other MMUs within a system, including one or more MMUs associated with one or more application processor(s) 1705, image processors 1715, and/or video processors 1720 of FIG. 17, such that each processor 1705-1720 can participate in a shared or unified virtual memory system. In at least one embodiment, one or more circuit interconnect(s) 1830A-1830B enable graphics processor 1810 to interface with other IP cores within SoC, either via an internal bus of SoC or via a direct connection.

In at least one embodiment, graphics processor 1840 includes one or more shader core(s) 1855A-1855N (e.g., 1855A, 1855B, 1855C, 1855D, 1855E, 1855F, through 1855N-1, and 1855N) as shown in FIG. 18B, which provides for a unified shader core architecture in which a single core or type or core can execute all types of programmable shader code, including shader program code to implement vertex shaders, fragment shaders, and/or compute shaders. In at least one embodiment, a number of shader cores can vary. In at least one embodiment, graphics processor 1840 includes an inter-core task manager 1845, which acts as a thread dispatcher to dispatch execution threads to one or more shader cores 1855A-1855N and a tiling unit 1858 to accelerate tiling operations for tile-based rendering, in which rendering operations for a scene are subdivided in image space, for example to exploit local spatial coherence within a scene or to optimize use of internal caches.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, inference and/or training logic 815 may be used in integrated circuit 18A and/or 18B for inferencing or predicting operations based, at least in part, on weight parameters calculated using neural network training operations, neural network functions and/or architectures, or neural network use cases described herein.

In at least one embodiment, one or more systems depicted in FIGS. 18A-18B are utilized to generate segmentation and confidence values for pixels of an image. In at least one embodiment, one or more systems depicted in FIGS. 18A-18B are utilized to implement one or more networks and processes such as those described in connection with FIGS. 1-7. In at least one embodiment, one or more systems depicted in FIGS. 18A-18B are utilized to implement a system for segmentation and confidence value determination.

Figure 19A:
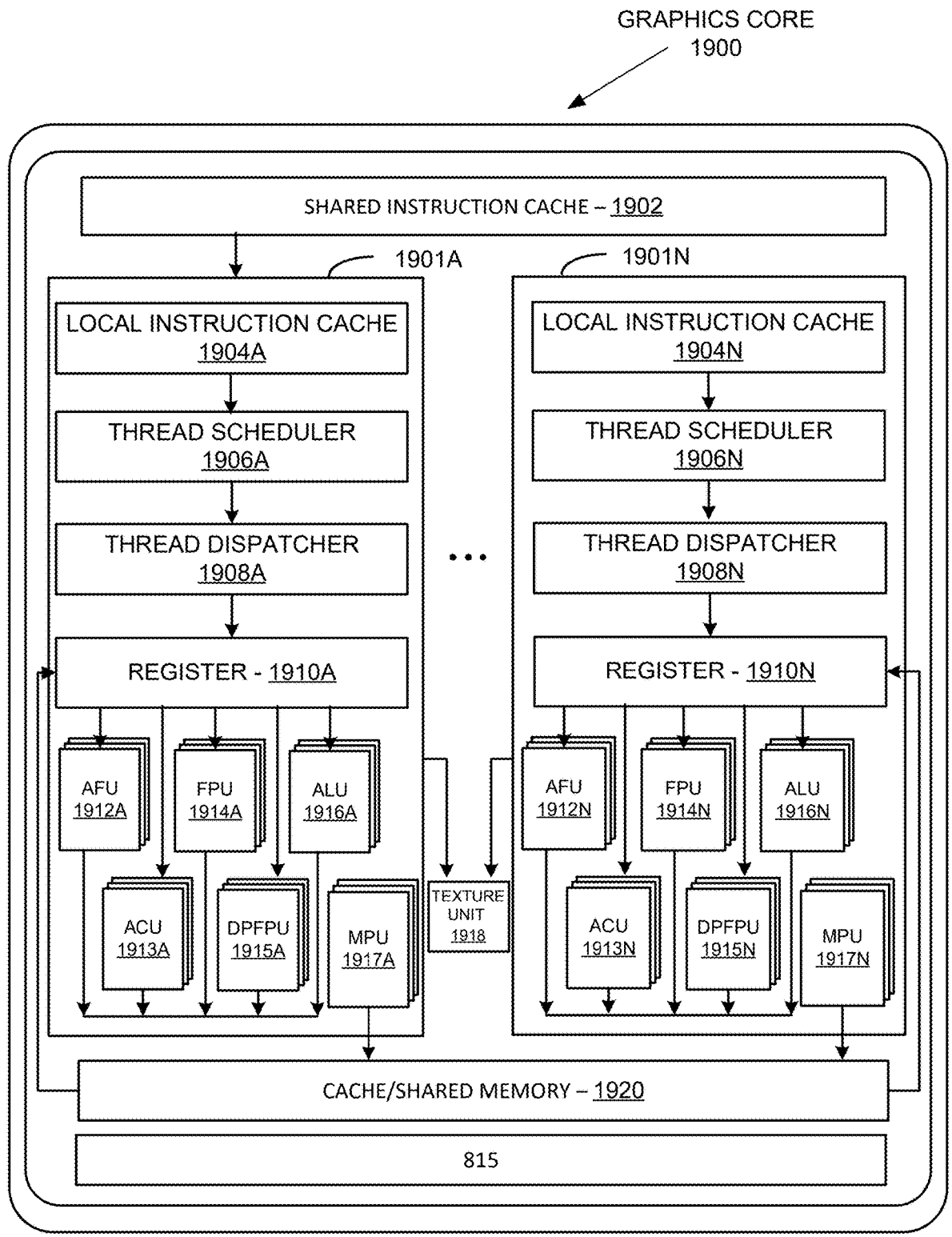
FIGS. 19A and 19B illustrate additional exemplary graphics processor logic according to at least one embodiment.
Figure 19B:
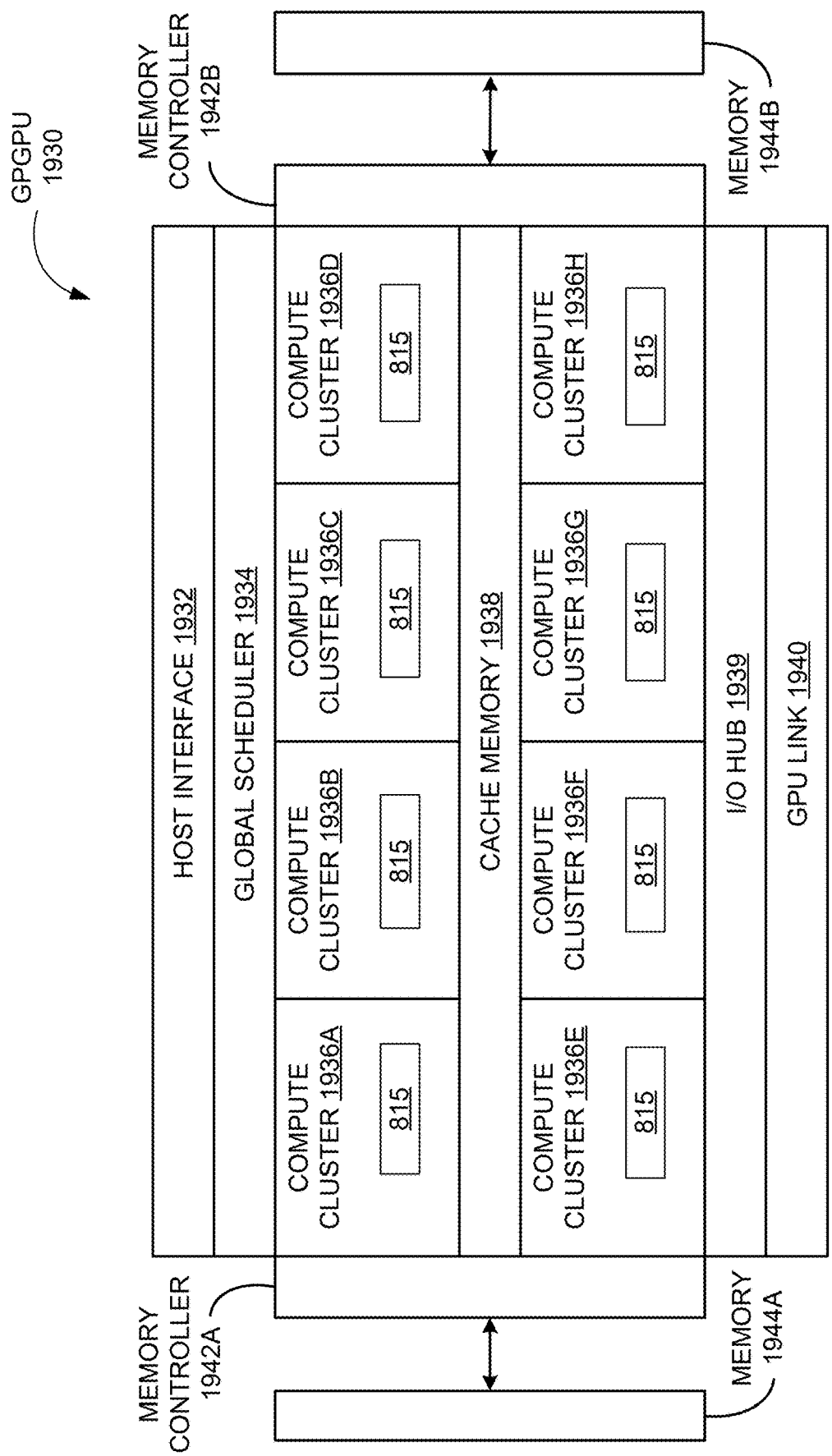

FIGS. 19A-19B illustrate additional exemplary graphics processor logic according to embodiments described herein. FIG. 19A illustrates a graphics core 1900 that may be included within graphics processor 1710 of FIG. 17, in at least one embodiment, and may be a unified shader core 1855A-1855N as in FIG. 18B in at least one embodiment. FIG. 19B illustrates a highly-parallel general-purpose graphics processing unit ("GPGPU") 1930 suitable for deployment on a multi-chip module in at least one embodiment.

In at least one embodiment, graphics core 1900 includes a shared instruction cache 1902, a texture unit 1918, and a cache/shared memory 1920 that are common to execution resources within graphics core 1900. In at least one embodiment, graphics core 1900 can include multiple slices 1901A-1901N or a partition for each core, and a graphics processor can include multiple instances of graphics core 1900. In at least one embodiment, slices 1901A-1901N can include support logic including a local instruction cache 1904A-1904N, a thread scheduler 1906A-1906N, a thread dispatcher 1908A-1908N, and a set of registers 1910A-1910N. In at least one embodiment, slices 1901A-1901N can include a set of additional function units (AFUs 1912A-1912N), floating-point units (FPUs 1914A-1914N), integer arithmetic logic units (ALUs 1916A-1916N), address computational units (ACUs 1913A-1913N), double-precision floating-point units (DPFPUs 1915A-1915N), and matrix processing units (MPUs 1917A-1917N).

In at least one embodiment, FPUs 1914A-1914N can perform single-precision (32-bit) and half-precision (16-bit) floating point operations, while DPFPUs 1915A-1915N perform double precision (64-bit) floating point operations. In at least one embodiment, ALUs 1916A-1916N can perform variable precision integer operations at 8-bit, 16-bit, and 32-bit precision, and can be configured for mixed precision operations. In at least one embodiment, MPUs 1917A-1917N can also be configured for mixed precision matrix operations, including half-precision floating point and 8-bit integer operations. In at least one embodiment, MPUs 1917-1917N can perform a variety of matrix operations to accelerate machine learning application frameworks, including enabling support for accelerated general matrix to matrix multiplication (GEMM). In at least one embodiment, AFUs 1912A-1912N can perform additional logic operations not supported by floating-point or integer units, including trigonometric operations (e.g., sine, cosine, etc.).

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, inference and/or training logic 815 may be used in graphics core 1900 for inferencing or predicting operations based, at least in part, on weight parameters calculated using neural network training operations, neural network functions and/or architectures, or neural network use cases described herein.

FIG. 19B illustrates a general-purpose processing unit (GPGPU) 1930 that can be configured to enable highly-parallel compute operations to be performed by an array of graphics processing units, in at least one embodiment. In at least one embodiment, GPGPU 1930 can be linked directly to other instances of GPGPU 1930 to create a multi-GPU cluster to improve training speed for deep neural networks. In at least one embodiment, GPGPU 1930 includes a host interface 1932 to enable a connection with a host processor. In at least one embodiment, host interface 1932 is a PCI Express interface. In at least one embodiment, host interface 1932 can be a vendor-specific communications interface or communications fabric. In at least one embodiment, GPGPU 1930 receives commands from a host processor and uses a global scheduler 1934 to distribute execution threads associated with those commands to a set of compute clusters 1936A-1936H. In at least one embodiment, compute clusters 1936A-1936H share a cache memory 1938. In at least one embodiment, cache memory 1938 can serve as a higher-level cache for cache memories within compute clusters 1936A-1936H.

In at least one embodiment, GPGPU 1930 includes memory 1944A-1944B coupled with compute clusters 1936A-1936H via a set of memory controllers 1942A-1942B. In at least one embodiment, memory 1944A-1944B can include various types of memory devices including dynamic random access memory (DRAM) or graphics random access memory, such as synchronous graphics random access memory (SGRAM), including graphics double data rate (GDDR) memory.

In at least one embodiment, compute clusters 1936A-1936H each include a set of graphics cores, such as graphics core 1900 of FIG. 19A, which can include multiple types of integer and floating point logic units that can perform computational operations at a range of precisions including suited for machine learning computations. For example, in at least one embodiment, at least a subset of floating point units in each of compute clusters 1936A-1936H can be configured to perform 16-bit or 32-bit floating point operations, while a different subset of floating point units can be configured to perform 64-bit floating point operations.

In at least one embodiment, multiple instances of GPGPU 1930 can be configured to operate as a compute cluster. In at least one embodiment, communication used by compute clusters 1936A-1936H for synchronization and data exchange varies across embodiments. In at least one embodiment, multiple instances of GPGPU 1930 communicate over host interface 1932. In at least one embodiment, GPGPU 1930 includes an I/O hub 1939 that couples GPGPU 1930 with a GPU link 1940 that enables a direct connection to other instances of GPGPU 1930. In at least one embodiment, GPU link 1940 is coupled to a dedicated GPU-to-GPU bridge that enables communication and synchronization between multiple instances of GPGPU 1930. In at least one embodiment, GPU link 1940 couples with a high-speed interconnect to transmit and receive data to other GPGPUs or parallel processors. In at least one embodiment, multiple instances of GPGPU 1930 are located in separate data processing systems and communicate via a network device that is accessible via host interface 1932. In at least one embodiment GPU link 1940 can be configured to enable a connection to a host processor in addition to or as an alternative to host interface 1932.

In at least one embodiment, GPGPU 1930 can be configured to train neural networks. In at least one embodiment, GPGPU 1930 can be used within an inferencing platform. In at least one embodiment, in which GPGPU 1930 is used for inferencing, GPGPU 1930 may include fewer compute clusters 1936A-1936H relative to when GPGPU 1930 is used for training a neural network. In at least one embodiment, memory technology associated with memory 1944A-1944B may differ between inferencing and training configurations, with higher bandwidth memory technologies devoted to training configurations. In at least one embodiment, an inferencing configuration of GPGPU 1930 can support inferencing specific instructions. For example, in at least one embodiment, an inferencing configuration can provide support for one or more 8-bit integer dot product instructions, which may be used during inferencing operations for deployed neural networks.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, inference and/or training logic 815 may be used in GPGPU 1930 for inferencing or predicting operations based, at least in part, on weight parameters calculated using neural network training operations, neural network functions and/or architectures, or neural network use cases described herein.

In at least one embodiment, one or more systems depicted in FIGS. 19A-19B are utilized to generate segmentation and confidence values for pixels of an image. In at least one embodiment, one or more systems depicted in FIGS. 19A-19B are utilized to implement one or more networks and processes such as those described in connection with FIGS. 1-7. In at least one embodiment, one or more systems depicted in FIGS. 19A-19B are utilized to implement a system for segmentation and confidence value determination.

Figure 20:
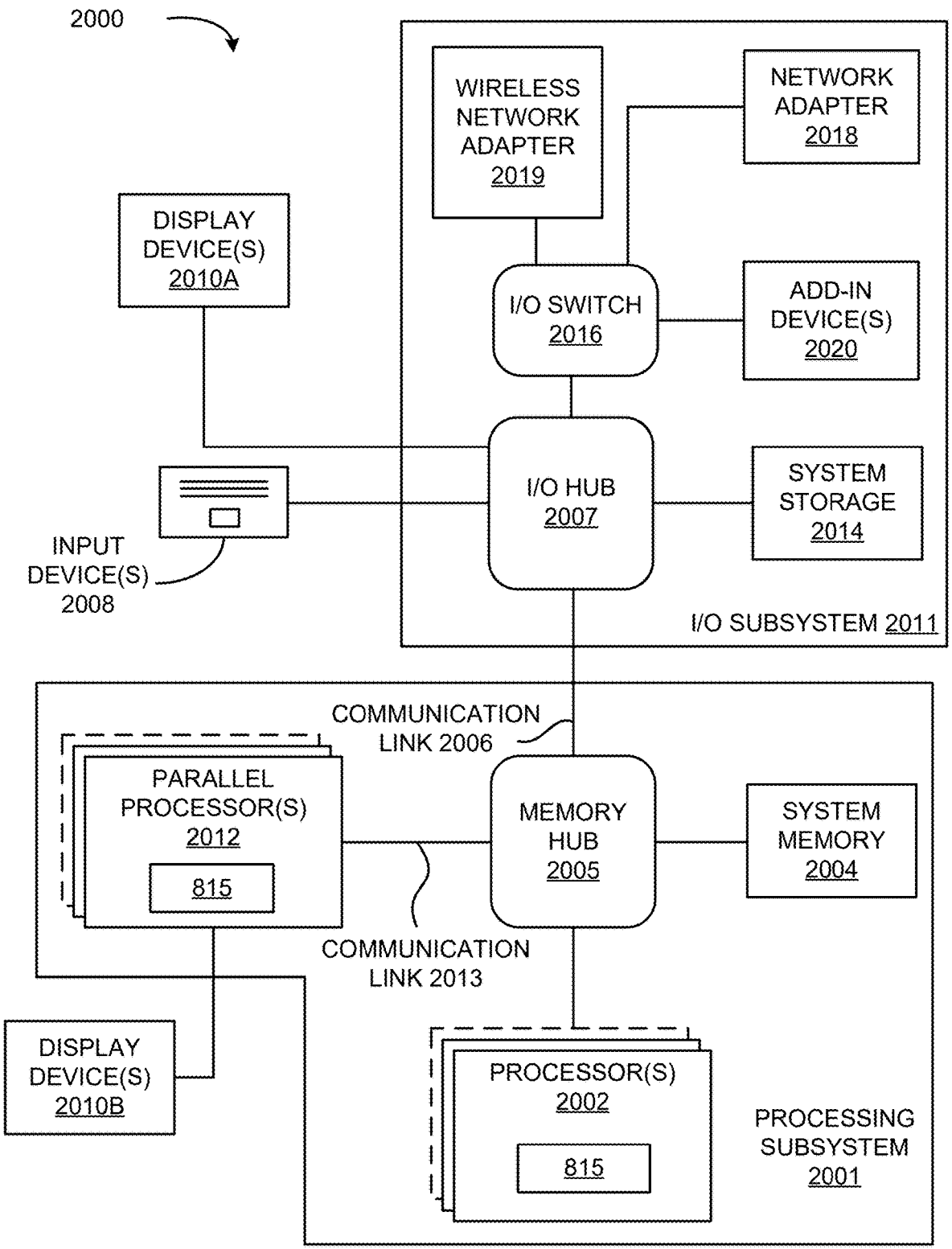
FIG. 20 illustrates a computer system, according to at least one embodiment.

FIG. 20 is a block diagram illustrating a computing system 2000 according to at least one embodiment. In at least one embodiment, computing system 2000 includes a processing subsystem 2001 having one or more processor(s) 2002 and a system memory 2004 communicating via an interconnection path that may include a memory hub 2005. In at least one embodiment, memory hub 2005 may be a separate component within a chipset component or may be integrated within one or more processor(s) 2002. In at least one embodiment, memory hub 2005 couples with an I/O subsystem 2011 via a communication link 2006. In at least one embodiment, I/O subsystem 2011 includes an I/O hub 2007 that can enable computing system 2000 to receive input from one or more input device(s) 2008. In at least one embodiment, I/O hub 2007 can enable a display controller, which may be included in one or more processor(s) 2002, to provide outputs to one or more display device(s) 2010A. In at least one embodiment, one or more display device(s) 2010A coupled with I/O hub 2007 can include a local, internal, or embedded display device.

In at least one embodiment, processing subsystem 2001 includes one or more parallel processor(s) 2012 coupled to memory hub 2005 via a bus or other communication link 2013. In at least one embodiment, communication link 2013 may use one of any number of standards based communication link technologies or protocols, such as, but not limited to PCI Express, or may be a vendor-specific communications interface or communications fabric. In at least one embodiment, one or more parallel processor(s) 2012 form a computationally focused parallel or vector processing system that can include a large number of processing cores and/or processing clusters, such as a many-integrated core (MIC) processor. In at least one embodiment, some or all of parallel processor(s) 2012 form a graphics processing subsystem that can output pixels to one of one or more display device(s) 2010A coupled via I/O Hub 2007. In at least one embodiment, parallel processor(s) 2012 can also include a display controller and display interface (not shown) to enable a direct connection to one or more display device(s) 2010B.

In at least one embodiment, a system storage unit 2014 can connect to I/O hub 2007 to provide a storage mechanism for computing system 2000. In at least one embodiment, an I/O switch 2016 can be used to provide an interface mechanism to enable connections between I/O hub 2007 and other components, such as a network adapter 2018 and/or a wireless network adapter 2019 that may be integrated into platform, and various other devices that can be added via one or more add-in device(s) 2020. In at least one embodiment, network adapter 2018 can be an Ethernet adapter or another wired network adapter. In at least one embodiment, wireless network adapter 2019 can include one or more of a Wi-Fi, Bluetooth, near field communication (NFC), or other network device that includes one or more wireless radios.

In at least one embodiment, computing system 2000 can include other components not explicitly shown, including USB or other port connections, optical storage drives, video capture devices, and like, may also be connected to I/O hub 2007. In at least one embodiment, communication paths interconnecting various components in FIG. 20 may be implemented using any suitable protocols, such as PCI (Peripheral Component Interconnect) based protocols (e.g., PCI-Express), or other bus or point-to-point communication interfaces and/or protocol(s), such as NV-Link high-speed interconnect, or interconnect protocols.

In at least one embodiment, parallel processor(s) 2012 incorporate circuitry optimized for graphics and video processing, including, for example, video output circuitry, and constitutes a graphics processing unit (GPU). In at least one embodiment, parallel processor(s) 2012 incorporate circuitry optimized for general purpose processing. In at least embodiment, components of computing system 2000 may be integrated with one or more other system elements on a single integrated circuit. For example, in at least one embodiment, parallel processor(s) 2012, memory hub 2005, processor(s) 2002, and I/O hub 2007 can be integrated into a system on chip (SoC) integrated circuit. In at least one embodiment, components of computing system 2000 can be integrated into a single package to form a system in package (SIP) configuration. In at least one embodiment, at least a portion of components of computing system 2000 can be integrated into a multi-chip module (MCM), which can be interconnected with other multi-chip modules into a modular computing system.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, inference and/or training logic 815 may be used in system FIG. 2000 for inferencing or predicting operations based, at least in part, on weight parameters calculated using neural network training operations, neural network functions and/or architectures, or neural network use cases described herein.

In at least one embodiment, one or more systems depicted in FIG. 20 are utilized to generate segmentation and confidence values for pixels of an image. In at least one embodiment, one or more systems depicted in FIG. 20 are utilized to implement one or more networks and processes such as those described in connection with FIGS. 1-7. In at least one embodiment, one or more systems depicted in FIG. 20 are utilized to implement a system for segmentation and confidence value determination.

Processors

Figure 21A:
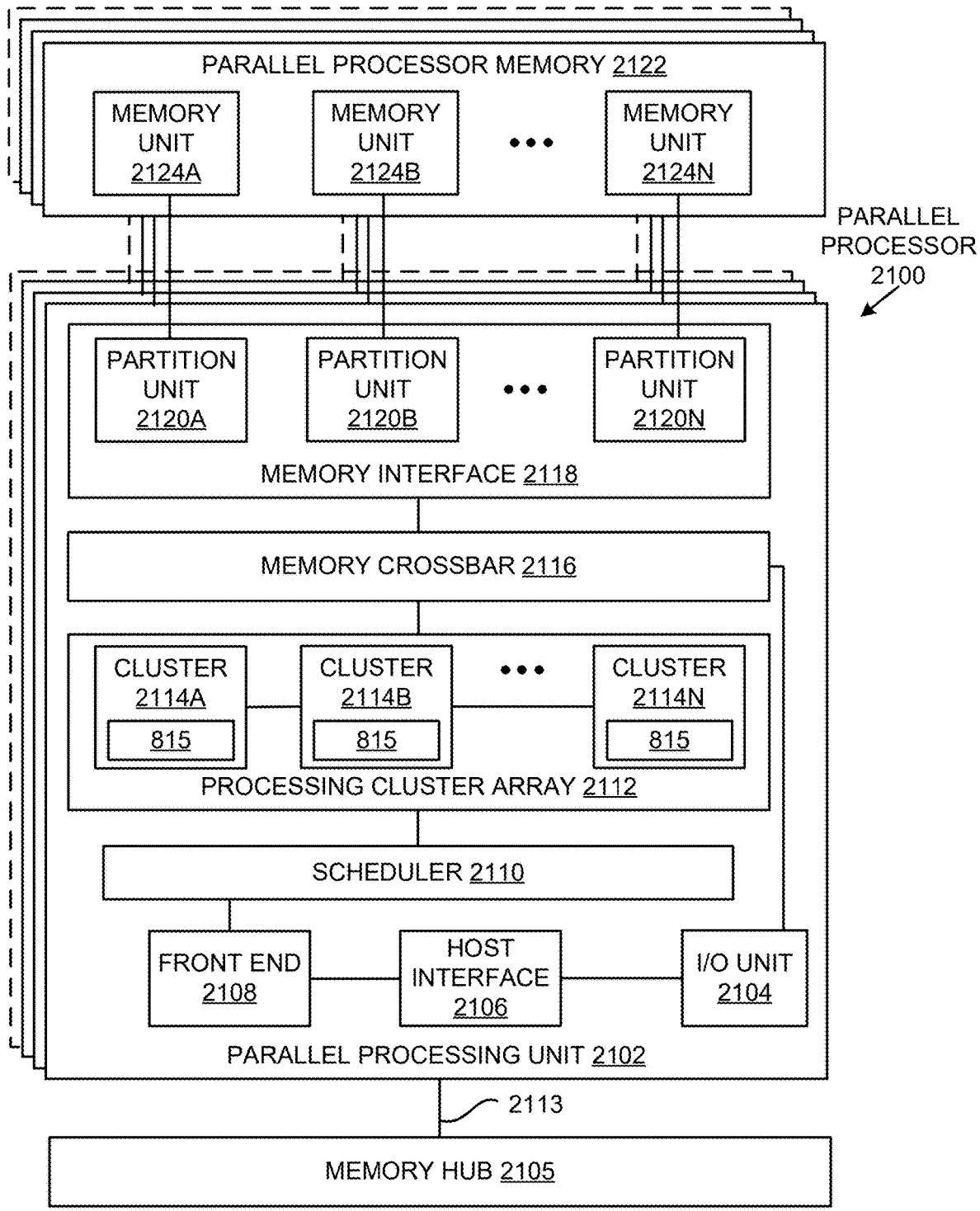
FIG. 21A illustrates a parallel processor, according to at least one embodiment.

FIG. 21A illustrates a parallel processor 2100 according to at least one embodiment. In at least one embodiment, various components of parallel processor 2100 may be implemented using one or more integrated circuit devices, such as programmable processors, application specific integrated circuits (ASICs), or field programmable gate arrays (FPGA). In at least one embodiment, illustrated parallel processor 2100 is a variant of one or more parallel processor(s) 2012 shown in FIG. 20 according to an exemplary embodiment.

In at least one embodiment, parallel processor 2100 includes a parallel processing unit 2102. In at least one embodiment, parallel processing unit 2102 includes an I/O unit 2104 that enables communication with other devices, including other instances of parallel processing unit 2102. In at least one embodiment, I/O unit 2104 may be directly connected to other devices. In at least one embodiment, I/O unit 2104 connects with other devices via use of a hub or switch interface, such as a memory hub 2105. In at least one embodiment, connections between memory hub 2105 and I/O unit 2104 form a communication link 2113. In at least one embodiment, I/O unit 2104 connects with a host interface 2106 and a memory crossbar 2116, where host interface 2106 receives commands directed to performing processing operations and memory crossbar 2116 receives commands directed to performing memory operations.

In at least one embodiment, when host interface 2106 receives a command buffer via I/O unit 2104, host interface 2106 can direct work operations to perform those commands to a front end 2108. In at least one embodiment, front end 2108 couples with a scheduler 2110, which is configured to distribute commands or other work items to a processing cluster array 2112. In at least one embodiment, scheduler 2110 ensures that processing cluster array 2112 is properly configured and in a valid state before tasks are distributed to a cluster of processing cluster array 2112. In at least one embodiment, scheduler 2110 is implemented via firmware logic executing on a microcontroller. In at least one embodiment, microcontroller implemented scheduler 2110 is configurable to perform complex scheduling and work distribution operations at coarse and fine granularity, enabling rapid preemption and context switching of threads executing on processing array 2112. In at least one embodiment, host software can prove workloads for scheduling on processing cluster array 2112 via one of multiple graphics processing paths. In at least one embodiment, workloads can then be automatically distributed across processing array cluster 2112 by scheduler 2110 logic within a microcontroller including scheduler 2110.

In at least one embodiment, processing cluster array 2112 can include up to "N" processing clusters (e.g., cluster 2114A, cluster 2114B, through cluster 2114N), where "N" represents a positive integer (which may be a different integer "N" than used in other figures). In at least one embodiment, each cluster 2114A-2114N of processing cluster array 2112 can execute a large number of concurrent threads. In at least one embodiment, scheduler 2110 can allocate work to clusters 2114A-2114N of processing cluster array 2112 using various scheduling and/or work distribution algorithms, which may vary depending on workload arising for each type of program or computation. In at least one embodiment, scheduling can be handled dynamically by scheduler 2110, or can be assisted in part by compiler logic during compilation of program logic configured for execution by processing cluster array 2112. In at least one embodiment, different clusters 2114A-2114N of processing cluster array 2112 can be allocated for processing different types of programs or for performing different types of computations.

In at least one embodiment, processing cluster array 2112 can be configured to perform various types of parallel processing operations. In at least one embodiment, processing cluster array 2112 is configured to perform general-purpose parallel compute operations. For example, in at least one embodiment, processing cluster array 2112 can include logic to execute processing tasks including filtering of video and/or audio data, performing modeling operations, including physics operations, and performing data transformations.

In at least one embodiment, processing cluster array 2112 is configured to perform parallel graphics processing operations. In at least one embodiment, processing cluster array 2112 can include additional logic to support execution of such graphics processing operations, including but not limited to, texture sampling logic to perform texture operations, as well as tessellation logic and other vertex processing logic. In at least one embodiment, processing cluster array 2112 can be configured to execute graphics processing related shader programs such as, but not limited to, vertex shaders, tessellation shaders, geometry shaders, and pixel shaders. In at least one embodiment, parallel processing unit 2102 can transfer data from system memory via I/O unit 2104 for processing. In at least one embodiment, during processing, transferred data can be stored to on-chip memory (e.g., parallel processor memory 2122) during processing, then written back to system memory.

In at least one embodiment, when parallel processing unit 2102 is used to perform graphics processing, scheduler 2110 can be configured to divide a processing workload into approximately equal sized tasks, to better enable distribution of graphics processing operations to multiple clusters 2114A-2114N of processing cluster array 2112. In at least one embodiment, portions of processing cluster array 2112 can be configured to perform different types of processing. For example, in at least one embodiment, a first portion may be configured to perform vertex shading and topology generation, a second portion may be configured to perform tessellation and geometry shading, and a third portion may be configured to perform pixel shading or other screen space operations, to produce a rendered image for display. In at least one embodiment, intermediate data produced by one or more of clusters 2114A-2114N may be stored in buffers to allow intermediate data to be transmitted between clusters 2114A-2114N for further processing.

In at least one embodiment, processing cluster array 2112 can receive processing tasks to be executed via scheduler 2110, which receives commands defining processing tasks from front end 2108. In at least one embodiment, processing tasks can include indices of data to be processed, e.g., surface (patch) data, primitive data, vertex data, and/or pixel data, as well as state parameters and commands defining how data is to be processed (e.g., what program is to be executed). In at least one embodiment, scheduler 2110 may be configured to fetch indices corresponding to tasks or may receive indices from front end 2108. In at least one embodiment, front end 2108 can be configured to ensure processing cluster array 2112 is configured to a valid state before a workload specified by incoming command buffers (e.g., batch-buffers, push buffers, etc.) is initiated.

In at least one embodiment, each of one or more instances of parallel processing unit 2102 can couple with a parallel processor memory 2122. In at least one embodiment, parallel processor memory 2122 can be accessed via memory crossbar 2116, which can receive memory requests from processing cluster array 2112 as well as I/O unit 2104. In at least one embodiment, memory crossbar 2116 can access parallel processor memory 2122 via a memory interface 2118. In at least one embodiment, memory interface 2118 can include multiple partition units (e.g., partition unit 2120A, partition unit 2120B, through partition unit 2120N) that can each couple to a portion (e.g., memory unit) of parallel processor memory 2122. In at least one embodiment, a number of partition units 2120A-2120N is configured to be equal to a number of memory units, such that a first partition unit 2120A has a corresponding first memory unit 2124A, a second partition unit 2120B has a corresponding memory unit 2124B, and an N-th partition unit 2120N has a corresponding N-th memory unit 2124N. In at least one embodiment, a number of partition units 2120A-2120N may not be equal to a number of memory units.

In at least one embodiment, memory units 2124A-2124N can include various types of memory devices, including dynamic random access memory (DRAM) or graphics random access memory, such as synchronous graphics random access memory (SGRAM), including graphics double data rate (GDDR) memory. In at least one embodiment, memory units 2124A-2124N may also include 3D stacked memory, including but not limited to high bandwidth memory (HBM). In at least one embodiment, render targets, such as frame buffers or texture maps may be stored across memory units 2124A-2124N, allowing partition units 2120A-2120N to write portions of each render target in parallel to efficiently use available bandwidth of parallel processor memory 2122. In at least one embodiment, a local instance of parallel processor memory 2122 may be excluded in favor of a unified memory design that utilizes system memory in conjunction with local cache memory.

In at least one embodiment, any one of clusters 2114A-2114N of processing cluster array 2112 can process data that will be written to any of memory units 2124A-2124N within parallel processor memory 2122. In at least one embodiment, memory crossbar 2116 can be configured to transfer an output of each cluster 2114A-2114N to any partition unit 2120A-2120N or to another cluster 2114A-2114N, which can perform additional processing operations on an output. In at least one embodiment, each cluster 2114A-2114N can communicate with memory interface 2118 through memory crossbar 2116 to read from or write to various external memory devices. In at least one embodiment, memory crossbar 2116 has a connection to memory interface 2118 to communicate with I/O unit 2104, as well as a connection to a local instance of parallel processor memory 2122, enabling processing units within different processing clusters 2114A-2114N to communicate with system memory or other memory that is not local to parallel processing unit 2102. In at least one embodiment, memory crossbar 2116 can use virtual channels to separate traffic streams between clusters 2114A-2114N and partition units 2120A-2120N.

In at least one embodiment, multiple instances of parallel processing unit 2102 can be provided on a single add-in card, or multiple add-in cards can be interconnected. In at least one embodiment, different instances of parallel processing unit 2102 can be configured to interoperate even if different instances have different numbers of processing cores, different amounts of local parallel processor memory, and/or other configuration differences. For example, in at least one embodiment, some instances of parallel processing unit 2102 can include higher precision floating point units relative to other instances. In at least one embodiment, systems incorporating one or more instances of parallel processing unit 2102 or parallel processor 2100 can be implemented in a variety of configurations and form factors, including but not limited to desktop, laptop, or handheld personal computers, servers, workstations, game consoles, and/or embedded systems.

Figure 21B:
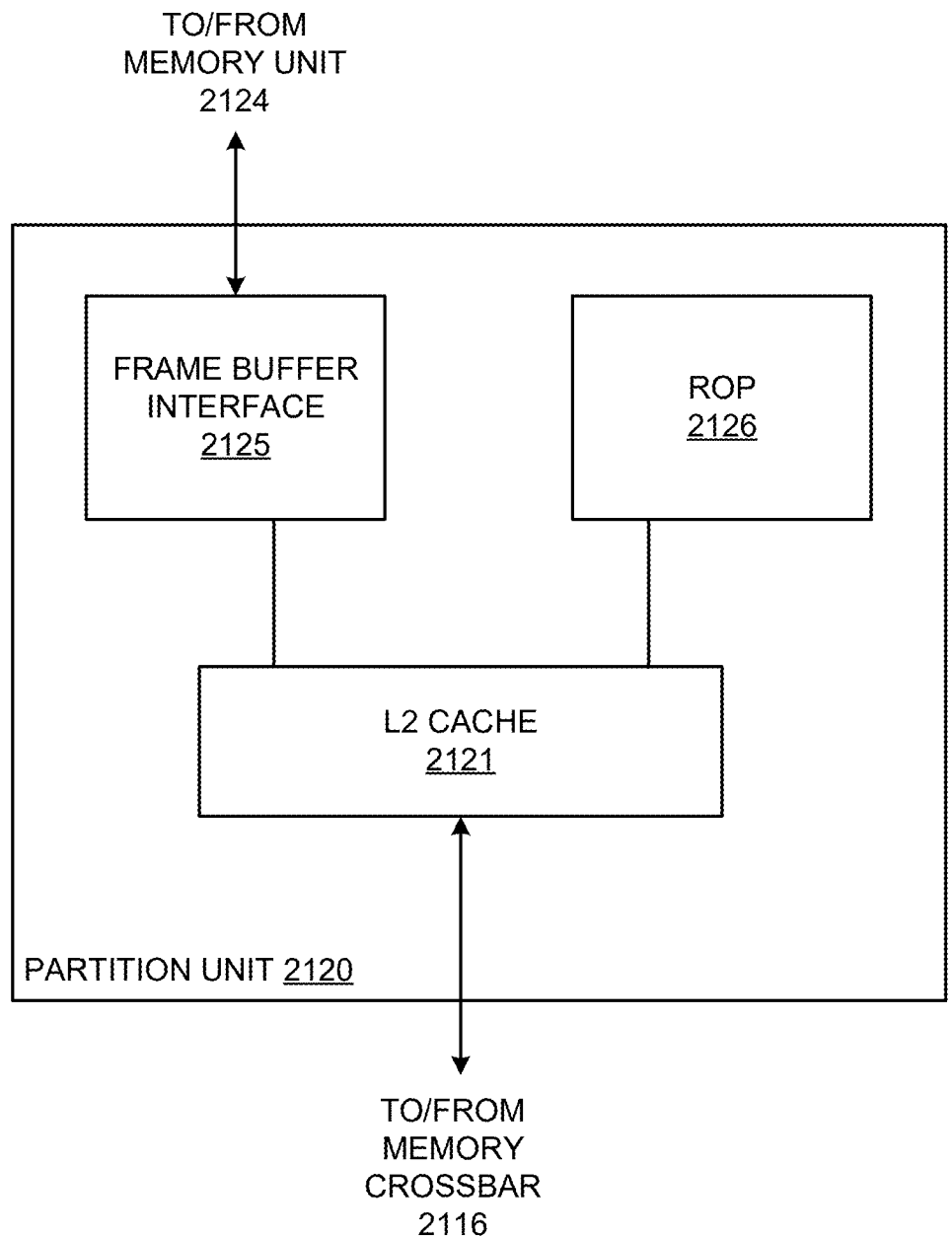
FIG. 21B illustrates a partition unit, according to at least one embodiment.

FIG. 21B is a block diagram of a partition unit 2120 according to at least one embodiment. In at least one embodiment, partition unit 2120 is an instance of one of partition units 2120A-2120N of FIG. 21A. In at least one embodiment, partition unit 2120 includes an L2 cache 2121, a frame buffer interface 2125, and a ROP 2126 (raster operations unit). In at least one embodiment, L2 cache 2121 is a read/write cache that is configured to perform load and store operations received from memory crossbar 2116 and ROP 2126. In at least one embodiment, read misses and urgent write-back requests are output by L2 cache 2121 to frame buffer interface 2125 for processing. In at least one embodiment, updates can also be sent to a frame buffer via frame buffer interface 2125 for processing. In at least one embodiment, frame buffer interface 2125 interfaces with one of memory units in parallel processor memory, such as memory units 2124A-2124N of FIG. 21 (e.g., within parallel processor memory 2122).

In at least one embodiment, ROP 2126 is a processing unit that performs raster operations such as stencil, z test, blending, etc. In at least one embodiment, ROP 2126 then outputs processed graphics data that is stored in graphics memory. In at least one embodiment, ROP 2126 includes compression logic to compress depth or color data that is written to memory and decompress depth or color data that is read from memory. In at least one embodiment, compression logic can be lossless compression logic that makes use of one or more of multiple compression algorithms. In at least one embodiment, a type of compression that is performed by ROP 2126 can vary based on statistical characteristics of data to be compressed. For example, in at least one embodiment, delta color compression is performed on depth and color data on a per-tile basis.

In at least one embodiment, ROP 2126 is included within each processing cluster (e.g., cluster 2114A-2114N of FIG. 21A) instead of within partition unit 2120. In at least one embodiment, read and write requests for pixel data are transmitted over memory crossbar 2116 instead of pixel fragment data. In at least one embodiment, processed graphics data may be displayed on a display device, such as one of one or more display device(s) 2010 of FIG. 20, routed for further processing by processor(s) 2002, or routed for further processing by one of processing entities within parallel processor 2100 of FIG. 21A.

Figure 21C:
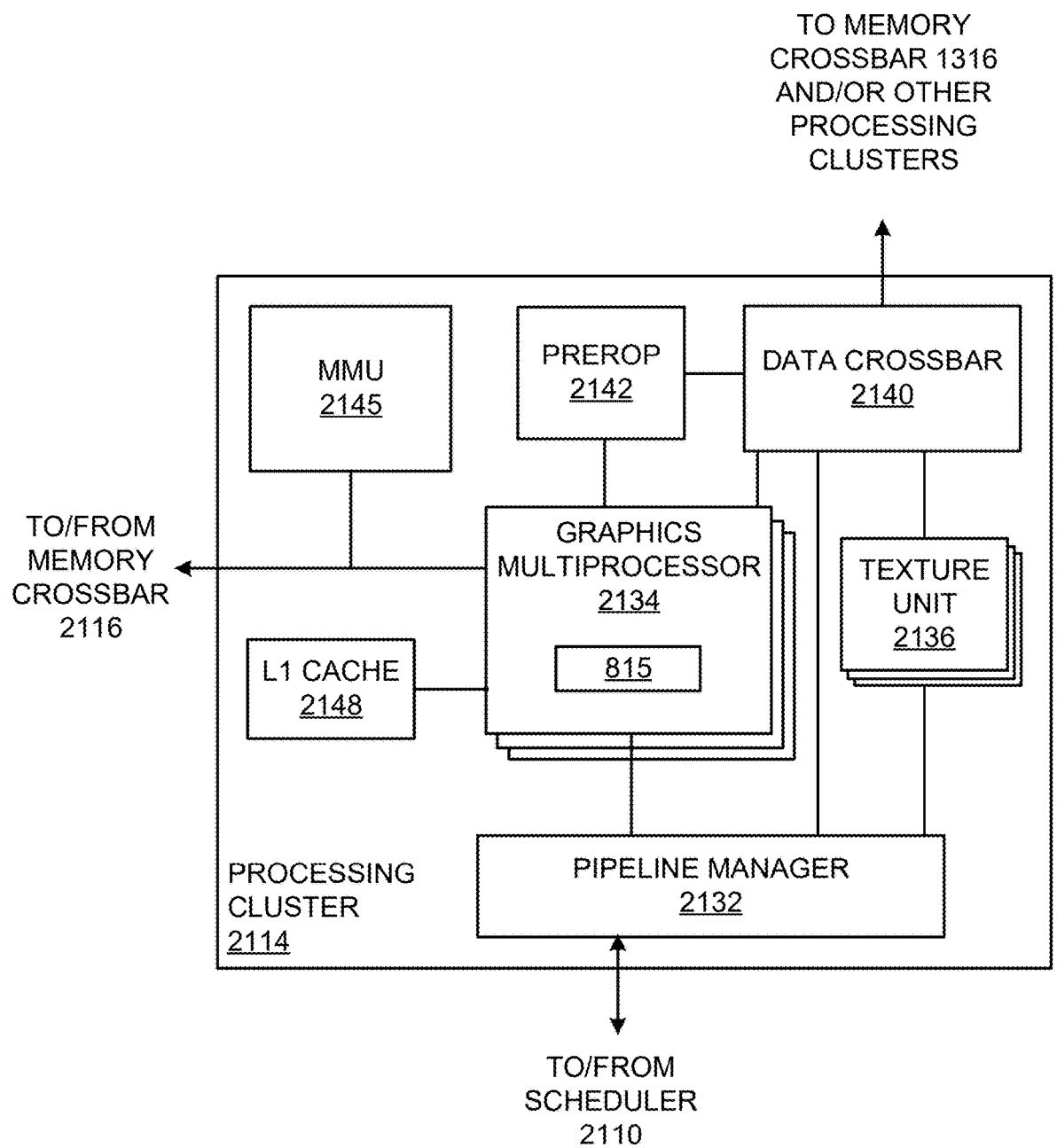
FIG. 21C illustrates a processing cluster, according to at least one embodiment.

FIG. 21C is a block diagram of a processing cluster 2114 within a parallel processing unit according to at least one embodiment. In at least one embodiment, a processing cluster is an instance of one of processing clusters 2114A-2114N of FIG. 21A. In at least one embodiment, processing cluster 2114 can be configured to execute many threads in parallel, where "thread" refers to an instance of a particular program executing on a particular set of input data. In at least one embodiment, single-instruction, multiple-data (SIMD) instruction issue techniques are used to support parallel execution of a large number of threads without providing multiple independent instruction units. In at least one embodiment, single-instruction, multiple-thread (SIMT) techniques are used to support parallel execution of a large number of generally synchronized threads, using a common instruction unit configured to issue instructions to a set of processing engines within each one of processing clusters.

In at least one embodiment, operation of processing cluster 2114 can be controlled via a pipeline manager 2132 that distributes processing tasks to SIMT parallel processors. In at least one embodiment, pipeline manager 2132 receives instructions from scheduler 2110 of FIG. 21A and manages execution of those instructions via a graphics multiprocessor 2134 and/or a texture unit 2136. In at least one embodiment, graphics multiprocessor 2134 is an exemplary instance of a SIMT parallel processor. However, in at least one embodiment, various types of SIMT parallel processors of differing architectures may be included within processing cluster 2114. In at least one embodiment, one or more instances of graphics multiprocessor 2134 can be included within a processing cluster 2114. In at least one embodiment, graphics multiprocessor 2134 can process data and a data crossbar 2140 can be used to distribute processed data to one of multiple possible destinations, including other shader units. In at least one embodiment, pipeline manager 2132 can facilitate distribution of processed data by specifying destinations for processed data to be distributed via data crossbar 2140.

In at least one embodiment, each graphics multiprocessor 2134 within processing cluster 2114 can include an identical set of functional execution logic (e.g., arithmetic logic units, load-store units, etc.). In at least one embodiment, functional execution logic can be configured in a pipelined manner in which new instructions can be issued before previous instructions are complete. In at least one embodiment, functional execution logic supports a variety of operations including integer and floating point arithmetic, comparison operations, Boolean operations, bit-shifting, and computation of various algebraic functions. In at least one embodiment, same functional-unit hardware can be leveraged to perform different operations and any combination of functional units may be present.

In at least one embodiment, instructions transmitted to processing cluster 2114 constitute a thread. In at least one embodiment, a set of threads executing across a set of parallel processing engines is a thread group. In at least one embodiment, a thread group executes a common program on different input data. In at least one embodiment, each thread within a thread group can be assigned to a different processing engine within a graphics multiprocessor 2134. In at least one embodiment, a thread group may include fewer threads than a number of processing engines within graphics multiprocessor 2134. In at least one embodiment, when a thread group includes fewer threads than a number of processing engines, one or more of processing engines may be idle during cycles in which that thread group is being processed. In at least one embodiment, a thread group may also include more threads than a number of processing engines within graphics multiprocessor 2134. In at least one embodiment, when a thread group includes more threads than number of processing engines within graphics multiprocessor 2134, processing can be performed over consecutive clock cycles. In at least one embodiment, multiple thread groups can be executed concurrently on a graphics multiprocessor 2134.

In at least one embodiment, graphics multiprocessor 2134 includes an internal cache memory to perform load and store operations. In at least one embodiment, graphics multiprocessor 2134 can forego an internal cache and use a cache memory (e.g., L1 cache 2148) within processing cluster 2114. In at least one embodiment, each graphics multiprocessor 2134 also has access to L2 caches within partition units (e.g., partition units 2120A-2120N of FIG. 21A) that are shared among all processing clusters 2114 and may be used to transfer data between threads. In at least one embodiment, graphics multiprocessor 2134 may also access off-chip global memory, which can include one or more of local parallel processor memory and/or system memory. In at least one embodiment, any memory external to parallel processing unit 2102 may be used as global memory. In at least one embodiment, processing cluster 2114 includes multiple instances of graphics multiprocessor 2134 and can share common instructions and data, which may be stored in L1 cache 2148.

In at least one embodiment, each processing cluster 2114 may include an MMU 2145 (memory management unit) that is configured to map virtual addresses into physical addresses. In at least one embodiment, one or more instances of MMU 2145 may reside within memory interface 2118 of FIG. 21A. In at least one embodiment, MMU 2145 includes a set of page table entries (PTEs) used to map a virtual address to a physical address of a tile and optionally a cache line index. In at least one embodiment, MMU 2145 may include address translation lookaside buffers (TLB) or caches that may reside within graphics multiprocessor 2134 or L1 2148 cache or processing cluster 2114. In at least one embodiment, a physical address is processed to distribute surface data access locally to allow for efficient request interleaving among partition units. In at least one embodiment, a cache line index may be used to determine whether a request for a cache line is a hit or miss.

In at least one embodiment, a processing cluster 2114 may be configured such that each graphics multiprocessor 2134 is coupled to a texture unit 2136 for performing texture mapping operations, e.g., determining texture sample positions, reading texture data, and filtering texture data. In at least one embodiment, texture data is read from an internal texture L1 cache (not shown) or from an L1 cache within graphics multiprocessor 2134 and is fetched from an L2 cache, local parallel processor memory, or system memory, as needed. In at least one embodiment, each graphics multiprocessor 2134 outputs processed tasks to data crossbar 2140 to provide processed task to another processing cluster 2114 for further processing or to store processed task in an L2 cache, local parallel processor memory, or system memory via memory crossbar 2116. In at least one embodiment, a preROP 2142 (pre-raster operations unit) is configured to receive data from graphics multiprocessor 2134, and direct data to ROP units, which may be located with partition units as described herein (e.g., partition units 2120A-2120N of FIG. 21A). In at least one embodiment, preROP 2142 unit can perform optimizations for color blending, organizing pixel color data, and performing address translations.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, inference and/or training logic 815 may be used in graphics processing cluster 2114 for inferencing or predicting operations based, at least in part, on weight parameters calculated using neural network training operations, neural network functions and/or architectures, or neural network use cases described herein.

Figure 21D:
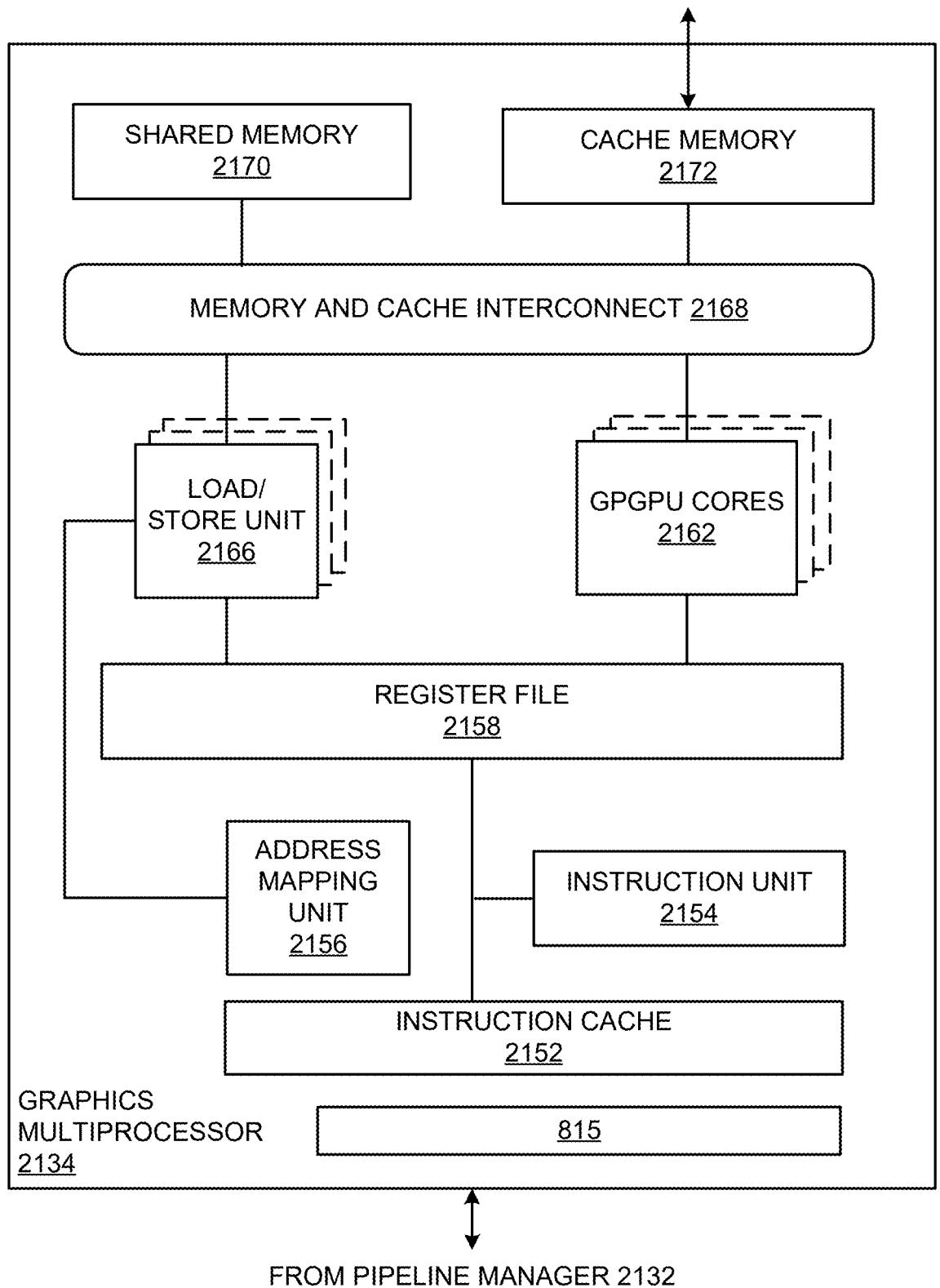
FIG. 21D illustrates a graphics multiprocessor, according to at least one embodiment.

FIG. 21D shows a graphics multiprocessor 2134 according to at least one embodiment. In at least one embodiment, graphics multiprocessor 2134 couples with pipeline manager 2132 of processing cluster 2114. In at least one embodiment, graphics multiprocessor 2134 has an execution pipeline including but not limited to an instruction cache 2152, an instruction unit 2154, an address mapping unit 2156, a register file 2158, one or more general purpose graphics processing unit (GPGPU) cores 2162, and one or more load/store units 2166. In at least one embodiment, GPGPU cores 2162 and load/store units 2166 are coupled with cache memory 2172 and shared memory 2170 via a memory and cache interconnect 2168.

In at least one embodiment, instruction cache 2152 receives a stream of instructions to execute from pipeline manager 2132. In at least one embodiment, instructions are cached in instruction cache 2152 and dispatched for execution by an instruction unit 2154. In at least one embodiment, instruction unit 2154 can dispatch instructions as thread groups (e.g., warps), with each thread of thread group assigned to a different execution unit within GPGPU cores 2162. In at least one embodiment, an instruction can access any of a local, shared, or global address space by specifying an address within a unified address space. In at least one embodiment, address mapping unit 2156 can be used to translate addresses in a unified address space into a distinct memory address that can be accessed by load/store units 2166.

In at least one embodiment, register file 2158 provides a set of registers for functional units of graphics multiprocessor 2134. In at least one embodiment, register file 2158 provides temporary storage for operands connected to data paths of functional units (e.g., GPGPU cores 2162, load/store units 2166) of graphics multiprocessor 2134. In at least one embodiment, register file 2158 is divided between each of functional units such that each functional unit is allocated a dedicated portion of register file 2158. In at least one embodiment, register file 2158 is divided between different warps being executed by graphics multiprocessor 2134.

In at least one embodiment, GPGPU cores 2162 can each include floating point units (FPUs) and/or integer arithmetic logic units (ALUs) that are used to execute instructions of graphics multiprocessor 2134. In at least one embodiment, GPGPU cores 2162 can be similar in architecture or can differ in architecture. In at least one embodiment, a first portion of GPGPU cores 2162 include a single precision FPU and an integer ALU while a second portion of GPGPU cores include a double precision FPU. In at least one embodiment, FPUs can implement IEEE 754-2008 standard floating point arithmetic or enable variable precision floating point arithmetic. In at least one embodiment, graphics multiprocessor 2134 can additionally include one or more fixed function or special function units to perform specific functions such as copy rectangle or pixel blending operations. In at least one embodiment, one or more of GPGPU cores 2162 can also include fixed or special function logic.

In at least one embodiment, GPGPU cores 2162 include SIMD logic capable of performing a single instruction on multiple sets of data. In at least one embodiment, GPGPU cores 2162 can physically execute SIMD4, SIMD8, and SIMD16 instructions and logically execute SIMD1, SIMD2, and SIMD32 instructions. In at least one embodiment, SIMD instructions for GPGPU cores can be generated at compile time by a shader compiler or automatically generated when executing programs written and compiled for single program multiple data (SPMD) or SIMT architectures. In at least one embodiment, multiple threads of a program configured for an SIMT execution model can executed via a single SIMD instruction. For example, in at least one embodiment, eight SIMT threads that perform same or similar operations can be executed in parallel via a single SIMD8 logic unit.

In at least one embodiment, memory and cache interconnect 2168 is an interconnect network that connects each functional unit of graphics multiprocessor 2134 to register file 2158 and to shared memory 2170. In at least one embodiment, memory and cache interconnect 2168 is a crossbar interconnect that allows load/store unit 2166 to implement load and store operations between shared memory 2170 and register file 2158. In at least one embodiment, register file 2158 can operate at a same frequency as GPGPU cores 2162, thus data transfer between GPGPU cores 2162 and register file 2158 can have very low latency. In at least one embodiment, shared memory 2170 can be used to enable communication between threads that execute on functional units within graphics multiprocessor 2134. In at least one embodiment, cache memory 2172 can be used as a data cache for example, to cache texture data communicated between functional units and texture unit 2136. In at least one embodiment, shared memory 2170 can also be used as a program managed cache. In at least one embodiment, threads executing on GPGPU cores 2162 can programmatically store data within shared memory in addition to automatically cached data that is stored within cache memory 2172.

In at least one embodiment, a parallel processor or GPGPU as described herein is communicatively coupled to host/processor cores to accelerate graphics operations, machine-learning operations, pattern analysis operations, and various general purpose GPU (GPGPU) functions. In at least one embodiment, a GPU may be communicatively coupled to host processor/cores over a bus or other interconnect (e.g., a high-speed interconnect such as PCIe or NVLink). In at least one embodiment, a GPU may be integrated on a package or chip as cores and communicatively coupled to cores over an internal processor bus/interconnect internal to a package or chip. In at least one embodiment, regardless a manner in which a GPU is connected, processor cores may allocate work to such GPU in a form of sequences of commands/instructions contained in a work descriptor. In at least one embodiment, that GPU then uses dedicated circuitry/logic for efficiently processing these commands/instructions.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, inference and/or training logic 815 may be used in graphics multiprocessor 2134 for inferencing or predicting operations based, at least in part, on weight parameters calculated using neural network training operations, neural network functions and/or architectures, or neural network use cases described herein.

In at least one embodiment, one or more systems depicted in FIGS. 21A-21D are utilized to generate segmentation and confidence values for pixels of an image. In at least one embodiment, one or more systems depicted in FIGS. 21A-21D are utilized to implement one or more networks and processes such as those described in connection with FIGS. 1-7. In at least one embodiment, one or more systems depicted in FIGS. 21A-21D are utilized to implement a system for segmentation and confidence value determination.

Figure 22:
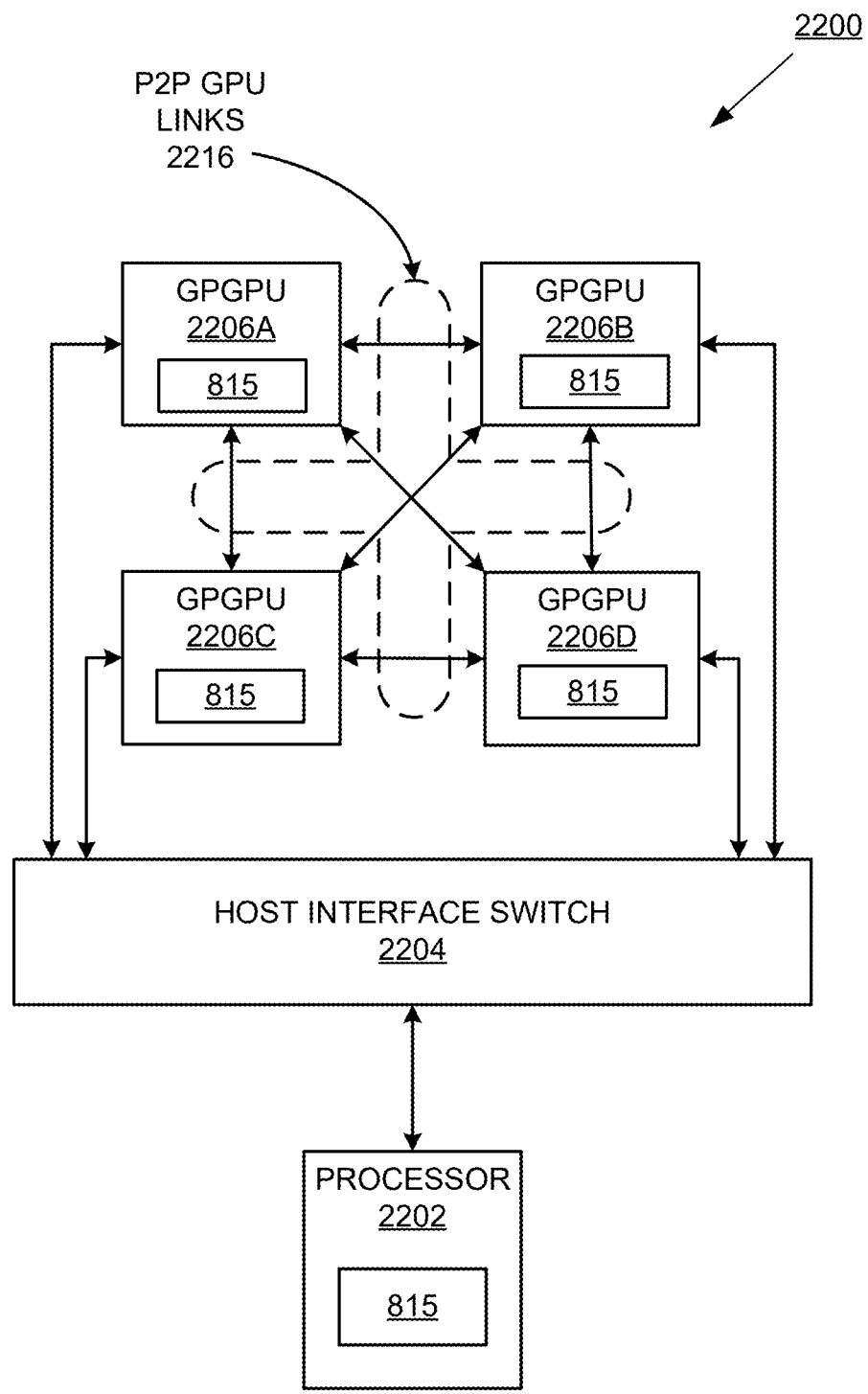
FIG. 22 illustrates a multi-graphics processing unit (GPU) system, according to at least one embodiment.

FIG. 22 illustrates a multi-GPU computing system 2200, according to at least one embodiment. In at least one embodiment, multi-GPU computing system 2200 can include a processor 2202 coupled to multiple general purpose graphics processing units (GPGPUs) 2206A-D via a host interface switch 2204. In at least one embodiment, host interface switch 2204 is a PCI express switch device that couples processor 2202 to a PCI express bus over which processor 2202 can communicate with GPGPUs 2206A-D. In at least one embodiment, GPGPUs 2206A-D can interconnect via a set of high-speed point-to-point GPU-to-GPU links 2216. In at least one embodiment, GPU-to-GPU links 2216 connect to each of GPGPUs 2206A-D via a dedicated GPU link. In at least one embodiment, P2P GPU links 2216 enable direct communication between each of GPGPUs 2206A-D without requiring communication over host interface bus 2204 to which processor 2202 is connected. In at least one embodiment, with GPU-to-GPU traffic directed to P2P GPU links 2216, host interface bus 2204 remains available for system memory access or to communicate with other instances of multi-GPU computing system 2200, for example, via one or more network devices. While in at least one embodiment GPGPUs 2206A-D connect to processor 2202 via host interface switch 2204, in at least one embodiment processor 2202 includes direct support for P2P GPU links 2216 and can connect directly to GPGPUs 2206A-D.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, inference and/or training logic 815 may be used in multi-GPU computing system 2200 for inferencing or predicting operations based, at least in part, on weight parameters calculated using neural network training operations, neural network functions and/or architectures, or neural network use cases described herein.

In at least one embodiment, one or more systems depicted in FIG. 22 are utilized to generate segmentation and confidence values for pixels of an image. In at least one embodiment, one or more systems depicted in FIG. 22 are utilized to implement one or more networks and processes such as those described in connection with FIGS. 1-7. In at least one embodiment, one or more systems depicted in FIG. 22 are utilized to implement a system for segmentation and confidence value determination.

Figure 23:
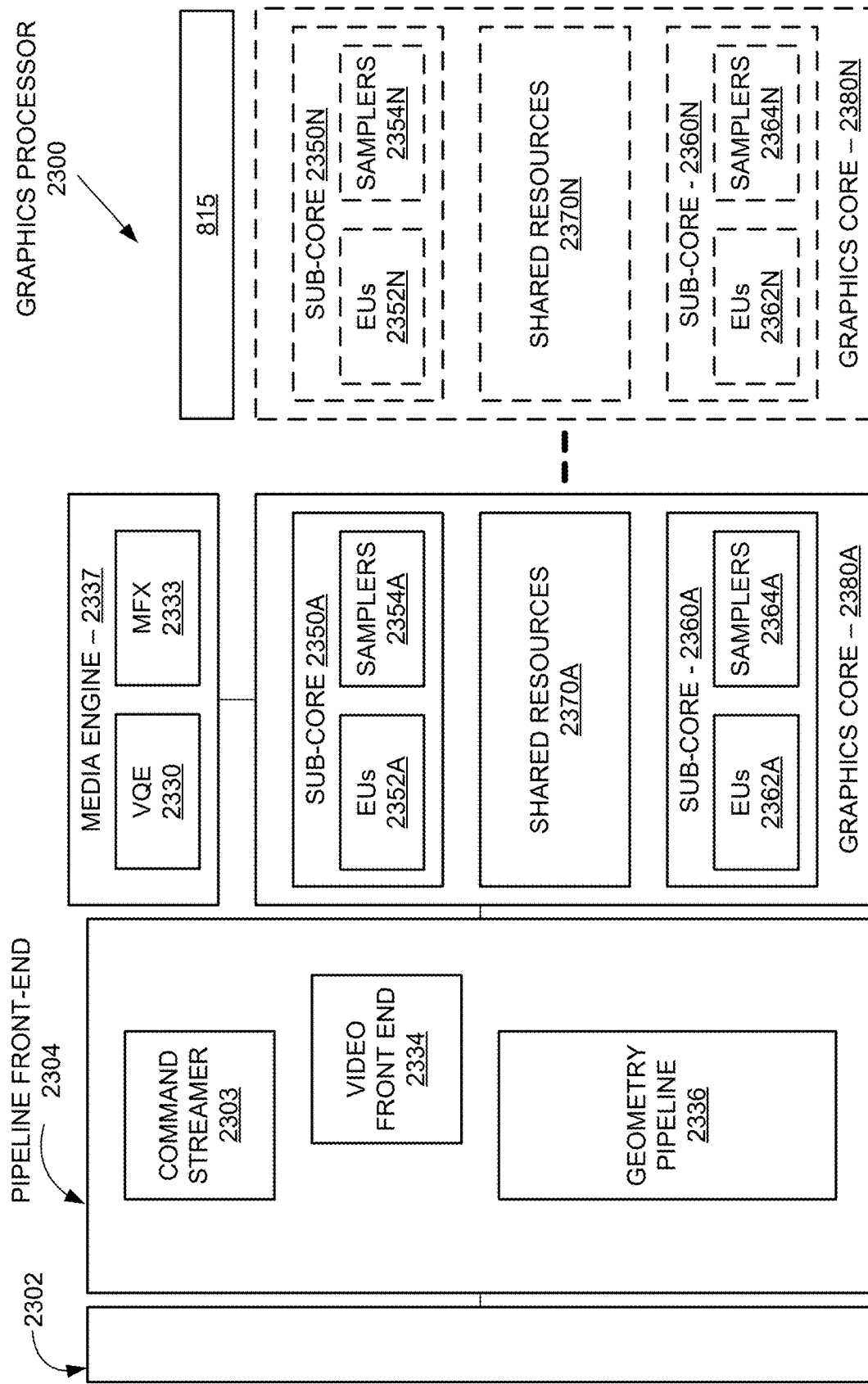
FIG. 23 illustrates a graphics processor, according to at least one embodiment.

FIG. 23 is a block diagram of a graphics processor 2300, according to at least one embodiment. In at least one embodiment, graphics processor 2300 includes a ring interconnect 2302, a pipeline front-end 2304, a media engine 2337, and graphics cores 2380A-2380N. In at least one embodiment, ring interconnect 2302 couples graphics processor 2300 to other processing units, including other graphics processors or one or more general-purpose processor cores. In at least one embodiment, graphics processor 2300 is one of many processors integrated within a multi-core processing system.

In at least one embodiment, graphics processor 2300 receives batches of commands via ring interconnect 2302. In at least one embodiment, incoming commands are interpreted by a command streamer 2303 in pipeline front-end 2304. In at least one embodiment, graphics processor 2300 includes scalable execution logic to perform 3D geometry processing and media processing via graphics core(s) 2380A-2380N. In at least one embodiment, for 3D geometry processing commands, command streamer 2303 supplies commands to geometry pipeline 2336. In at least one embodiment, for at least some media processing commands, command streamer 2303 supplies commands to a video front end 2334, which couples with media engine 2337. In at least one embodiment, media engine 2337 includes a Video Quality Engine (VQE) 2330 for video and image post-processing and a multi-format encode/decode (MFX) 2333 engine to provide hardware-accelerated media data encoding and decoding. In at least one embodiment, geometry pipeline 2336 and media engine 2337 each generate execution threads for thread execution resources provided by at least one graphics core 2380.

In at least one embodiment, graphics processor 2300 includes scalable thread execution resources featuring graphics cores 2380A-2380N (which can be modular and are sometimes referred to as core slices), each having multiple sub-cores 2350A-50N, 2360A-2360N (sometimes referred to as core sub-slices). In at least one embodiment, graphics processor 2300 can have any number of graphics cores 2380A. In at least one embodiment, graphics processor 2300 includes a graphics core 2380A having at least a first sub-core 2350A and a second sub-core 2360A. In at least one embodiment, graphics processor 2300 is a low power processor with a single sub-core (e.g., 2350A). In at least one embodiment, graphics processor 2300 includes multiple graphics cores 2380A-2380N, each including a set of first sub-cores 2350A-2350N and a set of second sub-cores 2360A-2360N. In at least one embodiment, each sub-core in first sub-cores 2350A-2350N includes at least a first set of execution units 2352A-2352N and media/texture samplers 2354A-2354N. In at least one embodiment, each sub-core in second sub-cores 2360A-2360N includes at least a second set of execution units 2362A-2362N and samplers 2364A-2364N. In at least one embodiment, each sub-core 2350A-2350N, 2360A-2360N shares a set of shared resources 2370A-2370N. In at least one embodiment, shared resources include shared cache memory and pixel operation logic.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, inference and/or training logic 815 may be used in graphics processor 2300 for inferencing or predicting operations based, at least in part, on weight parameters calculated using neural network training operations, neural network functions and/or architectures, or neural network use cases described herein.

In at least one embodiment, one or more systems depicted in FIG. 23 are utilized to generate segmentation and confidence values for pixels of an image. In at least one embodiment, one or more systems depicted in FIG. 23 are utilized to implement one or more networks and processes such as those described in connection with FIGS. 1-7. In at least one embodiment, one or more systems depicted in FIG. 23 are utilized to implement a system for segmentation and confidence value determination.

Figure 24:
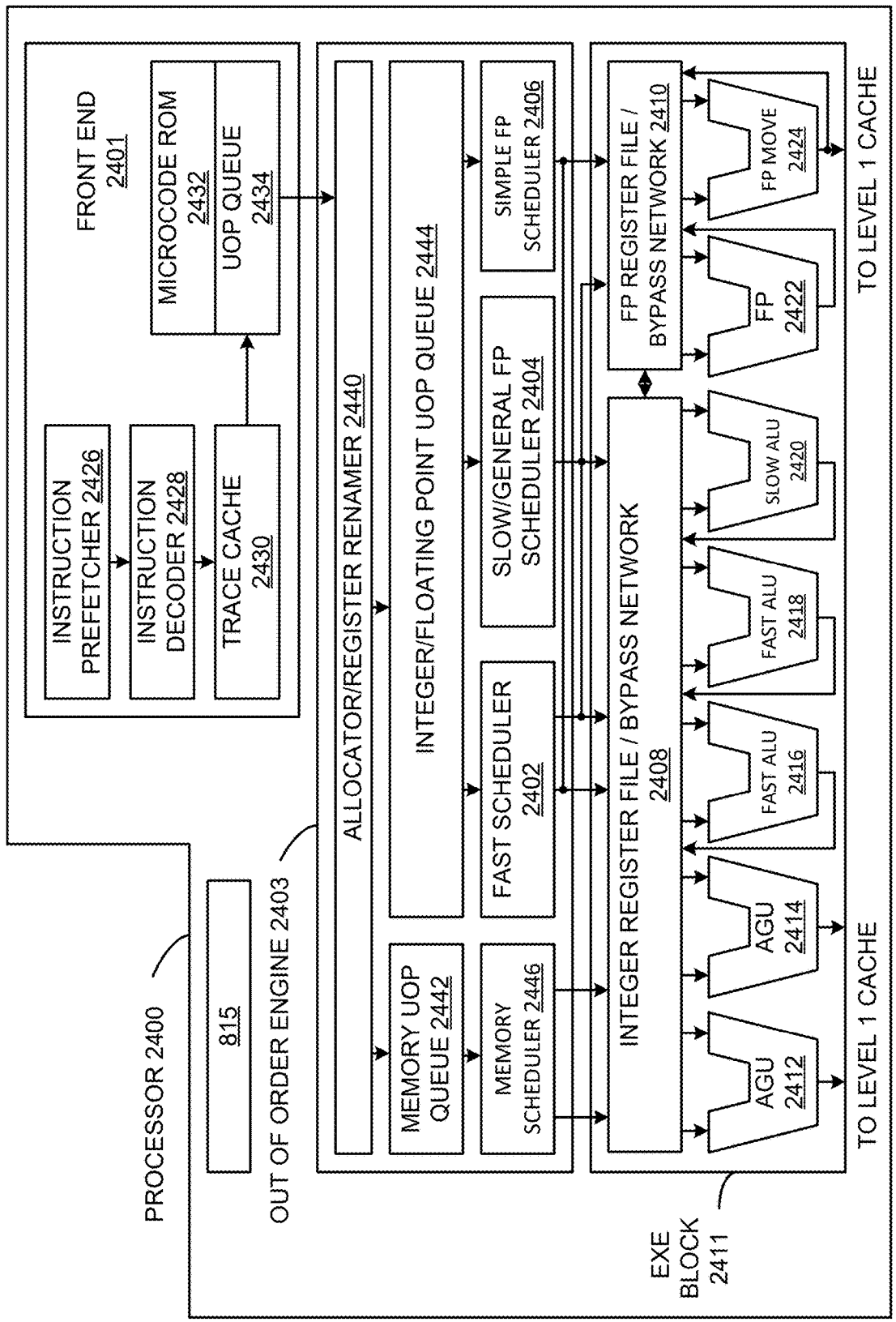
FIG. 24 is a block diagram illustrating a processor microarchitecture for a processor, according to at least one embodiment.

FIG. 24 is a block diagram illustrating micro-architecture for a processor 2400 that may include logic circuits to perform instructions, according to at least one embodiment. In at least one embodiment, processor 2400 may perform instructions, including x86 instructions, ARM instructions, specialized instructions for application-specific integrated circuits (ASICs), etc. In at least one embodiment, processor 2400 may include registers to store packed data, such as 64-bit wide MMX™ registers in microprocessors enabled with MMX technology from Intel Corporation of Santa Clara, Calif. In at least one embodiment, MMX registers, available in both integer and floating point forms, may operate with packed data elements that accompany single instruction, multiple data ("SIMD") and streaming SIMD extensions ("SSE") instructions. In at least one embodiment, 128-bit wide XMM registers relating to SSE2, SSE3, SSE4, AVX, or beyond (referred to generically as "SSEx") technology may hold such packed data operands. In at least one embodiment, processor 2400 may perform instructions to accelerate machine learning or deep learning algorithms, training, or inferencing.

In at least one embodiment, processor 2400 includes an in-order front end ("front end") 2401 to fetch instructions to be executed and prepare instructions to be used later in a processor pipeline. In at least one embodiment, front end 2401 may include several units. In at least one embodiment, an instruction prefetcher 2426 fetches instructions from memory and feeds instructions to an instruction decoder 2428 which in turn decodes or interprets instructions. For example, in at least one embodiment, instruction decoder 2428 decodes a received instruction into one or more operations called "micro-instructions" or "micro-operations" (also called "micro ops" or "uops") that a machine may execute. In at least one embodiment, instruction decoder 2428 parses an instruction into an opcode and corresponding data and control fields that may be used by micro-architecture to perform operations in accordance with at least one embodiment. In at least one embodiment, a trace cache 2430 may assemble decoded uops into program ordered sequences or traces in a uop queue 2434 for execution. In at least one embodiment, when trace cache 2430 encounters a complex instruction, a microcode ROM 2432 provides uops needed to complete an operation.

In at least one embodiment, some instructions may be converted into a single micro-op, whereas others need several micro-ops to complete full operation. In at least one embodiment, if more than four micro-ops are needed to complete an instruction, instruction decoder 2428 may access microcode ROM 2432 to perform that instruction. In at least one embodiment, an instruction may be decoded into a small number of micro-ops for processing at instruction decoder 2428. In at least one embodiment, an instruction may be stored within microcode ROM 2432 should a number of micro-ops be needed to accomplish such operation. In at least one embodiment, trace cache 2430 refers to an entry point programmable logic array ("PLA") to determine a correct micro-instruction pointer for reading microcode sequences to complete one or more instructions from microcode ROM 2432 in accordance with at least one embodiment. In at least one embodiment, after microcode ROM 2432 finishes sequencing micro-ops for an instruction, front end 2401 of a machine may resume fetching micro-ops from trace cache 2430.

In at least one embodiment, out-of-order execution engine ("out of order engine") 2403 may prepare instructions for execution. In at least one embodiment, out-of-order execution logic has a number of buffers to smooth out and re-order flow of instructions to optimize performance as they go down a pipeline and get scheduled for execution. In at least one embodiment, out-of-order execution engine 2403 includes, without limitation, an allocator/register renamer 2440, a memory uop queue 2442, an integer/floating point uop queue 2444, a memory scheduler 2446, a fast scheduler 2402, a slow/general floating point scheduler ("slow/general FP scheduler") 2404, and a simple floating point scheduler ("simple FP scheduler") 2406. In at least one embodiment, fast schedule 2402, slow/general floating point scheduler 2404, and simple floating point scheduler 2406 are also collectively referred to herein as "uop schedulers 2402, 2404, 2406." In at least one embodiment, allocator/register renamer 2440 allocates machine buffers and resources that each uop needs in order to execute. In at least one embodiment, allocator/register renamer 2440 renames logic registers onto entries in a register file. In at least one embodiment, allocator/register renamer 2440 also allocates an entry for each uop in one of two uop queues, memory uop queue 2442 for memory operations and integer/floating point uop queue 2444 for non-memory operations, in front of memory scheduler 2446 and uop schedulers 2402, 2404, 2406. In at least one embodiment, uop schedulers 2402, 2404, 2406, determine when a uop is ready to execute based on readiness of their dependent input register operand sources and availability of execution resources uops need to complete their operation. In at least one embodiment, fast scheduler 2402 may schedule on each half of a main clock cycle while slow/general floating point scheduler 2404 and simple floating point scheduler 2406 may schedule once per main processor clock cycle. In at least one embodiment, uop schedulers 2402, 2404, 2406 arbitrate for dispatch ports to schedule uops for execution.

In at least one embodiment, execution block 2411 includes, without limitation, an integer register file/bypass network 2408, a floating point register file/bypass network ("FP register file/bypass network") 2410, address generation units ("AGUs") 2412 and 2414, fast Arithmetic Logic Units (ALUs) ("fast ALUs") 2416 and 2418, a slow Arithmetic Logic Unit ("slow ALU") 2420, a floating point ALU ("FP") 2422, and a floating point move unit ("FP move") 2424. In at least one embodiment, integer register file/bypass network 2408 and floating point register file/bypass network 2410 are also referred to herein as "register files 2408, 2410." In at least one embodiment, AGUSs 2412 and 2414, fast ALUs 2416 and 2418, slow ALU 2420, floating point ALU 2422, and floating point move unit 2424 are also referred to herein as "execution units 2412, 2414, 2416, 2418, 2420, 2422, and 2424." In at least one embodiment, execution block 2411 may include, without limitation, any number (including zero) and type of register files, bypass networks, address generation units, and execution units, in any combination.

In at least one embodiment, register networks 2408, 2410 may be arranged between uop schedulers 2402, 2404, 2406, and execution units 2412, 2414, 2416, 2418, 2420, 2422, and 2424. In at least one embodiment, integer register file/bypass network 2408 performs integer operations. In at least one embodiment, floating point register file/bypass network 2410 performs floating point operations. In at least one embodiment, each of register networks 2408, 2410 may include, without limitation, a bypass network that may bypass or forward just completed results that have not yet been written into a register file to new dependent uops. In at least one embodiment, register networks 2408, 2410 may communicate data with each other. In at least one embodiment, integer register file/bypass network 2408 may include, without limitation, two separate register files, one register file for a low-order thirty-two bits of data and a second register file for a high order thirty-two bits of data. In at least one embodiment, floating point register file/bypass network 2410 may include, without limitation, 128-bit wide entries because floating point instructions typically have operands from 64 to 128 bits in width.

In at least one embodiment, execution units 2412, 2414, 2416, 2418, 2420, 2422, 2424 may execute instructions. In at least one embodiment, register networks 2408, 2410 store integer and floating point data operand values that micro-instructions need to execute. In at least one embodiment, processor 2400 may include, without limitation, any number and combination of execution units 2412, 2414, 2416, 2418, 2420, 2422, 2424. In at least one embodiment, floating point ALU 2422 and floating point move unit 2424, may execute floating point, MMX, SIMD, AVX and SSE, or other operations, including specialized machine learning instructions. In at least one embodiment, floating point ALU 2422 may include, without limitation, a 64-bit by 64-bit floating point divider to execute divide, square root, and remainder micro ops. In at least one embodiment, instructions involving a floating point value may be handled with floating point hardware. In at least one embodiment, ALU operations may be passed to fast ALUs 2416, 2418. In at least one embodiment, fast ALUS 2416, 2418 may execute fast operations with an effective latency of half a clock cycle. In at least one embodiment, most complex integer operations go to slow ALU 2420 as slow ALU 2420 may include, without limitation, integer execution hardware for long-latency type of operations, such as a multiplier, shifts, flag logic, and branch processing. In at least one embodiment, memory load/store operations may be executed by AGUs 2412, 2414. In at least one embodiment, fast ALU 2416, fast ALU 2418, and slow ALU 2420 may perform integer operations on 64-bit data operands. In at least one embodiment, fast ALU 2416, fast ALU 2418, and slow ALU 2420 may be implemented to support a variety of data bit sizes including sixteen, thirty-two, 128, 256, etc. In at least one embodiment, floating point ALU 2422 and floating point move unit 2424 may be implemented to support a range of operands having bits of various widths, such as 128-bit wide packed data operands in conjunction with SIMD and multimedia instructions.

In at least one embodiment, uop schedulers 2402, 2404, 2406 dispatch dependent operations before a parent load has finished executing. In at least one embodiment, as uops may be speculatively scheduled and executed in processor 2400, processor 2400 may also include logic to handle memory misses. In at least one embodiment, if a data load misses in a data cache, there may be dependent operations in flight in a pipeline that have left a scheduler with temporarily incorrect data. In at least one embodiment, a replay mechanism tracks and re-executes instructions that use incorrect data. In at least one embodiment, dependent operations might need to be replayed and independent ones may be allowed to complete. In at least one embodiment, schedulers and a replay mechanism of at least one embodiment of a processor may also be designed to catch instruction sequences for text string comparison operations.

In at least one embodiment, "registers" may refer to on-board processor storage locations that may be used as part of instructions to identify operands. In at least one embodiment, registers may be those that may be usable from outside of a processor (from a programmer's perspective). In at least one embodiment, registers might not be limited to a particular type of circuit. Rather, in at least one embodiment, a register may store data, provide data, and perform functions described herein. In at least one embodiment, registers described herein may be implemented by circuitry within a processor using any number of different techniques, such as dedicated physical registers, dynamically allocated physical registers using register renaming, combinations of dedicated and dynamically allocated physical registers, etc. In at least one embodiment, integer registers store 32-bit integer data. A register file of at least one embodiment also contains eight multimedia SIMD registers for packed data.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment portions or all of inference and/or training logic 815 may be incorporated into execution block 2411 and other memory or registers shown or not shown. For example, in at least one embodiment, training and/or inferencing techniques described herein may use one or more of ALUs illustrated in execution block 2411. Moreover, weight parameters may be stored in on-chip or off-chip memory and/or registers (shown or not shown) that configure ALUs of execution block 2411 to perform one or more machine learning algorithms, neural network architectures, use cases, or training techniques described herein.

In at least one embodiment, one or more systems depicted in FIG. 24 are utilized to generate segmentation and confidence values for pixels of an image. In at least one embodiment, one or more systems depicted in FIG. 24 are utilized to implement one or more networks and processes such as those described in connection with FIGS. 1-7. In at least one embodiment, one or more systems depicted in FIG. 24 are utilized to implement a system for segmentation and confidence value determination.

Figure 25:
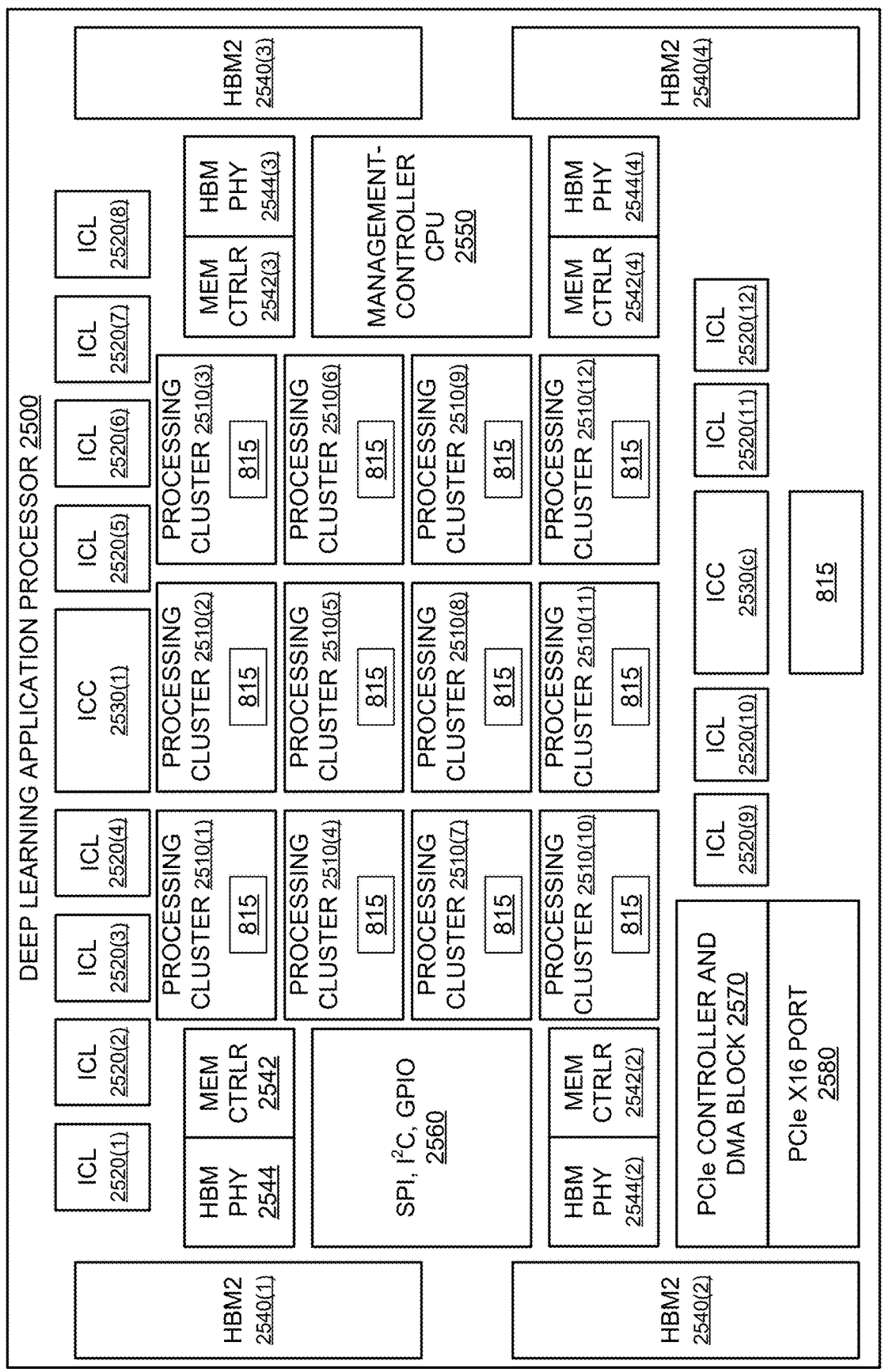
FIG. 25 illustrates a deep learning application processor, according to at least one embodiment.

FIG. 25 illustrates a deep learning application processor 2500, according to at least one embodiment. In at least one embodiment, deep learning application processor 2500 uses instructions that, if executed by deep learning application processor 2500, cause deep learning application processor 2500 to perform some or all of processes and techniques described throughout this disclosure. In at least one embodiment, deep learning application processor 2500 is an application-specific integrated circuit (ASIC). In at least one embodiment, application processor 2500 performs matrix multiply operations either "hard-wired" into hardware as a result of performing one or more instructions or both. In at least one embodiment, deep learning application processor 2500 includes, without limitation, processing clusters 2510(1)-2510(12), Inter-Chip Links ("ICLs") 2520(1)-2520(12), Inter-Chip Controllers ("ICCs") 2530(1)-2530(2), high-bandwidth memory second generation ("HBM2") 2540(1)-2540(4), memory controllers ("Mem Ctrlrs") 2542(1)-2542(4), high bandwidth memory physical layer ("HBM PHY") 2544(1)-2544(4), a management-controller central processing unit ("management-controller CPU") 2550, a Serial Peripheral Interface, Inter-Integrated Circuit, and General Purpose Input/Output block ("SPI, I²C, GPIO") 2560, a peripheral component interconnect express controller and direct memory access block ("PCIe Controller and DMA") 2570, and a sixteen-lane peripheral component interconnect express port ("PCI Express×16") 2580.

In at least one embodiment, processing clusters 2510 may perform deep learning operations, including inference or prediction operations based on weight parameters calculated one or more training techniques, including those described herein. In at least one embodiment, each processing cluster 2510 may include, without limitation, any number and type of processors. In at least one embodiment, deep learning application processor 2500 may include any number and type of processing clusters 2500. In at least one embodiment, Inter-Chip Links 2520 are bi-directional. In at least one embodiment, Inter-Chip Links 2520 and Inter-Chip Controllers 2530 enable multiple deep learning application processors 2500 to exchange information, including activation information resulting from performing one or more machine learning algorithms embodied in one or more neural networks. In at least one embodiment, deep learning application processor 2500 may include any number (including zero) and type of ICLs 2520 and ICCs 2530.

In at least one embodiment, HBM2s 2540 provide a total of 32 Gigabytes (GB) of memory. In at least one embodiment, HBM2 2540(i) is associated with both memory controller 2542(i) and HBM PHY 2544(i) where "i" is an arbitrary integer. In at least one embodiment, any number of HBM2s 2540 may provide any type and total amount of high bandwidth memory and may be associated with any number (including zero) and type of memory controllers 2542 and HBM PHYs 2544. In at least one embodiment, SPI, I²C, GPIO 2560, PCIe Controller and DMA 2570, and/or PCIe 2580 may be replaced with any number and type of blocks that enable any number and type of communication standards in any technically feasible fashion.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, deep learning application processor is used to train a machine learning model, such as a neural network, to predict or infer information provided to deep learning application processor 2500. In at least one embodiment, deep learning application processor 2500 is used to infer or predict information based on a trained machine learning model (e.g., neural network) that has been trained by another processor or system or by deep learning application processor 2500. In at least one embodiment, processor 2500 may be used to perform one or more neural network use cases described herein.

In at least one embodiment, one or more systems depicted in FIG. 25 are utilized to generate segmentation and confidence values for pixels of an image. In at least one embodiment, one or more systems depicted in FIG. 25 are utilized to implement one or more networks and processes such as those described in connection with FIGS. 1-7. In at least one embodiment, one or more systems depicted in FIG. 25 are utilized to implement a system for segmentation and confidence value determination.

Figure 26:
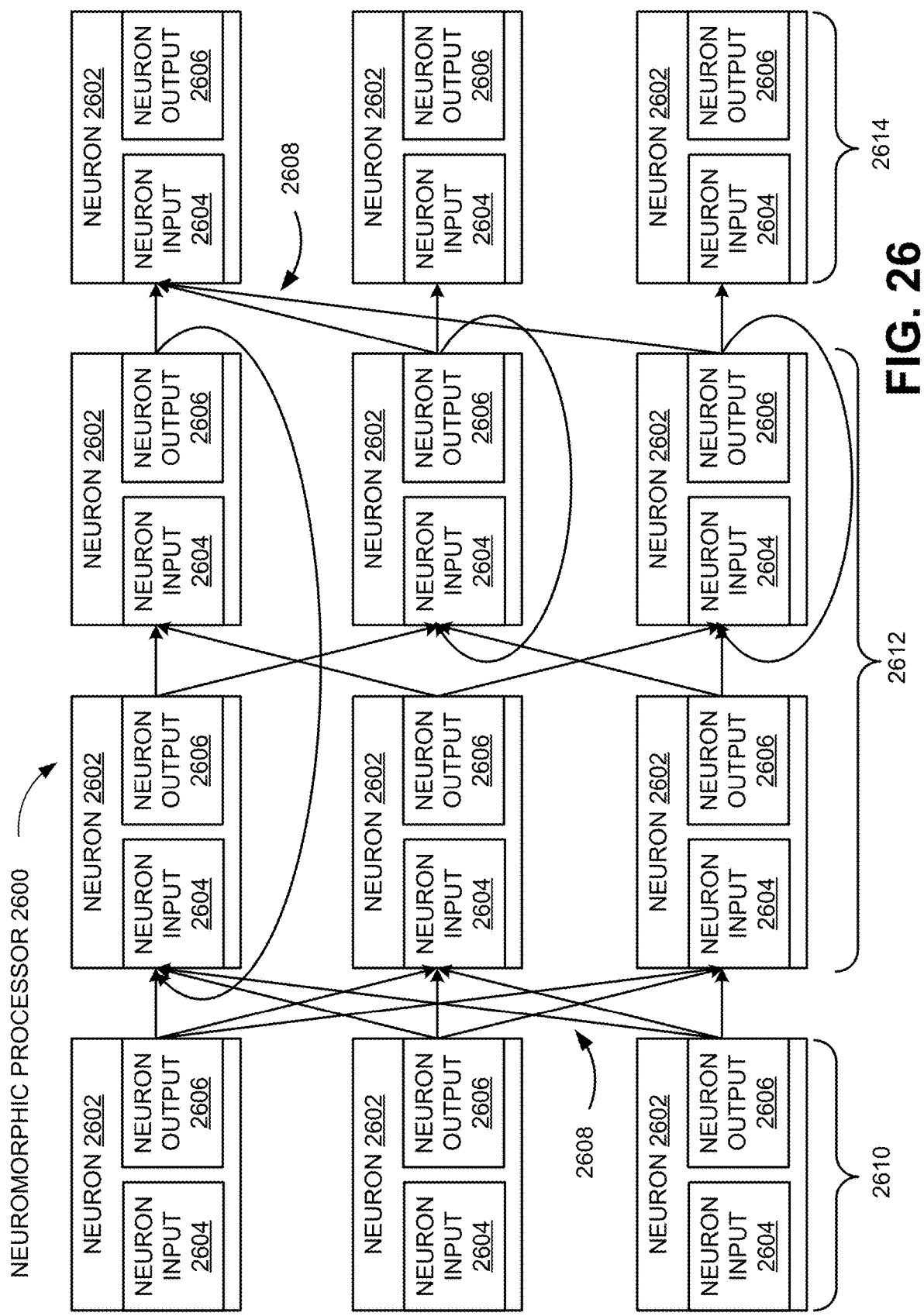
FIG. 26 is a block diagram illustrating an example neuromorphic processor, according to at least one embodiment.

FIG. 26 is a block diagram of a neuromorphic processor 2600, according to at least one embodiment. In at least one embodiment, neuromorphic processor 2600 may receive one or more inputs from sources external to neuromorphic processor 2600. In at least one embodiment, these inputs may be transmitted to one or more neurons 2602 within neuromorphic processor 2600. In at least one embodiment, neurons 2602 and components thereof may be implemented using circuitry or logic, including one or more arithmetic logic units (ALUs). In at least one embodiment, neuromorphic processor 2600 may include, without limitation, thousands or millions of instances of neurons 2602, but any suitable number of neurons 2602 may be used. In at least one embodiment, each instance of neuron 2602 may include a neuron input 2604 and a neuron output 2606. In at least one embodiment, neurons 2602 may generate outputs that may be transmitted to inputs of other instances of neurons 2602. For example, in at least one embodiment, neuron inputs 2604 and neuron outputs 2606 may be interconnected via synapses 2608.

In at least one embodiment, neurons 2602 and synapses 2608 may be interconnected such that neuromorphic processor 2600 operates to process or analyze information received by neuromorphic processor 2600. In at least one embodiment, neurons 2602 may transmit an output pulse (or "fire" or "spike") when inputs received through neuron input 2604 exceed a threshold. In at least one embodiment, neurons 2602 may sum or integrate signals received at neuron inputs 2604. For example, in at least one embodiment, neurons 2602 may be implemented as leaky integrate-and-fire neurons, wherein if a sum (referred to as a "membrane potential") exceeds a threshold value, neuron 2602 may generate an output (or "fire") using a transfer function such as a sigmoid or threshold function. In at least one embodiment, a leaky integrate-and-fire neuron may sum signals received at neuron inputs 2604 into a membrane potential and may also apply a decay factor (or leak) to reduce a membrane potential. In at least one embodiment, a leaky integrate-and-fire neuron may fire if multiple input signals are received at neuron inputs 2604 rapidly enough to exceed a threshold value (i.e., before a membrane potential decays too low to fire). In at least one embodiment, neurons 2602 may be implemented using circuits or logic that receive inputs, integrate inputs into a membrane potential, and decay a membrane potential. In at least one embodiment, inputs may be averaged, or any other suitable transfer function may be used. Furthermore, in at least one embodiment, neurons 2602 may include, without limitation, comparator circuits or logic that generate an output spike at neuron output 2606 when result of applying a transfer function to neuron input 2604 exceeds a threshold. In at least one embodiment, once neuron 2602 fires, it may disregard previously received input information by, for example, resetting a membrane potential to 0 or another suitable default value. In at least one embodiment, once membrane potential is reset to 0, neuron 2602 may resume normal operation after a suitable period of time (or refractory period).

In at least one embodiment, neurons 2602 may be interconnected through synapses 2608. In at least one embodiment, synapses 2608 may operate to transmit signals from an output of a first neuron 2602 to an input of a second neuron 2602. In at least one embodiment, neurons 2602 may transmit information over more than one instance of synapse 2608. In at least one embodiment, one or more instances of neuron output 2606 may be connected, via an instance of synapse 2608, to an instance of neuron input 2604 in same neuron 2602. In at least one embodiment, an instance of neuron 2602 generating an output to be transmitted over an instance of synapse 2608 may be referred to as a "presynaptic neuron" with respect to that instance of synapse 2608. In at least one embodiment, an instance of neuron 2602 receiving an input transmitted over an instance of synapse 2608 may be referred to as a "post-synaptic neuron" with respect to that instance of synapse 2608. Because an instance of neuron 2602 may receive inputs from one or more instances of synapse 2608, and may also transmit outputs over one or more instances of synapse 2608, a single instance of neuron 2602 may therefore be both a "presynaptic neuron" and "post-synaptic neuron," with respect to various instances of synapses 2608, in at least one embodiment.

In at least one embodiment, neurons 2602 may be organized into one or more layers. In at least one embodiment, each instance of neuron 2602 may have one neuron output 2606 that may fan out through one or more synapses 2608 to one or more neuron inputs 2604. In at least one embodiment, neuron outputs 2606 of neurons 2602 in a first layer 2610 may be connected to neuron inputs 2604 of neurons 2602 in a second layer 2612. In at least one embodiment, layer 2610 may be referred to as a "feed-forward layer." In at least one embodiment, each instance of neuron 2602 in an instance of first layer 2610 may fan out to each instance of neuron 2602 in second layer 2612. In at least one embodiment, first layer 2610 may be referred to as a "fully connected feed-forward layer." In at least one embodiment, each instance of neuron 2602 in an instance of second layer 2612 may fan out to fewer than all instances of neuron 2602 in a third layer 2614. In at least one embodiment, second layer 2612 may be referred to as a "sparsely connected feed-forward layer." In at least one embodiment, neurons 2602 in second layer 2612 may fan out to neurons 2602 in multiple other layers, including to neurons 2602 also in second layer 2612. In at least one embodiment, second layer 2612 may be referred to as a "recurrent layer." In at least one embodiment, neuromorphic processor 2600 may include, without limitation, any suitable combination of recurrent layers and feed-forward layers, including, without limitation, both sparsely connected feed-forward layers and fully connected feed-forward layers.

In at least one embodiment, neuromorphic processor 2600 may include, without limitation, a reconfigurable interconnect architecture or dedicated hard-wired interconnects to connect synapse 2608 to neurons 2602. In at least one embodiment, neuromorphic processor 2600 may include, without limitation, circuitry or logic that allows synapses to be allocated to different neurons 2602 as needed based on neural network topology and neuron fan-in/out. For example, in at least one embodiment, synapses 2608 may be connected to neurons 2602 using an interconnect fabric, such as network-on-chip, or with dedicated connections. In at least one embodiment, synapse interconnections and components thereof may be implemented using circuitry or logic.

In at least one embodiment, one or more systems depicted in FIG. 26 are utilized to generate segmentation and confidence values for pixels of an image. In at least one embodiment, one or more systems depicted in FIG. 26 are utilized to implement one or more networks and processes such as those described in connection with FIGS. 1-7. In at least one embodiment, one or more systems depicted in FIG. 26 are utilized to implement a system for segmentation and confidence value determination.

Figure 27:
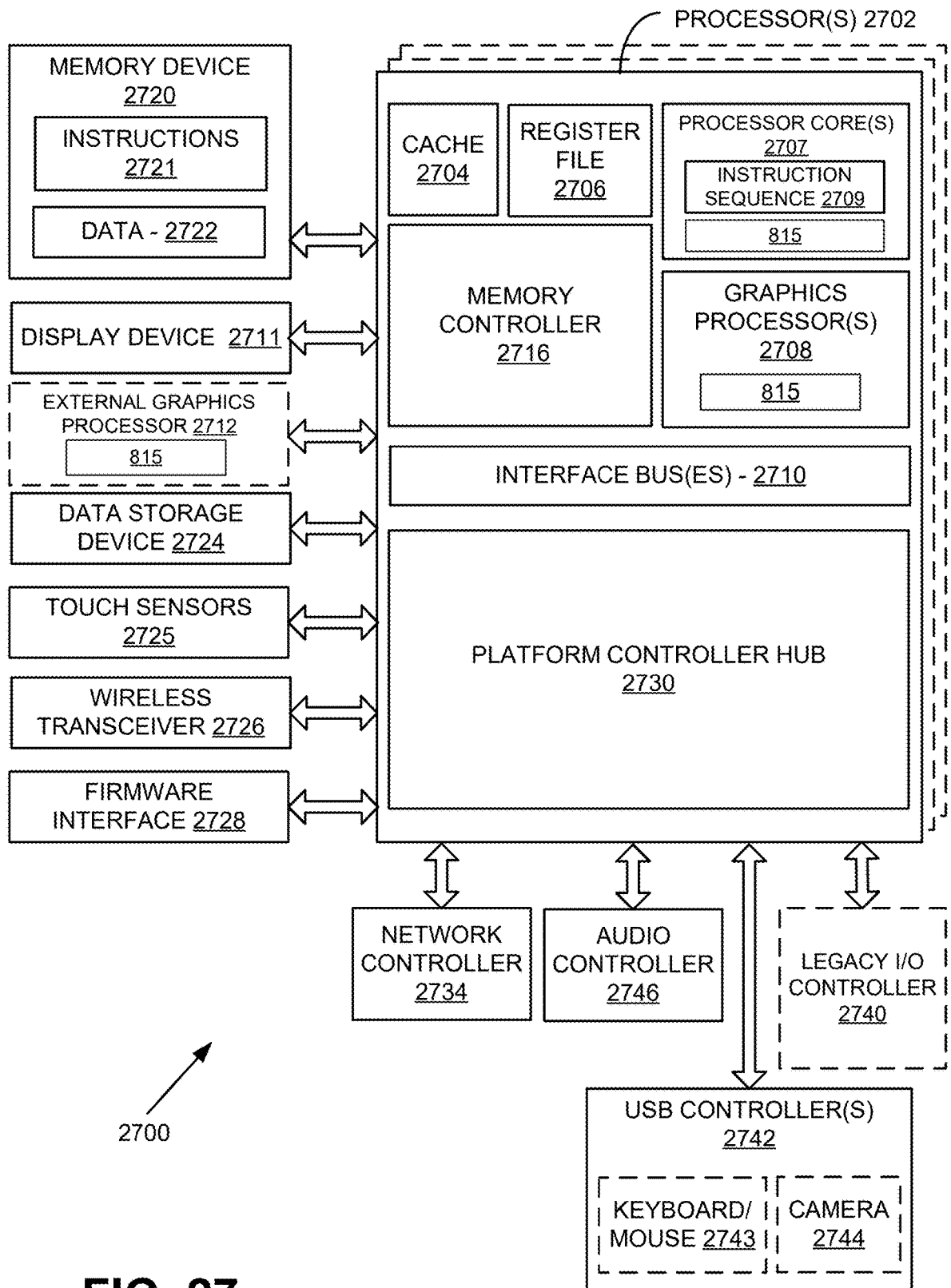
FIG. 27 illustrates at least portions of a graphics processor, according to one or more embodiments.

FIG. 27 is a block diagram of a processing system, according to at least one embodiment. In at least one embodiment, system 2700 includes one or more processors 2702 and one or more graphics processors 2708, and may be a single processor desktop system, a multiprocessor workstation system, or a server system having a large number of processors 2702 or processor cores 2707. In at least one embodiment, system 2700 is a processing platform incorporated within a system-on-a-chip (SoC) integrated circuit for use in mobile, handheld, or embedded devices.

In at least one embodiment, system 2700 can include, or be incorporated within a server-based gaming platform, a game console, including a game and media console, a mobile gaming console, a handheld game console, or an online game console. In at least one embodiment, system 2700 is a mobile phone, a smart phone, a tablet computing device or a mobile Internet device. In at least one embodiment, processing system 2700 can also include, couple with, or be integrated within a wearable device, such as a smart watch wearable device, a smart eyewear device, an augmented reality device, or a virtual reality device. In at least one embodiment, processing system 2700 is a television or set top box device having one or more processors 2702 and a graphical interface generated by one or more graphics processors 2708.

In at least one embodiment, one or more processors 2702 each include one or more processor cores 2707 to process instructions which, when executed, perform operations for system and user software. In at least one embodiment, each of one or more processor cores 2707 is configured to process a specific instruction sequence 2709. In at least one embodiment, instruction sequence 2709 may facilitate Complex Instruction Set Computing (CISC), Reduced Instruction Set Computing (RISC), or computing via a Very Long Instruction Word (VLIW). In at least one embodiment, processor cores 2707 may each process a different instruction sequence 2709, which may include instructions to facilitate emulation of other instruction sequences. In at least one embodiment, processor core 2707 may also include other processing devices, such a Digital Signal Processor (DSP).

In at least one embodiment, processor 2702 includes a cache memory 2704. In at least one embodiment, processor 2702 can have a single internal cache or multiple levels of internal cache. In at least one embodiment, cache memory is shared among various components of processor 2702. In at least one embodiment, processor 2702 also uses an external cache (e.g., a Level-3 (L3) cache or Last Level Cache (LLC)) (not shown), which may be shared among processor cores 2707 using known cache coherency techniques. In at least one embodiment, a register file 2706 is additionally included in processor 2702, which may include different types of registers for storing different types of data (e.g., integer registers, floating point registers, status registers, and an instruction pointer register). In at least one embodiment, register file 2706 may include general-purpose registers or other registers.

In at least one embodiment, one or more processor(s) 2702 are coupled with one or more interface bus(es) 2710 to transmit communication signals such as address, data, or control signals between processor 2702 and other components in system 2700. In at least one embodiment, interface bus 2710 can be a processor bus, such as a version of a Direct Media Interface (DMI) bus. In at least one embodiment, interface bus 2710 is not limited to a DMI bus, and may include one or more Peripheral Component Interconnect buses (e.g., PCI, PCI Express), memory busses, or other types of interface busses. In at least one embodiment processor(s) 2702 include an integrated memory controller 2716 and a platform controller hub 2730. In at least one embodiment, memory controller 2716 facilitates communication between a memory device and other components of system 2700, while platform controller hub (PCH) 2730 provides connections to I/O devices via a local I/O bus.

In at least one embodiment, a memory device 2720 can be a dynamic random access memory (DRAM) device, a static random access memory (SRAM) device, flash memory device, phase-change memory device, or some other memory device having suitable performance to serve as process memory. In at least one embodiment, memory device 2720 can operate as system memory for system 2700, to store data 2722 and instructions 2721 for use when one or more processors 2702 executes an application or process. In at least one embodiment, memory controller 2716 also couples with an optional external graphics processor 2712, which may communicate with one or more graphics processors 2708 in processors 2702 to perform graphics and media operations. In at least one embodiment, a display device 2711 can connect to processor(s) 2702. In at least one embodiment, display device 2711 can include one or more of an internal display device, as in a mobile electronic device or a laptop device, or an external display device attached via a display interface (e.g., DisplayPort, etc.). In at least one embodiment, display device 2711 can include a head mounted display (HMD) such as a stereoscopic display device for use in virtual reality (VR) applications or augmented reality (AR) applications.

In at least one embodiment, platform controller hub 2730 enables peripherals to connect to memory device 2720 and processor 2702 via a high-speed I/O bus. In at least one embodiment, I/O peripherals include, but are not limited to, an audio controller 2746, a network controller 2734, a firmware interface 2728, a wireless transceiver 2726, touch sensors 2725, a data storage device 2724 (e.g., hard disk drive, flash memory, etc.). In at least one embodiment, data storage device 2724 can connect via a storage interface (e.g., SATA) or via a peripheral bus, such as a Peripheral Component Interconnect bus (e.g., PCI, PCI Express). In at least one embodiment, touch sensors 2725 can include touch screen sensors, pressure sensors, or fingerprint sensors. In at least one embodiment, wireless transceiver 2726 can be a Wi-Fi transceiver, a Bluetooth transceiver, or a mobile network transceiver such as a 3G, 4G, or Long Term Evolution (LTE) transceiver. In at least one embodiment, firmware interface 2728 enables communication with system firmware, and can be, for example, a unified extensible firmware interface (UEFI). In at least one embodiment, network controller 2734 can enable a network connection to a wired network. In at least one embodiment, a high-performance network controller (not shown) couples with interface bus 2710. In at least one embodiment, audio controller 2746 is a multi-channel high definition audio controller. In at least one embodiment, system 2700 includes an optional legacy I/O controller 2740 for coupling legacy (e.g., Personal System 2 (PS/2)) devices to system 2700. In at least one embodiment, platform controller hub 2730 can also connect to one or more Universal Serial Bus (USB) controllers 2742 connect input devices, such as keyboard and mouse 2743 combinations, a camera 2744, or other USB input devices.

In at least one embodiment, an instance of memory controller 2716 and platform controller hub 2730 may be integrated into a discreet external graphics processor, such as external graphics processor 2712. In at least one embodiment, platform controller hub 2730 and/or memory controller 2716 may be external to one or more processor(s) 2702. For example, in at least one embodiment, system 2700 can include an external memory controller 2716 and platform controller hub 2730, which may be configured as a memory controller hub and peripheral controller hub within a system chipset that is in communication with processor(s) 2702.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment portions or all of inference and/or training logic 815 may be incorporated into graphics processor 2700. For example, in at least one embodiment, training and/or inferencing techniques described herein may use one or more of ALUs embodied in a 3D pipeline. Moreover, in at least one embodiment, inferencing and/or training operations described herein may be done using logic other than logic illustrated in FIG. 8A or 8B. In at least one embodiment, weight parameters may be stored in on-chip or off-chip memory and/or registers (shown or not shown) that configure ALUs of graphics processor 2700 to perform one or more machine learning algorithms, neural network architectures, use cases, or training techniques described herein.

In at least one embodiment, one or more systems depicted in FIG. 27 are utilized to generate segmentation and confidence values for pixels of an image. In at least one embodiment, one or more systems depicted in FIG. 27 are utilized to implement one or more networks and processes such as those described in connection with FIGS. 1-7. In at least one embodiment, one or more systems depicted in FIG. 27 are utilized to implement a system for segmentation and confidence value determination.

Figure 28:
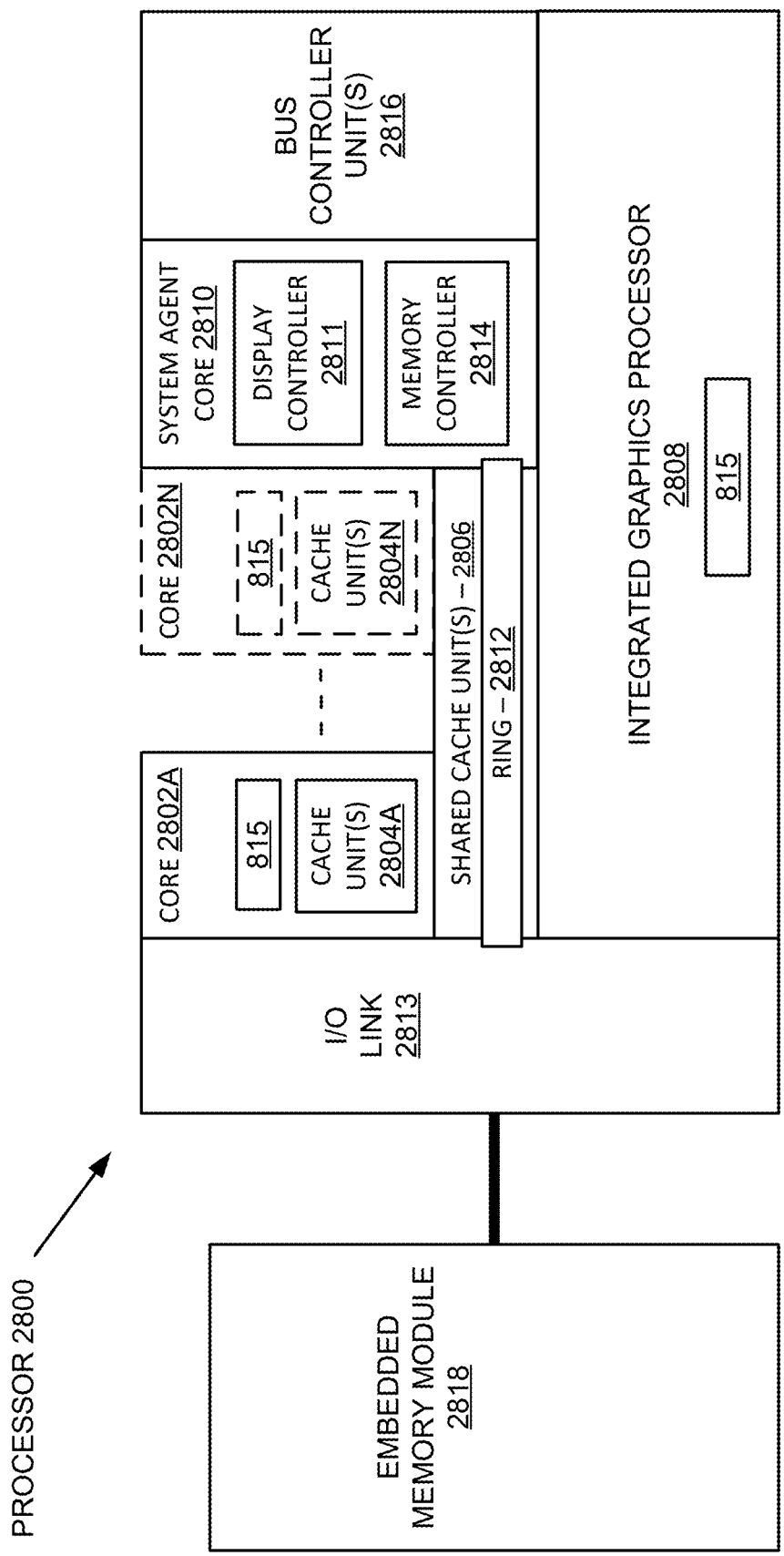
FIG. 28 illustrates at least portions of a graphics processor, according to one or more embodiments.

FIG. 28 is a block diagram of a processor 2800 having one or more processor cores 2802A-2802N, an integrated memory controller 2814, and an integrated graphics processor 2808, according to at least one embodiment. In at least one embodiment, processor 2800 can include additional cores up to and including additional core 2802N represented by dashed lined boxes. In at least one embodiment, each of processor cores 2802A-2802N includes one or more internal cache units 2804A-2804N. In at least one embodiment, each processor core also has access to one or more shared cached units 2806.

In at least one embodiment, internal cache units 2804A-2804N and shared cache units 2806 represent a cache memory hierarchy within processor 2800. In at least one embodiment, cache memory units 2804A-2804N may include at least one level of instruction and data cache within each processor core and one or more levels of shared mid-level cache, such as a Level 2 (L2), Level 3 (L3), Level 4 (L4), or other levels of cache, where a highest level of cache before external memory is classified as an LLC. In at least one embodiment, cache coherency logic maintains coherency between various cache units 2806 and 2804A-2804N.

In at least one embodiment, processor 2800 may also include a set of one or more bus controller units 2816 and a system agent core 2810. In at least one embodiment, bus controller units 2816 manage a set of peripheral buses, such as one or more PCI or PCI express busses. In at least one embodiment, system agent core 2810 provides management functionality for various processor components. In at least one embodiment, system agent core 2810 includes one or more integrated memory controllers 2814 to manage access to various external memory devices (not shown).

In at least one embodiment, one or more of processor cores 2802A-2802N include support for simultaneous multi-threading. In at least one embodiment, system agent core 2810 includes components for coordinating and operating cores 2802A-2802N during multi-threaded processing. In at least one embodiment, system agent core 2810 may additionally include a power control unit (PCU), which includes logic and components to regulate one or more power states of processor cores 2802A-2802N and graphics processor 2808.

In at least one embodiment, processor 2800 additionally includes graphics processor 2808 to execute graphics processing operations. In at least one embodiment, graphics processor 2808 couples with shared cache units 2806, and system agent core 2810, including one or more integrated memory controllers 2814. In at least one embodiment, system agent core 2810 also includes a display controller 2811 to drive graphics processor output to one or more coupled displays. In at least one embodiment, display controller 2811 may also be a separate module coupled with graphics processor 2808 via at least one interconnect, or may be integrated within graphics processor 2808.

In at least one embodiment, a ring-based interconnect unit 2812 is used to couple internal components of processor 2800. In at least one embodiment, an alternative interconnect unit may be used, such as a point-to-point interconnect, a switched interconnect, or other techniques. In at least one embodiment, graphics processor 2808 couples with ring interconnect 2812 via an I/O link 2813.

In at least one embodiment, I/O link 2813 represents at least one of multiple varieties of I/O interconnects, including an on package I/O interconnect which facilitates communication between various processor components and a high-performance embedded memory module 2818, such as an eDRAM module. In at least one embodiment, each of processor cores 2802A-2802N and graphics processor 2808 use embedded memory module 2818 as a shared Last Level Cache.

In at least one embodiment, processor cores 2802A-2802N are homogeneous cores executing a common instruction set architecture. In at least one embodiment, processor cores 2802A-2802N are heterogeneous in terms of instruction set architecture (ISA), where one or more of processor cores 2802A-2802N execute a common instruction set, while one or more other cores of processor cores 2802A-2802N executes a subset of a common instruction set or a different instruction set. In at least one embodiment, processor cores 2802A-2802N are heterogeneous in terms of microarchitecture, where one or more cores having a relatively higher power consumption couple with one or more power cores having a lower power consumption. In at least one embodiment, processor 2800 can be implemented on one or more chips or as an SoC integrated circuit.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment portions or all of inference and/or training logic 815 may be incorporated into graphics processor 2810. For example, in at least one embodiment, training and/or inferencing techniques described herein may use one or more of ALUs embodied in a 3D pipeline, graphics core(s) 2802, shared function logic, or other logic in FIG. 28. Moreover, in at least one embodiment, inferencing and/or training operations described herein may be done using logic other than logic illustrated in FIG. 8A or 8B. In at least one embodiment, weight parameters may be stored in on-chip or off-chip memory and/or registers (shown or not shown) that configure ALUs of processor 2800 to perform one or more machine learning algorithms, neural network architectures, use cases, or training techniques described herein.

In at least one embodiment, one or more systems depicted in FIG. 28 are utilized to generate segmentation and confidence values for pixels of an image. In at least one embodiment, one or more systems depicted in FIG. 28 are utilized to implement one or more networks and processes such as those described in connection with FIGS. 1-7. In at least one embodiment, one or more systems depicted in FIG. 28 are utilized to implement a system for segmentation and confidence value determination.

Figure 29:
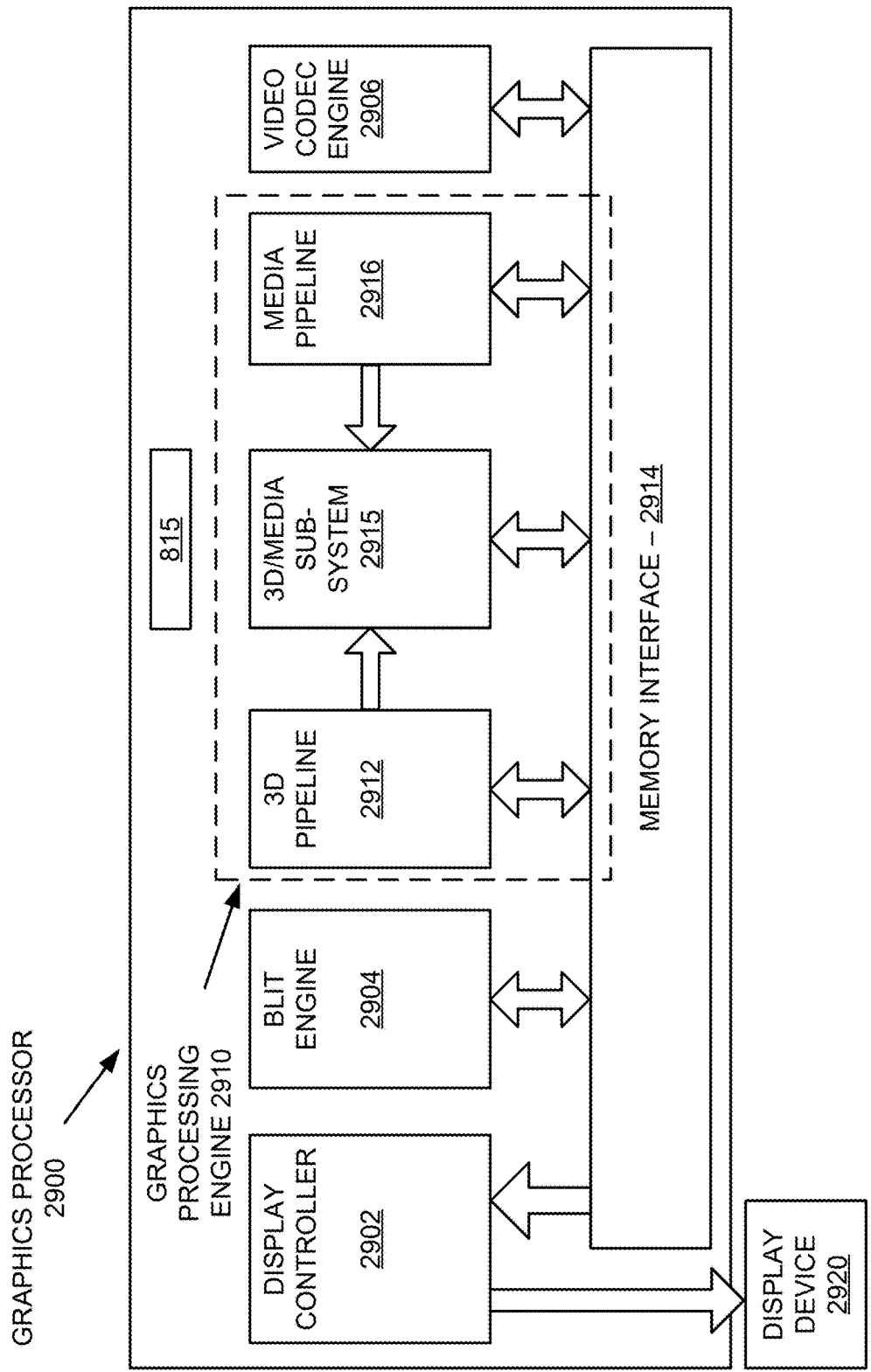
FIG. 29 illustrates at least portions of a graphics processor, according to one or more embodiments.

FIG. 29 is a block diagram of a graphics processor 2900, which may be a discrete graphics processing unit, or may be a graphics processor integrated with a plurality of processing cores. In at least one embodiment, graphics processor 2900 communicates via a memory mapped I/O interface to registers on graphics processor 2900 and with commands placed into memory. In at least one embodiment, graphics processor 2900 includes a memory interface 2914 to access memory. In at least one embodiment, memory interface 2914 is an interface to local memory, one or more internal caches, one or more shared external caches, and/or to system memory.

In at least one embodiment, graphics processor 2900 also includes a display controller 2902 to drive display output data to a display device 2920. In at least one embodiment, display controller 2902 includes hardware for one or more overlay planes for display device 2920 and composition of multiple layers of video or user interface elements. In at least one embodiment, display device 2920 can be an internal or external display device. In at least one embodiment, display device 2920 is a head mounted display device, such as a virtual reality (VR) display device or an augmented reality (AR) display device. In at least one embodiment, graphics processor 2900 includes a video codec engine 2906 to encode, decode, or transcode media to, from, or between one or more media encoding formats, including, but not limited to Moving Picture Experts Group (MPEG) formats such as MPEG-2, Advanced Video Coding (AVC) formats such as H.264/MPEG-4 AVC, as well as the Society of Motion Picture & Television Engineers (SMPTE) 421M/VC-1, and Joint Photographic Experts Group (JPEG) formats such as JPEG, and Motion JPEG (MJPEG) formats.

In at least one embodiment, graphics processor 2900 includes a block image transfer (BLIT) engine 2904 to perform two-dimensional (2D) rasterizer operations including, for example, bit-boundary block transfers. However, in at least one embodiment, 2D graphics operations are performed using one or more components of a graphics processing engine (GPE) 2910. In at least one embodiment, GPE 2910 is a compute engine for performing graphics operations, including three-dimensional (3D) graphics operations and media operations.

In at least one embodiment, GPE 2910 includes a 3D pipeline 2912 for performing 3D operations, such as rendering three-dimensional images and scenes using processing functions that act upon 3D primitive shapes (e.g., rectangle, triangle, etc.). In at least one embodiment, 3D pipeline 2912 includes programmable and fixed function elements that perform various tasks and/or spawn execution threads to a 3D/Media sub-system 2915. While 3D pipeline 2912 can be used to perform media operations, in at least one embodiment, GPE 2910 also includes a media pipeline 2916 that is used to perform media operations, such as video post-processing and image enhancement.

In at least one embodiment, media pipeline 2916 includes fixed function or programmable logic units to perform one or more specialized media operations, such as video decode acceleration, video de-interlacing, and video encode acceleration in place of, or on behalf of, video codec engine 2906. In at least one embodiment, media pipeline 2916 additionally includes a thread spawning unit to spawn threads for execution on 3D/Media sub-system 2915. In at least one embodiment, spawned threads perform computations for media operations on one or more graphics execution units included in 3D/Media sub-system 2915.

In at least one embodiment, 3D/Media subsystem 2915 includes logic for executing threads spawned by 3D pipeline 2912 and media pipeline 2916. In at least one embodiment, 3D pipeline 2912 and media pipeline 2916 send thread execution requests to 3D/Media subsystem 2915, which includes thread dispatch logic for arbitrating and dispatching various requests to available thread execution resources. In at least one embodiment, execution resources include an array of graphics execution units to process 3D and media threads. In at least one embodiment, 3D/Media subsystem 2915 includes one or more internal caches for thread instructions and data. In at least one embodiment, subsystem 2915 also includes shared memory, including registers and addressable memory, to share data between threads and to store output data.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment portions or all of inference and/or training logic 815 may be incorporated into graphics processor 2900. For example, in at least one embodiment, training and/or inferencing techniques described herein may use one or more of ALUs embodied in 3D pipeline 2912. Moreover, in at least one embodiment, inferencing and/or training operations described herein may be done using logic other than logic illustrated in FIG. 8A or 8B. In at least one embodiment, weight parameters may be stored in on-chip or off-chip memory and/or registers (shown or not shown) that configure ALUs of graphics processor 2900 to perform one or more machine learning algorithms, neural network architectures, use cases, or training techniques described herein.

In at least one embodiment, one or more systems depicted in FIG. 29 are utilized to generate segmentation and confidence values for pixels of an image. In at least one embodiment, one or more systems depicted in FIG. 29 are utilized to implement one or more networks and processes such as those described in connection with FIGS. 1-7. In at least one embodiment, one or more systems depicted in FIG. 29 are utilized to implement a system for segmentation and confidence value determination.

Figure 30:
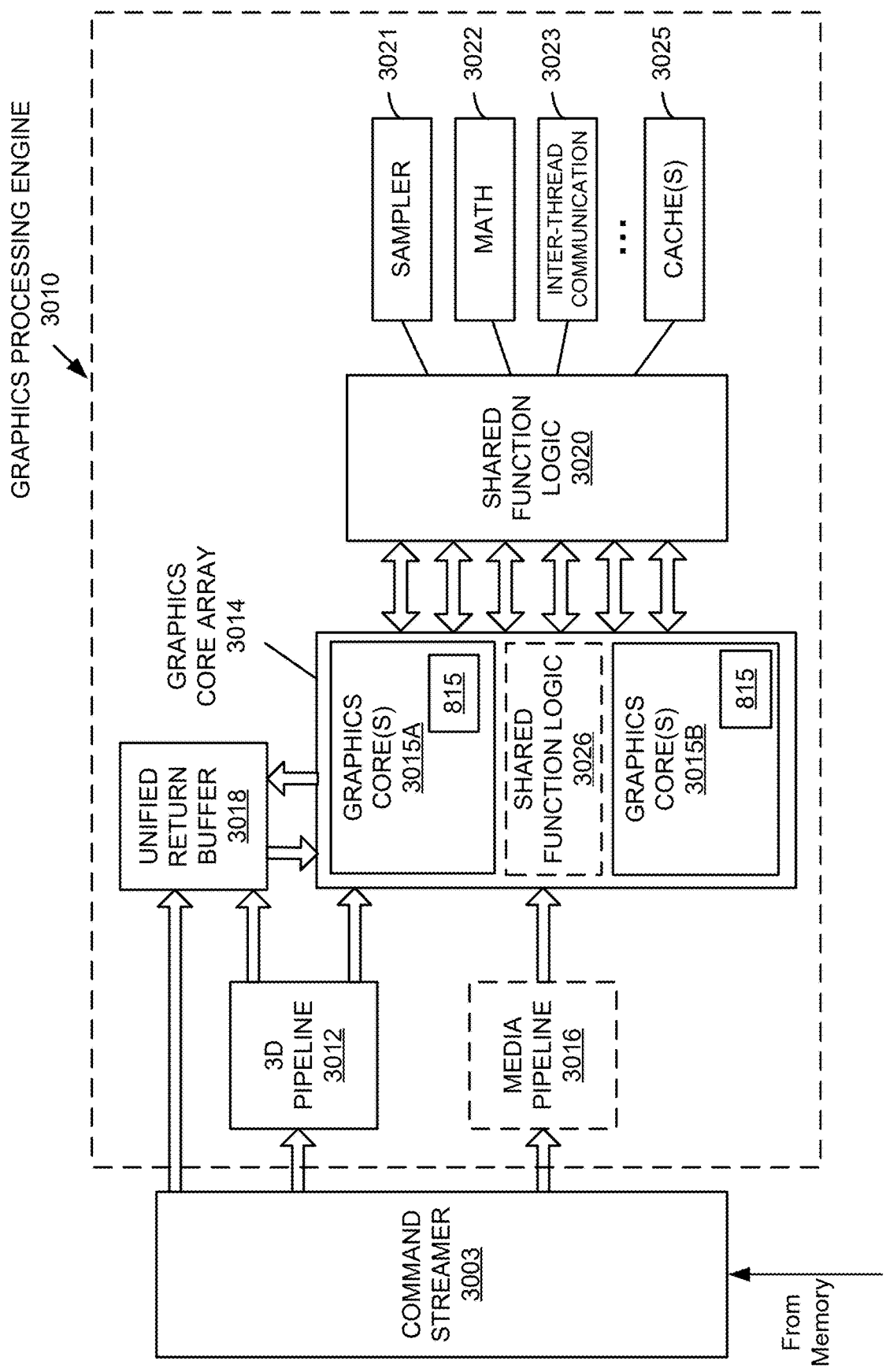
FIG. 30 is a block diagram of a graphics processing engine of a graphics processor in accordance with at least one embodiment.

FIG. 30 is a block diagram of a graphics processing engine 3010 of a graphics processor in accordance with at least one embodiment. In at least one embodiment, graphics processing engine (GPE) 3010 is a version of GPE 2910 shown in FIG. 29. In at least one embodiment, a media pipeline 3016 is optional and may not be explicitly included within GPE 3010. In at least one embodiment, a separate media and/or image processor is coupled to GPE 3010.

In at least one embodiment, GPE 3010 is coupled to or includes a command streamer 3003, which provides a command stream to a 3D pipeline 3012 and/or media pipeline 3016. In at least one embodiment, command streamer 3003 is coupled to memory, which can be system memory, or one or more of internal cache memory and shared cache memory. In at least one embodiment, command streamer 3003 receives commands from memory and sends commands to 3D pipeline 3012 and/or media pipeline 3016. In at least one embodiment, commands are instructions, primitives, or micro-operations fetched from a ring buffer, which stores commands for 3D pipeline 3012 and media pipeline 3016. In at least one embodiment, a ring buffer can additionally include batch command buffers storing batches of multiple commands. In at least one embodiment, commands for 3D pipeline 3012 can also include references to data stored in memory, such as, but not limited to, vertex and geometry data for 3D pipeline 3012 and/or image data and memory objects for media pipeline 3016. In at least one embodiment, 3D pipeline 3012 and media pipeline 3016 process commands and data by performing operations or by dispatching one or more execution threads to a graphics core array 3014. In at least one embodiment, graphics core array 3014 includes one or more blocks of graphics cores (e.g., graphics core(s) 3015A, graphics core(s) 3015B), each block including one or more graphics cores. In at least one embodiment, each graphics core includes a set of graphics execution resources that includes general-purpose and graphics specific execution logic to perform graphics and compute operations, as well as fixed function texture processing and/or machine learning and artificial intelligence acceleration logic, including inference and/or training logic 815 in FIG. 8A and FIG. 8B.

In at least one embodiment, 3D pipeline 3012 includes fixed function and programmable logic to process one or more shader programs, such as vertex shaders, geometry shaders, pixel shaders, fragment shaders, compute shaders, or other shader programs, by processing instructions and dispatching execution threads to graphics core array 3014. In at least one embodiment, graphics core array 3014 provides a unified block of execution resources for use in processing shader programs. In at least one embodiment, a multi-purpose execution logic (e.g., execution units) within graphics core(s) 3015A-3015B of graphic core array 3014 includes support for various 3D API shader languages and can execute multiple simultaneous execution threads associated with multiple shaders.

In at least one embodiment, graphics core array 3014 also includes execution logic to perform media functions, such as video and/or image processing. In at least one embodiment, execution units additionally include general-purpose logic that is programmable to perform parallel general-purpose computational operations, in addition to graphics processing operations.

In at least one embodiment, output data generated by threads executing on graphics core array 3014 can output data to memory in a unified return buffer (URB) 3018. In at least one embodiment, URB 3018 can store data for multiple threads. In at least one embodiment, URB 3018 may be used to send data between different threads executing on graphics core array 3014. In at least one embodiment, URB 3018 may additionally be used for synchronization between threads on graphics core array 3014 and fixed function logic within shared function logic 3020.

In at least one embodiment, graphics core array 3014 is scalable, such that graphics core array 3014 includes a variable number of graphics cores, each having a variable number of execution units based on a target power and performance level of GPE 3010. In at least one embodiment, execution resources are dynamically scalable, such that execution resources may be enabled or disabled as needed.

In at least one embodiment, graphics core array 3014 is coupled to shared function logic 3020 that includes multiple resources that are shared between graphics cores in graphics core array 3014. In at least one embodiment, shared functions performed by shared function logic 3020 are embodied in hardware logic units that provide specialized supplemental functionality to graphics core array 3014. In at least one embodiment, shared function logic 3020 includes but is not limited to a sampler unit 3021, a math unit 3022, and inter-thread communication (ITC) logic 3023. In at least one embodiment, one or more cache(s) 3025 are included in, or coupled to, shared function logic 3020.

In at least one embodiment, a shared function is used if demand for a specialized function is insufficient for inclusion within graphics core array 3014. In at least one embodiment, a single instantiation of a specialized function is used in shared function logic 3020 and shared among other execution resources within graphics core array 3014. In at least one embodiment, specific shared functions within shared function logic 3020 that are used extensively by graphics core array 3014 may be included within shared function logic 3316 within graphics core array 3014. In at least one embodiment, shared function logic 3316 within graphics core array 3014 can include some or all logic within shared function logic 3020. In at least one embodiment, all logic elements within shared function logic 3020 may be duplicated within shared function logic 3026 of graphics core array 3014. In at least one embodiment, shared function logic 3020 is excluded in favor of shared function logic 3026 within graphics core array 3014.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment portions or all of inference and/or training logic 815 may be incorporated into graphics processor 3010. For example, in at least one embodiment, training and/or inferencing techniques described herein may use one or more of ALUs embodied in 3D pipeline 3012, graphics core(s) 3015, shared function logic 3026, shared function logic 3020, or other logic in FIG. 30. Moreover, in at least one embodiment, inferencing and/or training operations described herein may be done using logic other than logic illustrated in FIG. 8A or 8B. In at least one embodiment, weight parameters may be stored in on-chip or off-chip memory and/or registers (shown or not shown) that configure ALUs of graphics processor 3010 to perform one or more machine learning algorithms, neural network architectures, use cases, or training techniques described herein.

In at least one embodiment, one or more systems depicted in FIG. 30 are utilized to generate segmentation and confidence values for pixels of an image. In at least one embodiment, one or more systems depicted in FIG. 30 are utilized to implement one or more networks and processes such as those described in connection with FIGS. 1-7. In at least one embodiment, one or more systems depicted in FIG. 30 are utilized to implement a system for segmentation and confidence value determination.

Figure 31:
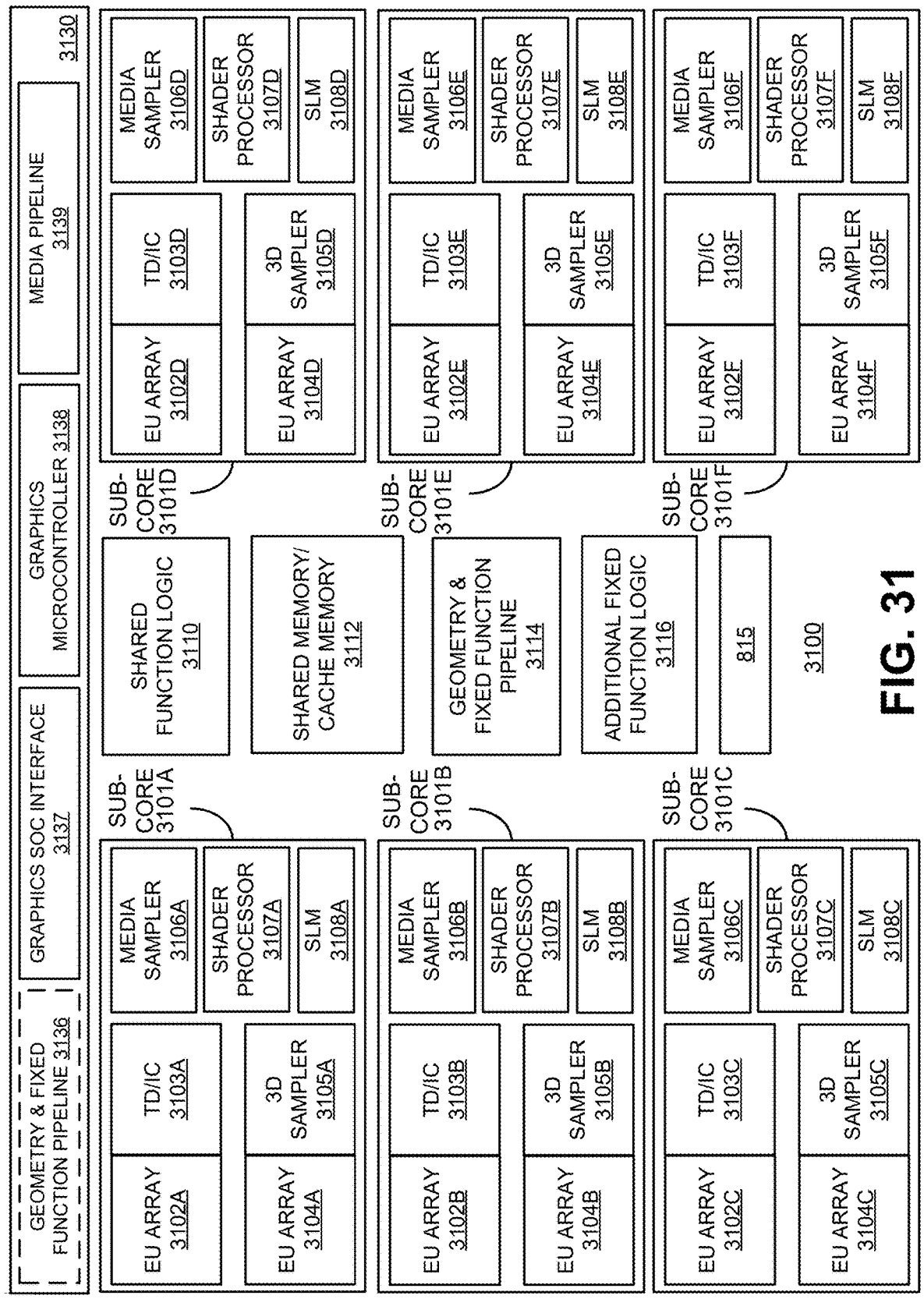
FIG. 31 is a block diagram of at least portions of a graphics processor core, according to at least one embodiment.

FIG. 31 is a block diagram of hardware logic of a graphics processor core 3100, according to at least one embodiment described herein. In at least one embodiment, graphics processor core 3100 is included within a graphics core array. In at least one embodiment, graphics processor core 3100, sometimes referred to as a core slice, can be one or multiple graphics cores within a modular graphics processor. In at least one embodiment, graphics processor core 3100 is exemplary of one graphics core slice, and a graphics processor as described herein may include multiple graphics core slices based on target power and performance envelopes. In at least one embodiment, each graphics core 3100 can include a fixed function block 3130 coupled with multiple sub-cores 3101A-3101F, also referred to as sub-slices, that include modular blocks of general-purpose and fixed function logic.

In at least one embodiment, fixed function block 3130 includes a geometry and fixed function pipeline 3136 that can be shared by all sub-cores in graphics processor 3100, for example, in lower performance and/or lower power graphics processor implementations. In at least one embodiment, geometry and fixed function pipeline 3136 includes a 3D fixed function pipeline, a video front-end unit, a thread spawner and thread dispatcher, and a unified return buffer manager, which manages unified return buffers.

In at least one embodiment, fixed function block 3130 also includes a graphics SoC interface 3137, a graphics microcontroller 3138, and a media pipeline 3139. In at least one embodiment, graphics SoC interface 3137 provides an interface between graphics core 3100 and other processor cores within a system on a chip integrated circuit. In at least one embodiment, graphics microcontroller 3138 is a programmable sub-processor that is configurable to manage various functions of graphics processor 3100, including thread dispatch, scheduling, and pre-emption. In at least one embodiment, media pipeline 3139 includes logic to facilitate decoding, encoding, pre-processing, and/or post-processing of multimedia data, including image and video data. In at least one embodiment, media pipeline 3139 implements media operations via requests to compute or sampling logic within sub-cores 3101A-3101F.

In at least one embodiment, SoC interface 3137 enables graphics core 3100 to communicate with general-purpose application processor cores (e.g., CPUs) and/or other components within an SoC, including memory hierarchy elements such as a shared last level cache memory, system RAM, and/or embedded on-chip or on-package DRAM. In at least one embodiment, SoC interface 3137 can also enable communication with fixed function devices within an SoC, such as camera imaging pipelines, and enables use of and/or implements global memory atomics that may be shared between graphics core 3100 and CPUs within an SoC. In at least one embodiment, graphics SoC interface 3137 can also implement power management controls for graphics processor core 3100 and enable an interface between a clock domain of graphics processor core 3100 and other clock domains within an SoC. In at least one embodiment, SoC interface 3137 enables receipt of command buffers from a command streamer and global thread dispatcher that are configured to provide commands and instructions to each of one or more graphics cores within a graphics processor. In at least one embodiment, commands and instructions can be dispatched to media pipeline 3139, when media operations are to be performed, or a geometry and fixed function pipeline (e.g., geometry and fixed function pipeline 3136, and/or a geometry and fixed function pipeline 3114) when graphics processing operations are to be performed.

In at least one embodiment, graphics microcontroller 3138 can be configured to perform various scheduling and management tasks for graphics core 3100. In at least one embodiment, graphics microcontroller 3138 can perform graphics and/or compute workload scheduling on various graphics parallel engines within execution unit (EU) arrays 3102A-3102F, 3104A-3104F within sub-cores 3101A-3101F. In at least one embodiment, host software executing on a CPU core of an SoC including graphics core 3100 can submit workloads to one of multiple graphic processor paths, which invokes a scheduling operation on an appropriate graphics engine. In at least one embodiment, scheduling operations include determining which workload to run next, submitting a workload to a command streamer, pre-empting existing workloads running on an engine, monitoring progress of a workload, and notifying host software when a workload is complete. In at least one embodiment, graphics microcontroller 3138 can also facilitate low-power or idle states for graphics core 3100, providing graphics core 3100 with an ability to save and restore registers within graphics core 3100 across low-power state transitions independently from an operating system and/or graphics driver software on a system.

In at least one embodiment, graphics core 3100 may have greater than or fewer than illustrated sub-cores 3101A-3101F, up to N modular sub-cores. For each set of N sub-cores, in at least one embodiment, graphics core 3100 can also include shared function logic 3110, shared and/or cache memory 3112, geometry/fixed function pipeline 3114, as well as additional fixed function logic 3116 to accelerate various graphics and compute processing operations. In at least one embodiment, shared function logic 3110 can include logic units (e.g., sampler, math, and/or inter-thread communication logic) that can be shared by each N sub-cores within graphics core 3100. In at least one embodiment, shared and/or cache memory 3112 can be a last-level cache for N sub-cores 3101A-3101F within graphics core 3100 and can also serve as shared memory that is accessible by multiple sub-cores. In at least one embodiment, geometry/fixed function pipeline 3114 can be included instead of geometry/fixed function pipeline 3136 within fixed function block 3130 and can include similar logic units.

In at least one embodiment, graphics core 3100 includes additional fixed function logic 3116 that can include various fixed function acceleration logic for use by graphics core 3100. In at least one embodiment, additional fixed function logic 3116 includes an additional geometry pipeline for use in position-only shading. In position-only shading, at least two geometry pipelines exist, whereas in a full geometry pipeline within geometry and fixed function pipelines 3114, 3136, and a cull pipeline, which is an additional geometry pipeline that may be included within additional fixed function logic 3116. In at least one embodiment, a cull pipeline is a trimmed down version of a full geometry pipeline. In at least one embodiment, a full pipeline and a cull pipeline can execute different instances of an application, each instance having a separate context. In at least one embodiment, position only shading can hide long cull runs of discarded triangles, enabling shading to be completed earlier in some instances. For example, in at least one embodiment, cull pipeline logic within additional fixed function logic 3116 can execute position shaders in parallel with a main application and generally generates critical results faster than a full pipeline, as a cull pipeline fetches and shades position attributes of vertices, without performing rasterization and rendering of pixels to a frame buffer. In at least one embodiment, a cull pipeline can use generated critical results to compute visibility information for all triangles without regard to whether those triangles are culled. In at least one embodiment, a full pipeline (which in this instance may be referred to as a replay pipeline) can consume visibility information to skip culled triangles to shade only visible triangles that are finally passed to a rasterization phase.

In at least one embodiment, additional fixed function logic 3116 can also include machine-learning acceleration logic, such as fixed function matrix multiplication logic, for implementations including optimizations for machine learning training or inferencing.

In at least one embodiment, within each graphics sub-core 3101A-3101F includes a set of execution resources that may be used to perform graphics, media, and compute operations in response to requests by graphics pipeline, media pipeline, or shader programs. In at least one embodiment, graphics sub-cores 3101A-3101F include multiple EU arrays 3102A-3102F, 3104A-3104F, thread dispatch and inter-thread communication (TD/IC) logic 3103A-3103F, a 3D (e.g., texture) sampler 3105A-3105F, a media sampler 3106A-3106F, a shader processor 3107A-3107F, and shared local memory (SLM) 3108A-3108F. In at least one embodiment, EU arrays 3102A-3102F, 3104A-3104F each include multiple execution units, which are general-purpose graphics processing units capable of performing floating-point and integer/fixed-point logic operations in service of a graphics, media, or compute operation, including graphics, media, or compute shader programs. In at least one embodiment, TD/IC logic 3103A-3103F performs local thread dispatch and thread control operations for execution units within a sub-core and facilitates communication between threads executing on execution units of a sub-core. In at least one embodiment, 3D samplers 3105A-3105F can read texture or other 3D graphics related data into memory. In at least one embodiment, 3D samplers can read texture data differently based on a configured sample state and texture format associated with a given texture. In at least one embodiment, media samplers 3106A-3106F can perform similar read operations based on a type and format associated with media data. In at least one embodiment, each graphics sub-core 3101A-3101F can alternately include a unified 3D and media sampler. In at least one embodiment, threads executing on execution units within each of sub-cores 3101A-3101F can make use of shared local memory 3108A-3108F within each sub-core, to enable threads executing within a thread group to execute using a common pool of on-chip memory.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, portions or all of inference and/or training logic 815 may be incorporated into graphics processor 3110. For example, in at least one embodiment, training and/or inferencing techniques described herein may use one or more of ALUs embodied in a 3D pipeline, graphics microcontroller 3138, geometry and fixed function pipeline 3114 and 3136, or other logic in FIG. 31. Moreover, in at least one embodiment, inferencing and/or training operations described herein may be done using logic other than logic illustrated in FIG. 8A or 8B. In at least one embodiment, weight parameters may be stored in on-chip or off-chip memory and/or registers (shown or not shown) that configure ALUs of graphics processor 3100 to perform one or more machine learning algorithms, neural network architectures, use cases, or training techniques described herein.

In at least one embodiment, one or more systems depicted in FIG. 31 are utilized to generate segmentation and confidence values for pixels of an image. In at least one embodiment, one or more systems depicted in FIG. 31 are utilized to implement one or more networks and processes such as those described in connection with FIGS. 1-7. In at least one embodiment, one or more systems depicted in FIG. 31 are utilized to implement a system for segmentation and confidence value determination.

Figure 32A:
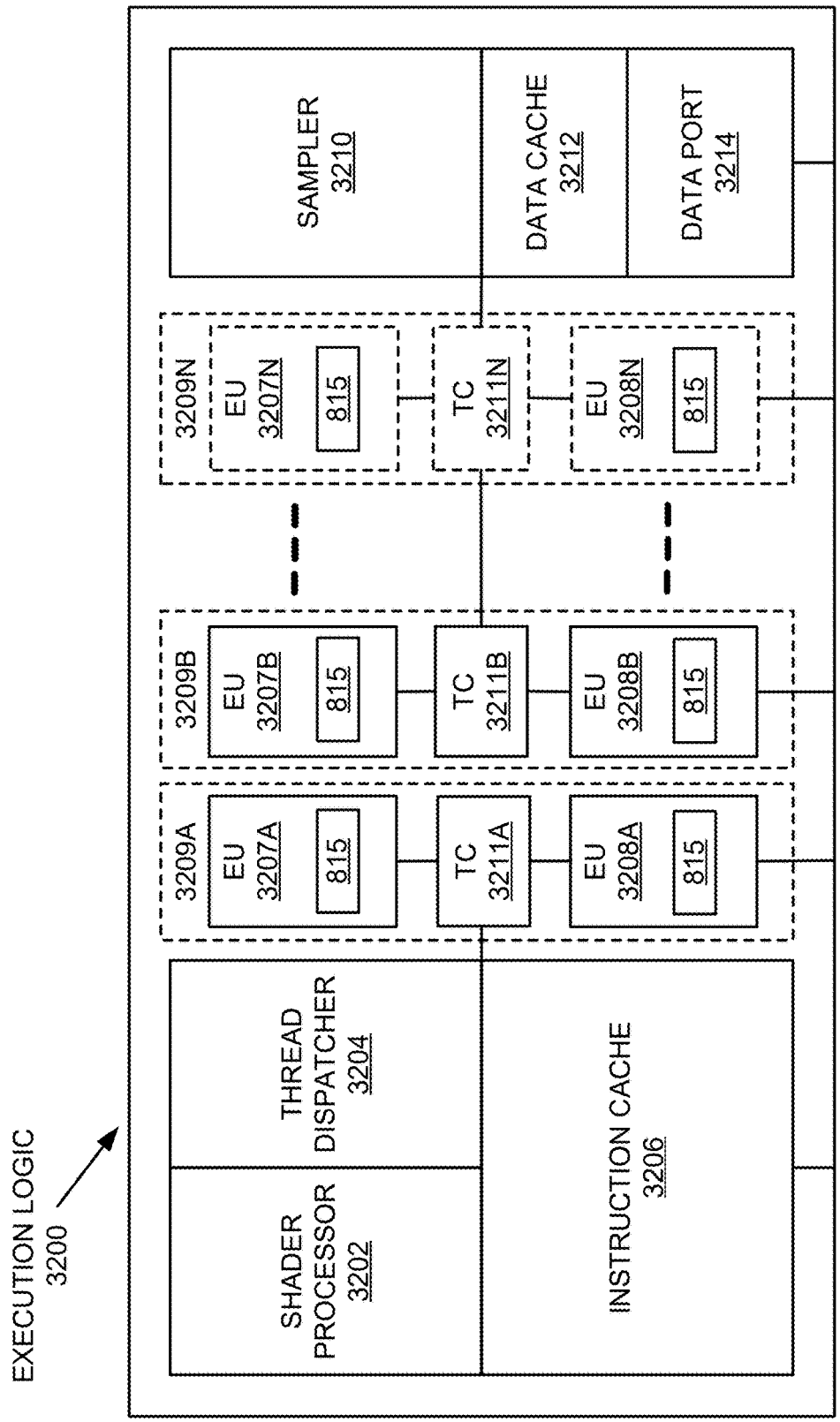
FIGS. 32A and 32B illustrate thread execution logic including an array of processing elements of a graphics processor core according to at least one embodiment.
Figure 32B:
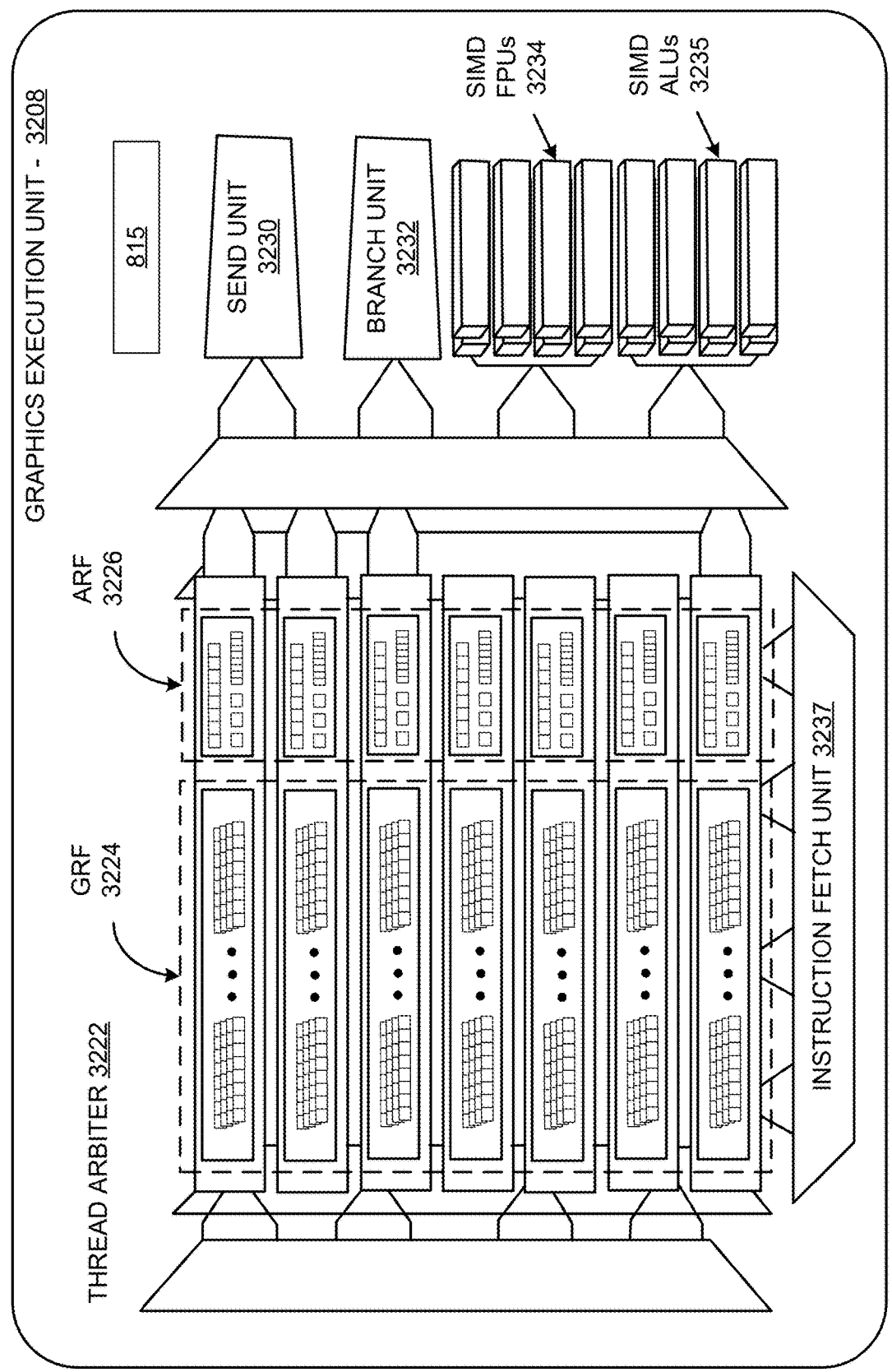

FIGS. 32A-32B illustrate thread execution logic 3200 including an array of processing elements of a graphics processor core according to at least one embodiment. FIG. 32A illustrates at least one embodiment, in which thread execution logic 3200 is used. FIG. 32B illustrates exemplary internal details of a graphics execution unit 3208, according to at least one embodiment.

As illustrated in FIG. 32A, in at least one embodiment, thread execution logic 3200 includes a shader processor 3202, a thread dispatcher 3204, an instruction cache 3206, a scalable execution unit array including a plurality of execution units 3207A-3207N and 3208A-3208N, a sampler 3210, a data cache 3212, and a data port 3214. In at least one embodiment, a scalable execution unit array can dynamically scale by enabling or disabling one or more execution units (e.g., any of execution unit 3208A-N or 3207A-N) based on computational requirements of a workload, for example. In at least one embodiment, scalable execution units are interconnected via an interconnect fabric that links to each execution unit. In at least one embodiment, thread execution logic 3200 includes one or more connections to memory, such as system memory or cache memory, through one or more of instruction cache 3206, data port 3214, sampler 3210, and execution units 3207 or 3208. In at least one embodiment, each execution unit (e.g., 3207A) is a stand-alone programmable general-purpose computational unit that is capable of executing multiple simultaneous hardware threads while processing multiple data elements in parallel for each thread. In at least one embodiment, array of execution units 3207 and/or 3208 is scalable to include any number individual execution units.

In at least one embodiment, execution units 3207 and/or 3208 are primarily used to execute shader programs. In at least one embodiment, shader processor 3202 can process various shader programs and dispatch execution threads associated with shader programs via a thread dispatcher 3204. In at least one embodiment, thread dispatcher 3204 includes logic to arbitrate thread initiation requests from graphics and media pipelines and instantiate requested threads on one or more execution units in execution units 3207 and/or 3208. For example, in at least one embodiment, a geometry pipeline can dispatch vertex, tessellation, or geometry shaders to thread execution logic for processing. In at least one embodiment, thread dispatcher 3204 can also process runtime thread spawning requests from executing shader programs.

In at least one embodiment, execution units 3207 and/or 3208 support an instruction set that includes native support for many standard 3D graphics shader instructions, such that shader programs from graphics libraries (e.g., Direct 3D and OpenGL) are executed with a minimal translation. In at least one embodiment, execution units support vertex and geometry processing (e.g., vertex programs, geometry programs, and/or vertex shaders), pixel processing (e.g., pixel shaders, fragment shaders) and general-purpose processing (e.g., compute and media shaders). In at least one embodiment, each of execution units 3207 and/or 3208, which include one or more arithmetic logic units (ALUs), is capable of multi-issue single instruction multiple data (SIMD) execution and multi-threaded operation enables an efficient execution environment despite higher latency memory accesses. In at least one embodiment, each hardware thread within each execution unit has a dedicated high-bandwidth register file and associated independent thread-state. In at least one embodiment, execution is multi-issue per clock to pipelines capable of integer, single and double precision floating point operations, SIMD branch capability, logical operations, transcendental operations, and other miscellaneous operations. In at least one embodiment, while waiting for data from memory or one of shared functions, dependency logic within execution units 3207 and/or 3208 causes a waiting thread to sleep until requested data has been returned. In at least one embodiment, while an awaiting thread is sleeping, hardware resources may be devoted to processing other threads. For example, in at least one embodiment, during a delay associated with a vertex shader operation, an execution unit can perform operations for a pixel shader, fragment shader, or another type of shader program, including a different vertex shader.

In at least one embodiment, each execution unit in execution units 3207 and/or 3208 operates on arrays of data elements. In at least one embodiment, a number of data elements is an "execution size," or number of channels for an instruction. In at least one embodiment, an execution channel is a logical unit of execution for data element access, masking, and flow control within instructions. In at least one embodiment, a number of channels may be independent of a number of physical arithmetic logic units (ALUs) or floating point units (FPUs) for a particular graphics processor. In at least one embodiment, execution units 3207 and/or 3208 support integer and floating-point data types.

In at least one embodiment, an execution unit instruction set includes SIMD instructions. In at least one embodiment, various data elements can be stored as a packed data type in a register and execution unit will process various elements based on data size of elements. For example, in at least one embodiment, when operating on a 256-bit wide vector, 256 bits of a vector are stored in a register and an execution unit operates on a vector as four separate 64-bit packed data elements (Quad-Word (QW) size data elements), eight separate 32-bit packed data elements (Double Word (DW) size data elements), sixteen separate 16-bit packed data elements (Word (W) size data elements), or thirty-two separate 8-bit data elements (byte (B) size data elements). However, in at least one embodiment, different vector widths and register sizes are possible.

In at least one embodiment, one or more execution units can be combined into a fused execution unit 3209A-3209N having thread control logic (3211A-3211N) that is common to fused EUs such as execution unit 3207A fused with execution unit 3208A into fused execution unit 3209A. In at least one embodiment, multiple EUs can be fused into an EU group. In at least one embodiment, each EU in a fused EU group can be configured to execute a separate SIMD hardware thread, with a number of EUs in a fused EU group possibly varying according to various embodiments. In at least one embodiment, various SIMD widths can be performed per-EU, including but not limited to SIMD8, SIMD16, and SIMD32. In at least one embodiment, each fused graphics execution unit 3209A-3209N includes at least two execution units. For example, in at least one embodiment, fused execution unit 3209A includes a first EU 3207A, second EU 3208A, and thread control logic 3211A that is common to first EU 3207A and second EU 3208A. In at least one embodiment, thread control logic 3211A controls threads executed on fused graphics execution unit 3209A, allowing each EU within fused execution units 3209A-3209N to execute using a common instruction pointer register.

In at least one embodiment, one or more internal instruction caches (e.g., 3206) are included in thread execution logic 3200 to cache thread instructions for execution units. In at least one embodiment, one or more data caches (e.g., 3212) are included to cache thread data during thread execution. In at least one embodiment, sampler 3210 is included to provide texture sampling for 3D operations and media sampling for media operations. In at least one embodiment, sampler 3210 includes specialized texture or media sampling functionality to process texture or media data during sampling process before providing sampled data to an execution unit.

During execution, in at least one embodiment, graphics and media pipelines send thread initiation requests to thread execution logic 3200 via thread spawning and dispatch logic. In at least one embodiment, once a group of geometric objects has been processed and rasterized into pixel data, pixel processor logic (e.g., pixel shader logic, fragment shader logic, etc.) within shader processor 3202 is invoked to further compute output information and cause results to be written to output surfaces (e.g., color buffers, depth buffers, stencil buffers, etc.). In at least one embodiment, a pixel shader or a fragment shader calculates values of various vertex attributes that are to be interpolated across a rasterized object. In at least one embodiment, pixel processor logic within shader processor 3202 then executes an application programming interface (API)-supplied pixel or fragment shader program. In at least one embodiment, to execute a shader program, shader processor 3202 dispatches threads to an execution unit (e.g., 3208A) via thread dispatcher 3204. In at least one embodiment, shader processor 3202 uses texture sampling logic in sampler 3210 to access texture data in texture maps stored in memory. In at least one embodiment, arithmetic operations on texture data and input geometry data compute pixel color data for each geometric fragment, or discards one or more pixels from further processing.

In at least one embodiment, data port 3214 provides a memory access mechanism for thread execution logic 3200 to output processed data to memory for further processing on a graphics processor output pipeline. In at least one embodiment, data port 3214 includes or couples to one or more cache memories (e.g., data cache 3212) to cache data for memory access via a data port.

As illustrated in FIG. 32B, in at least one embodiment, a graphics execution unit 3208 can include an instruction fetch unit 3237, a general register file array (GRF) 3224, an architectural register file array (ARF) 3226, a thread arbiter 3222, a send unit 3230, a branch unit 3232, a set of SIMD floating point units (FPUs) 3234, and a set of dedicated integer SIMD ALUs 3235. In at least one embodiment, GRF 3224 and ARF 3226 includes a set of general register files and architecture register files associated with each simultaneous hardware thread that may be active in graphics execution unit 3208. In at least one embodiment, per thread architectural state is maintained in ARF 3226, while data used during thread execution is stored in GRF 3224. In at least one embodiment, execution state of each thread, including instruction pointers for each thread, can be held in thread-specific registers in ARF 3226.

In at least one embodiment, graphics execution unit 3208 has an architecture that is a combination of Simultaneous Multi-Threading (SMT) and fine-grained Interleaved Multi-Threading (IMT). In at least one embodiment, architecture has a modular configuration that can be fine-tuned at design time based on a target number of simultaneous threads and number of registers per execution unit, where execution unit resources are divided across logic used to execute multiple simultaneous threads.

In at least one embodiment, graphics execution unit 3208 can co-issue multiple instructions, which may each be different instructions. In at least one embodiment, thread arbiter 3222 of graphics execution unit thread 3208 can dispatch instructions to one of send unit 3230, branch unit 3232, or SIMD FPU(s) 3234 for execution. In at least one embodiment, each execution thread can access 128 general-purpose registers within GRF 3224, where each register can store 32 bytes, accessible as a SIMD 8-element vector of 32-bit data elements. In at least one embodiment, each execution unit thread has access to 4 kilobytes within GRF 3224, although embodiments are not so limited, and greater or fewer register resources may be provided in other embodiments. In at least one embodiment, up to seven threads can execute simultaneously, although a number of threads per execution unit can also vary according to embodiments. In at least one embodiment, in which seven threads may access 4 kilobytes, GRF 3224 can store a total of 28 kilobytes. In at least one embodiment, flexible addressing modes can permit registers to be addressed together to build effectively wider registers or to represent strided rectangular block data structures.

In at least one embodiment, memory operations, sampler operations, and other longer-latency system communications are dispatched via "send" instructions that are executed by message passing to send unit 3230. In at least one embodiment, branch instructions are dispatched to branch unit 3232 to facilitate SIMD divergence and eventual convergence.

In at least one embodiment, graphics execution unit 3208 includes one or more SIMD floating point units (FPU(s)) 3234 to perform floating-point operations. In at least one embodiment, FPU(s) 3234 also support integer computation. In at least one embodiment, FPU(s) 3234 can SIMD execute up to M number of 32-bit floating-point (or integer) operations, or SIMD execute up to 2M 16-bit integer or 16-bit floating-point operations. In at least one embodiment, at least one FPU provides extended math capability to support high-throughput transcendental math functions and double precision 64-bit floating-point. In at least one embodiment, a set of 8-bit integer SIMD ALUs 3235 are also present, and may be specifically optimized to perform operations associated with machine learning computations.

In at least one embodiment, arrays of multiple instances of graphics execution unit 3208 can be instantiated in a graphics sub-core grouping (e.g., a sub-slice). In at least one embodiment, execution unit 3208 can execute instructions across a plurality of execution channels. In at least one embodiment, each thread executed on graphics execution unit 3208 is executed on a different channel.

Inference and/or training logic 815 are used to perform inferencing and/or training operations associated with one or more embodiments. Details regarding inference and/or training logic 815 are provided herein in conjunction with FIGS.

8A and/or 8B. In at least one embodiment, portions or all of inference and/or training logic 815 may be incorporated into thread execution logic 3200. Moreover, in at least one embodiment, inferencing and/or training operations described herein may be done using logic other than logic illustrated in FIG. 8A or 8B. In at least one embodiment, weight parameters may be stored in on-chip or off-chip memory and/or registers (shown or not shown) that configure ALUs thread of execution logic 3200 to perform one or more machine learning algorithms, neural network architectures, use cases, or training techniques described herein.

In at least one embodiment, one or more systems depicted in FIGS. 32A-32B are utilized to generate segmentation and confidence values for pixels of an image. In at least one embodiment, one or more systems depicted in FIGS. 32A-32B are utilized to implement one or more networks and processes such as those described in connection with FIGS. 1-7. In at least one embodiment, one or more systems depicted in FIGS. 32A-32B are utilized to implement a system for segmentation and confidence value determination.

Figure 33:
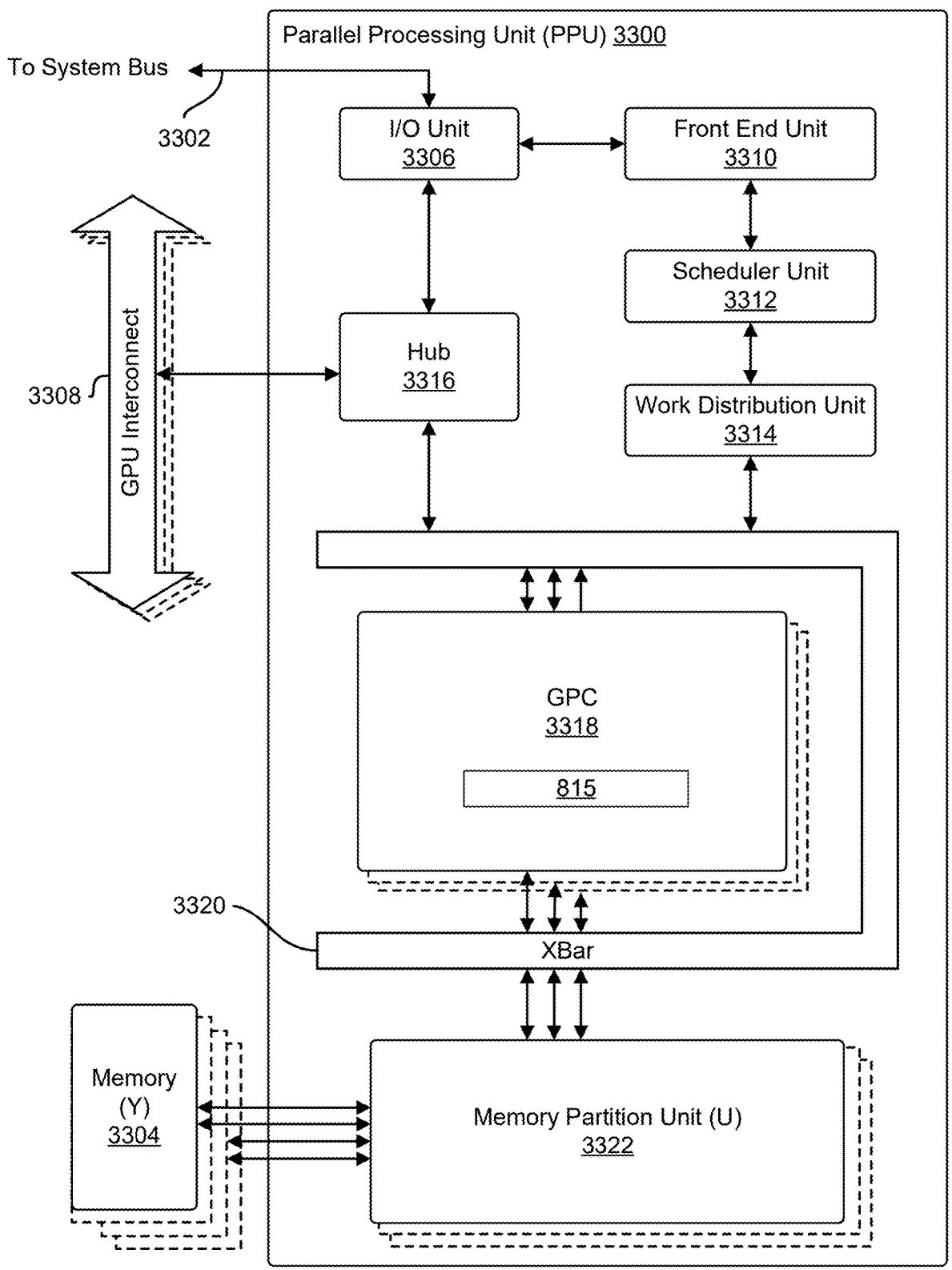
FIG. 33 illustrates a parallel processing unit ("PPU"), according to at least one embodiment.

FIG. 33 illustrates a parallel processing unit ("PPU") 3300, according to at least one embodiment. In at least one embodiment, PPU 3300 is configured with machine-readable code that, if executed by PPU 3300, causes PPU 3300 to perform some or all of processes and techniques described throughout this disclosure. In at least one embodiment, PPU 3300 is a multi-threaded processor that is implemented on one or more integrated circuit devices and that utilizes multithreading as a latency-hiding technique designed to process computer-readable instructions (also referred to as machine-readable instructions or simply instructions) on multiple threads in parallel. In at least one embodiment, a thread refers to a thread of execution and is an instantiation of a set of instructions configured to be executed by PPU 3300. In at least one embodiment, PPU 3300 is a graphics processing unit ("GPU") configured to implement a graphics rendering pipeline for processing three-dimensional ("3D") graphics data in order to generate two-dimensional ("2D") image data for display on a display device such as a liquid crystal display ("LCD") device. In at least one embodiment, PPU 3300 is utilized to perform computations such as linear algebra operations and machine-learning operations. FIG. 33 illustrates an example parallel processor for illustrative purposes only and should be construed as a non-limiting example of processor architectures contemplated within scope of this disclosure and that any suitable processor may be employed to supplement and/or substitute for same.

In at least one embodiment, one or more PPUs 3300 are configured to accelerate High Performance Computing ("HPC"), data center, and machine learning applications. In at least one embodiment, PPU 3300 is configured to accelerate deep learning systems and applications including following non-limiting examples: autonomous vehicle platforms, deep learning, high-accuracy speech, image, text recognition systems, intelligent video analytics, molecular simulations, drug discovery, disease diagnosis, weather forecasting, big data analytics, astronomy, molecular dynamics simulation, financial modeling, robotics, factory automation, real-time language translation, online search optimizations, and personalized user recommendations, and more.

In at least one embodiment, PPU 3300 includes, without limitation, an Input/Output ("I/O") unit 3306, a front-end unit 3310, a scheduler unit 3312, a work distribution unit 3314, a hub 3316, a crossbar ("XBar") 3320, one or more general processing clusters ("GPCs") 3318, and one or more partition units ("memory partition units") 3322. In at least one embodiment, PPU 3300 is connected to a host processor or other PPUs 3300 via one or more high-speed GPU interconnects ("GPU interconnects") 3308. In at least one embodiment, PPU 3300 is connected to a host processor or other peripheral devices via a system bus 3302. In at least one embodiment, PPU 3300 is connected to a local memory comprising one or more memory devices ("memory") 3304. In at least one embodiment, memory devices 3304 include, without limitation, one or more dynamic random access memory ("DRAM") devices. In at least one embodiment, one or more DRAM devices are configured and/or configurable as high-bandwidth memory ("HBM") subsystems, with multiple DRAM dies stacked within each device.

In at least one embodiment, high-speed GPU interconnect 3308 may refer to a wire-based multi-lane communications link that is used by systems to scale and include one or more PPUs 3300 combined with one or more central processing units ("CPUs"), supports cache coherence between PPUs 3300 and CPUs, and CPU mastering. In at least one embodiment, data and/or commands are transmitted by high-speed GPU interconnect 3308 through hub 3316 to/from other units of PPU 3300 such as one or more copy engines, video encoders, video decoders, power management units, and other components which may not be explicitly illustrated in FIG. 33.

In at least one embodiment, I/O unit 3306 is configured to transmit and receive communications (e.g., commands, data) from a host processor (not illustrated in FIG. 33) over system bus 3302. In at least one embodiment, I/O unit 3306 communicates with host processor directly via system bus 3302 or through one or more intermediate devices such as a memory bridge. In at least one embodiment, I/O unit 3306 may communicate with one or more other processors, such as one or more of PPUs 3300 via system bus 3302. In at least one embodiment, I/O unit 3306 implements a Peripheral Component Interconnect Express ("PCIe") interface for communications over a PCIe bus. In at least one embodiment, I/O unit 3306 implements interfaces for communicating with external devices.

In at least one embodiment, I/O unit 3306 decodes packets received via system bus 3302. In at least one embodiment, at least some packets represent commands configured to cause PPU 3300 to perform various operations. In at least one embodiment, I/O unit 3306 transmits decoded commands to various other units of PPU 3300 as specified by commands. In at least one embodiment, commands are transmitted to front-end unit 3310 and/or transmitted to hub 3316 or other units of PPU 3300 such as one or more copy engines, a video encoder, a video decoder, a power management unit, etc. (not explicitly illustrated in FIG. 33). In at least one embodiment, I/O unit 3306 is configured to route communications between and among various logical units of PPU 3300.

In at least one embodiment, a program executed by host processor encodes a command stream in a buffer that provides workloads to PPU 3300 for processing. In at least one embodiment, a workload comprises instructions and data to be processed by those instructions. In at least one embodiment, a buffer is a region in a memory that is accessible (e.g., read/write) by both a host processor and PPU 3300—a host interface unit may be configured to access that buffer in a system memory connected to system bus 3302 via memory requests transmitted over system bus 3302 by I/O unit 3306. In at least one embodiment, a host processor writes a command stream to a buffer and then transmits a pointer to a start of a command stream to PPU 3300 such that front-end unit 3310 receives pointers to one or more command streams and manages one or more command streams, reading commands from command streams and forwarding commands to various units of PPU 3300.

In at least one embodiment, front-end unit 3310 is coupled to scheduler unit 3312 that configures various GPCs 3318 to process tasks defined by one or more command streams. In at least one embodiment, scheduler unit 3312 is configured to track state information related to various tasks managed by scheduler unit 3312 where state information may indicate which of GPCs 3318 a task is assigned to, whether task is active or inactive, a priority level associated with task, and so forth. In at least one embodiment, scheduler unit 3312 manages execution of a plurality of tasks on one or more of GPCs 3318.

In at least one embodiment, scheduler unit 3312 is coupled to work distribution unit 3314 that is configured to dispatch tasks for execution on GPCs 3318. In at least one embodiment, work distribution unit 3314 tracks a number of scheduled tasks received from scheduler unit 3312 and work distribution unit 3314 manages a pending task pool and an active task pool for each of GPCs 3318. In at least one embodiment, pending task pool comprises a number of slots (e.g., 32 slots) that contain tasks assigned to be processed by a particular GPC 3318; an active task pool may comprise a number of slots (e.g., 4 slots) for tasks that are actively being processed by GPCs 3318 such that as one of GPCs 3318 completes execution of a task, that task is evicted from that active task pool for GPC 3318 and another task from a pending task pool is selected and scheduled for execution on GPC 3318. In at least one embodiment, if an active task is idle on GPC 3318, such as while waiting for a data dependency to be resolved, then that active task is evicted from GPC 3318 and returned to that pending task pool while another task in that pending task pool is selected and scheduled for execution on GPC 3318.

In at least one embodiment, work distribution unit 3314 communicates with one or more GPCs 3318 via XBar 3320. In at least one embodiment, XBar 3320 is an interconnect network that couples many of units of PPU 3300 to other units of PPU 3300 and can be configured to couple work distribution unit 3314 to a particular GPC 3318. In at least one embodiment, one or more other units of PPU 3300 may also be connected to XBar 3320 via hub 3316.

In at least one embodiment, tasks are managed by scheduler unit 3312 and dispatched to one of GPCs 3318 by work distribution unit 3314. In at least one embodiment, GPC 3318 is configured to process task and generate results. In at least one embodiment, results may be consumed by other tasks within GPC 3318, routed to a different GPC 3318 via XBar 3320, or stored in memory 3304. In at least one embodiment, results can be written to memory 3304 via partition units 3322, which implement a memory interface for reading and writing data to/from memory 3304. In at least one embodiment, results can be transmitted to another PPU 3304 or CPU via high-speed GPU interconnect 3308. In at least one embodiment, PPU 3300 includes, without limitation, a number U of partition units 3322 that is equal to a number of separate and distinct memory devices 3304 coupled to PPU 3300, as described in more detail herein in conjunction with FIG. 35.

In at least one embodiment, a host processor executes a driver kernel that implements an application programming interface ("API") that enables one or more applications executing on a host processor to schedule operations for execution on PPU 3300. In at least one embodiment, multiple compute applications are simultaneously executed by PPU 3300 and PPU 3300 provides isolation, quality of service ("QoS"), and independent address spaces for multiple compute applications. In at least one embodiment, an application generates instructions (e.g., in form of API calls) that cause a driver kernel to generate one or more tasks for execution by PPU 3300 and that driver kernel outputs tasks to one or more streams being processed by PPU 3300. In at least one embodiment, each task comprises one or more groups of related threads, which may be referred to as a warp. In at least one embodiment, a warp comprises a plurality of related threads (e.g., 32 threads) that can be executed in parallel. In at least one embodiment, cooperating threads can refer to a plurality of threads including instructions to perform task and that exchange data through shared memory. In at least one embodiment, threads and cooperating threads are described in more detail in conjunction with FIG. 35.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, deep learning application processor is used to train a machine learning model, such as a neural network, to predict or infer information provided to PPU 3300. In at least one embodiment, deep learning application processor 3300 is used to infer or predict information based on a trained machine learning model (e.g., neural network) that has been trained by another processor or system or by PPU 3300. In at least one embodiment, PPU 3300 may be used to perform one or more neural network use cases described herein.

In at least one embodiment, one or more systems depicted in FIG. 33 are utilized to generate segmentation and confidence values for pixels of an image. In at least one embodiment, one or more systems depicted in FIG. 33 are utilized to implement one or more networks and processes such as those described in connection with FIGS. 1-7. In at least one embodiment, one or more systems depicted in FIG. 33 are utilized to implement a system for segmentation and confidence value determination.

Figure 34:
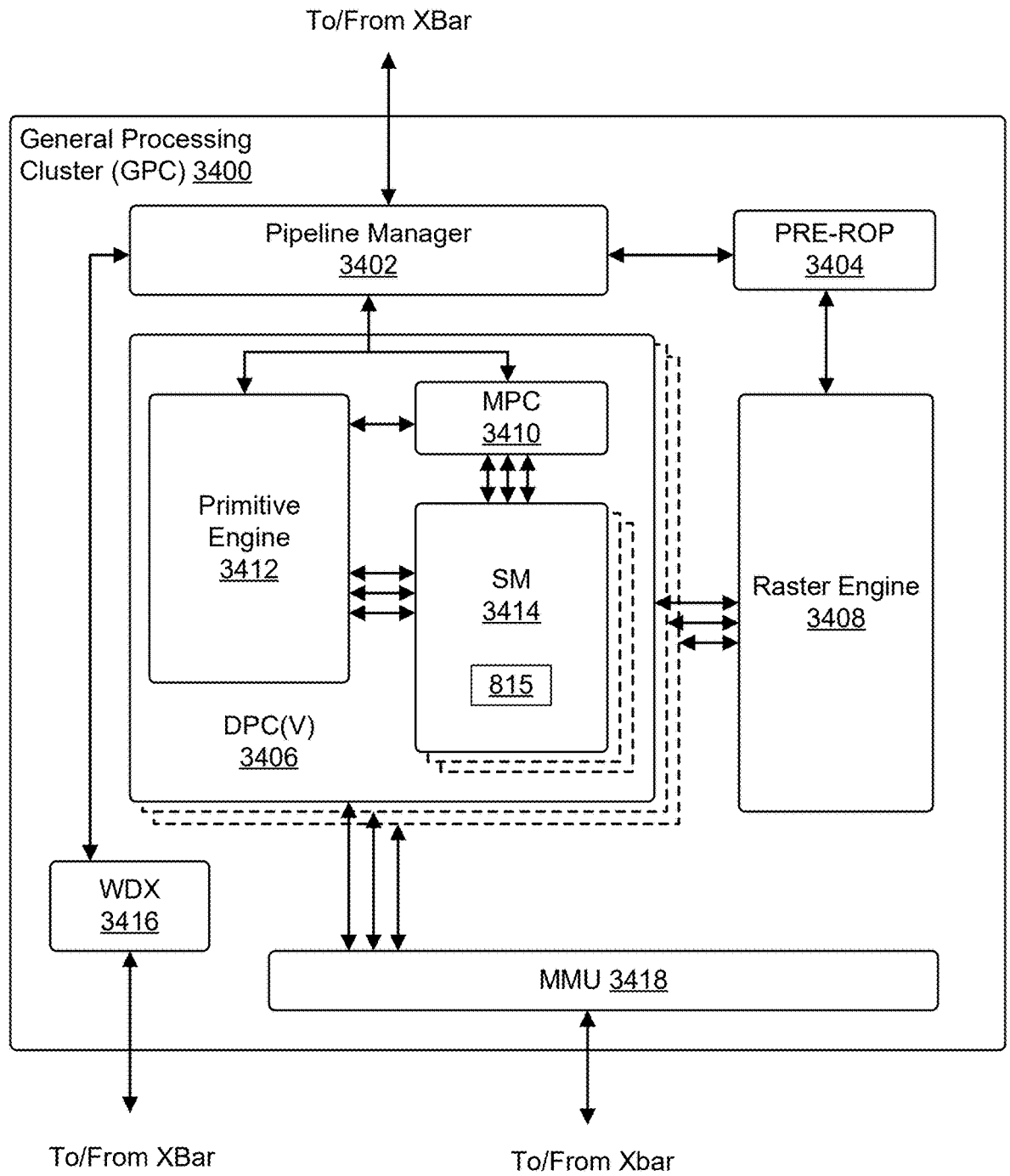
FIG. 34 illustrates a general processing cluster ("GPC"), according to at least one embodiment.

FIG. 34 illustrates a general processing cluster ("GPC") 3400, according to at least one embodiment. In at least one embodiment, GPC 3400 is GPC 3318 of FIG. 33. In at least one embodiment, each GPC 3400 includes, without limitation, a number of hardware units for processing tasks and each GPC 3400 includes, without limitation, a pipeline manager 3402, a pre-raster operations unit ("preROP") 3404, a raster engine 3408, a work distribution crossbar ("WDX") 3416, a memory management unit ("MMU") 3418, one or more Data Processing Clusters ("DPCs") 3406, and any suitable combination of parts.

In at least one embodiment, operation of GPC 3400 is controlled by pipeline manager 3402. In at least one embodiment, pipeline manager 3402 manages configuration of one or more DPCs 3406 for processing tasks allocated to GPC 3400. In at least one embodiment, pipeline manager 3402 configures at least one of one or more DPCs 3406 to implement at least a portion of a graphics rendering pipeline. In at least one embodiment, DPC 3406 is configured to execute a vertex shader program on a programmable streaming multi-processor ("SM") 3414. In at least one embodiment, pipeline manager 3402 is configured to route packets received from a work distribution unit to appropriate logical units within GPC 3400, in at least one embodiment, and some packets may be routed to fixed function hardware units in preROP 3404 and/or raster engine 3408 while other packets may be routed to DPCs 3406 for processing by a primitive engine 3412 or SM 3414. In at least one embodiment, pipeline manager 3402 configures at least one of DPCs 3406 to implement a neural network model and/or a computing pipeline.

In at least one embodiment, preROP unit 3404 is configured, in at least one embodiment, to route data generated by raster engine 3408 and DPCs 3406 to a Raster Operations ("ROP") unit in partition unit 3322, described in more detail above in conjunction with FIG. 33. In at least one embodiment, preROP unit 3404 is configured to perform optimizations for color blending, organize pixel data, perform address translations, and more. In at least one embodiment, raster engine 3408 includes, without limitation, a number of fixed function hardware units configured to perform various raster operations, in at least one embodiment, and raster engine 3408 includes, without limitation, a setup engine, a coarse raster engine, a culling engine, a clipping engine, a fine raster engine, a tile coalescing engine, and any suitable combination thereof. In at least one embodiment, setup engine receives transformed vertices and generates plane equations associated with geometric primitive defined by vertices; plane equations are transmitted to a coarse raster engine to generate coverage information (e.g., an x, y coverage mask for a tile) for primitive; output of a coarse raster engine is transmitted to a culling engine where fragments associated with a primitive that fail a z-test are culled, and transmitted to a clipping engine where fragments lying outside a viewing frustum are clipped. In at least one embodiment, fragments that survive clipping and culling are passed to a fine raster engine to generate attributes for pixel fragments based on plane equations generated by a setup engine. In at least one embodiment, an output of raster engine 3408 comprises fragments to be processed by any suitable entity, such as by a fragment shader implemented within DPC 3406.

In at least one embodiment, each DPC 3406 included in GPC 3400 comprises, without limitation, an M-Pipe Controller ("MPC") 3410; primitive engine 3412; one or more SMs 3414; and any suitable combination thereof. In at least one embodiment, MPC 3410 controls operation of DPC 3406, routing packets received from pipeline manager 3402 to appropriate units in DPC 3406. In at least one embodiment, packets associated with a vertex are routed to primitive engine 3412, which is configured to fetch vertex attributes associated with a vertex from memory; in contrast, packets associated with a shader program may be transmitted to SM 3414.

In at least one embodiment, SM 3414 comprises, without limitation, a programmable streaming processor that is configured to process tasks represented by a number of threads. In at least one embodiment, SM 3414 is multi-threaded and configured to execute a plurality of threads (e.g., 32 threads) from a particular group of threads concurrently and implements a Single-Instruction, Multiple-Data ("SIMD") architecture where each thread in a group of threads (e.g., a warp) is configured to process a different set of data based on same set of instructions. In at least one embodiment, all threads in group of threads execute a common set of instructions. In at least one embodiment, SM 3414 implements a Single-Instruction, Multiple Thread ("SIMT") architecture wherein each thread in a group of threads is configured to process a different set of data based on that common set of instructions, but where individual threads in a group of threads are allowed to diverge during execution. In at least one embodiment, a program counter, call stack, and execution state is maintained for each warp, enabling concurrency between warps and serial execution within warps when threads within a warp diverge. In another embodiment, a program counter, call stack, and execution state is maintained for each individual thread, enabling equal concurrency between all threads, within and between warps. In at least one embodiment, execution state is maintained for each individual thread and threads executing common instructions may be converged and executed in parallel for better efficiency. At least one embodiment of SM 3414 is described in more detail herein.

In at least one embodiment, MMU 3418 provides an interface between GPC 3400 and a memory partition unit (e.g., partition unit 3322 of FIG. 33) and MMU 3418 provides translation of virtual addresses into physical addresses, memory protection, and arbitration of memory requests. In at least one embodiment, MMU 3418 provides one or more translation lookaside buffers ("TLBs") for performing translation of virtual addresses into physical addresses in memory.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, deep learning application processor is used to train a machine learning model, such as a neural network, to predict or infer information provided to GPC 3400. In at least one embodiment, GPC 3400 is used to infer or predict information based on a trained machine learning model (e.g., neural network) that has been trained by another processor or system or by GPC 3400. In at least one embodiment, GPC 3400 may be used to perform one or more neural network use cases described herein.

In at least one embodiment, one or more systems depicted in FIG. 34 are utilized to generate segmentation and confidence values for pixels of an image. In at least one embodiment, one or more systems depicted in FIG. 34 are utilized to implement one or more networks and processes such as those described in connection with FIGS. 1-7. In at least one embodiment, one or more systems depicted in FIG. 34 are utilized to implement a system for segmentation and confidence value determination.

Figure 35:
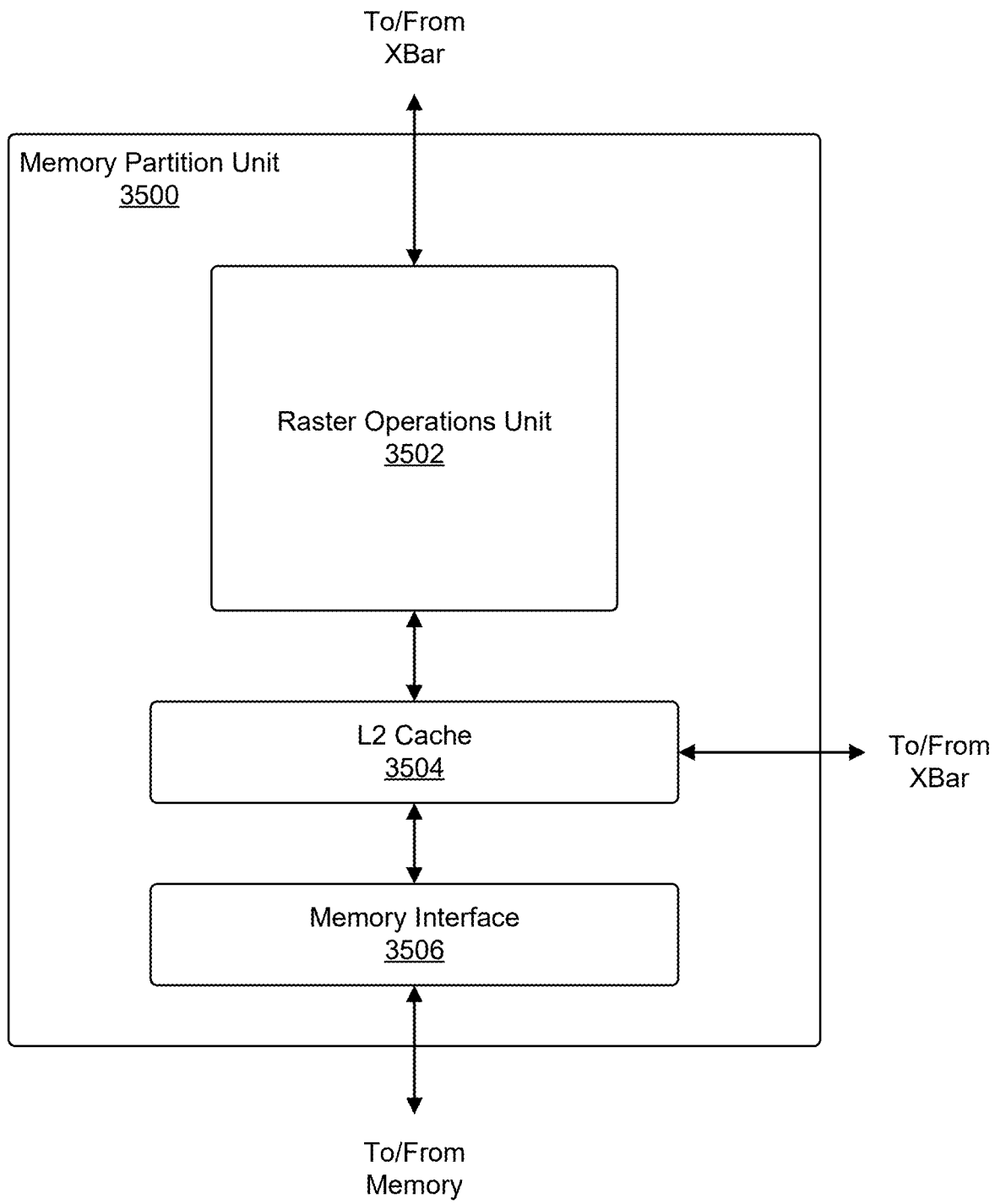
FIG. 35 illustrates a memory partition unit of a parallel processing unit ("PPU"), according to at least one embodiment.

FIG. 35 illustrates a memory partition unit 3500 of a parallel processing unit ("PPU"), in accordance with at least one embodiment. In at least one embodiment, memory partition unit 3500 includes, without limitation, a Raster Operations ("ROP") unit 3502, a level two ("L2") cache 3504, a memory interface 3506, and any suitable combination thereof. In at least one embodiment, memory interface 3506 is coupled to memory. In at least one embodiment, memory interface 3506 may implement 32, 64, 128, 1024-bit data buses, or like, for high-speed data transfer. In at least one embodiment, PPU incorporates U memory interfaces 3506 where U is a positive integer, with one memory interface 3506 per pair of partition units 3500, where each pair of partition units 3500 is connected to a corresponding memory device. For example, in at least one embodiment, PPU may be connected to up to Y memory devices, such as high bandwidth memory stacks or graphics double-data-rate, version 5, synchronous dynamic random access memory ("GDDR5 SDRAM").

In at least one embodiment, memory interface 3506 implements a high bandwidth memory second generation ("HBM2") memory interface and Y equals half of U. In at least one embodiment, HBM2 memory stacks are located on a physical package with a PPU, providing substantial power and area savings compared with conventional GDDR5 SDRAM systems. In at least one embodiment, each HBM2 stack includes, without limitation, four memory dies with Y=4, with each HBM2 stack including two 128-bit channels per die for a total of 8 channels and a data bus width of 1024 bits. In at least one embodiment, that memory supports Single-Error Correcting Double-Error Detecting ("SECDED") Error Correction Code ("ECC") to protect data. In at least one embodiment, ECC can provide higher reliability for compute applications that are sensitive to data corruption.

In at least one embodiment, PPU implements a multi-level memory hierarchy. In at least one embodiment, memory partition unit 3500 supports a unified memory to provide a single unified virtual address space for central processing unit ("CPU") and PPU memory, enabling data sharing between virtual memory systems. In at least one embodiment frequency of accesses by a PPU to a memory located on other processors is traced to ensure that memory pages are moved to physical memory of PPU that is accessing pages more frequently. In at least one embodiment, high-speed GPU interconnect 3308 supports address translation services allowing PPU to directly access a CPU's page tables and providing full access to CPU memory by a PPU.

In at least one embodiment, copy engines transfer data between multiple PPUs or between PPUs and CPUs. In at least one embodiment, copy engines can generate page faults for addresses that are not mapped into page tables and memory partition unit 3500 then services page faults, mapping addresses into page table, after which copy engine performs a transfer. In at least one embodiment, memory is pinned (i.e., non-pageable) for multiple copy engine operations between multiple processors, substantially reducing available memory. In at least one embodiment, with hardware page faulting, addresses can be passed to copy engines without regard as to whether memory pages are resident, and a copy process is transparent.

Data from memory 3304 of FIG. 33 or other system memory is fetched by memory partition unit 3500 and stored in L2 cache 3504, which is located on-chip and is shared between various GPCs, in accordance with at least one embodiment. Each memory partition unit 3500, in at least one embodiment, includes, without limitation, at least a portion of L2 cache associated with a corresponding memory device. In at least one embodiment, lower level caches are implemented in various units within GPCs. In at least one embodiment, each of SMs 3414 in FIG. 34 may implement a Level 1 ("L1") cache wherein that L1 cache is private memory that is dedicated to a particular SM 3414 and data from L2 cache 3504 is fetched and stored in each L1 cache for processing in functional units of SMs 3414. In at least one embodiment, L2 cache 3504 is coupled to memory interface 3506 and XBar 3320 shown in FIG. 33.

ROP unit 3502 performs graphics raster operations related to pixel color, such as color compression, pixel blending, and more, in at least one embodiment. ROP unit 3502, in at least one embodiment, implements depth testing in conjunction with raster engine 3408, receiving a depth for a sample location associated with a pixel fragment from a culling engine of raster engine 3408. In at least one embodiment, depth is tested against a corresponding depth in a depth buffer for a sample location associated with a fragment. In at least one embodiment, if that fragment passes that depth test for that sample location, then ROP unit 3502 updates depth buffer and transmits a result of that depth test to raster engine 3408. It will be appreciated that a number of partition units 3500 may be different than a number of GPCs and, therefore, each ROP unit 3502 can, in at least one embodiment, be coupled to each GPC. In at least one embodiment, ROP unit 3502 tracks packets received from different GPCs and determines whether a result generated by ROP unit 3502 is to be routed to through XBar 3320.

In at least one embodiment, one or more systems depicted in FIG. 35 are utilized to generate segmentation and confidence values for pixels of an image. In at least one embodiment, one or more systems depicted in FIG. 35 are utilized to implement one or more networks and processes such as those described in connection with FIGS. 1-7. In at least one embodiment, one or more systems depicted in FIG. 35 are utilized to implement a system for segmentation and confidence value determination.

Figure 36:
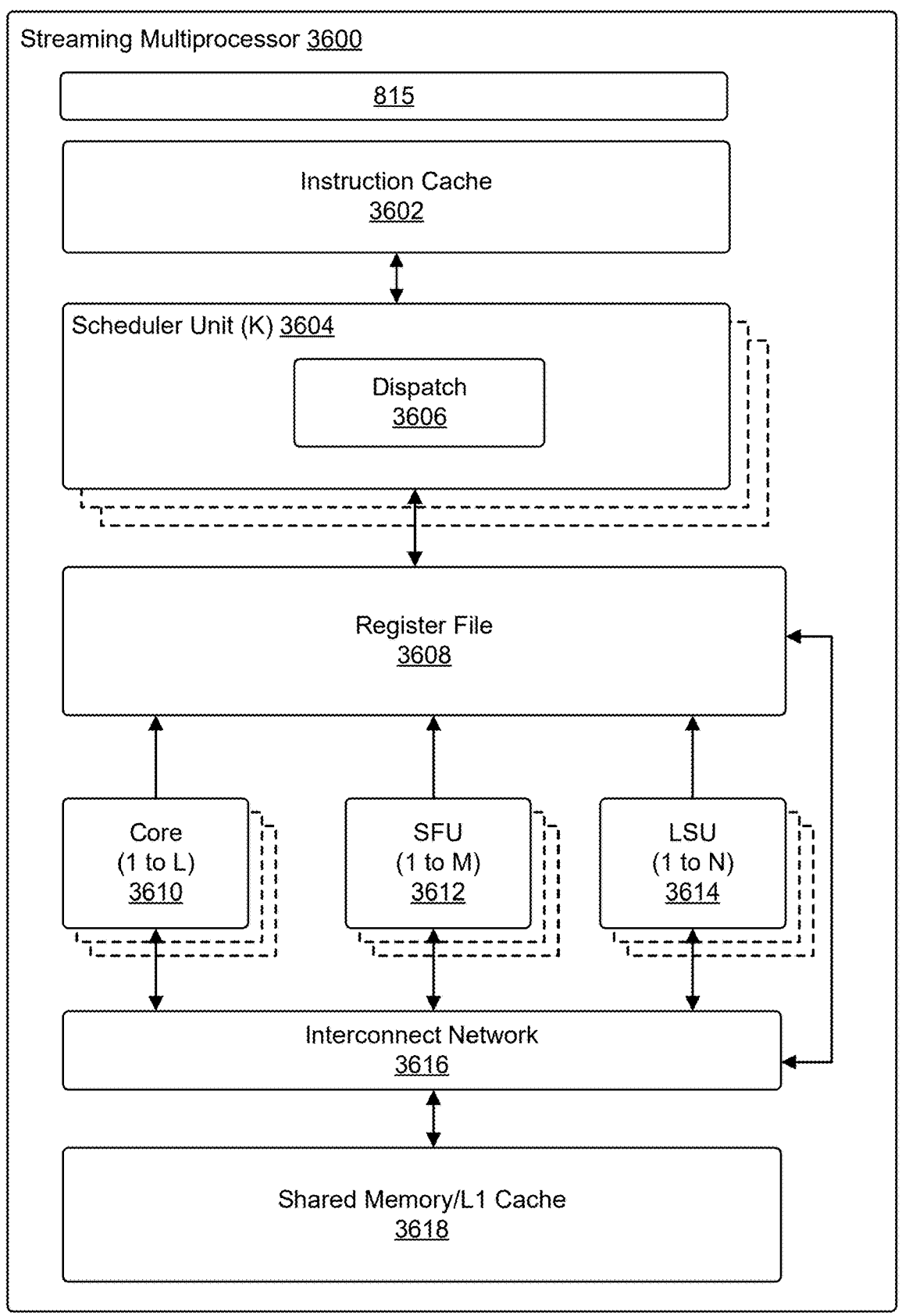
FIG. 36 illustrates a streaming multi-processor, according to at least one embodiment.

FIG. 36 illustrates a streaming multi-processor ("SM") 3600, according to at least one embodiment. In at least one embodiment, SM 3600 is SM of FIG. 34. In at least one embodiment, SM 3600 includes, without limitation, an instruction cache 3602, one or more scheduler units 3604, a register file 3608, one or more processing cores ("cores") 3610, one or more special function units ("SFUs") 3612, one or more load/store units ("LSUs") 3614, an interconnect network 3616, a shared memory/level one ("L1") cache 3618, and/or any suitable combination thereof.

In at least one embodiment, a work distribution unit dispatches tasks for execution on general processing clusters ("GPCs") of parallel processing units ("PPUs") and each task is allocated to a particular Data Processing Cluster ("DPC") within a GPC and, if a task is associated with a shader program, that task is allocated to one of SMs 3600. In at least one embodiment, scheduler unit 3604 receives tasks from a work distribution unit and manages instruction scheduling for one or more thread blocks assigned to SM 3600. In at least one embodiment, scheduler unit 3604 schedules thread blocks for execution as warps of parallel threads, wherein each thread block is allocated at least one warp. In at least one embodiment, each warp executes threads. In at least one embodiment, scheduler unit 3604 manages a plurality of different thread blocks, allocating warps to different thread blocks and then dispatching instructions from plurality of different cooperative groups to various functional units (e.g., processing cores 3610, SFUs 3612, and LSUs 3614) during each clock cycle.

In at least one embodiment, Cooperative Groups may refer to a programming model for organizing groups of communicating threads that allows developers to express granularity at which threads are communicating, enabling expression of richer, more efficient parallel decompositions. In at least one embodiment, cooperative launch APIs support synchronization amongst thread blocks for execution of parallel algorithms. In at least one embodiment, applications of conventional programming models provide a single, simple construct for synchronizing cooperating threads: a barrier across all threads of a thread block (e.g., syncthreads( ) function). However, in at least one embodiment, programmers may define groups of threads at smaller than thread block granularities and synchronize within defined groups to enable greater performance, design flexibility, and software reuse in form of collective group-wide function interfaces. In at least one embodiment, Cooperative Groups enables programmers to define groups of threads explicitly at sub-block (i.e., as small as a single thread) and multi-block granularities, and to perform collective operations such as synchronization on threads in a cooperative group. In at least one embodiment, that programming model supports clean composition across software boundaries, so that libraries and utility functions can synchronize safely within their local context without having to make assumptions about convergence. In at least one embodiment, Cooperative Groups primitives enable new patterns of cooperative parallelism, including, without limitation, producer-consumer parallelism, opportunistic parallelism, and global synchronization across an entire grid of thread blocks.

In at least one embodiment, a dispatch unit 3606 is configured to transmit instructions to one or more functional units and scheduler unit 3604 and includes, without limitation, two dispatch units 3606 that enable two different instructions from a common warp to be dispatched during each clock cycle. In at least one embodiment, each scheduler unit 3604 includes a single dispatch unit 3606 or additional dispatch units 3606.

In at least one embodiment, each SM 3600, in at least one embodiment, includes, without limitation, register file 3608 that provides a set of registers for functional units of SM 3600. In at least one embodiment, register file 3608 is divided between each functional unit such that each functional unit is allocated a dedicated portion of register file 3608. In at least one embodiment, register file 3608 is divided between different warps being executed by SM 3600 and register file 3608 provides temporary storage for operands connected to data paths of functional units. In at least one embodiment, each SM 3600 comprises, without limitation, a plurality of L processing cores 3610, where L is a positive integer. In at least one embodiment, SM 3600 includes, without limitation, a large number (e.g., 128 or more) of distinct processing cores 3610. In at least one embodiment, each processing core 3610 includes, without limitation, a fully-pipelined, single-precision, double-precision, and/or mixed precision processing unit that includes, without limitation, a floating point arithmetic logic unit and an integer arithmetic logic unit. In at least one embodiment, floating point arithmetic logic units implement IEEE 754-2008 standard for floating point arithmetic. In at least one embodiment, processing cores 3610 include, without limitation, 64 single-precision (32-bit) floating point cores, 64 integer cores, 32 double-precision (64-bit) floating point cores, and 8 tensor cores.

Tensor cores are configured to perform matrix operations in accordance with at least one embodiment. In at least one embodiment, one or more tensor cores are included in processing cores 3610. In at least one embodiment, tensor cores are configured to perform deep learning matrix arithmetic, such as convolution operations for neural network training and inferencing. In at least one embodiment, each tensor core operates on a 4×4 matrix and performs a matrix multiply and accumulate operation, D=A×B+C, where A, B, C, and D are 4×4 matrices.

In at least one embodiment, matrix multiply inputs A and B are 16-bit floating point matrices and accumulation matrices C and D are 16-bit floating point or 32-bit floating point matrices. In at least one embodiment, tensor cores operate on 16-bit floating point input data with 32-bit floating point accumulation. In at least one embodiment, 16-bit floating point multiply uses 64 operations and results in a full precision product that is then accumulated using 32-bit floating point addition with other intermediate products for a 4×4×4 matrix multiply. Tensor cores are used to perform much larger two-dimensional or higher dimensional matrix operations, built up from these smaller elements, in at least one embodiment. In at least one embodiment, an API, such as a CUDA 9 C++ API, exposes specialized matrix load, matrix multiply and accumulate, and matrix store operations to efficiently use tensor cores from a CUDA-C++ program. In at least one embodiment, at a CUDA level, a warp-level interface assumes 16×16 size matrices spanning all 32 threads of warp.

In at least one embodiment, each SM 3600 comprises, without limitation, M SFUs 3612 that perform special functions (e.g., attribute evaluation, reciprocal square root, and like). In at least one embodiment, SFUs 3612 include, without limitation, a tree traversal unit configured to traverse a hierarchical tree data structure. In at least one embodiment, SFUs 3612 include, without limitation, a texture unit configured to perform texture map filtering operations. In at least one embodiment, texture units are configured to load texture maps (e.g., a 2D array of texels) from memory and sample texture maps to produce sampled texture values for use in shader programs executed by SM 3600. In at least one embodiment, texture maps are stored in shared memory/L1 cache 3618. In at least one embodiment, texture units implement texture operations such as filtering operations using mip-maps (e.g., texture maps of varying levels of detail), in accordance with at least one embodiment. In at least one embodiment, each SM 3600 includes, without limitation, two texture units.

Each SM 3600 comprises, without limitation, N LSUs 3614 that implement load and store operations between shared memory/L1 cache 3618 and register file 3608, in at least one embodiment. Interconnect network 3616 connects each functional unit to register file 3608 and LSU 3614 to register file 3608 and shared memory/L1 cache 3618 in at least one embodiment. In at least one embodiment, interconnect network 3616 is a crossbar that can be configured to connect any functional units to any registers in register file 3608 and connect LSUs 3614 to register file 3608 and memory locations in shared memory/L1 cache 3618.

In at least one embodiment, shared memory/L1 cache 3618 is an array of on-chip memory that allows for data storage and communication between SM 3600 and primitive engine and between threads in SM 3600, in at least one embodiment. In at least one embodiment, shared memory/L1 cache 3618 comprises, without limitation, 128 KB of storage capacity and is in a path from SM 3600 to a partition unit. In at least one embodiment, shared memory/L1 cache 3618, in at least one embodiment, is used to cache reads and writes. In at least one embodiment, one or more of shared memory/L1 cache 3618, L2 cache, and memory are backing stores.

Combining data cache and shared memory functionality into a single memory block provides improved performance for both types of memory accesses, in at least one embodiment. In at least one embodiment, capacity is used or is usable as a cache by programs that do not use shared memory, such as if shared memory is configured to use half of a capacity, and texture and load/store operations can use remaining capacity. Integration within shared memory/L1 cache 3618 enables shared memory/L1 cache 3618 to function as a high-throughput conduit for streaming data while simultaneously providing high-bandwidth and low-latency access to frequently reused data, in accordance with at least one embodiment. In at least one embodiment, when configured for general purpose parallel computation, a simpler configuration can be used compared with graphics processing. In at least one embodiment, fixed function graphics processing units are bypassed, creating a much simpler programming model. In a general purpose parallel computation configuration, a work distribution unit assigns and distributes blocks of threads directly to DPCs, in at least one embodiment. In at least one embodiment, threads in a block execute a common program, using a unique thread ID in calculation to ensure each thread generates unique results, using SM 3600 to execute program and perform calculations, shared memory/L1 cache 3618 to communicate between threads, and LSU 3614 to read and write global memory through shared memory/L1 cache 3618 and memory partition unit. In at least one embodiment, when configured for general purpose parallel computation, SM 3600 writes commands that scheduler unit 3604 can use to launch new work on DPCs.

In at least one embodiment, a PPU is included in or coupled to a desktop computer, a laptop computer, a tablet computer, servers, supercomputers, a smart-phone (e.g., a wireless, hand-held device), personal digital assistant ("PDA"), a digital camera, a vehicle, a head mounted display, a hand-held electronic device, and more. In at least one embodiment, a PPU is embodied on a single semiconductor substrate. In at least one embodiment, a PPU is included in a system-on-a-chip ("SoC") along with one or more other devices such as additional PPUs, memory, a reduced instruction set computer ("RISC") CPU, a memory management unit ("MMU"), a digital-to-analog converter ("DAC"), and like.

In at least one embodiment, a PPU may be included on a graphics card that includes one or more memory devices. In at least one embodiment, that graphics card may be configured to interface with a PCIe slot on a motherboard of a desktop computer. In at least one embodiment, that PPU may be an integrated graphics processing unit ("iGPU") included in chipset of a motherboard.

Inference and/or training logic 815 are used to perform inferencing and/or training operations associated with one or more embodiments. Details regarding inference and/or training logic 815 are provided herein in conjunction with FIGS. 8A and/or 8B. In at least one embodiment, deep learning application processor is used to train a machine learning model, such as a neural network, to predict or infer information provided to SM 3600. In at least one embodiment, SM 3600 is used to infer or predict information based on a trained machine learning model (e.g., neural network) that has been trained by another processor or system or by SM 3600. In at least one embodiment, SM 3600 may be used to perform one or more neural network use cases described herein.

In at least one embodiment, one or more systems depicted in FIG. 36 are utilized to generate segmentation and confidence values for pixels of an image. In at least one embodiment, one or more systems depicted in FIG. 36 are utilized to implement one or more networks and processes such as those described in connection with FIGS. 1-7. In at least one embodiment, one or more systems depicted in FIG. 36 are utilized to implement a system for segmentation and confidence value determination.

Embodiments are disclosed related a virtualized computing platform for advanced computing, such as image inferencing and image processing in medical applications. Without limitation, embodiments may include radiography, magnetic resonance imaging (MRI), nuclear medicine, ultrasound, sonography, elastography, photoacoustic imaging, tomography, echocardiography, functional near-infrared spectroscopy, and magnetic particle imaging, or a combination thereof. In at least one embodiment, a virtualized computing platform and associated processes described herein may additionally or alternatively be used, without limitation, in forensic science analysis, sub-surface detection and imaging (e.g., oil exploration, archaeology, paleontology, etc.), topography, oceanography, geology, osteology, meteorology, intelligent area or object tracking and monitoring, sensor data processing (e.g., RADAR, SONAR, LIDAR, etc.), and/or genomics and gene sequencing.

Figure 37:
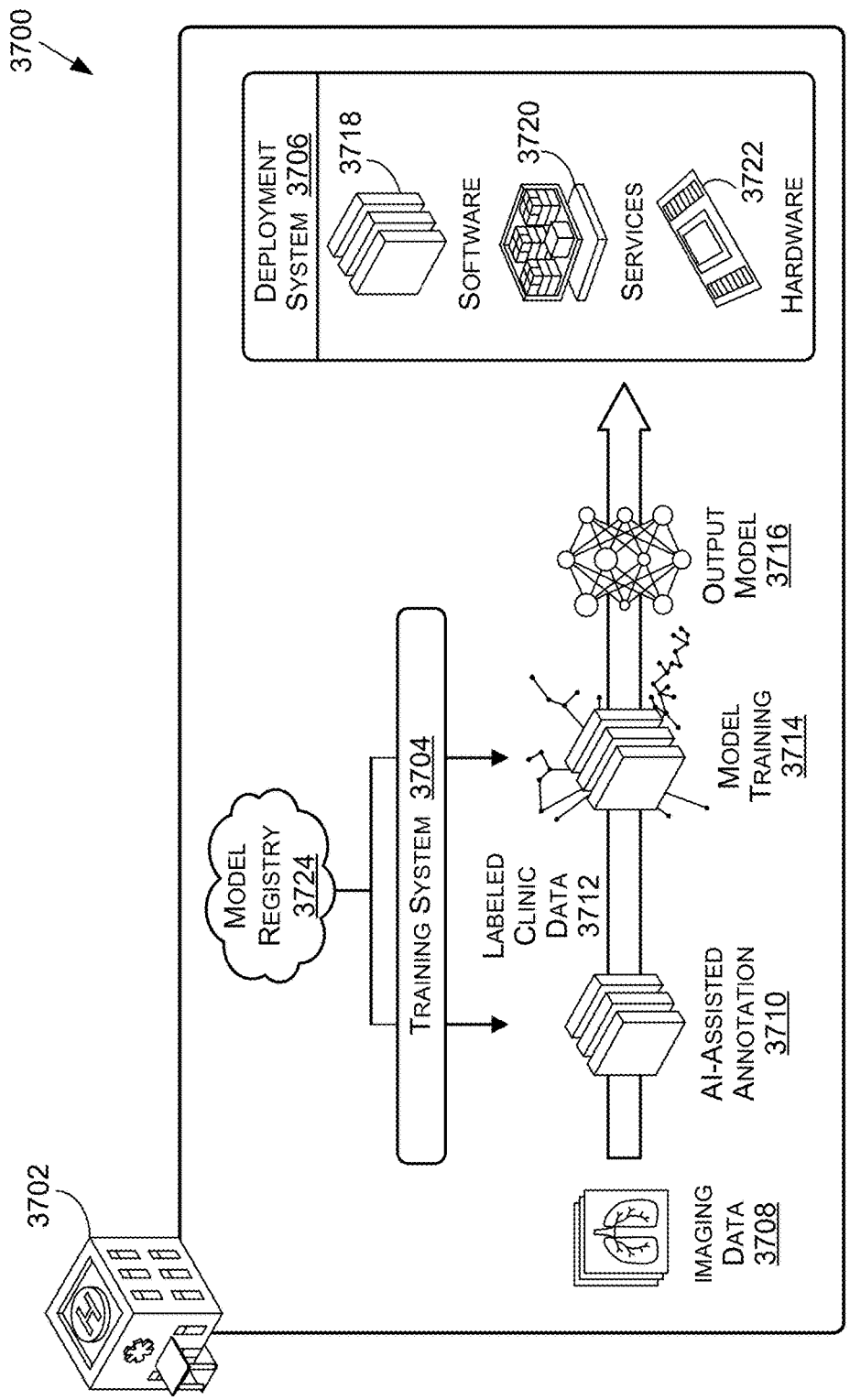
FIG. 37 is an example data flow diagram for an advanced computing pipeline, in accordance with at least one embodiment.

With reference to FIG. 37, FIG. 37 is an example data flow diagram for a process 3700 of generating and deploying an image processing and inferencing pipeline, in accordance with at least one embodiment. In at least one embodiment, process 3700 may be deployed for use with imaging devices, processing devices, genomics devices, gene sequencing devices, radiology devices, and/or other device types at one or more facilities 3702, such as medical facilities, hospitals, healthcare institutes, clinics, research or diagnostic labs, etc. In at least one embodiment, process 3700 may be deployed to perform genomics analysis and inferencing on sequencing data. Examples of genomic analyses that may be performed using systems and processes described herein include, without limitation, variant calling, mutation detection, and gene expression quantification.

In at least one embodiment, process 3700 may be executed within a training system 3704 and/or a deployment system 3706. In at least one embodiment, training system 3704 may be used to perform training, deployment, and implementation of machine learning models (e.g., neural networks, object detection algorithms, computer vision algorithms, etc.) for use in deployment system 3706. In at least one embodiment, deployment system 3706 may be configured to offload processing and compute resources among a distributed computing environment to reduce infrastructure requirements at facility 3702. In at least one embodiment, deployment system 3706 may provide a streamlined platform for selecting, customizing, and implementing virtual instruments for use with imaging devices (e.g., MRI, CT Scan, X-Ray, Ultrasound, etc.) or sequencing devices at facility 3702. In at least one embodiment, virtual instruments may include software-defined applications for performing one or more processing operations with respect to imaging data generated by imaging devices, sequencing devices, radiology devices, and/or other device types. In at least one embodiment, one or more applications in a pipeline may use or call upon services (e.g., inference, visualization, compute, AI, etc.) of deployment system 3706 during execution of applications.

In at least one embodiment, some of applications used in advanced processing and inferencing pipelines may use machine learning models or other AI to perform one or more processing steps. In at least one embodiment, machine learning models may be trained at facility 3702 using data 3708 (such as imaging data) generated at facility 3702 (and stored on one or more picture archiving and communication system (PACS) servers at facility 3702), may be trained using imaging or sequencing data 3708 from another facility or facilities (e.g., a different hospital, lab, clinic, etc.), or a combination thereof. In at least one embodiment, training system 3704 may be used to provide applications, services, and/or other resources for generating working, deployable machine learning models for deployment system 3706.

In at least one embodiment, a model registry 3724 may be backed by object storage that may support versioning and object metadata. In at least one embodiment, object storage may be accessible through, for example, a cloud storage (e.g., a cloud 3826 of FIG. 38) compatible application programming interface (API) from within a cloud platform. In at least one embodiment, machine learning models within model registry 3724 may uploaded, listed, modified, or deleted by developers or partners of a system interacting with an API. In at least one embodiment, an API may provide access to methods that allow users with appropriate credentials to associate models with applications, such that models may be executed as part of execution of containerized instantiations of applications.

In at least one embodiment, a training pipeline 3804 (FIG. 38) may include a scenario where facility 3702 is training their own machine learning model, or has an existing machine learning model that needs to be optimized or updated. In at least one embodiment, imaging data 3708 generated by imaging device(s), sequencing devices, and/or other device types may be received. In at least one embodiment, once imaging data 3708 is received, AI-assisted annotation 3710 may be used to aid in generating annotations corresponding to imaging data 3708 to be used as ground truth data for a machine learning model. In at least one embodiment, AI-assisted annotation 3710 may include one or more machine learning models (e.g., convolutional neural networks (CNNs)) that may be trained to generate annotations corresponding to certain types of imaging data 3708 (e.g., from certain devices) and/or certain types of anomalies in imaging data 3708. In at least one embodiment, AI-assisted annotations 3710 may then be used directly, or may be adjusted or fine-tuned using an annotation tool (e.g., by a researcher, a clinician, a doctor, a scientist, etc.), to generate ground truth data. In at least one embodiment, in some examples, labeled clinic data 3712 (e.g., annotations provided by a clinician, doctor, scientist, technician, etc.) may be used as ground truth data for training a machine learning model. In at least one embodiment, AI-assisted annotations 3710, labeled clinic data 3712, or a combination thereof may be used as ground truth data for training a machine learning model. In at least one embodiment, a trained machine learning model may be referred to as an output model 3716, and may be used by deployment system 3706, as described herein.

In at least one embodiment, training pipeline 3804 (FIG. 38) may include a scenario where facility 3702 needs a machine learning model for use in performing one or more processing tasks for one or more applications in deployment system 3706, but facility 3702 may not currently have such a machine learning model (or may not have a model that is optimized, efficient, or effective for such purposes). In at least one embodiment, an existing machine learning model may be selected from model registry 3724. In at least one embodiment, model registry 3724 may include machine learning models trained to perform a variety of different inference tasks on imaging data. In at least one embodiment, machine learning models in model registry 3724 may have been trained on imaging data from different facilities than facility 3702 (e.g., facilities remotely located). In at least one embodiment, machine learning models may have been trained on imaging data from one location, two locations, or any number of locations. In at least one embodiment, when being trained on imaging data from a specific location, training may take place at that location, or at least in a manner that protects confidentiality of imaging data or restricts imaging data from being transferred off-premises (e.g., to comply with HIPAA regulations, privacy regulations, etc.). In at least one embodiment, once a model is trained (or partially trained) at one location, a machine learning model may be added to model registry 3724. In at least one embodiment, a machine learning model may then be retrained, or updated, at any number of other facilities, and a retrained or updated model may be made available in model registry 3724. In at least one embodiment, a machine learning model may then be selected from model registry 3724 (and referred to as output model 3716) and may be used in deployment system 3706 to perform one or more processing tasks for one or more applications of a deployment system.

In at least one embodiment, training pipeline 3804 (FIG. 38) may be used in a scenario that includes facility 3702 requiring a machine learning model for use in performing one or more processing tasks for one or more applications in deployment system 3706, but facility 3702 may not currently have such a machine learning model (or may not have a model that is optimized, efficient, or effective for such purposes). In at least one embodiment, a machine learning model selected from model registry 3724 might not be fine-tuned or optimized for imaging data 3708 generated at facility 3702 because of differences in populations, genetic variations, robustness of training data used to train a machine learning model, diversity in anomalies of training data, and/or other issues with training data. In at least one embodiment, AI-assisted annotation 3710 may be used to aid in generating annotations corresponding to imaging data 3708 to be used as ground truth data for retraining or updating a machine learning model. In at least one embodiment, labeled clinic data 3712 (e.g., annotations provided by a clinician, doctor, scientist, etc.) may be used as ground truth data for training a machine learning model. In at least one embodiment, retraining or updating a machine learning model may be referred to as model training 3714. In at least one embodiment, model training 3714 (e.g., AI-assisted annotations 3710, labeled clinic data 3712, or a combination thereof) may be used as ground truth data for retraining or updating a machine learning model.

In at least one embodiment, deployment system 3706 may include software 3718, services 3720, hardware 3722, and/or other components, features, and functionality. In at least one embodiment, deployment system 3706 may include a software "stack," such that software 3718 may be built on top of services 3720 and may use services 3720 to perform some or all of processing tasks, and services 3720 and software 3718 may be built on top of hardware 3722 and use hardware 3722 to execute processing, storage, and/or other compute tasks of deployment system 3706.

In at least one embodiment, software 3718 may include any number of different containers, where each container may execute an instantiation of an application. In at least one embodiment, each application may perform one or more processing tasks in an advanced processing and inferencing pipeline (e.g., inferencing, object detection, feature detection, segmentation, image enhancement, calibration, etc.). In at least one embodiment, for each type of imaging device (e.g., CT, MRI, X-Ray, ultrasound, sonography, echocardiography, etc.), sequencing device, radiology device, genomics device, etc., there may be any number of containers that may perform a data processing task with respect to imaging data 3708 (or other data types, such as those described herein) generated by a device. In at least one embodiment, an advanced processing and inferencing pipeline may be defined based on selections of different containers that are desired or required for processing imaging data 3708, in addition to containers that receive and configure imaging data for use by each container and/or for use by facility 3702 after processing through a pipeline (e.g., to convert outputs back to a usable data type, such as digital imaging and communications in medicine (DICOM) data, radiology information system (RIS) data, clinical information system (CIS) data, remote procedure call (RPC) data, data substantially compliant with a representation state transfer (REST) interface, data substantially compliant with a file-based interface, and/or raw data, for storage and display at facility 3702). In at least one embodiment, a combination of containers within software 3718 (e.g., that make up a pipeline) may be referred to as a virtual instrument (as described in more detail herein), and a virtual instrument may leverage services 3720 and hardware 3722 to execute some or all processing tasks of applications instantiated in containers.

In at least one embodiment, a data processing pipeline may receive input data (e.g., imaging data 3708) in a DICOM, RIS, CIS, REST compliant, RPC, raw, and/or other format in response to an inference request (e.g., a request from a user of deployment system 3706, such as a clinician, a doctor, a radiologist, etc.). In at least one embodiment, input data may be representative of one or more images, video, and/or other data representations generated by one or more imaging devices, sequencing devices, radiology devices, genomics devices, and/or other device types. In at least one embodiment, data may undergo pre-processing as part of data processing pipeline to prepare data for processing by one or more applications. In at least one embodiment, post-processing may be performed on an output of one or more inferencing tasks or other processing tasks of a pipeline to prepare an output data for a next application and/or to prepare output data for transmission and/or use by a user (e.g., as a response to an inference request). In at least one embodiment, inferencing tasks may be performed by one or more machine learning models, such as trained or deployed neural networks, which may include output models 3716 of training system 3704.

In at least one embodiment, tasks of data processing pipeline may be encapsulated in a container(s) that each represent a discrete, fully functional instantiation of an application and virtualized computing environment that is able to reference machine learning models. In at least one embodiment, containers or applications may be published into a private (e.g., limited access) area of a container registry (described in more detail herein), and trained or deployed models may be stored in model registry 3724 and associated with one or more applications. In at least one embodiment, images of applications (e.g., container images) may be available in a container registry, and once selected by a user from a container registry for deployment in a pipeline, an image may be used to generate a container for an instantiation of an application for use by a user's system.

In at least one embodiment, developers (e.g., software developers, clinicians, doctors, etc.) may develop, publish, and store applications (e.g., as containers) for performing image processing and/or inferencing on supplied data. In at least one embodiment, development, publishing, and/or storing may be performed using a software development kit (SDK) associated with a system (e.g., to ensure that an application and/or container developed is compliant with or compatible with a system). In at least one embodiment, an application that is developed may be tested locally (e.g., at a first facility, on data from a first facility) with an SDK which may support at least some of services 3720 as a system (e.g., system 3800 of FIG. 38). In at least one embodiment, because DICOM objects may contain anywhere from one to hundreds of images or other data types, and due to a variation in data, a developer may be responsible for managing (e.g., setting constructs for, building pre-processing into an application, etc.) extraction and preparation of incoming DICOM data. In at least one embodiment, once validated by system 3800 (e.g., for accuracy, safety, patient privacy, etc.), an application may be available in a container registry for selection and/or implementation by a user (e.g., a hospital, clinic, lab, healthcare provider, etc.) to perform one or more processing tasks with respect to data at a facility (e.g., a second facility) of a user.

Figure 38:
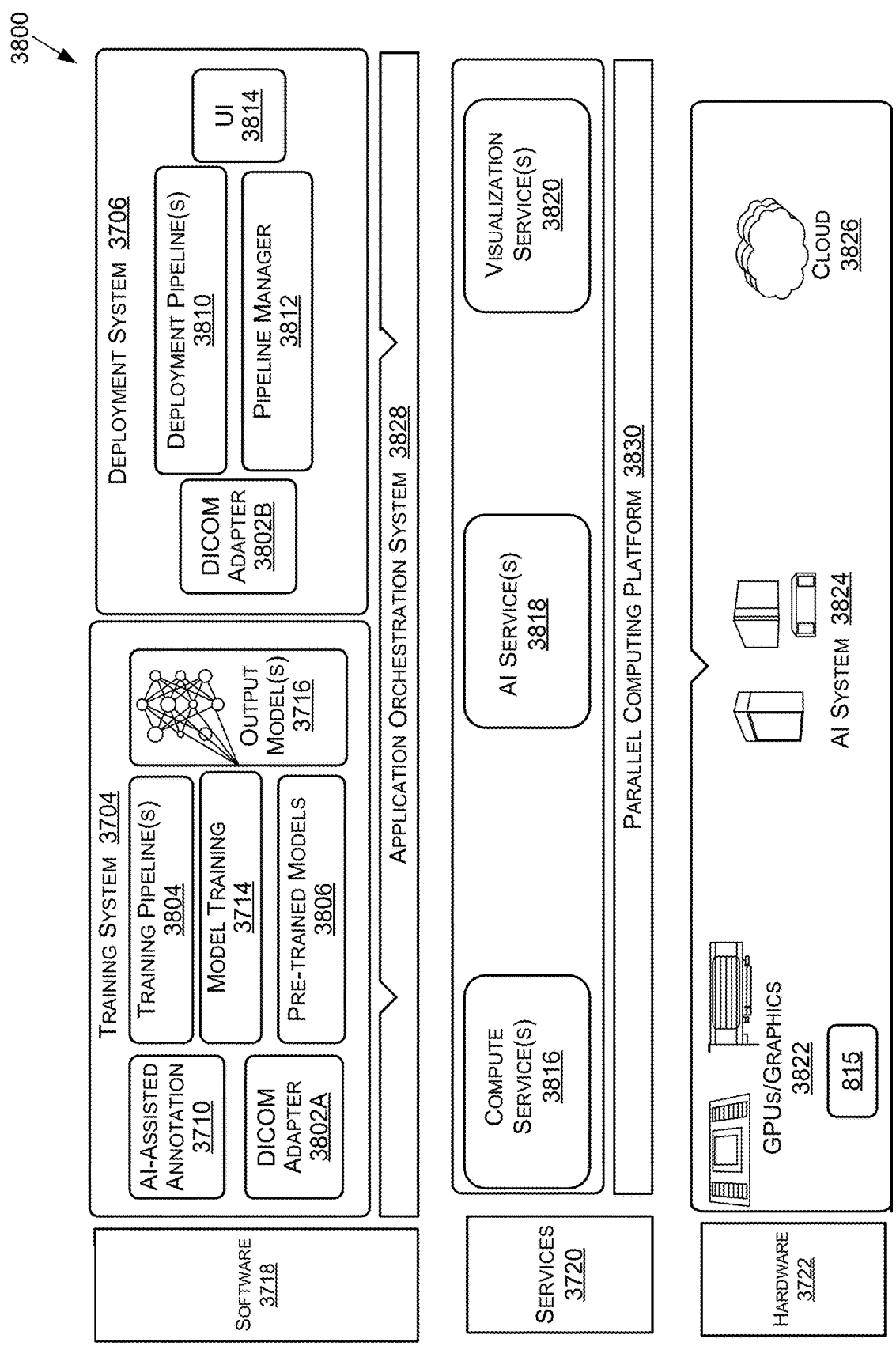
FIG. 38 is a system diagram for an example system for training, adapting, instantiating and deploying machine learning models in an advanced computing pipeline, in accordance with at least one embodiment.

In at least one embodiment, developers may then share applications or containers through a network for access and use by users of a system (e.g., system 3800 of FIG. 38). In at least one embodiment, completed and validated applications or containers may be stored in a container registry and associated machine learning models may be stored in model registry 3724. In at least one embodiment, a requesting entity (e.g., a user at a medical facility), who provides an inference or image processing request, may browse a container registry and/or model registry 3724 for an application, container, dataset, machine learning model, etc., select a desired combination of elements for inclusion in data processing pipeline, and submit an imaging processing request. In at least one embodiment, a request may include input data (and associated patient data, in some examples) that is necessary to perform a request, and/or may include a selection of application(s) and/or machine learning models to be executed in processing a request. In at least one embodiment, a request may then be passed to one or more components of deployment system 3706 (e.g., a cloud) to perform processing of data processing pipeline. In at least one embodiment, processing by deployment system 3706 may include referencing selected elements (e.g., applications, containers, models, etc.) from a container registry and/or model registry 3724. In at least one embodiment, once results are generated by a pipeline, results may be returned to a user for reference (e.g., for viewing in a viewing application suite executing on a local, on-premises workstation or terminal). In at least one embodiment, a radiologist may receive results from an data processing pipeline including any number of application and/or containers, where results may include anomaly detection in X-rays, CT scans, MRIs, etc.

In at least one embodiment, to aid in processing or execution of applications or containers in pipelines, services 3720 may be leveraged. In at least one embodiment, services 3720 may include compute services, artificial intelligence (AI) services, visualization services, and/or other service types. In at least one embodiment, services 3720 may provide functionality that is common to one or more applications in software 3718, so functionality may be abstracted to a service that may be called upon or leveraged by applications. In at least one embodiment, functionality provided by services 3720 may run dynamically and more efficiently, while also scaling well by allowing applications to process data in parallel (e.g., using a parallel computing platform 3830 (FIG. 38)). In at least one embodiment, rather than each application that shares a same functionality offered by a service 3720 being required to have a respective instance of service 3720, service 3720 may be shared between and among various applications. In at least one embodiment, services may include an inference server or engine that may be used for executing detection or segmentation tasks, as non-limiting examples. In at least one embodiment, a model training service may be included that may provide machine learning model training and/or retraining capabilities. In at least one embodiment, a data augmentation service may further be included that may provide GPU accelerated data (e.g., DICOM, RIS, CIS, REST compliant, RPC, raw, etc.) extraction, resizing, scaling, and/or other augmentation. In at least one embodiment, a visualization service may be used that may add image rendering effects (such as ray-tracing, rasterization, denoising, sharpening, etc.) to add realism to two-dimensional (2D) and/or three-dimensional (3D) models. In at least one embodiment, virtual instrument services may be included that provide for beam-forming, segmentation, inferencing, imaging, and/or support for other applications within pipelines of virtual instruments.

In at least one embodiment, where a service 3720 includes an AI service (e.g., an inference service), one or more machine learning models associated with an application for anomaly detection (e.g., tumors, growth abnormalities, scarring, etc.) may be executed by calling upon (e.g., as an API call) an inference service (e.g., an inference server) to execute machine learning model(s), or processing thereof, as part of application execution. In at least one embodiment, where another application includes one or more machine learning models for segmentation tasks, an application may call upon an inference service to execute machine learning models for performing one or more of processing operations associated with segmentation tasks. In at least one embodiment, software 3718 implementing advanced processing and inferencing pipeline that includes segmentation application and anomaly detection application may be streamlined because each application may call upon a same inference service to perform one or more inferencing tasks.

In at least one embodiment, hardware 3722 may include GPUs, CPUs, graphics cards, an AI/deep learning system (e.g., an AI supercomputer, such as NVIDIA's DGX supercomputer system), a cloud platform, or a combination thereof. In at least one embodiment, different types of hardware 3722 may be used to provide efficient, purpose-built support for software 3718 and services 3720 in deployment system 3706. In at least one embodiment, use of GPU processing may be implemented for processing locally (e.g., at facility 3702), within an AI/deep learning system, in a cloud system, and/or in other processing components of deployment system 3706 to improve efficiency, accuracy, and efficacy of image processing, image reconstruction, segmentation, MRI exams, stroke or heart attack detection (e.g., in real-time), image quality in rendering, etc. In at least one embodiment, a facility may include imaging devices, genomics devices, sequencing devices, and/or other device types on-premises that may leverage GPUs to generate imaging data representative of a subject's anatomy.

In at least one embodiment, software 3718 and/or services 3720 may be optimized for GPU processing with respect to deep learning, machine learning, and/or high-performance computing, as non-limiting examples. In at least one embodiment, at least some of computing environment of deployment system 3706 and/or training system 3704 may be executed in a datacenter one or more supercomputers or high performance computing systems, with GPU optimized software (e.g., hardware and software combination of NVIDIA's DGX system). In at least one embodiment, datacenters may be compliant with provisions of HIPAA, such that receipt, processing, and transmission of imaging data and/or other patient data is securely handled with respect to privacy of patient data. In at least one embodiment, hardware 3722 may include any number of GPUs that may be called upon to perform processing of data in parallel, as described herein. In at least one embodiment, cloud platform may further include GPU processing for GPU-optimized execution of deep learning tasks, machine learning tasks, or other computing tasks. In at least one embodiment, cloud platform (e.g., NVIDIA's NGC) may be executed using an AI/deep learning supercomputer(s) and/or GPU-optimized software (e.g., as provided on NVIDIA's DGX systems) as a hardware abstraction and scaling platform. In at least one embodiment, cloud platform may integrate an application container clustering system or orchestration system (e.g., KUBERNETES) on multiple GPUs to enable seamless scaling and load balancing.

In at least one embodiment, one or more systems depicted in FIG. 37 are utilized to generate segmentation and confidence values for pixels of an image. In at least one embodiment, one or more systems depicted in FIG. 37 are utilized to implement one or more networks and processes such as those described in connection with FIGS. 1-7. In at least one embodiment, one or more systems depicted in FIG. 37 are utilized to implement a system for segmentation and confidence value determination.

FIG. 38 is a system diagram for an example system 3800 for generating and deploying an imaging deployment pipeline, in accordance with at least one embodiment. In at least one embodiment, system 3800 may be used to implement process 3700 of FIG. 37 and/or other processes including advanced processing and inferencing pipelines. In at least one embodiment, system 3800 may include training system 3704 and deployment system 3706. In at least one embodiment, training system 3704 and deployment system 3706 may be implemented using software 3718, services 3720, and/or hardware 3722, as described herein.

In at least one embodiment, system 3800 (e.g., training system 3704 and/or deployment system 3706) may implemented in a cloud computing environment (e.g., using cloud 3826). In at least one embodiment, system 3800 may be implemented locally with respect to a healthcare services facility, or as a combination of both cloud and local computing resources. In at least one embodiment, in embodiments where cloud computing is implemented, patient data may be separated from, or unprocessed by, by one or more components of system 3800 that would render processing non-compliant with HIPAA and/or other data handling and privacy regulations or laws. In at least one embodiment, access to APIs in cloud 3826 may be restricted to authorized users through enacted security measures or protocols. In at least one embodiment, a security protocol may include web tokens that may be signed by an authentication (e.g., AuthN, AuthZ, Gluecon, etc.) service and may carry appropriate authorization. In at least one embodiment, APIs of virtual instruments (described herein), or other instantiations of system 3800, may be restricted to a set of public IPs that have been vetted or authorized for interaction.

In at least one embodiment, various components of system 3800 may communicate between and among one another using any of a variety of different network types, including but not limited to local area networks (LANs) and/or wide area networks (WANs) via wired and/or wireless communication protocols. In at least one embodiment, communication between facilities and components of system 3800 (e.g., for transmitting inference requests, for receiving results of inference requests, etc.) may be communicated over a data bus or data busses, wireless data protocols (Wi-Fi), wired data protocols (e.g., Ethernet), etc.

In at least one embodiment, training system 3704 may execute training pipelines 3804, similar to those described herein with respect to FIG. 37. In at least one embodiment, where one or more machine learning models are to be used in deployment pipelines 3810 by deployment system 3706, training pipelines 3804 may be used to train or retrain one or more (e.g., pre-trained) models, and/or implement one or more of pre-trained models 3806 (e.g., without a need for retraining or updating). In at least one embodiment, as a result of training pipelines 3804, output model(s) 3716 may be generated. In at least one embodiment, training pipelines 3804 may include any number of processing steps, such as but not limited to imaging data (or other input data) conversion or adaption (e.g., using DICOM adapter 3802A to convert DICOM images to another format suitable for processing by respective machine learning models, such as Neuroimaging Informatics Technology Initiative (NIfTI) format), AI-assisted annotation 3710, labeling or annotating of imaging data 3708 to generate labeled clinic data 3712, model selection from a model registry, model training 3714, training, retraining, or updating models, and/or other processing steps. In at least one embodiment, for different machine learning models used by deployment system 3706, different training pipelines 3804 may be used. In at least one embodiment, training pipeline 3804 similar to a first example described with respect to FIG. 37 may be used for a first machine learning model, training pipeline 3804 similar to a second example described with respect to FIG. 37 may be used for a second machine learning model, and training pipeline 3804 similar to a third example described with respect to FIG. 37 may be used for a third machine learning model. In at least one embodiment, any combination of tasks within training system 3704 may be used depending on what is required for each respective machine learning model. In at least one embodiment, one or more of machine learning models may already be trained and ready for deployment so machine learning models may not undergo any processing by training system 3704, and may be implemented by deployment system 3706.

In at least one embodiment, output model(s) 3716 and/or pre-trained model(s) 3806 may include any types of machine learning models depending on implementation or embodiment. In at least one embodiment, and without limitation, machine learning models used by system 3800 may include machine learning model(s) using linear regression, logistic regression, decision trees, support vector machines (SVM), Naïve Bayes, k-nearest neighbor (Knn), K means clustering, random forest, dimensionality reduction algorithms, gradient boosting algorithms, neural networks (e.g., auto-encoders, convolutional, recurrent, perceptrons, Long/Short Term Memory (LSTM), Hopfield, Boltzmann, deep belief, deconvolutional, generative adversarial, liquid state machine, etc.), and/or other types of machine learning models.

Figure 41A:
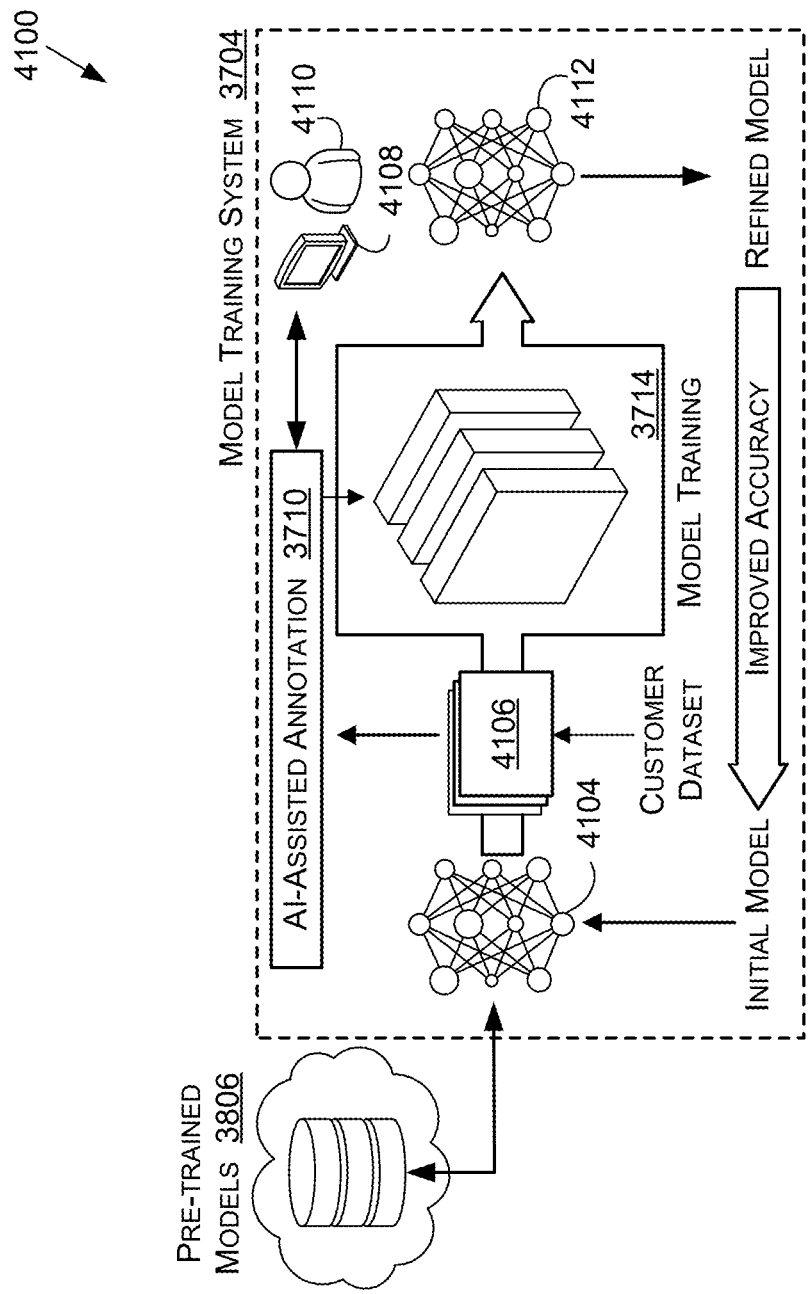
FIG. 41A illustrates a data flow diagram for a process to train a machine learning model, in accordance with at least one embodiment.
Figure 41B:
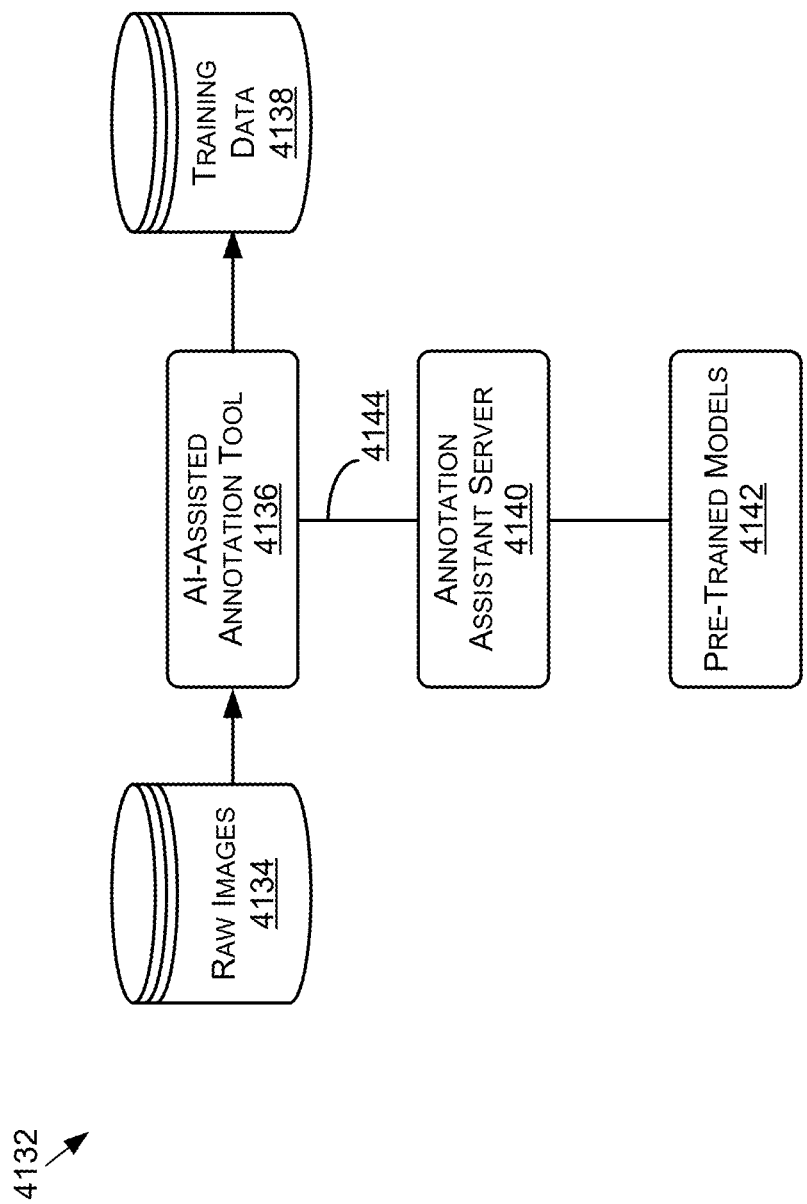
FIG. 41B is an example illustration of a client-server architecture to enhance annotation tools with pre-trained annotation models, in accordance with at least one embodiment.

In at least one embodiment, training pipelines 3804 may include AI-assisted annotation, as described in more detail herein with respect to at least FIG. 41B. In at least one embodiment, labeled clinic data 3712 (e.g., traditional annotation) may be generated by any number of techniques. In at least one embodiment, labels or other annotations may be generated within a drawing program (e.g., an annotation program), a computer aided design (CAD) program, a labeling program, another type of program suitable for generating annotations or labels for ground truth, and/or may be hand drawn, in some examples. In at least one embodiment, ground truth data may be synthetically produced (e.g., generated from computer models or renderings), real produced (e.g., designed and produced from real-world data), machine-automated (e.g., using feature analysis and learning to extract features from data and then generate labels), human annotated (e.g., labeler, or annotation expert, defines location of labels), and/or a combination thereof. In at least one embodiment, for each instance of imaging data 3708 (or other data type used by machine learning models), there may be corresponding ground truth data generated by training system 3704. In at least one embodiment, AI-assisted annotation may be performed as part of deployment pipelines 3810; either in addition to, or in lieu of AI-assisted annotation included in training pipelines 3804. In at least one embodiment, system 3800 may include a multi-layer platform that may include a software layer (e.g., software 3718) of diagnostic applications (or other application types) that may perform one or more medical imaging and diagnostic functions. In at least one embodiment, system 3800 may be communicatively coupled to (e.g., via encrypted links) PACS server networks of one or more facilities. In at least one embodiment, system 3800 may be configured to access and referenced data (e.g., DICOM data, RIS data, raw data, CIS data, REST compliant data, RPC data, raw data, etc.) from PACS servers (e.g., via a DICOM adapter 3802, or another data type adapter such as RIS, CIS, REST compliant, RPC, raw, etc.) to perform operations, such as training machine learning models, deploying machine learning models, image processing, inferencing, and/or other operations.

In at least one embodiment, a software layer may be implemented as a secure, encrypted, and/or authenticated API through which applications or containers may be invoked (e.g., called) from an external environment(s) (e.g., facility 3702). In at least one embodiment, applications may then call or execute one or more services 3720 for performing compute, AI, or visualization tasks associated with respective applications, and software 3718 and/or services 3720 may leverage hardware 3722 to perform processing tasks in an effective and efficient manner.

In at least one embodiment, deployment system 3706 may execute deployment pipelines 3810. In at least one embodiment, deployment pipelines 3810 may include any number of applications that may be sequentially, non-sequentially, or otherwise applied to imaging data (and/or other data types) generated by imaging devices, sequencing devices, genomics devices, etc., including AI-assisted annotation, as described above. In at least one embodiment, as described herein, a deployment pipeline 3810 for an individual device may be referred to as a virtual instrument for a device (e.g., a virtual ultrasound instrument, a virtual CT scan instrument, a virtual sequencing instrument, etc.). In at least one embodiment, for a single device, there may be more than one deployment pipeline 3810 depending on information desired from data generated by a device. In at least one embodiment, where detections of anomalies are desired from an MRI machine, there may be a first deployment pipeline 3810, and where image enhancement is desired from output of an MRI machine, there may be a second deployment pipeline 3810.

In at least one embodiment, applications available for deployment pipelines 3810 may include any application that may be used for performing processing tasks on imaging data or other data from devices. In at least one embodiment, different applications may be responsible for image enhancement, segmentation, reconstruction, anomaly detection, object detection, feature detection, treatment planning, dosimetry, beam planning (or other radiation treatment procedures), and/or other analysis, image processing, or inferencing tasks. In at least one embodiment, deployment system 3706 may define constructs for each of applications, such that users of deployment system 3706 (e.g., medical facilities, labs, clinics, etc.) may understand constructs and adapt applications for implementation within their respective facility. In at least one embodiment, an application for image reconstruction may be selected for inclusion in deployment pipeline 3810, but data type generated by an imaging device may be different from a data type used within an application. In at least one embodiment, DICOM adapter 3802B (and/or a DICOM reader) or another data type adapter or reader (e.g., RIS, CIS, REST compliant, RPC, raw, etc.) may be used within deployment pipeline 3810 to convert data to a form useable by an application within deployment system 3706. In at least one embodiment, access to DICOM, RIS, CIS, REST compliant, RPC, raw, and/or other data type libraries may be accumulated and pre-processed, including decoding, extracting, and/or performing any convolutions, color corrections, sharpness, gamma, and/or other augmentations to data. In at least one embodiment, DICOM, RIS, CIS, REST compliant, RPC, and/or raw data may be unordered and a pre-pass may be executed to organize or sort collected data. In at least one embodiment, because various applications may share common image operations, in some embodiments, a data augmentation library (e.g., as one of services 3720) may be used to accelerate these operations. In at least one embodiment, to avoid bottlenecks of conventional processing approaches that rely on CPU processing, parallel computing platform 3830 may be used for GPU acceleration of these processing tasks.

In at least one embodiment, an image reconstruction application may include a processing task that includes use of a machine learning model. In at least one embodiment, a user may desire to use their own machine learning model, or to select a machine learning model from model registry 3724. In at least one embodiment, a user may implement their own machine learning model or select a machine learning model for inclusion in an application for performing a processing task. In at least one embodiment, applications may be selectable and customizable, and by defining constructs of applications, deployment and implementation of applications for a particular user are presented as a more seamless user experience. In at least one embodiment, by leveraging other features of system 3800 (such as services 3720 and hardware 3722) deployment pipelines 3810 may be even more user friendly, provide for easier integration, and produce more accurate, efficient, and timely results.

In at least one embodiment, deployment system 3706 may include a user interface 3814 (e.g., a graphical user interface, a web interface, etc.) that may be used to select applications for inclusion in deployment pipeline(s) 3810, arrange applications, modify or change applications or parameters or constructs thereof, use and interact with deployment pipeline(s) 3810 during set-up and/or deployment, and/or to otherwise interact with deployment system 3706. In at least one embodiment, although not illustrated with respect to training system 3704, user interface 3814 (or a different user interface) may be used for selecting models for use in deployment system 3706, for selecting models for training, or retraining, in training system 3704, and/or for otherwise interacting with training system 3704.

Figure 39:
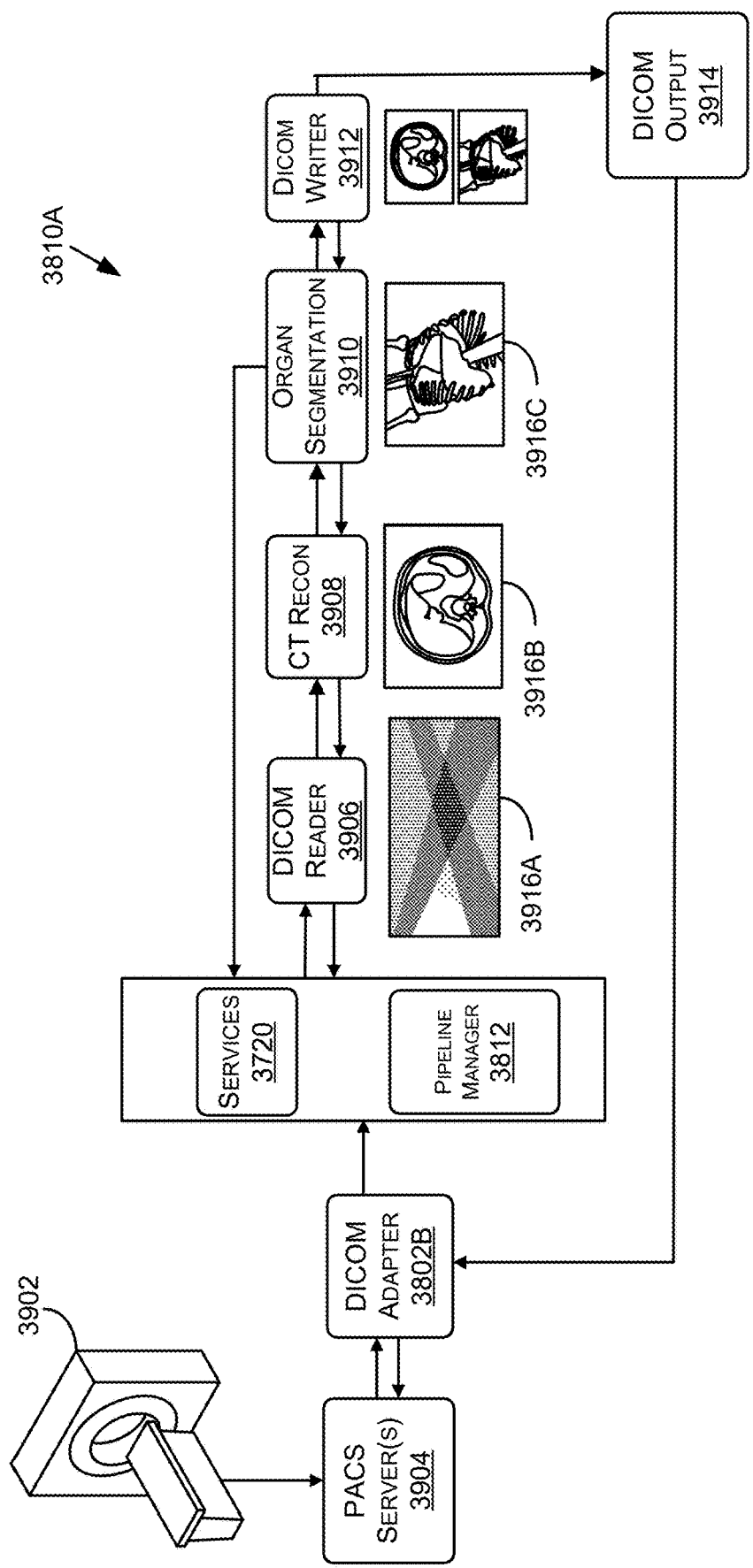
FIG. 39 includes an example illustration of an advanced computing pipeline 3810A for processing imaging data, in accordance with at least one embodiment.

In at least one embodiment, pipeline manager 3812 may be used, in addition to an application orchestration system 3828, to manage interaction between applications or containers of deployment pipeline(s) 3810 and services 3720 and/or hardware 3722. In at least one embodiment, pipeline manager 3812 may be configured to facilitate interactions from application to application, from application to service 3720, and/or from application or service to hardware 3722. In at least one embodiment, although illustrated as included in software 3718, this is not intended to be limiting, and in some examples (e.g., as illustrated in FIG. 39) pipeline manager 3812 may be included in services 3720. In at least one embodiment, application orchestration system 3828 (e.g., Kubernetes, DOCKER, etc.) may include a container orchestration system that may group applications into containers as logical units for coordination, management, scaling, and deployment. In at least one embodiment, by associating applications from deployment pipeline(s) 3810 (e.g., a reconstruction application, a segmentation application, etc.) with individual containers, each application may execute in a self-contained environment (e.g., at a kernel level) to increase speed and efficiency.

In at least one embodiment, each application and/or container (or image thereof) may be individually developed, modified, and deployed (e.g., a first user or developer may develop, modify, and deploy a first application and a second user or developer may develop, modify, and deploy a second application separate from a first user or developer), which may allow for focus on, and attention to, a task of a single application and/or container(s) without being hindered by tasks of another application(s) or container(s). In at least one embodiment, communication, and cooperation between different containers or applications may be aided by pipeline manager 3812 and application orchestration system 3828. In at least one embodiment, so long as an expected input and/or output of each container or application is known by a system (e.g., based on constructs of applications or containers), application orchestration system 3828 and/or pipeline manager 3812 may facilitate communication among and between, and sharing of resources among and between, each of applications or containers. In at least one embodiment, because one or more of applications or containers in deployment pipeline(s) 3810 may share same services and resources, application orchestration system 3828 may orchestrate, load balance, and determine sharing of services or resources between and among various applications or containers. In at least one embodiment, a scheduler may be used to track resource requirements of applications or containers, current usage or planned usage of these resources, and resource availability. In at least one embodiment, a scheduler may thus allocate resources to different applications and distribute resources between and among applications in view of requirements and availability of a system. In some examples, a scheduler (and/or other component of application orchestration system 3828) may determine resource availability and distribution based on constraints imposed on a system (e.g., user constraints), such as quality of service (QoS), urgency of need for data outputs (e.g., to determine whether to execute real-time processing or delayed processing), etc.

In at least one embodiment, services 3720 leveraged by and shared by applications or containers in deployment system 3706 may include compute services 3816, AI services 3818, visualization services 3820, and/or other service types. In at least one embodiment, applications may call (e.g., execute) one or more of services 3720 to perform processing operations for an application. In at least one embodiment, compute services 3816 may be leveraged by applications to perform super-computing or other high-performance computing (HPC) tasks. In at least one embodiment, compute service(s) 3816 may be leveraged to perform parallel processing (e.g., using a parallel computing platform 3830) for processing data through one or more of applications and/or one or more tasks of a single application, substantially simultaneously. In at least one embodiment, parallel computing platform 3830 (e.g., NVIDIA's CUDA) may enable general purpose computing on GPUs (GPGPU) (e.g., GPUs 3822). In at least one embodiment, a software layer of parallel computing platform 3830 may provide access to virtual instruction sets and parallel computational elements of GPUs, for execution of compute kernels. In at least one embodiment, parallel computing platform 3830 may include memory and, in some embodiments, a memory may be shared between and among multiple containers, and/or between and among different processing tasks within a single container. In at least one embodiment, inter-process communication (IPC) calls may be generated for multiple containers and/or for multiple processes within a container to use same data from a shared segment of memory of parallel computing platform 3830 (e.g., where multiple different stages of an application or multiple applications are processing same information). In at least one embodiment, rather than making a copy of data and moving data to different locations in memory (e.g., a read/write operation), same data in same location of a memory may be used for any number of processing tasks (e.g., at a same time, at different times, etc.). In at least one embodiment, as data is used to generate new data as a result of processing, this information of a new location of data may be stored and shared between various applications. In at least one embodiment, location of data and a location of updated or modified data may be part of a definition of how a payload is understood within containers.

In at least one embodiment, AI services 3818 may be leveraged to perform inferencing services for executing machine learning model(s) associated with applications (e.g., tasked with performing one or more processing tasks of an application). In at least one embodiment, AI services 3818 may leverage AI system 3824 to execute machine learning model(s) (e.g., neural networks, such as CNNs) for segmentation, reconstruction, object detection, feature detection, classification, and/or other inferencing tasks. In at least one embodiment, applications of deployment pipeline(s) 3810 may use one or more of output models 3716 from training system 3704 and/or other models of applications to perform inference on imaging data (e.g., DICOM data, RIS data, CIS data, REST compliant data, RPC data, raw data, etc.). In at least one embodiment, two or more examples of inferencing using application orchestration system 3828 (e.g., a scheduler) may be available. In at least one embodiment, a first category may include a high priority/low latency path that may achieve higher service level agreements, such as for performing inference on urgent requests during an emergency, or for a radiologist during diagnosis. In at least one embodiment, a second category may include a standard priority path that may be used for requests that may be non-urgent or where analysis may be performed at a later time. In at least one embodiment, application orchestration system 3828 may distribute resources (e.g., services 3720 and/or hardware 3722) based on priority paths for different inferencing tasks of AI services 3818.

In at least one embodiment, shared storage may be mounted to AI services 3818 within system 3800. In at least one embodiment, shared storage may operate as a cache (or other storage device type) and may be used to process inference requests from applications. In at least one embodiment, when an inference request is submitted, a request may be received by a set of API instances of deployment system 3706, and one or more instances may be selected (e.g., for best fit, for load balancing, etc.) to process a request. In at least one embodiment, to process a request, a request may be entered into a database, a machine learning model may be located from model registry 3724 if not already in a cache, a validation step may ensure appropriate machine learning model is loaded into a cache (e.g., shared storage), and/or a copy of a model may be saved to a cache. In at least one embodiment, a scheduler (e.g., of pipeline manager 3812) may be used to launch an application that is referenced in a request if an application is not already running or if there are not enough instances of an application. In at least one embodiment, if an inference server is not already launched to execute a model, an inference server may be launched. In at least one embodiment, any number of inference servers may be launched per model. In at least one embodiment, in a pull model, in which inference servers are clustered, models may be cached whenever load balancing is advantageous. In at least one embodiment, inference servers may be statically loaded in corresponding, distributed servers.

In at least one embodiment, inferencing may be performed using an inference server that runs in a container. In at least one embodiment, an instance of an inference server may be associated with a model (and optionally a plurality of versions of a model). In at least one embodiment, if an instance of an inference server does not exist when a request to perform inference on a model is received, a new instance may be loaded. In at least one embodiment, when starting an inference server, a model may be passed to an inference server such that a same container may be used to serve different models so long as inference server is running as a different instance.

In at least one embodiment, during application execution, an inference request for a given application may be received, and a container (e.g., hosting an instance of an inference server) may be loaded (if not already), and a start procedure may be called. In at least one embodiment, pre-processing logic in a container may load, decode, and/or perform any additional pre-processing on incoming data (e.g., using a CPU(s) and/or GPU(s)). In at least one embodiment, once data is prepared for inference, a container may perform inference as necessary on data. In at least one embodiment, this may include a single inference call on one image (e.g., a hand X-ray), or may require inference on hundreds of images (e.g., a chest CT). In at least one embodiment, an application may summarize results before completing, which may include, without limitation, a single confidence score, pixel level-segmentation, voxel-level segmentation, generating a visualization, or generating text to summarize findings. In at least one embodiment, different models or applications may be assigned different priorities. For example, some models may have a real-time (TAT less than one minute) priority while others may have lower priority (e.g., TAT less than 10 minutes). In at least one embodiment, model execution times may be measured from requesting institution or entity and may include partner network traversal time, as well as execution on an inference service.

In at least one embodiment, transfer of requests between services 3720 and inference applications may be hidden behind a software development kit (SDK), and robust transport may be provide through a queue. In at least one embodiment, a request will be placed in a queue via an API for an individual application/tenant ID combination and an SDK will pull a request from a queue and give a request to an application. In at least one embodiment, a name of a queue may be provided in an environment from where an SDK will pick it up. In at least one embodiment, asynchronous communication through a queue may be useful as it may allow any instance of an application to pick up work as it becomes available. In at least one embodiment, results may be transferred back through a queue, to ensure no data is lost. In at least one embodiment, queues may also provide an ability to segment work, as highest priority work may go to a queue with most instances of an application connected to it, while lowest priority work may go to a queue with a single instance connected to it that processes tasks in an order received. In at least one embodiment, an application may run on a GPU-accelerated instance generated in cloud 3826, and an inference service may perform inferencing on a GPU.

In at least one embodiment, visualization services 3820 may be leveraged to generate visualizations for viewing outputs of applications and/or deployment pipeline(s) 3810.

In at least one embodiment, GPUs 3822 may be leveraged by visualization services 3820 to generate visualizations. In at least one embodiment, rendering effects, such as ray-tracing, may be implemented by visualization services 3820 to generate higher quality visualizations. In at least one embodiment, visualizations may include, without limitation, 2D image renderings, 3D volume renderings, 3D volume reconstruction, 2D tomographic slices, virtual reality displays, augmented reality displays, etc. In at least one embodiment, virtualized environments may be used to generate a virtual interactive display or environment (e.g., a virtual environment) for interaction by users of a system (e.g., doctors, nurses, radiologists, etc.). In at least one embodiment, visualization services 3820 may include an internal visualizer, cinematics, and/or other rendering or image processing capabilities or functionality (e.g., ray tracing, rasterization, internal optics, etc.).

In at least one embodiment, hardware 3722 may include GPUs 3822, AI system 3824, cloud 3826, and/or any other hardware used for executing training system 3704 and/or deployment system 3706. In at least one embodiment, GPUs 3822 (e.g., NVIDIA's TESLA and/or QUADRO GPUs) may include any number of GPUs that may be used for executing processing tasks of compute services 3816, AI services 3818, visualization services 3820, other services, and/or any of features or functionality of software 3718. For example, with respect to AI services 3818, GPUs 3822 may be used to perform pre-processing on imaging data (or other data types used by machine learning models), post-processing on outputs of machine learning models, and/or to perform inferencing (e.g., to execute machine learning models). In at least one embodiment, cloud 3826, AI system 3824, and/or other components of system 3800 may use GPUs 3822. In at least one embodiment, cloud 3826 may include a GPU-optimized platform for deep learning tasks. In at least one embodiment, AI system 3824 may use GPUs, and cloud 3826 (or at least a portion tasked with deep learning or inferencing) may be executed using one or more AI systems 3824. As such, although hardware 3722 is illustrated as discrete components, this is not intended to be limiting, and any components of hardware 3722 may be combined with, or leveraged by, any other components of hardware 3722.

In at least one embodiment, AI system 3824 may include a purpose-built computing system (e.g., a super-computer or an HPC) configured for inferencing, deep learning, machine learning, and/or other artificial intelligence tasks. In at least one embodiment, AI system 3824 (e.g., NVIDIA's DGX) may include GPU-optimized software (e.g., a software stack) that may be executed using a plurality of GPUs 3822, in addition to CPUs, RAM, storage, and/or other components, features, or functionality. In at least one embodiment, one or more AI systems 3824 may be implemented in cloud 3826 (e.g., in a data center) for performing some or all of AI-based processing tasks of system 3800.

In at least one embodiment, cloud 3826 may include a GPU-accelerated infrastructure (e.g., NVIDIA's NGC) that may provide a GPU-optimized platform for executing processing tasks of system 3800. In at least one embodiment, cloud 3826 may include an AI system(s) 3824 for performing one or more of AI-based tasks of system 3800 (e.g., as a hardware abstraction and scaling platform). In at least one embodiment, cloud 3826 may integrate with application orchestration system 3828 leveraging multiple GPUs to enable seamless scaling and load balancing between and among applications and services 3720. In at least one embodiment, cloud 3826 may tasked with executing at least some of services 3720 of system 3800, including compute services 3816, AI services 3818, and/or visualization services 3820, as described herein.

In at least one embodiment, cloud 3826 may perform small and large batch inference (e.g., executing NVIDIA's TENSOR RT), provide an accelerated parallel computing API and platform 3830 (e.g., NVIDIA's CUDA), execute application orchestration system 3828 (e.g., KUBERNETES), provide a graphics rendering API and platform (e.g., for ray-tracing, 2D graphics, 3D graphics, and/or other rendering techniques to produce higher quality cinematics), and/or may provide other functionality for system 3800.

In at least one embodiment, in an effort to preserve patient confidentiality (e.g., where patient data or records are to be used off-premises), cloud 3826 may include a registry, such as a deep learning container registry. In at least one embodiment, a registry may store containers for instantiations of applications that may perform pre-processing, post-processing, or other processing tasks on patient data. In at least one embodiment, cloud 3826 may receive data that includes patient data as well as sensor data in containers, perform requested processing for just sensor data in those containers, and then forward a resultant output and/or visualizations to appropriate parties and/or devices (e.g., on-premises medical devices used for visualization or diagnoses), all without having to extract, store, or otherwise access patient data. In at least one embodiment, confidentiality of patient data is preserved in compliance with HIPAA and/or other data regulations.

In at least one embodiment, one or more systems depicted in FIG. 38 are utilized to generate segmentation and confidence values for pixels of an image. In at least one embodiment, one or more systems depicted in FIG. 38 are utilized to implement one or more networks and processes such as those described in connection with FIGS. 1-7. In at least one embodiment, one or more systems depicted in FIG. 38 are utilized to implement a system for segmentation and confidence value determination.

FIG. 39 includes an example illustration of a deployment pipeline 3810A for processing imaging data, in accordance with at least one embodiment. In at least one embodiment, system 3800 (and specifically deployment system 3706) may be used to customize, update, and/or integrate deployment pipeline(s) 3810A into one or more production environments. In at least one embodiment, deployment pipeline 3810A of FIG. 39 includes a non-limiting example of a deployment pipeline 3810A that may be custom defined by a particular user (or team of users) at a facility (e.g., at a hospital, clinic, lab, research environment, etc.). In at least one embodiment, to define deployment pipelines 3810A for a CT scanner 3902, a user may select (from a container registry, for example) one or more applications that perform specific functions or tasks with respect to imaging data generated by CT scanner 3902. In at least one embodiment, applications may be applied to deployment pipeline 3810A as containers that may leverage services 3720 and/or hardware 3722 of system 3800. In addition, deployment pipeline 3810A may include additional processing tasks or applications that may be implemented to prepare data for use by applications (e.g., DICOM adapter 3802B and DICOM reader 3906 may be used in deployment pipeline 3810A to prepare data for use by CT reconstruction 3908, organ segmentation 3910, etc.). In at least one embodiment, deployment pipeline 3810A may be customized or selected for consistent deployment, one time use, or for another frequency or interval. In at least one embodiment, a user may desire to have CT reconstruction 3908 and organ segmentation 3910 for several subjects over a specific interval, and thus may deploy pipeline 3810A for that period of time. In at least one embodiment, a user may select, for each request from system 3800, applications that a user wants to perform processing on that data for that request. In at least one embodiment, deployment pipeline 3810A may be adjusted at any interval and, because of adaptability and scalability of a container structure within system 3800, this may be a seamless process.

In at least one embodiment, deployment pipeline 3810A of FIG. 39 may include CT scanner 3902 generating imaging data of a patient or subject. In at least one embodiment, imaging data from CT scanner 3902 may be stored on a PACS server(s) 3904 associated with a facility housing CT scanner 3902. In at least one embodiment, PACS server(s) 3904 may include software and/or hardware components that may directly interface with imaging modalities (e.g., CT scanner 3902) at a facility. In at least one embodiment, DICOM adapter 3802B may enable sending and receipt of DICOM objects using DICOM protocols. In at least one embodiment, DICOM adapter 3802B may aid in preparation or configuration of DICOM data from PACS server(s) 3904 for use by deployment pipeline 3810A. In at least one embodiment, once DICOM data is processed through DICOM adapter 3802B, pipeline manager 3812 may route data through to deployment pipeline 3810A. In at least one embodiment, DICOM reader 3906 may extract image files and any associated metadata from DICOM data (e.g., raw sinogram data, as illustrated in visualization 3916A). In at least one embodiment, working files that are extracted may be stored in a cache for faster processing by other applications in deployment pipeline 3810A. In at least one embodiment, once DICOM reader 3906 has finished extracting and/or storing data, a signal of completion may be communicated to pipeline manager 3812. In at least one embodiment, pipeline manager 3812 may then initiate or call upon one or more other applications or containers in deployment pipeline 3810A.

In at least one embodiment, CT reconstruction 3908 application and/or container may be executed once data (e.g., raw sinogram data) is available for processing by CT reconstruction 3908 application. In at least one embodiment, CT reconstruction 3908 may read raw sinogram data from a cache, reconstruct an image file out of raw sinogram data (e.g., as illustrated in visualization 3916B), and store resulting image file in a cache. In at least one embodiment, at completion of reconstruction, pipeline manager 3812 may be signaled that reconstruction task is complete. In at least one embodiment, once reconstruction is complete, and a reconstructed image file may be stored in a cache (or other storage device), organ segmentation 3910 application and/or container may be triggered by pipeline manager 3812. In at least one embodiment, organ segmentation 3910 application and/or container may read an image file from a cache, normalize or convert an image file to format suitable for inference (e.g., convert an image file to an input resolution of a machine learning model), and run inference against a normalized image. In at least one embodiment, to run inference on a normalized image, organ segmentation 3910 application and/or container may rely on services 3720, and pipeline manager 3812 and/or application orchestration system 3828 may facilitate use of services 3720 by organ segmentation 3910 application and/or container. In at least one embodiment, for example, organ segmentation 3910 application and/or container may leverage AI services 3818 to perform inference on a normalized image, and AI services 3818 may leverage hardware 3722 (e.g., AI system 3824) to execute AI services 3818. In at least one embodiment, a result of an inference may be a mask file (e.g., as illustrated in visualization 3916C) that may be stored in a cache (or other storage device).

In at least one embodiment, once applications that process DICOM data and/or data extracted from DICOM data have completed processing, a signal may be generated for pipeline manager 3812. In at least one embodiment, pipeline manager 3812 may then execute DICOM writer 3912 to read results from a cache (or other storage device), package results into a DICOM format (e.g., as DICOM output 3914) for use by users at a facility who generated a request. In at least one embodiment, DICOM output 3914 may then be transmitted to DICOM adapter 3802B to prepare DICOM output 3914 for storage on PACS server(s) 3904 (e.g., for viewing by a DICOM viewer at a facility). In at least one embodiment, in response to a request for reconstruction and segmentation, visualizations 3916B and 3916C may be generated and available to a user for diagnoses, research, and/or for other purposes.

Although illustrated as consecutive application in deployment pipeline 3810A, CT reconstruction 3908 and organ segmentation 3910 applications may be processed in parallel in at least one embodiment. In at least one embodiment, where applications do not have dependencies on one another, and data is available for each application (e.g., after DICOM reader 3906 extracts data), applications may be executed at a same time, substantially at a same time, or with some overlap. In at least one embodiment, where two or more applications require similar services 3720, a scheduler of system 3800 may be used to load balance and distribute compute or processing resources between and among various applications. In at least one embodiment, in some embodiments, parallel computing platform 3830 may be used to perform parallel processing for applications to decrease run-time of deployment pipeline 3810A to provide real-time results.

Figure 40A:
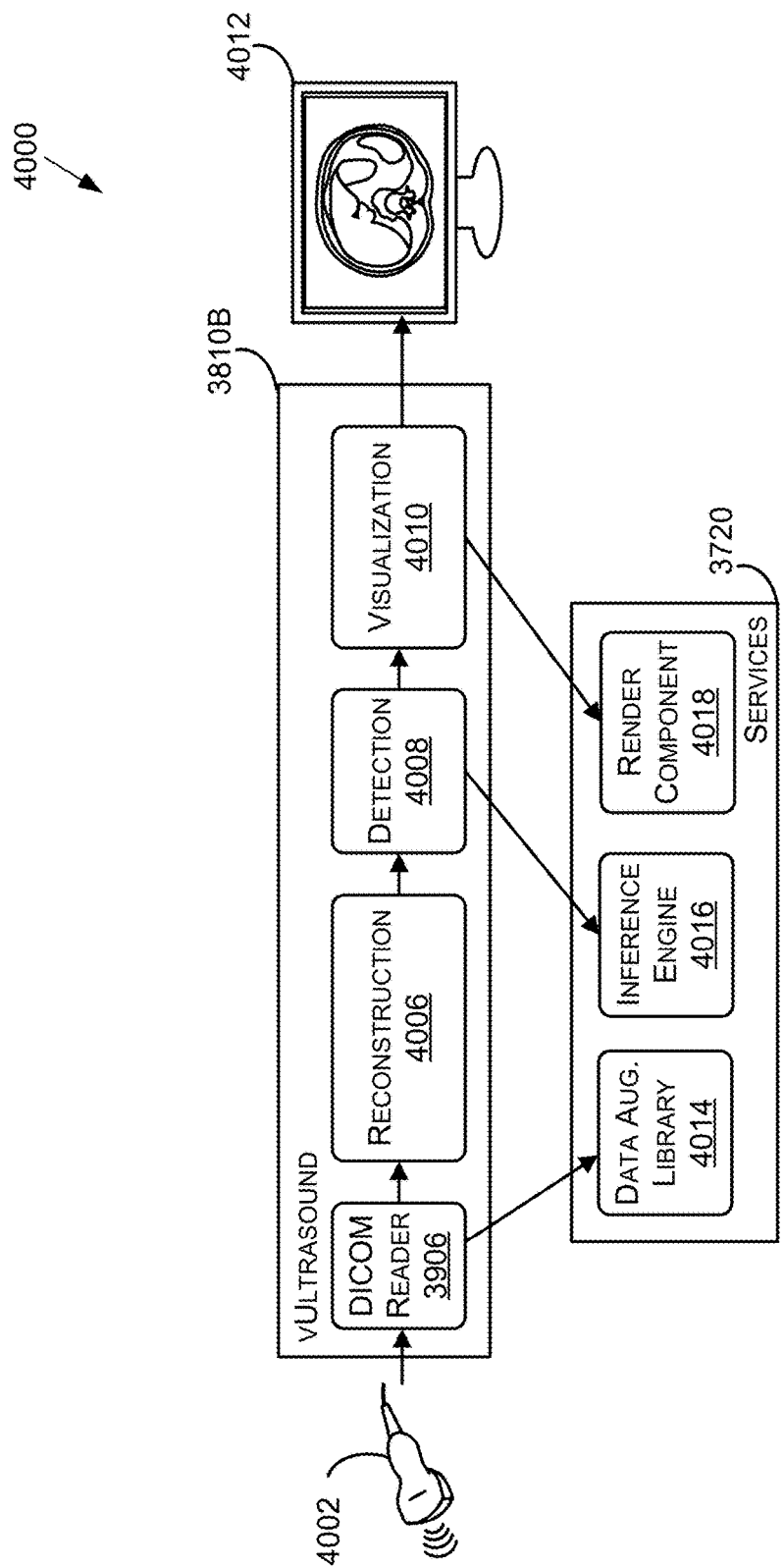
FIG. 40A includes an example data flow diagram of a virtual instrument supporting an ultrasound device, in accordance with at least one embodiment.
Figure 40B:
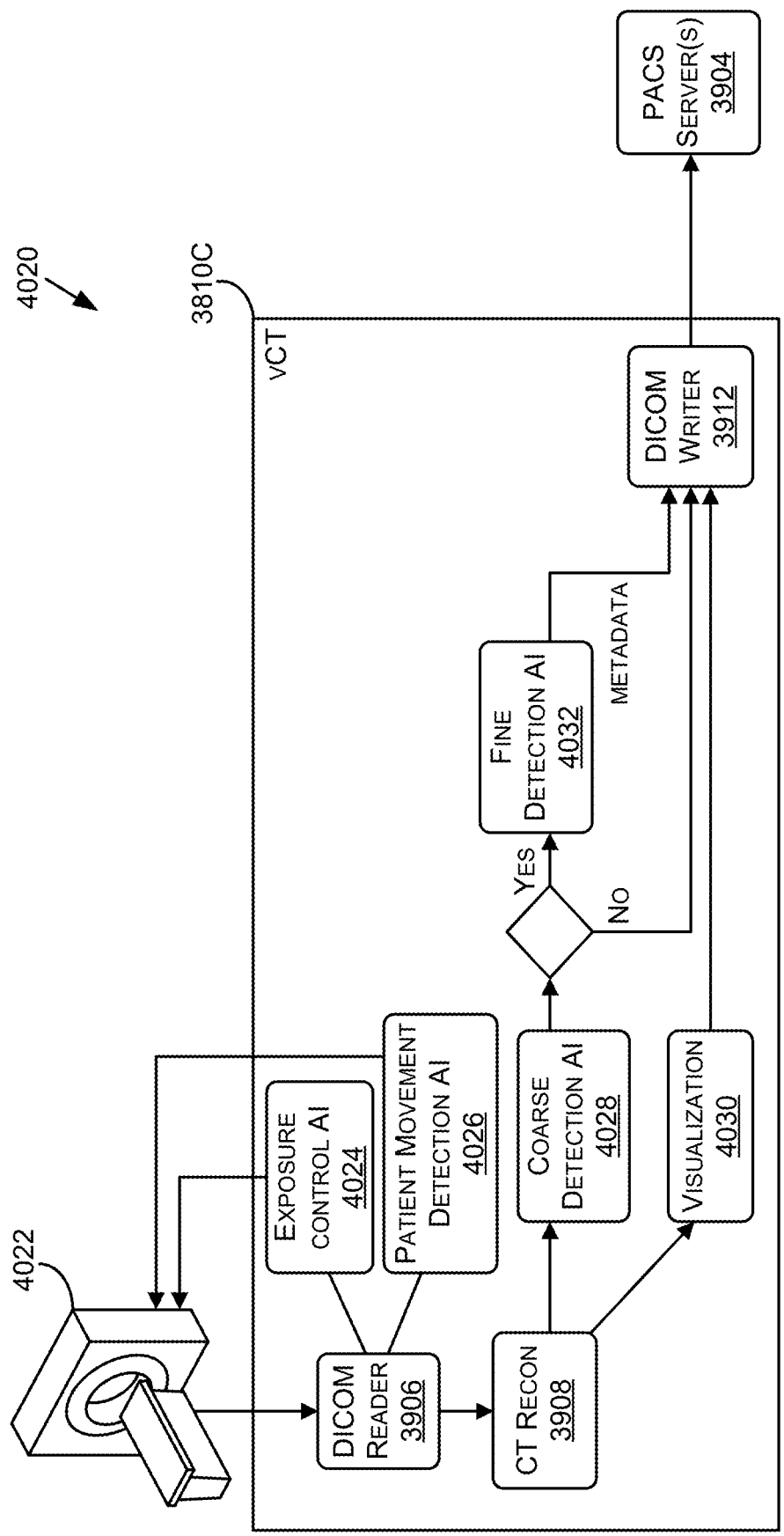
FIG. 40B includes an example data flow diagram of a virtual instrument supporting an CT scanner, in accordance with at least one embodiment.

In at least one embodiment, and with reference to FIGS. 40A-40B, deployment system 3706 may be implemented as one or more virtual instruments to perform different functionalities (such as image processing, segmentation, enhancement, AI, visualization, and inferencing) with imaging devices (e.g., CT scanners, X-ray machines, MRI machines, etc.), sequencing devices, genomics devices, and/or other device types. In at least one embodiment, system 3800 may allow for creation and provision of virtual instruments that may include a software-defined deployment pipeline 3810 that may receive raw/unprocessed input data generated by a device(s) and output processed/reconstructed data. In at least one embodiment, deployment pipelines 3810 (e.g., 3810A and 3810B) that represent virtual instruments may implement intelligence into a pipeline, such as by leveraging machine learning models, to provide containerized inference support to a system. In at least one embodiment, virtual instruments may execute any number of containers each including instantiations of applications.

In at least one embodiment, such as where real-time processing is desired, deployment pipelines 3810 representing virtual instruments may be static (e.g., containers and/or applications may be set), while in other examples, container and/or applications for virtual instruments may be selected (e.g., on a per-request basis) from a pool of applications or resources (e.g., within a container registry).

In at least one embodiment, system 3800 may be instantiated or executed as one or more virtual instruments on-premise at a facility in, for example, a computing system deployed next to or otherwise in communication with a radiology machine, an imaging device, and/or another device type at a facility. In at least one embodiment, however, an on-premise installation may be instantiated or executed within a computing system of a device itself (e.g., a computing system integral to an imaging device), in a local datacenter (e.g., a datacenter on-premise), and/or in a cloud-environment (e.g., in cloud 3826). In at least one embodiment, deployment system 3706, operating as a virtual instrument, may be instantiated by a supercomputer or other HPC system in some examples. In at least one embodiment, on-premise installation may allow for high-bandwidth uses (via, for example, higher throughput local communication interfaces, such as RF over Ethernet) for real-time processing. In at least one embodiment, real-time or near real-time processing may be particularly useful where a virtual instrument supports an ultrasound device or other imaging modality where immediate visualizations are expected or required for accurate diagnoses and analyses. In at least one embodiment, a cloud-computing architecture may be capable of dynamic bursting to a cloud computing service provider, or other compute cluster, when local demand exceeds on-premise capacity or capability. In at least one embodiment, a cloud architecture, when implemented, may be tuned for training neural networks or other machine learning models, as described herein with respect to training system 3704. In at least one embodiment, with training pipelines in place, machine learning models may be continuously learn and improve as they process additional data from devices they support. In at least one embodiment, virtual instruments may be continually improved using additional data, new data, existing machine learning models, and/or new or updated machine learning models.

In at least one embodiment, a computing system may include some or all of hardware 3722 described herein, and hardware 3722 may be distributed in any of a number of ways including within a device, as part of a computing device coupled to and located proximate a device, in a local datacenter at a facility, and/or in cloud 3826. In at least one embodiment, because deployment system 3706 and associated applications or containers are created in software (e.g., as discrete containerized instantiations of applications), behavior, operation, and configuration of virtual instruments, as well as outputs generated by virtual instruments, may be modified or customized as desired, without having to change or alter raw output of a device that a virtual instrument supports.

In at least one embodiment, one or more systems depicted in FIG. 39 are utilized to generate segmentation and confidence values for pixels of an image. In at least one embodiment, one or more systems depicted in FIG. 39 are utilized to implement one or more networks and processes such as those described in connection with FIGS. 1-7. In at least one embodiment, one or more systems depicted in FIG. 39 are utilized to implement a system for segmentation and confidence value determination.

FIG. 40A includes an example data flow diagram of a virtual instrument supporting an ultrasound device, in accordance with at least one embodiment. In at least one embodiment, deployment pipeline 3810B may leverage one or more of services 3720 of system 3800. In at least one embodiment, deployment pipeline 3810B and services 3720 may leverage hardware 3722 of a system either locally or in cloud 3826. In at least one embodiment, although not illustrated, process 4000 may be facilitated by pipeline manager 3812, application orchestration system 3828, and/or parallel computing platform 3830.

In at least one embodiment, process 4000 may include receipt of imaging data from an ultrasound device 4002. In at least one embodiment, imaging data may be stored on PACS server(s) in a DICOM format (or other format, such as RIS, CIS, REST compliant, RPC, raw, etc.), and may be received by system 3800 for processing through deployment pipeline 3810 selected or customized as a virtual instrument (e.g., a virtual ultrasound) for ultrasound device 4002. In at least one embodiment, imaging data may be received directly from an imaging device (e.g., ultrasound device 4002) and processed by a virtual instrument. In at least one embodiment, a transducer or other signal converter communicatively coupled between an imaging device and a virtual instrument may convert signal data generated by an imaging device to image data that may be processed by a virtual instrument. In at least one embodiment, raw data and/or image data may be applied to DICOM reader 3906 to extract data for use by applications or containers of deployment pipeline 3810B. In at least one embodiment, DICOM reader 3906 may leverage data augmentation library 4014 (e.g., NVIDIA's DALI) as a service 3720 (e.g., as one of compute service(s) 3816) for extracting, resizing, rescaling, and/or otherwise preparing data for use by applications or containers.

In at least one embodiment, once data is prepared, a reconstruction 4006 application and/or container may be executed to reconstruct data from ultrasound device 4002 into an image file. In at least one embodiment, after reconstruction 4006, or at a same time as reconstruction 4006, a detection 4008 application and/or container may be executed for anomaly detection, object detection, feature detection, and/or other detection tasks related to data. In at least one embodiment, an image file generated during reconstruction 4006 may be used during detection 4008 to identify anomalies, objects, features, etc. In at least one embodiment, detection 4008 application may leverage an inference engine 4016 (e.g., as one of AI service(s) 3818) to perform inference on data to generate detections. In at least one embodiment, one or more machine learning models (e.g., from training system 3704) may be executed or called by detection 4008 application.

In at least one embodiment, once reconstruction 4006 and/or detection 4008 is/are complete, data output from these application and/or containers may be used to generate visualizations 4010, such as visualization 4012 (e.g., a grayscale output) displayed on a workstation or display terminal. In at least one embodiment, visualization may allow a technician or other user to visualize results of deployment pipeline 3810B with respect to ultrasound device 4002. In at least one embodiment, visualization 4010 may be executed by leveraging a render component 4018 of system 3800 (e.g., one of visualization service(s) 3820). In at least one embodiment, render component 4018 may execute a 2D, OpenGL, or ray-tracing service to generate visualization 4012.

FIG. 40B includes an example data flow diagram of a virtual instrument supporting a CT scanner, in accordance with at least one embodiment. In at least one embodiment, deployment pipeline 3810C may leverage one or more of services 3720 of system 3800. In at least one embodiment, deployment pipeline 3810C and services 3720 may leverage hardware 3722 of a system either locally or in cloud 3826. In at least one embodiment, although not illustrated, process 4020 may be facilitated by pipeline manager 3812, application orchestration system 3828, and/or parallel computing platform 3830.

In at least one embodiment, process 4020 may include CT scanner 4022 generating raw data that may be received by DICOM reader 3906 (e.g., directly, via a PACS server 3904, after processing, etc.). In at least one embodiment, a Virtual CT (instantiated by deployment pipeline 3810C) may include a first, real-time pipeline for monitoring a patient (e.g., patient movement detection AI 4026) and/or for adjusting or optimizing exposure of CT scanner 4022 (e.g., using exposure control AI 4024). In at least one embodiment, one or more of applications (e.g., 4024 and 4026) may leverage a service 3720, such as AI service(s) 3818. In at least one embodiment, outputs of exposure control AI 4024 application (or container) and/or patient movement detection AI 4026 application (or container) may be used as feedback to CT scanner 4022 and/or a technician for adjusting exposure (or other settings of CT scanner 4022) and/or informing a patient to move less.

In at least one embodiment, deployment pipeline 3810C may include a non-real-time pipeline for analyzing data generated by CT scanner 4022. In at least one embodiment, a second pipeline may include CT reconstruction 3908 application and/or container, a coarse detection AI 4028 application and/or container, a fine detection AI 4032 application and/or container (e.g., where certain results are detected by coarse detection AI 4028), a visualization 4030 application and/or container, and a DICOM writer 3912 (and/or other data type writer, such as RIS, CIS, REST compliant, RPC, raw, etc.) application and/or container. In at least one embodiment, raw data generated by CT scanner 4022 may be passed through pipelines of deployment pipeline 3810C (instantiated as a virtual CT instrument) to generate results. In at least one embodiment, results from DICOM writer 3912 may be transmitted for display and/or may be stored on PACS server(s) 3904 for later retrieval, analysis, or display by a technician, practitioner, or other user.

In at least one embodiment, one or more systems depicted in FIGS. 40A-40B are utilized to generate segmentation and confidence values for pixels of an image. In at least one embodiment, one or more systems depicted in FIGS. 40A-40B are utilized to implement one or more networks and processes such as those described in connection with FIGS. 1-7. In at least one embodiment, one or more systems depicted in FIGS. 40A-40B are utilized to implement a system for segmentation and confidence value determination.

FIG. 41A illustrates a data flow diagram for a process 4100 to train, retrain, or update a machine learning model, in accordance with at least one embodiment. In at least one embodiment, process 4100 may be executed using, as a non-limiting example, system 3800 of FIG. 38. In at least one embodiment, process 4100 may leverage services 3720 and/or hardware 3722 of system 3800, as described herein. In at least one embodiment, refined models 4112 generated by process 4100 may be executed by deployment system 3706 for one or more containerized applications in deployment pipelines 3810.

In at least one embodiment, model training 3714 may include retraining or updating an initial model 4104 (e.g., a pre-trained model) using new training data (e.g., new input data, such as customer dataset 4106, and/or new ground truth data associated with input data). In at least one embodiment, to retrain, or update, initial model 4104, output or loss layer(s) of initial model 4104 may be reset, or deleted, and/or replaced with an updated or new output or loss layer(s). In at least one embodiment, initial model 4104 may have previously fine-tuned parameters (e.g., weights and/or biases) that remain from prior training, so training or retraining 3714 may not take as long or require as much processing as training a model from scratch. In at least one embodiment, during model training 3714, by having reset or replaced output or loss layer(s) of initial model 4104, parameters may be updated and re-tuned for a new data set based on loss calculations associated with accuracy of output or loss layer(s) at generating predictions on new, customer dataset 4106 (e.g., image data 3708 of FIG. 37).

In at least one embodiment, pre-trained models 3806 may be stored in a data store, or registry (e.g., model registry 3724 of FIG. 37). In at least one embodiment, pre-trained models 3806 may have been trained, at least in part, at one or more facilities other than a facility executing process 4100. In at least one embodiment, to protect privacy and rights of patients, subjects, or clients of different facilities, pre-trained models 3806 may have been trained, on-premise, using customer or patient data generated on-premise. In at least one embodiment, pre-trained models 3806 may be trained using cloud 3826 and/or other hardware 3722, but confidential, privacy protected patient data may not be transferred to, used by, or accessible to any components of cloud 3826 (or other off premise hardware). In at least one embodiment, where a pre-trained model 3806 is trained at using patient data from more than one facility, pre-trained model 3806 may have been individually trained for each facility prior to being trained on patient or customer data from another facility. In at least one embodiment, such as where a customer or patient data has been released of privacy concerns (e.g., by waiver, for experimental use, etc.), or where a customer or patient data is included in a public data set, a customer or patient data from any number of facilities may be used to train pre-trained model 3806 on-premise and/or off premise, such as in a datacenter or other cloud computing infrastructure.

In at least one embodiment, when selecting applications for use in deployment pipelines 3810, a user may also select machine learning models to be used for specific applications. In at least one embodiment, a user may not have a model for use, so a user may select a pre-trained model 3806 to use with an application. In at least one embodiment, pre-trained model 3806 may not be optimized for generating accurate results on customer dataset 4106 of a facility of a user (e.g., based on patient diversity, demographics, types of medical imaging devices used, etc.). In at least one embodiment, prior to deploying pre-trained model 3806 into deployment pipeline 3810 for use with an application(s), pre-trained model 3806 may be updated, retrained, and/or fine-tuned for use at a respective facility.

In at least one embodiment, a user may select pre-trained model 3806 that is to be updated, retrained, and/or fine-tuned, and pre-trained model 3806 may be referred to as initial model 4104 for training system 3704 within process 4100. In at least one embodiment, customer dataset 4106 (e.g., imaging data, genomics data, sequencing data, or other data types generated by devices at a facility) may be used to perform model training 3714 (which may include, without limitation, transfer learning) on initial model 4104 to generate refined model 4112. In at least one embodiment, ground truth data corresponding to customer dataset 4106 may be generated by training system 3704. In at least one embodiment, ground truth data may be generated, at least in part, by clinicians, scientists, doctors, practitioners, at a facility (e.g., as labeled clinic data 3712 of FIG. 37).

In at least one embodiment, AI-assisted annotation 3710 may be used in some examples to generate ground truth data. In at least one embodiment, AI-assisted annotation 3710 (e.g., implemented using an AI-assisted annotation SDK) may leverage machine learning models (e.g., neural networks) to generate suggested or predicted ground truth data for a customer dataset. In at least one embodiment, user 4110 may use annotation tools within a user interface (a graphical user interface (GUI)) on computing device 4108.

In at least one embodiment, user 4110 may interact with a GUI via computing device 4108 to edit or fine-tune annotations or auto-annotations. In at least one embodiment, a polygon editing feature may be used to move vertices of a polygon to more accurate or fine-tuned locations.

In at least one embodiment, once customer dataset 4106 has associated ground truth data, ground truth data (e.g., from AI-assisted annotation, manual labeling, etc.) may be used by during model training 3714 to generate refined model 4112. In at least one embodiment, customer dataset 4106 may be applied to initial model 4104 any number of times, and ground truth data may be used to update parameters of initial model 4104 until an acceptable level of accuracy is attained for refined model 4112. In at least one embodiment, once refined model 4112 is generated, refined model 4112 may be deployed within one or more deployment pipelines 3810 at a facility for performing one or more processing tasks with respect to medical imaging data.

In at least one embodiment, refined model 4112 may be uploaded to pre-trained models 3806 in model registry 3724 to be selected by another facility. In at least one embodiment, his process may be completed at any number of facilities such that refined model 4112 may be further refined on new datasets any number of times to generate a more universal model.

FIG. 41B is an example illustration of a client-server architecture 4132 to enhance annotation tools with pre-trained annotation models, in accordance with at least one embodiment. In at least one embodiment, AI-assisted annotation tools 4136 may be instantiated based on a client-server architecture 4132. In at least one embodiment, annotation tools 4136 in imaging applications may aid radiologists, for example, identify organs and abnormalities. In at least one embodiment, imaging applications may include software tools that help user 4110 to identify, as a non-limiting example, a few extreme points on a particular organ of interest in raw images 4134 (e.g., in a 3D MRI or CT scan) and receive auto-annotated results for all 2D slices of a particular organ. In at least one embodiment, results may be stored in a data store as training data 4138 and used as (for example and without limitation) ground truth data for training. In at least one embodiment, when computing device 4108 sends extreme points for AI-assisted annotation 3710, a deep learning model, for example, may receive this data as input and return inference results of a segmented organ or abnormality. In at least one embodiment, pre-instantiated annotation tools, such as AI-Assisted Annotation Tool 4136B in FIG. 41B, may be enhanced by making API calls (e.g., API Call 4144) to a server, such as an Annotation Assistant Server 4140 that may include a set of pre-trained models 4142 stored in an annotation model registry, for example. In at least one embodiment, an annotation model registry may store pre-trained models 4142 (e.g., machine learning models, such as deep learning models) that are pre-trained to perform AI-assisted annotation on a particular organ or abnormality. In at least one embodiment, these models may be further updated by using training pipelines 3804. In at least one embodiment, pre-installed annotation tools may be improved over time as new labeled clinic data 3712 is added.

Inference and/or training logic 815 are used to perform inferencing and/or training operations associated with one or more embodiments. Details regarding inference and/or training logic 815 are provided herein in conjunction with FIGS. 8A and/or 8B.

In at least one embodiment, one or more systems depicted in FIGS. 41A-41B are utilized to generate segmentation and confidence values for pixels of an image. In at least one embodiment, one or more systems depicted in FIGS. 41A-41B are utilized to implement one or more networks and processes such as those described in connection with FIGS. 1-7. In at least one embodiment, one or more systems depicted in FIGS. 41A-41B are utilized to implement a system for segmentation and confidence value determination.

At least one embodiment of the disclosure can be described in view of the following clauses:

Clause 1. A processor, comprising:
one or more circuits to use one or more neural networks to generate one or more confidence values associated with one or more objects identified by the one or more neural networks.

Clause 2. The processor of clause 1, wherein the one or more circuits are to further use the one or more neural networks to assign the one or more confidence values to one or more outputs indicating predicted classifications of the one or more objects identified by the one or more neural networks.

Clause 3. The processor of any of clauses 1-2, wherein the one or more neural networks comprise one or more image segmentation networks, and further wherein the one or more objects are identified as belonging to one or more segmentation classes.

Clause 4. The processor of any of clauses 1-3, wherein the one or more circuits are to further use the one or more neural networks to generate one or more class scores corresponding to the one or more objects.

Clause 5. The processor of any of clauses 1-4, wherein the one or more circuits are to further use the one or more neural networks to at least:
perform calibration on the one or more class scores; and
generate a label based at least in part on results from the calibration.

Clause 6. The processor of any of clauses 1-5, wherein the one or more circuits are to further cause a vehicle to perform one or more remedial actions in response to the one or more confidence values.

Clause 7. The processor of any of clauses 1-6, wherein the one or more remedial actions include activating one or more steering systems of the vehicle.

Clause 8. A system, comprising:
one or more computers having one or more processors to use one or more neural networks to generate one or more confidence values associated with one or more objects identified by the one or more neural networks.

Clause 9. The system of clause 8, wherein the one or more objects are identified from one or more images captured using one or more cameras of a vehicle.

Clause 10. The system of any of clauses 8-9, wherein the one or more neural networks output a vector of scores associated with one or more labels for each pixel of an image depicting the one or more objects.

Clause 11. The system of any of clauses 8-10, wherein the one or more processors are further to cause a semi-autonomous vehicle to perform one or more remedial actions in response to the vector of scores.

Clause 12. The system of any of clauses 8-11, wherein the one or more remedial actions include activating one or more acceleration systems of the vehicle.

Clause 13. The system of any of clauses 8-12, wherein the one or more remedial actions include activating one or more braking systems of the vehicle.

Clause 14. The system of any of clauses 8-13, wherein the one or more remedial actions include activating one or more warning systems of the vehicle.

Clause 15. A machine readable medium having stored thereon a set of instructions, which if performed by one or more processors, cause the one or more processors to use one or more neural networks to generate one or more confidence values associated with one or more objects identified by the one or more neural networks.

Clause 16. The machine readable medium of clause 15, wherein the one or more objects are identified from an image captured from one or more medical imaging devices.

Clause 17. The machine readable medium of any of clauses 15-16, wherein the one or more confidence values indicate one or more probabilities of whether one or more identifications of the one or more objects are correct.

Clause 18. The machine readable medium of any of clauses 15-17, wherein the set of instructions further include instructions, which if performed by the one or more processors, cause the one or more processors to use the one or more neural networks to:
determine whether the one or more confidence values are below a threshold; and
as a result of determining that the one or more confidence values are below the threshold, perform one or more actions.

Clause 19. The machine readable medium of any of clauses 15-18, wherein the one or more actions include activating one or more medical warning systems.

Clause 20. The machine readable medium of any of clauses 15-19, wherein the one or more actions include transmitting a notification to one or more medical systems indicating that the one or more confidence values associated with the one or more objects are below the threshold.

Clause 21. The machine readable medium of any of clauses 15-20, wherein the set of instructions further include instructions, which if performed by the one or more processors, cause the one or more processors to use the one or more neural networks to generate a segmentation map visualization indicating identifications of the one or more objects.

Clause 22. A processor, comprising:
one or more circuits to train one or more neural networks to generate one or more confidence values associated with one or more objects identified by the one or more neural networks.

Clause 23. The processor of clause 22, wherein the one or more confidence values are generated from one or more hidden layers of the one or more neural networks and provided with inferencing output.

Clause 24. The processor of any of clauses 22-23, wherein the one or more objects are identified from images captured by a geosensing imaging system, and further wherein the geosensing imaging system is a satellite.

Clause 25. The processor of any of clauses 22-24, wherein the one or more circuits are further to perform one or more actions based at least in part on multiple confidence values of the one or more objects.

Clause 26. The processor of any of clauses 22-25, wherein the one or more actions include transmitting an indication of the one or more confidence values to one or more geosensing systems.

Clause 27. The processor of any of clauses 22-26, wherein the one or more actions include causing the one or more neural networks to generate a different set of confidence values associated with the one or more objects.

Clause 28. A system, comprising:
one or more computers having one or more processors to train one or more neural networks to generate one or more confidence values associated with one or more objects identified by the one or more neural networks.

Clause 29. The system of clause 28, wherein the one or more processors are further to generate one or more classification scores associated with the one or more objects.

Clause 30. The system of any of clauses 28-29, wherein the one or more processors are further to perform one or more softmax processes on the one or more classification scores.

Clause 31. The system of any of clauses 28-30, wherein the one or more objects are identified from one or more images obtained from one or more agriculture devices.

Clause 32. The system of any of clauses 28-31, wherein the one or more processors are further to perform one or more actions based at least in part on the one or more confidence values.

Clause 33. The system of any of clauses 28-32, wherein the one or more actions include causing the one or more agriculture devices to at least activate one of:
one or more fertilization systems;
one or more watering systems; or
one or more weeding systems.

Clause 34. The system of any of clauses 28-33, wherein the one or more processors are further to train the one or more neural networks to generate the one or more confidence values for at least one of: instance segmentation, panoptic segmentation, optical flow, stereo disparity, classification, or detection processes.

In at least one embodiment, a single semiconductor platform may refer to a sole unitary semiconductor-based integrated circuit or chip. In at least one embodiment, multi-chip modules may be used with increased connectivity which simulate on-chip operation, and make substantial improvements over utilizing a conventional central processing unit ("CPU") and bus implementation. In at least one embodiment, various modules may also be situated separately or in various combinations of semiconductor platforms per desires of user.

In at least one embodiment, referring back to FIG. 14, computer programs in form of machine-readable executable code or computer control logic algorithms are stored in main memory 1404 and/or secondary storage. Computer programs, if executed by one or more processors, enable system 1400 to perform various functions in accordance with at least one embodiment. In at least one embodiment, memory 1404, storage, and/or any other storage are possible examples of computer-readable media. In at least one embodiment, secondary storage may refer to any suitable storage device or system such as a hard disk drive and/or a removable storage drive, representing a floppy disk drive, a magnetic tape drive, a compact disk drive, digital versatile disk ("DVD") drive, recording device, universal serial bus ("USB") flash memory, etc. In at least one embodiment, architecture and/or functionality of various previous figures are implemented in context of CPU 1402, parallel processing system 1412, an integrated circuit capable of at least a portion of capabilities of both CPU 1402, parallel processing system 1412, a chipset (e.g., a group of integrated circuits designed to work and sold as a unit for performing related functions, etc.), and/or any suitable combination of integrated circuit(s).

In at least one embodiment, architecture and/or functionality of various previous figures are implemented in context of a general computer system, a circuit board system, a game console system dedicated for entertainment purposes, an application-specific system, and more. In at least one embodiment, computer system 1400 may take form of a desktop computer, a laptop computer, a tablet computer, servers, supercomputers, a smart-phone (e.g., a wireless, hand-held device), personal digital assistant ("PDA"), a digital camera, a vehicle, a head mounted display, a hand-held electronic device, a mobile phone device, a television, workstation, game consoles, embedded system, and/or any other type of logic.

In at least one embodiment, parallel processing system 1412 includes, without limitation, a plurality of parallel processing units ("PPUs") 1414 and associated memories 1416. In at least one embodiment, PPUs 1414 are connected to a host processor or other peripheral devices via an interconnect 1418 and a switch 1420 or multiplexer. In at least one embodiment, parallel processing system 1412 distributes computational tasks across PPUs 1414 which can be parallelizable—for example, as part of distribution of computational tasks across multiple graphics processing unit ("GPU") thread blocks. In at least one embodiment, memory is shared and accessible (e.g., for read and/or write access) across some or all of PPUs 1414, although such shared memory may incur performance penalties relative to use of local memory and registers resident to a PPU 1414. In at least one embodiment, operation of PPUs 1414 is synchronized through use of a command such as _syncthreads( ), wherein all threads in a block (e.g., executed across multiple PPUs 1414) to reach a certain point of execution of code before proceeding.

Other variations are within spirit of present disclosure. Thus, while disclosed techniques are susceptible to various modifications and alternative constructions, certain illustrated embodiments thereof are shown in drawings and have been described above in detail. It should be understood, however, that there is no intention to limit disclosure to specific form or forms disclosed, but on contrary, intention is to cover all modifications, alternative constructions, and equivalents falling within spirit and scope of disclosure, as defined in appended claims.

Use of terms "a" and "an" and "the" and similar referents in context of describing disclosed embodiments (especially in context of following claims) are to be construed to cover both singular and plural, unless otherwise indicated herein or clearly contradicted by context, and not as a definition of a term. Terms "comprising," "having," "including," and "containing" are to be construed as open-ended terms (meaning "including, but not limited to,") unless otherwise noted. "Connected," when unmodified and referring to physical connections, is to be construed as partly or wholly contained within, attached to, or joined together, even if there is something intervening. Recitation of ranges of values herein are merely intended to serve as a shorthand method of referring individually to each separate value falling within range, unless otherwise indicated herein and each separate value is incorporated into specification as if it were individually recited herein. In at least one embodiment, use of term "set" (e.g., "a set of items") or "subset" unless otherwise noted or contradicted by context, is to be construed as a nonempty collection comprising one or more members. Further, unless otherwise noted or contradicted by context, term "subset" of a corresponding set does not necessarily denote a proper subset of corresponding set, but subset and corresponding set may be equal.

Conjunctive language, such as phrases of form "at least one of A, B, and C," or "at least one of A, B and C," unless specifically stated otherwise or otherwise clearly contradicted by context, is otherwise understood with context as used in general to present that an item, term, etc., may be either A or B or C, or any nonempty subset of set of A and B and C. For instance, in illustrative example of a set having three members, conjunctive phrases "at least one of A, B, and C" and "at least one of A, B and C" refer to any of following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present. In addition, unless otherwise noted or contradicted by context, term "plurality" indicates a state of being plural (e.g., "a plurality of items" indicates multiple items). In at least one embodiment, number of items in a plurality is at least two, but can be more when so indicated either explicitly or by context. Further, unless stated otherwise or otherwise clear from context, phrase "based on" means "based at least in part on" and not "based solely on."

Operations of processes described herein can be performed in any suitable order unless otherwise indicated herein or otherwise clearly contradicted by context. In at least one embodiment, a process such as those processes described herein (or variations and/or combinations thereof) is performed under control of one or more computer systems configured with executable instructions and is implemented as code (e.g., executable instructions, one or more computer programs or one or more applications) executing collectively on one or more processors, by hardware or combinations thereof. In at least one embodiment, code is stored on a computer-readable storage medium, for example, in form of a computer program comprising a plurality of instructions executable by one or more processors. In at least one embodiment, a computer-readable storage medium is a non-transitory computer-readable storage medium that excludes transitory signals (e.g., a propagating transient electric or electromagnetic transmission) but includes non-transitory data storage circuitry (e.g., buffers, cache, and queues) within transceivers of transitory signals. In at least one embodiment, code (e.g., executable code or source code) is stored on a set of one or more non-transitory computer-readable storage media having stored thereon executable instructions (or other memory to store executable instructions) that, when executed (i.e., as a result of being executed) by one or more processors of a computer system, cause computer system to perform operations described herein. In at least one embodiment, set of non-transitory computer-readable storage media comprises multiple non-transitory computer-readable storage media and one or more of individual non-transitory storage media of multiple non-transitory computer-readable storage media lack all of code while multiple non-transitory computer-readable storage media collectively store all of code. In at least one embodiment, executable instructions are executed such that different instructions are executed by different processors for example, a non-transitory computer-readable storage medium store instructions and a main central processing unit ("CPU") executes some of instructions while a graphics processing unit ("GPU") executes other instructions. In at least one embodiment, different components of a computer system have separate processors and different processors execute different subsets of instructions.

Accordingly, in at least one embodiment, computer systems are configured to implement one or more services that singly or collectively perform operations of processes described herein and such computer systems are configured with applicable hardware and/or software that enable performance of operations. Further, a computer system that implements at least one embodiment of present disclosure is a single device and, in another embodiment, is a distributed computer system comprising multiple devices that operate differently such that distributed computer system performs operations described herein and such that a single device does not perform all operations.

Use of any and all examples, or exemplary language (e.g., "such as") provided herein, is intended merely to better illuminate embodiments of disclosure and does not pose a limitation on scope of disclosure unless otherwise claimed. No language in specification should be construed as indicating any non-claimed element as essential to practice of disclosure.

All references, including publications, patent applications, and patents, cited herein are hereby incorporated by reference to same extent as if each reference were individually and specifically indicated to be incorporated by reference and were set forth in its entirety herein.

In description and claims, terms "coupled" and "connected," along with their derivatives, may be used. It should be understood that these terms may be not intended as synonyms for each other. Rather, in particular examples, "connected" or "coupled" may be used to indicate that two or more elements are in direct or indirect physical or electrical contact with each other. "Coupled" may also mean that two or more elements are not in direct contact with each other, but yet still co-operate or interact with each other.

Unless specifically stated otherwise, it may be appreciated that throughout specification terms such as "processing," "computing," "calculating," "determining," or like, refer to action and/or processes of a computer or computing system, or similar electronic computing device, that manipulate and/or transform data represented as physical, such as electronic, quantities within computing system's registers and/or memories into other data similarly represented as physical quantities within computing system's memories, registers or other such information storage, transmission or display devices.

In a similar manner, term "processor" may refer to any device or portion of a device that processes electronic data from registers and/or memory and transform that electronic data into other electronic data that may be stored in registers and/or memory. As non-limiting examples, "processor" may be a CPU or a GPU. A "computing platform" may comprise one or more processors. As used herein, "software" processes may include, for example, software and/or hardware entities that perform work over time, such as tasks, threads, and intelligent agents. Also, each process may refer to multiple processes, for carrying out instructions in sequence or in parallel, continuously or intermittently. In at least one embodiment, terms "system" and "method" are used herein interchangeably insofar as system may embody one or more methods and methods may be considered a system.

In present document, references may be made to obtaining, acquiring, receiving, or inputting analog or digital data into a subsystem, computer system, or computer-implemented machine. In at least one embodiment, process of obtaining, acquiring, receiving, or inputting analog and digital data can be accomplished in a variety of ways such as by receiving data as a parameter of a function call or a call to an application programming interface. In at least one embodiment, processes of obtaining, acquiring, receiving, or inputting analog or digital data can be accomplished by transferring data via a serial or parallel interface. In at least one embodiment, processes of obtaining, acquiring, receiving, or inputting analog or digital data can be accomplished by transferring data via a computer network from providing entity to acquiring entity. In at least one embodiment, references may also be made to providing, outputting, transmitting, sending, or presenting analog or digital data. In various examples, processes of providing, outputting, transmitting, sending, or presenting analog or digital data can be accomplished by transferring data as an input or output parameter of a function call, a parameter of an application programming interface or interprocess communication mechanism.

Although descriptions herein set forth example implementations of described techniques, other architectures may be used to implement described functionality, and are intended to be within scope of this disclosure. Furthermore, although specific distributions of responsibilities may be defined above for purposes of description, various functions and responsibilities might be distributed and divided in different ways, depending on circumstances.

Furthermore, although subject matter has been described in language specific to structural features and/or methodological acts, it is to be understood that subject matter claimed in appended claims is not necessarily limited to specific features or acts described. Rather, specific features and acts are disclosed as exemplary forms of implementing the claims.

What is claimed is:

1. One or more processors, comprising circuitry to use one or more neural networks to:
    identify one or more objects in one or more images based, at least in part, on segmentation of the one or more images;
    identify, based on the segmentation, one or more probabilities indicating that one or more pixels of the one or more objects is part of a corresponding object;
    generate one or more confidence values indicating predicted classifications to be associated with the one or more objects based, at least in part, on two or more probabilities generated for a same pixel; and
    in response to the one or more confidence values, cause one or more actions to be performed, wherein the one or more actions includes at least activating one or more steering systems of a vehicle.

2. The one or more processors of claim 1, wherein the one or more neural networks comprise one or more image segmentation networks, and further wherein the one or more objects are identified as belonging to one or more segmentation classes.

3. The one or more processors of claim 1, wherein the circuitry is to further use the one or more neural networks to generate one or more class scores corresponding to the one or more objects.

4. The one or more processors of claim 3, wherein the circuitry is to further use the one or more neural networks to at least:
    perform calibration on the one or more class scores; and
    generate a label based at least in part on results from the calibration.

5. The one or more processors of claim 1, wherein the circuitry is to further cause the vehicle to perform the one or more remedial actions in response to the one or more confidence values.

6. The one or more processors of claim 1, wherein the one or more actions include activating one or more warning systems of the vehicle.

7. The one or more processors of claim 1, wherein the one or more neural networks generate a confidence map that corresponds to a semantic segmentation of the one or more images.

8. The one or more processors of claim 7, wherein the confidence map comprises a visualization of one or more confidence values based, at least in part, on a gradient value.

9. The one or more processors of claim 1, wherein the one or more neural networks cause the vehicle to perform one or more actions based, at least in part, on one or more confidence values not satisfying a threshold value of confidence.

10. A system, comprising one or more processors to use one or more neural networks to:
   identify one or more objects in one or more images based, at least in part, on segmentation of the one or more images;
   identify, based on the segmentation, one or more probabilities indicating that one or more pixels of the one or more objects is part of a corresponding object;
   generate one or more confidence values indicating predicted classifications to be associated with the one or more objects based, at least in part, on two or more probabilities generated for a same pixel; and
   in response to the one or more confidence values, cause one or more actions to be performed, wherein the one or more actions includes at least activating one or more steering systems of a vehicle.

11. The system of claim 10, wherein the one or more objects are identified from one or more images captured using one or more cameras of a vehicle.

12. The system of claim 10, wherein the one or more outputs includes a vector of scores associated with one or more labels for each pixel of an image depicting the one or more objects.

13. The system of claim 12, wherein the one or more processors are further to cause a semi-autonomous vehicle to perform one or more remedial actions in response to the vector of scores.

14. The system of claim 13, wherein the one or more remedial actions include activating one or more acceleration systems of the semi-autonomous vehicle.

15. The system of claim 13, wherein the one or more remedial actions include activating one or more braking systems of the semi-autonomous vehicle.

16. The system of claim 13, wherein the one or more remedial actions include activating one or more warning systems of the semi-autonomous vehicle.

17. The system of claim 10, wherein the one or more neural networks further adjusts one or more confidence values based, at least in part, on one or more environmental conditions detected by one or more sensors of the vehicle.

18. A non-transitory machine-readable medium having stored thereon a set of instructions, which if performed by one or more processors, cause the one or more processors to use one or more neural networks to:
   identify one or more objects in one or more images based, at least in part, on segmentation of the one or more images;
   identify, based on the segmentation, one or more probabilities indicating that one or more pixels of the one or more objects is part of a corresponding object;
   generate one or more confidence values indicating predicted classifications to be associated with the one or more objects based, at least in part, on two or more probabilities generated for a same pixel; and
   in response to the one or more confidence values, cause one or more actions to be performed, wherein the one or more actions include activating one or more medical warning systems.

19. The non-transitory machine-readable medium of claim 18, wherein the one or more objects are identified from an image captured from one or more medical imaging devices.

20. The non-transitory machine-readable medium of claim 18, wherein one or more confidence values indicate one or more probabilities of whether one or more identifications of the one or more objects are correct.

21. The non-transitory machine-readable medium of claim 18, wherein the set of instructions further include instructions, which if performed by the one or more processors, cause the one or more processors to use the one or more neural networks to:
   determine whether one or more confidence values are below a threshold; and
   as a result of determining that the one or more confidence values are below the threshold, perform one or more actions.

22. The non-transitory machine-readable medium of claim 18, wherein the one or more actions include transmitting a notification to one or more medical systems.

23. The non-transitory machine-readable medium of claim 18, wherein the set of instructions further include instructions, which if performed by the one or more processors, cause the one or more processors to use the one or more neural networks to generate a segmentation map visualization indicating identifications of the one or more objects.

24. One or more processors, comprising circuitry to train one or more neural networks to:
   identify one or more objects in one or more images based, at least in part, on segmentation of the one or more images;
   identify, based on the segmentation, one or more probabilities indicating that one or more pixels of the one or more objects is part of a corresponding object;
   generate one or more confidence values indicating predicted classifications to be associated with the one or more objects based, at least in part, on two or more probabilities generated for a same pixel; and
   in response to the one or more confidence values, cause one or more actions to be performed, wherein the one or more actions include activating one or more warning systems.

25. The one or more processors of claim 24, wherein one or more confidence values are generated from one or more hidden layers of the one or more neural networks and provided with inferencing output.

26. The one or more processors of claim 24, wherein the one or more objects are identified from images captured by one or more geosensing imaging system, and further wherein an indication of multiple confidence values are transmitted to the one or more geosensing imaging systems.

27. The one or more processors of claim 24, wherein the circuitry is further to cause the one or more images to be segmented into one or more types of objects based, at least in part, on a comparison of how likely the one or more objects belong to at least one of two different semantic classes.

28. The one or more processors of claim 27, wherein the comparison is performed by the one or more neural networks based, at least in part, on the two or more probabilities for the same pixel indicating probabilities of different predicted classes.

29. The one or more processors of claim 27, wherein the circuitry is to further perform one or more actions causing the one or more neural networks to generate a different set of confidence values associated with the one or more objects.

30. A system, comprising one or more processors to train one or more neural networks to:
- identify one or more objects in one or more images based, at least in part, on segmentation of the one or more images;
- identify, based on the segmentation, one or more probabilities indicating that one or more pixels of the one or more objects is part of a corresponding object;
- generate one or more confidence values indicating predicted classifications to be associated with the one or more objects based, at least in part, on two or more probabilities generated for a same pixel; and
- in response to the one or more confidence values, cause one or more actions to be performed, wherein the one or more actions include causing to at least activate one of:
  - one or more fertilization systems;
  - one or more watering systems; or
  - one or more weeding systems.

31. The system of claim 30, wherein the one or more processors are further to generate one or more classification scores associated with the one or more objects.

32. The system of claim 31, wherein the one or more processors are further to perform one or more softmax processes on the one or more classification scores.

33. The system of claim 30, wherein the one or more objects are identified from one or more images obtained from one or more agriculture devices.

34. The system of claim 30, wherein the one or more processors are further to train the one or more neural networks to generate one or more confidence values for at least one of: instance segmentation, panoptic segmentation, optical flow, stereo disparity, classification, or detection processes.

* * * * *